US007745586B2

(12) United States Patent
Han et al.

(10) Patent No.: US 7,745,586 B2
(45) Date of Patent: Jun. 29, 2010

(54) HUMAN E3α UBIQUITIN LIGASE FAMILY

(75) Inventors: Hui-Quan Han, Thousand Oaks, CA (US); Keith Kwak, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 20 days.

(21) Appl. No.: 12/186,998

(22) Filed: Aug. 6, 2008

(65) Prior Publication Data

US 2009/0098575 A1  Apr. 16, 2009

Related U.S. Application Data

(62) Division of application No. 11/789,408, filed on Apr. 24, 2007, now Pat. No. 7,422,847, which is a division of application No. 10/758,636, filed on Jan. 15, 2004, now Pat. No. 7,220,547, which is a division of application No. 09/724,126, filed on Nov. 28, 2000, now Pat. No. 6,706,505.

(60) Provisional application No. 60/187,911, filed on Mar. 8, 2000.

(51) Int. Cl.
 C12P 21/08 (2006.01)
 G01N 33/563 (2006.01)
 G01N 33/536 (2006.01)
 G01N 33/543 (2006.01)

(52) U.S. Cl. ............... 530/387.9; 530/387.2; 530/387.3; 530/388.1; 530/388.15; 530/388.26; 436/512; 436/518; 436/536

(58) Field of Classification Search ........................ None
See application file for complete search history.

(56) References Cited

U.S. PATENT DOCUMENTS 5,861,312 A  1/1999  Varshavsky et al.
6,706,505 B1  3/2004  Han et al.

FOREIGN PATENT DOCUMENTS

WO  WO 98/23283  6/1998

OTHER PUBLICATIONS

Baracos et al., "Activation of the ATP-ubiquitin-proteasome pathway in skeletal muscle of cachetic rats bearing a hepatoma", *Am J Physiol* 268 (Endocrinol Metab):E996-1006, 1995.
Bartel et al., "The recognition component of the N-end rule pathway" *EMBO J* 9:3179-3189, 1990.
Ciechanover, "The ubiquitin-proteasome pathway: on protein death and cell life", *EMBO J* 17:7151-7160, 1998.
Hillier et al., Database GenBank. Accession No. AI929033, Aug. 23, 1999.
Kwon et al., "The mouse and human genes encoding the recognition component of the N-end rule pathway", *Proc Natl Acad Sci, USA* 95:7898-7903, 1998.

Lecker et al., "Muscle protein breakdown and the critical role of the ubiquitin-proteasome pathway in normal and disease states", *J Nutr* 129:227S-237S, 1999.
Matsumoto et al., "Tumor inoculation site-dependent induction of cachexia in mice bearing colon 26 carcinoma", *Brit J Cancer*79:764-769, 1999.
Mitch et al., "Mechanisms of muscle wasting: the role of ubiquitin-proteasome pathway", *New England J Med* 335:1897-1905, 1996.
Reiss et al., "Affinity purification of ubiquitin-protein ligase on immobilized protein substrates", *J Biol Chem* 265:3685-3690, 1990.
Solomon et al., "Rates of ubiquitin conjugation increase when muscles atrophy, largely through activation of the N-end rule pathway", *Proc Natl Acad Sci USA* 95:12602-12607, 1998.
Strausberg et al., Database GenBank. Accession No. AI361043, Feb. 15, 1999.
Tanaka et al., "Experimental cancer cachexia induced by transplantable colon 26 adenocarcinoma in mice", *Cancer Res* 50: 2290-2295, 1990.
Wilson et al., "2.2 Mb of contiguous nucleotide sequence from chromosome III of C. elegans", *Nature* 368:32-38, 1994.
Database GenBank. National Library of Medicine, (Bethesda, Maryland, US), Accession No. U88308, The C. elegans Sequencing Consortium, "Genome sequence of the nematode C. elegans: a platform for investigating biology: the C. elegans sequencing consortium", *Science* 282:2012-2018, 1998.
Database GenBank. National Library of Medicine, (Bethesda, Maryland, US), Accession No. AF061555, Kwon et al., "The mouse and human genes encoding the recognition component of the N-end rule pathway", Proc Natl Acad Sci, USA 95:7898-7903, 1998.
Database GenBank. National Library of Medicine, (Bethesda, Maryland, US), Accession No. AI187306, Strausberg, qf28h08.x1 Soares_testis_NHT *Homo sapiens* cDNA clone Image:1751391 3', mRNA sequence; National Cancer Institute, Cancer Genome Anatomy Project, 1997.
Database GenBank. National Library of Medicine, (Bethesda, Maryland, US), Accession No. AI192195, Strausberg, qc92e08.x1 Soares_pregnant_uterus_NbHPU *Homo sapiens* cDNA clone Image:I721702 3' similar to TR:O15057 O15057 KIAA0349; mRNA sequence; National Cancer Institute, Cancer Genome Anatomy Project, 1997.
Database GenBank. National Library of Medicine, (Bethesda, Maryland, US), Accession No. AI400279, Strausberg, tg43b12.x1 Soares_NFL_T_GBC_S1 *Homo sapiens* cDNA clone Image:2111519 3', mRNA sequence; National Cancer Institute, Cancer Genome Anatomy Project, 1997.
Database GenBank. National Library of Medicine, (Bethesda, Maryland, US), Accession No. AA002347, Marra et al., mg53g07.r1 Soares mouse embryo NbME13.5 14.5 Mus musculus cDNA clone Image:427548 5' similar to gb:U24428 Mus musculus mu-class glutathione s-transferase (Mouse); mRNA sequence, The WashU-HHMI Mouse EST Project, 1996.

*Primary Examiner*—David S Romeo
*Assistant Examiner*—Daniel C Gamett
(74) *Attorney, Agent, or Firm*—John A. Lamerdin

(57) ABSTRACT

The present invention relates to a novel polypeptide encoding a protein which is the full length human ortholog of E3α ubiquitin ligase. The invention also relates to vector, host cells, antibodies and recombinant methods for producing the polypeptide. In addition, the invention discloses therapeutic, diagnostic and research utilities for these and related products.

13 Claims, 23 Drawing Sheets

Figure 1A

| SEQ ID NO: | | | | | | |
|---|---|---|---|---|---|---|
| 6 | mouse_E3αI | MASEMEPEVQ | AID-RSLLEC | SAEEIAGRWL | QATDLNREVY | QHLAHCVPKI | 49 |
| 4 | human_E3αI | MASELEPEVQ | AID-RSLLEC | SAEEIAGKWL | QATDLTREVY | QHLAHYVPKI | 49 |
| 15 | mouse_E3αI | MADEEMDGAE | RMDVSPEPPL | APQRPASVWD | QQVDFYTAFL | HHLAQLVPEI | 50 |
| 2 | human_E3αI | MADEEAGGTE | RMEISAELPQ | TPQRLASVWD | QQVDFYTAFL | HHLAQLVPEI | 50 |
|  | Consensus | MA.E...... | ..D....L.. | .......A..W | Q..D...... | .HLA..VP.I | 50 |
| 6 | mouse_E3αI | YCRGPNPFPQ | KEDTLAQHIL | LGPMEWYICA | EDPALGFPKL | EQANKPSHLC | 99 |
| 4 | human_E3αI | YCRGPNPFPQ | KEDMLAQHVL | LGPMEWYLCG | EDPAFGFPKL | EQANKPSHLC | 99 |
| 15 | mouse_E3αI | YFAEMDPDLE | KQEESVQMSI | LTPLEWYLFG | EDPDICLEKL | KHSG-AFQLC | 99 |
| 2 | human_E3αI | YFAEMDPDLE | KQEESVQMSI | FTPLEWYLFG | EDPDICLEKL | KHSG-AFQLC | 99 |
|  | Consensus | Y......... | K........ | L.P.EWYL.G | EDP....... | ....KL.... | .LC | 100 |
| 6 | mouse_E3αII | GRVFKVGEPT | YSCRDCAVDP | TCVLCMECFL | GSIHRDHRYR | MTTSGGGFC | 149 |
| 4 | human_E3αII | GRVFKVGEPT | YSCRDCAVDP | TCVLCMECFL | GSIHRDHRYR | MTTSGGGGFC | 149 |
| 15 | mouse_E3αII | GKVFKSGETT | YSCRDCAIDP | TCVLCMDCFQ | SSVHKNHRYK | MHTSTGGGFC | 149 |
| 2 | human_E3αII | GRVFKSGETT | YSCRDCAIDP | TCVLCMDCFQ | DSVHKNHRYK | MHTSTGGGFC | 149 |
|  | Consensus | G.VFK.GE.T | YSCRDCA.DP | TCVLCM.CF. | .S.H..HRY. | M.TS.GGGFC | 150 |
| 6 | mouse_E3αII | DCGDTEAWKE | GPYCQKHKLS | SSEVVEEEDP | LVHLSEDVIA | RTYNIFAIMF | 199 |
| 4 | human_E3αII | DCGDTEAWKE | GPYCQKHELN | TSEIEEEEDP | LVHLSEDVIA | RTYNIFAITF | 199 |
| 15 | mouse_E3αII | DCGDTEAWKT | GPFCVDHEPG | RAGTTKESLH | -CPLNEEVIA | QARRIFPSVI | 198 |
| 2 | human_E3αII | DCGDTEAWKT | GPFCVNHEPG | RAGTIKENSR | -CPLNEEVIV | QARKIFPSVI | 198 |
|  | Consensus | DCGDTEAWK. | GP.C..HE.. | .......E.. | ....L.E.VIA | ....IF.... | 200 |

Figure 1B

```
6  mouse_E3αII   RYAVDILTWE KESELPEDLE VAEKSDTYYC MLFNDEVHTY EQVIYTLQKA  249
4  human_E3αII   RYAVEILTWE KESELPADLE MVEKSDTYYC MLFNDEVHTY EQVIYTLQKA  249
15 mouse_E3αI    KYIVEMTIWE EEKELPPELQ IREKNERYYC VLFNDEHHSY DHVIYSLQRA  248
2  human_E3αI    KYVVEMTIWE EEKELPPELQ IREKNERYYC VLFNDEHHSY DHVIYSLQRA  248
   Consensus     .Y..VE...WE .E.ELP..L. ..EK...YYC .LFNDE.H.Y ..VIY.LQ.A  250

6  mouse_E3αII   VNCTQKEAIG FATTVDRDGR RPVRYGDFQY CDQAKTVIVR NTSRQTK-PL  298
4  human_E3αII   VNCTQKEAIG FATTVDRDGR RSVRYGDFQY CEQAKSVIVR NTSRQTK-PL  298
15 mouse_E3αI    LDCELAEAQL HTTAIDKEGR RAVKAGVYAT CQEAKEDIKS HSENVSQHPL  298
2  human_E3αI    LDCELAEAQL HTTAIDKEGR RAVKAGAYAA CQEAKEDIKS HSENVSQHPL  298
   Consensus     ..C..EA.. ..T..D..GR R.V..G.... C..AK..I.. ........PL  300

6  mouse_E3αII   KVQVMHSSVA AHQNFGLKAL SWLGSVIGYS DGLRRIILCQV GLQEGPDGEN  348
4  human_E3αII   KVQVMHSSIV AHQNFGLKLL SWLGSIIGYS DGLRRIILCQV GLQEGPDGEN  348
15 mouse_E3αI    HVEVLHSVVM AHQKFALRLG SWMNKIMSYS SDFRQIFCQA CLVEEPGSEN  348
2  human_E3αI    HVEVLHSEIM AHQKFALRLG SWMNKIMSYS SDFRQIFCQA CLREEPDSEN  348
   Consensus     .V.V..HS... AHQ.F.L.L. SW..I..YS ...R.I.CQ. .L.E.PD.EN  350
```

Figure 1C

```
mouse_E3αII    SSLVDRLMLN DSKLWKGARS VYHQLFMSSL LMDLKYKKLF ALRFAKNYRQ   398
human_E3αII    SSLVDRLMLS DSKLWKGARS VYHQLFMSSL LMDLKYKKLF AVRFAKNYQQ   398
mouse_E3α      PCLISRLMLW DAKLYKGARK ILHELIFSSF FMEMEYKKLF AMEFVKYYKQ   398
human_E3α      PCLISRLMLW DAKLYKGARK ILHELIFSSF FMEMEYKKLF AMEFVKYYKQ   400
Consensus      ..L..RLML. D.KL.KGAR. ..H.L..SS. .M..YKKLF A..F.K.Y.Q mouse_E3αII    LQRDFMEDDH ERAVSVTALS VQFFTAPTLA RMLTEENLM  TVIIKAFMDH   448
human_E3αII    LQRDFMEDDH ERAVSVTALS VQFFTAPTLA RMLITEENLM SIIIKTFMDH   448
mouse_E3α      LQKEYISDDH ERSISITALS VQMLTVPTLA RHLIEEQNVI SVITETLLEV   448
human_E3α      LQKEYISDDH DRSISITALS VQMFTVPTLA RHLIEEQNVI SVITETLLEV   450
Consensus      LQ....DDH ER..S.TALS VQ.FT.PTLA R.LI.E.N. SVI..T...
```

| SEQ ID NO: | | | | | | |
|---|---|---|---|---|---|---|
| 6 | mouse_E3αII | LKHRDAQGRF | QFERYTALQA | FKFRRVQSLI | LDLKYVLISK | PTEWSDELRQ | 498 |
| 4 | human_E3αII | LRHRDAQGRF | QFERYTALQA | FKFRRVQSLI | LDLKYVLISK | PTEWSDELRQ | 498 |
| 15 | mouse_E3αI | LPEYLDRNN- | KFN-FQGYSQ | DKLGRVYAVI | CDLKYILISK | PVIWTERLRA | 496 |
| 2 | human_E3αI | LPEYLDRNN- | KFN-FQGYSQ | DKLGRVYAVI | CDLKYILISK | PTIWTERLRM | 496 |
| | Consensus | L........ | .F........ | .K..RV...I | .DLKY.LISK | PT.W...LR. | 500 |

| 6 | mouse_E3αII | KFLQGFDAFL | ELLKCMQGMD | PITRQVGQHI | EMEPEWEAAF | TLQMKLTHVI | 548 |
| 4 | human_E3αII | KFLEGFDAFL | ELLKCMQGMD | PITRQVGQHI | EMEPEWEAAF | TLQMKLTHVI | 548 |
| 15 | mouse_E3αI | QFLEGFRSFL | KILTCMQGME | EIRRQVGQHI | EVDPDWEAAI | AIQMQLKNIL | 546 |
| 2 | human_E3αI | QFLEGFRSFL | KILTCMQGME | EIRRQVGQHI | EVDPDWEAAI | AIQMQLKNIL | 546 |
| | Consensus | .FLEGF..FL | ..L.CMQGM. | .I.RQVGQHI | E..P.WEAA. | ..QML..... | 550 |

| 6 | mouse_E3αII | SMVQDWCALD | EKVLIEAYKK | CLAVLTQCHG | GFTDGEQPIT | LSICGHSVET | 598 |
| 4 | human_E3αII | SMVQDWCASD | EKVLIEAYKK | CLAVLMQCHG | GYTDGEQPIT | LSICGHSVET | 598 |
| 15 | mouse_E3αI | LMFQEWCACD | EDLLLVAYKE | CHKAVMRCST | NFMSSTKTV- | VQLCGHSLET | 595 |
| 2 | human_E3αI | LMFQEWCACD | EELLLVAYKE | CHKAVMRCST | SFISSSKTV- | VQSCGHSLET | 595 |
| | Consensus | .M.Q.WCA.D | E..L..AYK. | C.....M.C.. | .F........ | ...CGHS.ET | 600 |

Figure 1E

```
mouse_E3αII   6  IRYCVSQEKV SIHLPISRLL AGLHVLLSKS EVAYKFPELL PLSELSPPML  648
human_E3αII   4  IYCVSQEKV  SIHLPVSRLL AGLHVLLSKS EVAYKFPELL PLSELSPPML  648
mouse_E3αI   15  KSYKVSEDLV SIHLPLSRTL AGLHVRLSRL GAISRLHEFV PFDSFQVEVL   645
human_E3αI    2  KSYRVSEDLV SIHLPLSRTL AGLHVRLSRL GAVSRLHEFV SFEDFQVEVL   645
Consensus        ..Y.VS...V SIHLP.SR.L AGLHV.LS.. ........E.. P........L  650 mouse_E3αII   6  IEHPLRCLVL CAQVHAGMMR RNGFSLVNQI YYYHNVKCRR EMFDKDIVML  698
human_E3αII   4  IEHPLRCLVL CAQVHAGMMR RNGFSLVNQI YYYHNVKCRR EMFDKDVVML  698
mouse_E3αI   15  VEYPLRCLVL VAQVVAEMMR RNGLSLISQV FYYQDVKCRE EMYDKDIIML  695
human_E3αI    2  VEYPLRCLVL VAQVVAEMMR RNGLSLISQV FYYQDVKCRE EMYDKDIIML  695
Consensus        .E.PLRCLVL .AQV.A.MMR RNG.SL..Q. .YY..VKCR. EM.DKDI.ML  700 mouse_E3αII   6  QTGVSMMDPN HFLMMLSRF  ELYQLFSTPD YGKRFSSEVT HKDVVQQNNT  748
human_E3αII   4  QTGVSMMDPN HFLMMLSRF  ELYQIFSTPD YGKRFSSEIT HKDVVQQNNT  748
mouse_E3αI   15  QIGASIMDPN KFLLLVLQRY EL-----TDA FNKTIST--K DQDLIKQYNT  738
human_E3αI    2  QIGASLMDPN KFLLLVLQRY EL-----AEA FNKTIST--K DQDLIKQYNT  738
Consensus        Q.G.S.MDPN .FL...L.R. EL.....T.. ..K..S.... .D...Q.NT   750
```

Figure 1F

```
mouse_E3αII  LIEEMYLII  MLVGERFNPG  VGQVAATDEI  KREIIHQLSI  KPMAHSELVK  798
human_E3αII  LIEEMYLII  MLVGERFSPG  VGQVNATDEI  KREIIHQLSI  KPMAHSELVK  798
mouse_E3α    LIEEMQVLI  YIVGERYVPG  VGNVTREEVI  MREITHLLCI  EPMPHSAIAR  788
human_E3α    LIEEMQVLI  YIVGERYVPG  VGNVTKEEVT  MREIIHLLCI  EPMPHSAIAK  788
Consensus    .LIEEM...I ..VGER..PG  VG.V.....I  .REIIH.L.I  .PM.HS...K  800 mouse_E3αII  SLPEDENKET  GMESVIESVA  HFKKPGLTGR  GMYELKPECA  KEFNLYFYHF  848
human_E3αII  SLPEDENKET  GMESVIEAVA  HFKKPGLTGR  GMYELKPECA  KEFNLYFYHF  848
mouse_E3α    NLPENENNET  GLENVINKVA  TFKKPGVSGH  GVYELKDESL  KDFNMYFYHY  838
human_E3α    NLPENENNET  GLENVINKVA  TFKKPGVSGH  GVYELKDESL  KDFNMYFYHY  838
Consensus    .LPE.EN.ET  G.E.VI..VA  .FKKPG..G.  G.YELK.E..  K.FN.YFYH.  850 mouse_E3αII  SRAEQSKAEE  AQRKLKRENK  EDTALPPPAL  PPFCPLFASL  VNILQCDVM   898
human_E3αII  SRAEQSKAEE  AQRKLKRQNR  EDTALPPPVL  PPFCPLFASL  VNILQSDVM   898
mouse_E3α    SKTQHSKAEH  MQKKRRKQEN  KDEALPPPPP  PEFCPAFSKV  VNLLSCDVM   888
human_E3α    SKTQHSKAEH  MQKKRRKQEN  KDEALPPPPP  PEFCPAFSKV  INLLNCDIMM  888
Consensus    S....SKAE.  .Q.K...Q..  .D.ALPPP..  P.FCP.F...  VN.L.CDVM   900
```

Figure 1G

| SEQ ID NO: | | | | | | |
|---|---|---|---|---|---|---|
| 6 | mouse_E3αII | YIMGTILQWA | VEHHGSAWSE | SMLQRVLHLI | GMALQEEKHH LENAVEGHVQ | 948 |
| 4 | human_E3αII | CIMGTILQWA | VEHNGYAWSE | SMLQRVLHLI | GMALQEEKQH LENVTEEHVV | 948 |
| 15 | mouse_E3αI | YILRTIFERA | VDTESNLWTE | GMLQMAFHIL | ALGLLEEKQQ LQKAPEEEV- | 937 |
| 2 | human_E3αI | YILRTVFERA | IDTDSNLWTE | GMLQMAFHIL | ALGLLEEKQQ LQKAPEEEV- | 937 |
| | Consensus | YI..TI...A | V........W E | .MLQ...H.. | ...L.EEKQ. L..A.EE.V. | 950 |
| 6 | mouse_E3αII | TFTFTQKISK | PGDAPHNSPS | ILAMLETLQN | APSLEAHKDM IRWLLKMFNA | 998 |
| 4 | human_E3αII | TFTFTQKISK | PGEAPKNSPS | ILAMLETLQN | APYLEVHKDM IRWLKTFNA | 998 |
| 15 | mouse_E3αI | AFDFYHKASR | LGSSAMNAQN | IQMLERLKG | IPQLEGQKDM ITWLQMFDT | 987 |
| 2 | human_E3αI | TFDFYHKASR | LGSSAMNIQM | L---LEKLKG | IPQLEGQKDM ITWLQMFDT | 984 |
| | Consensus | TF.F..K.S. | .G......N.. | I...LE.L.. | .P.LE..KDM I..WL.MF.. | 1000 |
| 6 | mouse_E3αII | IKKIRE--CS | SSSPVAEAEG | TIMEESSRDK | DKAERKRKAE IARLRREKIM | 1046 |
| 4 | human_E3αII | VKKMRE--SS | PTSPVAETEG | TIMEESSRDK | DKAERKRKAE IARLRREKIM | 1046 |
| 15 | mouse_E3αI | VKRLREKSCL | VVATTSGLEC | IKSEEITHDK | EKAERKRKAE AARLHRQKIM | 1037 |
| 2 | human_E3αI | VKRLREKSCL | IVATTSGSES | IKNDEITHDK | EKAERKRKAE AARLHRQKIM | 1034 |
| | Consensus | VK..RE..C. | .........E. | ...EE...DK | .KAERKRKAE .ARL.R.KIM | 1050 |

Figure 1H

```
mouse_E3αII  6    AQMSEMQRHF IDENKELFQQ TLELDTSASA TL--DSSPPV SDAALTALGP  1094
human_E3αII  4    AQMSEMQRHF IDENKELFQQ TLELDASTSA VL--DHSPVA SDMTLTALGP  1094
mouse_E3α   15    AQMSALQKNF IETHKLMYDN TSEVTGKEDS IMEEESTSAV SEASRIALGP  1087
human_E3α    2    AQMSALQKNF IETHKLMYDN TSEMPGKEDS IMEEESTPAV SDYSRIALGP  1084
Consensus         AQMS..Q..F I.....K... T.E.......     ....S.P.V SD....ALGP  1100 mouse_E3αII  6    AQTQVPEPRQ FVTCILCQEE QEVTVGSRAM VLAAFVQRST VLSKDRTKTI  1144
human_E3αII  4    TQTQVPEQRQ FVTCILCQEE QEVKVESRAM VLAAFVQRST VLSKNRSKFI  1144
mouse_E3α   15    KRGPAVTEKE VLTCILCQEE QEVKLENNAM VLSACVQKST ALTQHRGKPV  1137
human_E3α    2    KRGPSVTEKE VLTCILCQEE QEVKIENNAM VLSACVQKST ALTQHRGKPI  1134
Consensus         .........  ..TCILCQEE QEVK.E..AM VL.A.VQ.ST .L..R.K.I  1150 mouse_E3αII  6    AD-PEKYDPL FMHPDLSCGT HTGSCGHVMH AHCWQRYFDS VQAKEQRRQQ  1193
human_E3αII  4    QD-PEKYDPL FMHPDLSCGT HTSSCGHIMH AHCWQRYFDS VQAKEQRRQQ  1193
mouse_E3α   15    DHLGETLDPL FMDPDLAHGT YTGSCGHVMH AVCWQKYFEA VQ--LSSQQ  1184
human_E3α    2    ELSGEALDPL FMDPDLAYGT YTGSCGHVMH AVCWQKYFEA VQ--LSSQQ  1181
Consensus         ...E..DPL FM PDL..GT .TGSCGHVMH A.CWQ.YF..  VQ......QQ  1200
```

Figure 1l

```
mouse_E3αII  6   RLRLHTSYDV ENGEFLCPLC ECLSNTVIPL L-LPPRSILS  RRLN-FSDQP  1241
human_E3αII  4   RLRLHTSYDV ENGEFLCPLC ECLSNTVIPL L-LPPRNIFN  NRLN-FSDQP  1241
mouse_E3α   15   RIHVDL-FDL ESGEYLCPLC KSLCNTVIPI IPLQPQKINS  ENAEALAQLL  1233
human_E3α    2   RIHVDL-FDL ESGEYLCPLC KSLCNTVIPI IPLQPQKINS  ENADALAQLL  1230
Consensus        R......D.  E.GE.LCPLC ..L.NTVIP.  ..L.P..I.S              1250 mouse_E3αII  6   DLAQWTRAVT QQIKVVQMLR RKHNAA-DTS SSEDTEAMNI  IPIPEGFRPD  1290
human_E3αII  4   NLTQWRTIS  QQIKALQFLR KEESTP-NNA STKNSENVDE  LQLPEGFRPD  1290
mouse_E3α   15   TLARWQTVL  ARISGYNIKH AKGEAPAVPV LFNQGMGDST  FEFHSILSFG  1283
human_E3α    2   TLARWQTVL  ARISGYNIRH AKGENP-IPI FFNQGMGDST  LEFHSILSFG  1279
Consensus        .LA.W.TV.  ..I........ .K...P-...               1300 mouse_E3αII  6   FYPRNPYSDS IKEMLTTFGT AAYKVGLKVH PNEGDPRVPI  LCWGTCAYTI  1340
human_E3αII  4   FRPKIPYSES IKEMLTTFGT ATYKVGLKVH PNEEDPRVPI  MCWGSCAYTI  1340
mouse_E3α   15   VQSSVKYSNS IKEMVILFAT TIYRIGLKVP PDELDPRVPM  MTWSTCAFTI  1333
human_E3α    2   VESSIKYSNS IKEMVILFAT TIYRIGLKVP PDERDPRVPM  LTWSTCAFTI  1329
Consensus        ......YS.S IKEM..F.T  ..Y..GLKV.  P.E.DPRVP.  ..WTCA.TI   1350
```

Figure 1J

| SEQ ID NO: | | | | | | |
|---|---|---|---|---|---|---|
| 6 mouse_E3αII | QSIERILSDE | EKPVFGPLPC | RLDDCLRSLT | RFAAAHWTVA | LLPVVQGHFC | 1390 |
| 4 human_E3αII | QSIERILSDE | DKPLFGPLPC | RLDDCLRSLT | RFAAAHWTVA | SVSVVQGHFC | 1390 |
| 15 mouse_E3αI | QAIENLLGDE | GKPLFGALQN | RQHSGLKALM | QFAVAQRATC | PQVLIHKHLA | 1383 |
| 2 human_E3αI | QAIENLLGDE | GKPLFGALQN | RQHNGLKALM | QFAVAQRITC | PQVLIQKHLV | 1379 |
| Consensus | Q.IE..L.DE | .KPLFG.L.. | R....L..L. | .FA.A..... | .....Q.H.. | 1400 |
| | | | | | | |
| 6 mouse_E3αII | KLFASLVPSD | SYEDLPCILD | IDMFHLLVGL | VLAFPALQCQ | D---FSGSSL | 1437 |
| 4 human_E3αII | KLFASLVPND | SHEELPCILD | IDMFHLLVGL | VLAFPALQCQ | D---FSGISL | 1437 |
| 15 mouse_E3αI | RLLSVILPNL | QSENTPGLLS | VDLFHVLVGA | VLAFPSLYWD | DTVDLQPSPL | 1433 |
| 2 human_E3αI | RLLSVVLPNI | KSEDTPCLLS | IDLFHVLVGA | VLAFPSLYWD | DPVDLQPSSV | 1429 |
| Consensus | .L......PN. | ..E..PC.L. | ID.FH.LVG. | VLAFP.L... | D.......SSL | 1450 |
| | | | | | | |
| 6 mouse_E3αII | ATG--DLHIF | HLVTMAHIVQ | ILLTSCTEEN | --GMDQENP | TGEEELAILS | 1482 |
| 4 human_E3αII | GTG--DLHIF | HLVTMAHIIQ | ILLTSCTEEN | --GMDQENP | PCEEESAVLA | 1482 |
| 15 mouse_E3αI | SSSYNHLYLF | HLITMAHMLQ | ILLTDTDLS | PGPPLAEGEE | DSEEARCASA | 1483 |
| 2 human_E3αI | SSSYNHLYLF | HLITMAHMLQ | ILLTVDTGL- | ---PLAQVQE | DSEEAHSASS | 1475 |
| Consensus | ....L..F | HL.TMAH..Q | ILLT..T... | ---...Q... | ....EE..... | 1500 |

Figure 1K

```
6  mouse_E3αII    LHKTLHQYTG  SALKEAPSGW  HLWRSVRAAI  MPFLKCSAL   FHYLNGVPAP  1532
4  human_E3αII    LYKTLHQYTG  SALKEIPSGW  HLWRSVRAGI  MPFLKCSALF  FHYLNGVPSP  1532
15 mouse_E3αI     FFVEVSQHTD  GLTGCGAPGW  YLWLSLRNGI  TPYLRCAALL  FHYLLGVAPP  1533
2  human_E3αI     FFAEISQYTS  GSIGCDIPGW  YLWVSLKNGI  TPYLRCAALF  FHYLLGVTPP  1525
   Consensus      ......QYT.  ........GW  .LW.S.R.GI  .P.L.C.ALF  FHYL.GV..P  1550

6  mouse_E3αII    PDLQV-SGTS  HFEHLCNYLS  LPTNLIHLFQ  ENSDIMNSLI  ESWCQNSEVK  1581
4  human_E3αII    PDIQV-PGTS  HFEHLCSYLS  LPNNLICLFQ  ENSEIMNSLI  ESWCRNSEVK  1581
15 mouse_E3αI     EELFANSAEG  EFSALCSYLS  LPTNLFLLFQ  EYWDTIRPLL  QRWCGDPALL  1583
2  human_E3αI     EELHTNSAEG  EYSALCSYLS  LPTNLFLLFQ  EYWDTVRPLL  QRWCADPALL  1575
   Consensus      ..L....S..  .F..LCSYLS  LPTNL..LFQ  E..D.....L  ..WC......  1600

6  mouse_E3αII    RYLNGERGAI  SYPRGANKLI  DLPEDYSSLI  NQASNFSCPK  SGGDKSRAPT  1631
4  human_E3αII    RYLEGERDAI  RYPRESNKLI  NLPEDYSSLI  NQASNFSCPK  SGGDKSRAPT  1631
15 mouse_E3αI     KSLKQKSAVV  RYPRKRNSLI  ELPEDYSCLL  NQASHFRCPR  SADDERKHPV  1633
2  human_E3αI     NCLKQKNTVV  RYPRKRNSLI  ELPDDYSCLL  NQASHFRCPR  SADDERKHPV  1625
   Consensus      ..L.......  RYPR..N.LI  .LPEDYS..L  NQAS.F.CP.  S..D.....P.  1650
```

Figure 1L

```
mouse_E3αII    LCLVCGSLLC  SQSYCCQAEL  EGEDVGACTA  HTYSCGSGAG  IFLRVRECQV  1681
human_E3αII    LCLVCGSLLC  SQSYCCQTEL  EGEDVGACTA  HTYSCGSGVG  IFLRVRECQV  1681
mouse_E3αI     LCLFCGAILC  SQNI CCQEIV  NGEEVGACVF  HALHCGAGVC  IFLKI RECRV 1683
human_E3αI     LCLFCGAILC  SQNI CCQEIV  NGEEVGACIF  HALHCGAGVC  IFLKI RECRV 1675
Consensus      LCL.CG..LC  SQ...CCQ..  .GE.VGAC..  H...CG.GV.  IFL..REC.V  1700 mouse_E3αII    LFLAGKTKGC  FYSPPYLDDY  GETDQGLRRG  NPLHLCQERF  RKI QKLWQQH 1731
human_E3αII    LFLAGKTKGC  FYSPPYLDDY  GETDQGLRRG  NPLHLCKERF  KKI QKLWHQH 1731
mouse_E3αI     VLVEGKARGC  AYPAPYLDEY  GETDPGLKRG  NPLHLSRERY  RKLHLVWQQH  1733
human_E3αI     VLVEGKARGC  AYPAPYLDEY  GETDPGLKRG  NPLHLSRERY  RKLHLVWQQH  1725
Consensus      ...GK..GC   .Y..PYLD.Y  GETD.GL.RG  NPLHL..ER.  RK....WQQH  1750 mouse_E3αII    SITEEI GHAQ  EANQTLVGI D  WQHL        1755
human_E3αII    SVTEEI GHAQ  EANQTLVGI D  WQHL        1755
mouse_E3αI     CIIEEI ARSQ  ETNQMLFGFN  WQLL        1757
human_E3αI     CIIEEI ARSQ  ETNQMLFGFN  WQLL        1749
Consensus      .I.EEI...Q   E.NQ.L.G..  WQ.L        1774
```

Tth Expression Profile of huE3α-II in Human Tissues

Tth Expression Profile of huE3α-I in Human Tissues

Ubiquitination of Endogenous Proteins

Transfection of Human E3α-I or E3α-II cDNA Stimulates Ubiquitin Conjugation in Cultured Muscle Cell Lines Rates of Ubiquitination of N-end Rule Substrate α-Lactalbumin in Skeletal Muscle Extracts Northern blot analysis of E3α-I & E3α-II expression in gastrocnemius muscles in YAH-130 exprimental cachexia model Northern blot analysis of E3α-I and E3α-II expression in gastrocnemius muscle and cardiac muscle in C26 experimental cachexia model IL-6 Elicits Accelerated Ubiquitination in C2C12 Myotube Cultures TNFα Elicits Accelerated Ubiquitination in C2C12 Myotube Cultures

SEQUENCE LISTING

<160> NUMBER OF SEQ ID NOS: 29

<210> SEQ ID NO 1
<211> LENGTH: 6308
<212> TYPE: DNA
<213> ORGANISM: Homo sapiens
<220> FEATURE:
<221> NAME/KEY: CDS
<222> LOCATION: (696)..(5942)

<400> SEQUENCE: 1

```
gccaagaatt cggcacgagg ggaaaagctg agcccaggaa ccaaattact tgctttacct      60
cattgtgtaa gacaagcgtc aaaaacagct tcaacctatc ttgaacaaga gaacttacct     120
ccaaaggctt atcatctgtc ttccacttat ccaacaagct gctatggcca ctgcctgtgc     180
cgcacctgga accaccgcca gcccactac tgcctccact accactggtt ctcccaccct     240
gatcagctgc ttgctgctgc catcttatcc gcttctgcct gttctgagta aatgtataca     300
caccctggaa accaccattc tactttctgt gtctatgaat ttgactactc tagctggatc     360
ccgagctttt ttgtacacat gtgcaagtgc ccacggggta gaatcctaaa aatagaagat     420
gtatgcaaca gttcccagca ccaaacccag atatacaacc attcagctac caagagctac     480
gcctgataaa ttagagggga aaaaaaaaat ctccagtccc ttcacgtcgt gacgcttgct     540
tccgggaagc gggccggaag ccactcctcg agtctgcgtc aaacccgact tcaggggccg     600
tcgtaaaagt gtcgtccctg tctctccgac cggccacagg tttccgcttg cctctggccg     660
ggggtcggca actgcaggcg tcagtttccc tcaag atg gcg gac gag gag gct       713
                                       Met Ala Asp Glu Glu Ala
                                        1               5 gga ggt act gag agg atg gaa atc agc gcg gag tta ccc cag acc cct     761
Gly Gly Thr Glu Arg Met Glu Ile Ser Ala Glu Leu Pro Gln Thr Pro
         10                  15                  20 cag cgt ctg gca tct tgg tgg gat cag caa gtt gat ttt tat act gct     809
Gln Arg Leu Ala Ser Trp Trp Asp Gln Gln Val Asp Phe Tyr Thr Ala
     25                  30                  35 ttc ttg cat cat ttg gca caa ttg gtg cca gaa att tac ttt gct gaa     857
Phe Leu His His Leu Ala Gln Leu Val Pro Glu Ile Tyr Phe Ala Glu
 40                  45                  50 atg gac cca gac ttg gaa aag cag gag gaa agt gta caa atg tca ata     905
Met Asp Pro Asp Leu Glu Lys Gln Glu Glu Ser Val Gln Met Ser Ile
55                  60                  65                  70 ttc act cca ctg gaa tgg tac tta ttt gga gaa gat cca gat att tgc     953
Phe Thr Pro Leu Glu Trp Tyr Leu Phe Gly Glu Asp Pro Asp Ile Cys
             75                  80                  85 tta gag aaa ttg aag cac agt gga gca ttt cag ctt tgt ggg agg gtt    1001
Leu Glu Lys Leu Lys His Ser Gly Ala Phe Gln Leu Cys Gly Arg Val
         90                  95                 100 ttc aaa agt gga gag aca acc tat tct tgc agg gat tgt gca att gat    1049
Phe Lys Ser Gly Glu Thr Thr Tyr Ser Cys Arg Asp Cys Ala Ile Asp
    105                 110                 115 cca aca tgt gta ctc tgt atg gac tgc ttc cag gac agt gtt cat aaa    1097
```

```
                Pro Thr Cys Val Leu Cys Met Asp Cys Phe Gln Asp Ser Val His Lys
                    120                 125                 130 aat cat cgt tac aag atg cat act tct act gga gga ggg ttc tgt gac              1145
Asn His Arg Tyr Lys Met His Thr Ser Thr Gly Gly Gly Phe Cys Asp
135                 140                 145                 150 tgt gga gac aca gag gca tgg aaa act ggc cct ttt tgt gta aat cat              1193
Cys Gly Asp Thr Glu Ala Trp Lys Thr Gly Pro Phe Cys Val Asn His
                155                 160                 165 gaa cct gga aga gca ggt act ata aaa gag aat tca cgc tgt ccg ttg              1241
Glu Pro Gly Arg Ala Gly Thr Ile Lys Glu Asn Ser Arg Cys Pro Leu
            170                 175                 180 aat gaa gag gta att gtc caa gcc agg aaa ata ttt cct tca gtg ata              1289
Asn Glu Glu Val Ile Val Gln Ala Arg Lys Ile Phe Pro Ser Val Ile
        185                 190                 195 aaa tat gtc gta gaa atg act ata tgg gaa gag aaa gaa ctg cct              1337
Lys Tyr Val Val Glu Met Thr Ile Trp Glu Glu Lys Glu Leu Pro
    200                 205                 210 cct gaa ctc cag ata agg gag aaa aat gaa aga tac tat tgt gtc ctt              1385
Pro Glu Leu Gln Ile Arg Glu Lys Asn Glu Arg Tyr Tyr Cys Val Leu
215                 220                 225                 230 ttc aat gat gaa cac cat tca tat gac cac gtc ata tac agc cta caa              1433
Phe Asn Asp Glu His His Ser Tyr Asp His Val Ile Tyr Ser Leu Gln
                235                 240                 245 aga gct ctt gac tgt gag ctc gca gag gcc cag ttg cat acc act gcc              1481
Arg Ala Leu Asp Cys Glu Leu Ala Glu Ala Gln Leu His Thr Thr Ala
                250                 255                 260 att gac aaa gag ggt cgt cgg gct gtt aaa gcg gga gct tat gct gct              1529
Ile Asp Lys Glu Gly Arg Arg Ala Val Lys Ala Gly Ala Tyr Ala Ala
            265                 270                 275 tgc cag gaa gca aag gaa gat ata aag agt cat tca gaa aat gtc tct              1577
Cys Gln Glu Ala Lys Glu Asp Ile Lys Ser His Ser Glu Asn Val Ser
        280                 285                 290 caa cat cca ctt cat gta gaa gta tta cac tca gag att atg gct cat              1625
Gln His Pro Leu His Val Glu Val Leu His Ser Glu Ile Met Ala His
295                 300                 305                 310 cag aaa ttt gct ttg cgt ctt ggt tcc tgg atg aac aaa att atg agc              1673
Gln Lys Phe Ala Leu Arg Leu Gly Ser Trp Met Asn Lys Ile Met Ser
                315                 320                 325 tat tca agt gac ttt agg cag atc ttt tgc caa gca tgc ctt aga gaa              1721
Tyr Ser Ser Asp Phe Arg Gln Ile Phe Cys Gln Ala Cys Leu Arg Glu
                330                 335                 340 gaa cct gac tcg gag aat ccc tgt ctc ata agc agg tta atg ctt tgg              1769
Glu Pro Asp Ser Glu Asn Pro Cys Leu Ile Ser Arg Leu Met Leu Trp
            345                 350                 355 gat gca aag ctt tat aaa ggt gcc cgt aag atc ctt cat gaa ttg atc              1817
Asp Ala Lys Leu Tyr Lys Gly Ala Arg Lys Ile Leu His Glu Leu Ile
        360                 365                 370 ttc agc agt ttt ttt atg gag atg gaa tac aaa aaa ctc ttt gct atg              1865
Phe Ser Ser Phe Phe Met Glu Met Glu Tyr Lys Lys Leu Phe Ala Met
375                 380                 385                 390 gaa ttt gtg aag tat tat aaa caa ctg cag aaa gaa tat atc agt gat              1913
Glu Phe Val Lys Tyr Tyr Lys Gln Leu Gln Lys Glu Tyr Ile Ser Asp
                395                 400                 405 gat cat gac aga agt atc tct ata act gca ctt tca gtt cag atg ttt              1961
Asp His Asp Arg Ser Ile Ser Ile Thr Ala Leu Ser Val Gln Met Phe
                410                 415                 420 act gtt cct act ctg gct cga cat ctt att gaa gag cag aat gtt atc              2009
Thr Val Pro Thr Leu Ala Arg His Leu Ile Glu Glu Gln Asn Val Ile
            425                 430                 435
```

```
tct gtc att act gaa act ctg cta gaa gtt tta cct gag tac ttg gac      2057
Ser Val Ile Thr Glu Thr Leu Leu Glu Val Leu Pro Glu Tyr Leu Asp
    440             445                 450 agg aac aat aaa ttc aac ttc cag ggt tat agc cag gac aaa ttg gga      2105
Arg Asn Asn Lys Phe Asn Phe Gln Gly Tyr Ser Gln Asp Lys Leu Gly
455                 460                 465                 470 aga gta tat gca gta ata tgt gac cta aag tat atc ctg atc agc aaa      2153
Arg Val Tyr Ala Val Ile Cys Asp Leu Lys Tyr Ile Leu Ile Ser Lys
                    475                 480                 485 ccc aca ata tgg aca gaa aga tta aga atg cag ttc ctt gaa ggt ttt      2201
Pro Thr Ile Trp Thr Glu Arg Leu Arg Met Gln Phe Leu Glu Gly Phe
                490                 495                 500 cga tct ttt ttg aag att ctt acc tgt atg cag gga atg gaa gaa atc      2249
Arg Ser Phe Leu Lys Ile Leu Thr Cys Met Gln Gly Met Glu Glu Ile
            505                 510                 515 cga aga cag gtt ggg caa cac att gaa gtg gat cct gat tgg gag gct      2297
Arg Arg Gln Val Gly Gln His Ile Glu Val Asp Pro Asp Trp Glu Ala
520                 525                 530 gcc att gct ata cag atg caa ttg aag aat att tta ctc atg ttc caa      2345
Ala Ile Ala Ile Gln Met Gln Leu Lys Asn Ile Leu Leu Met Phe Gln
535                 540                 545                 550 gag tgg tgt gct tgt gat gaa gaa ctc tta ctt gtg gct tat aaa gaa      2393
Glu Trp Cys Ala Cys Asp Glu Glu Leu Leu Leu Val Ala Tyr Lys Glu
                    555                 560                 565 tgt cac aaa gct gtg atg agg tgc agt acc agt ttc ata tct agt agc      2441
Cys His Lys Ala Val Met Arg Cys Ser Thr Ser Phe Ile Ser Ser Ser
                570                 575                 580 aag aca gta gta caa tcg tgt gga cat agt ttg gaa aca aag tcc tac      2489
Lys Thr Val Val Gln Ser Cys Gly His Ser Leu Glu Thr Lys Ser Tyr
            585                 590                 595 aga gta tct gag gat ctt gta agc ata cat ctg cca ctc tct agg acc      2537
Arg Val Ser Glu Asp Leu Val Ser Ile His Leu Pro Leu Ser Arg Thr
600                 605                 610 ctt gct ggt ctt cat gta cgt tta agc agg ctg ggt gct gtt tca aga      2585
Leu Ala Gly Leu His Val Arg Leu Ser Arg Leu Gly Ala Val Ser Arg
615                 620                 625                 630 ctg cat gaa ttt gtg tct ttt gag gac ttt caa gta gag gta cta gtg      2633
Leu His Glu Phe Val Ser Phe Glu Asp Phe Gln Val Glu Val Leu Val
                    635                 640                 645 gaa tat cct tta cgt tgt ctg gtg ttg gtt gcc cag gtt gtt gct gag      2681
Glu Tyr Pro Leu Arg Cys Leu Val Leu Val Ala Gln Val Val Ala Glu
                650                 655                 660 atg tgg cga aga aat gga ctg tct ctt att agc cag gtg ttt tat tac      2729
Met Trp Arg Arg Asn Gly Leu Ser Leu Ile Ser Gln Val Phe Tyr Tyr
            665                 670                 675 caa gat gtt aag tgc aga gaa gaa atg tat gat aaa gat atc atc atg      2777
Gln Asp Val Lys Cys Arg Glu Glu Met Tyr Asp Lys Asp Ile Ile Met
680                 685                 690 ctt cag att ggt gca tct tta atg gat ccc aat aag ttc ttg tta ctg      2825
Leu Gln Ile Gly Ala Ser Leu Met Asp Pro Asn Lys Phe Leu Leu Leu
695                 700                 705                 710 gta ctt cag agg tat gaa ctt gcc gag gct ttt aac aag acc ata tct      2873
Val Leu Gln Arg Tyr Glu Leu Ala Glu Ala Phe Asn Lys Thr Ile Ser
                    715                 720                 725 aca aaa gac cag gat ttg att aaa caa tat aat aca cta ata gaa gaa      2921
Thr Lys Asp Gln Asp Leu Ile Lys Gln Tyr Asn Thr Leu Ile Glu Glu
                730                 735                 740 atg ctt cag gtc ctc atc tat att gtg ggt gag cgt tat gta cct gga      2969
Met Leu Gln Val Leu Ile Tyr Ile Val Gly Glu Arg Tyr Val Pro Gly
            745                 750                 755
```

```
                                                              -continued gtg gga aat gtg acc aaa gaa gag gtc aca atg aga gaa atc att cac          3017
Val Gly Asn Val Thr Lys Glu Glu Val Thr Met Arg Glu Ile Ile His
    760                 765                 770 ttg ctt tgc att gaa ccc atg cca cac agt gcc att gcc aaa aat tta          3065
Leu Leu Cys Ile Glu Pro Met Pro His Ser Ala Ile Ala Lys Asn Leu
775                 780                 785                 790 cct gag aat gaa aat aat gaa act ggc tta gag aat gtc ata aac aaa          3113
Pro Glu Asn Glu Asn Asn Glu Thr Gly Leu Glu Asn Val Ile Asn Lys
                795                 800                 805 gtg gcc aca ttt aag aaa cca ggt gta tca ggc cat gga gtt tat gaa          3161
Val Ala Thr Phe Lys Lys Pro Gly Val Ser Gly His Gly Val Tyr Glu
            810                 815                 820 cta aaa gat gaa tca ctg aaa gac ttc aat atg tac ttt tat cat tac          3209
Leu Lys Asp Glu Ser Leu Lys Asp Phe Asn Met Tyr Phe Tyr His Tyr
        825                 830                 835 tcc aaa acc cag cat agc aag gct gaa cat atg cag aag aaa agg aga          3257
Ser Lys Thr Gln His Ser Lys Ala Glu His Met Gln Lys Lys Arg Arg
    840                 845                 850 aaa caa gaa aac aaa gat gaa gca ttg ccg cca cca cca cct cct gaa          3305
Lys Gln Glu Asn Lys Asp Glu Ala Leu Pro Pro Pro Pro Pro Pro Glu
855                 860                 865                 870 ttc tgc cct gct ttc agc aaa gtg att aac ctt ctc aac tgt gat atc          3353
Phe Cys Pro Ala Phe Ser Lys Val Ile Asn Leu Leu Asn Cys Asp Ile
                875                 880                 885 atg atg tac att ctc agg acc gta ttt gag cgg gca ata gac aca gat          3401
Met Met Tyr Ile Leu Arg Thr Val Phe Glu Arg Ala Ile Asp Thr Asp
            890                 895                 900 tct aac ttg tgg acc gaa ggg atg ctc caa atg gct ttt cat att ctg          3449
Ser Asn Leu Trp Thr Glu Gly Met Leu Gln Met Ala Phe His Ile Leu
        905                 910                 915 gca ttg ggt tta cta gaa gag aag caa cag ctt caa aaa gct cct gaa          3497
Ala Leu Gly Leu Leu Glu Glu Lys Gln Gln Leu Gln Lys Ala Pro Glu
    920                 925                 930 gaa gaa gta aca ttt gac ttt tat cat aag gct tca aga ttg gga agt          3545
Glu Glu Val Thr Phe Asp Phe Tyr His Lys Ala Ser Arg Leu Gly Ser
935                 940                 945                 950 tca gcc atg aat ata caa atg ctt ttg gaa aaa ctc aaa gga att ccc          3593
Ser Ala Met Asn Ile Gln Met Leu Leu Glu Lys Leu Lys Gly Ile Pro
                955                 960                 965 cag tta gaa ggc cag aag gac atg ata acg tgg ata ctt cag atg ttt          3641
Gln Leu Glu Gly Gln Lys Asp Met Ile Thr Trp Ile Leu Gln Met Phe
            970                 975                 980 gac aca gtg aag cga tta aga gaa aaa tct tgt tta att gta gca acc          3689
Asp Thr Val Lys Arg Leu Arg Glu Lys Ser Cys Leu Ile Val Ala Thr
        985                 990                 995 aca tca gga tcg gaa tct att   aag aat gat gag att   act cat gat          3734
Thr Ser Gly Ser Glu Ser Ile   Lys Asn Asp Glu Ile   Thr His Asp
    1000                1005                    1010 aaa gaa aaa gca gaa cga aaa   aga aaa gct gaa gct   gct agg cta          3779
Lys Glu Lys Ala Glu Arg Lys   Arg Lys Ala Glu Ala   Ala Arg Leu
    1015                1020                    1025 cat cgc cag aag atc atg gct   cag atg tct gcc tta   cag aaa aac          3824
His Arg Gln Lys Ile Met Ala   Gln Met Ser Ala Leu   Gln Lys Asn
    1030                1035                    1040 ttc att gaa act cat aaa ctc   atg tat gac aat aca   tca gaa atg          3869
Phe Ile Glu Thr His Lys Leu   Met Tyr Asp Asn Thr   Ser Glu Met
    1045                1050                    1055 cct ggg aaa gaa gat tcc att   atg gag gaa gag agc   acc cca gca          3914
Pro Gly Lys Glu Asp Ser Ile   Met Glu Glu Glu Ser   Thr Pro Ala
```

-continued

|  |  |  |  |  |  |  |  |  |  |  |  |  |  |  |  |
|---|---|---|---|---|---|---|---|---|---|---|---|---|---|---|---|
|  |  | 1060 |  |  |  | 1065 |  |  |  | 1070 |  |  |  |  |  |
| gtc | agt | gac | tac | tct | aga | att | gct | ttg | ggt | cct | aaa | cgg | ggt | cca | 3959 |
| Val | Ser | Asp | Tyr | Ser | Arg | Ile | Ala | Leu | Gly | Pro | Lys | Arg | Gly | Pro |  |
|  | 1075 |  |  |  | 1080 |  |  |  | 1085 |  |  |  |  |  |  |
| tct | gtt | act | gaa | aag | gag | gtg | ctg | acg | tgc | atc | ctt | tgc | caa | gaa | 4004 |
| Ser | Val | Thr | Glu | Lys | Glu | Val | Leu | Thr | Cys | Ile | Leu | Cys | Gln | Glu |  |
|  | 1090 |  |  |  | 1095 |  |  |  | 1100 |  |  |  |  |  |  |
| gaa | cag | gag | gtg | aaa | ata | gaa | aat | aat | gcc | atg | gta | tta | tcg | gca | 4049 |
| Glu | Gln | Glu | Val | Lys | Ile | Glu | Asn | Asn | Ala | Met | Val | Leu | Ser | Ala |  |
|  | 1105 |  |  |  | 1110 |  |  |  | 1115 |  |  |  |  |  |  |
| tgt | gtc | cag | aaa | tct | act | gcc | tta | acc | cag | cac | agg | gga | aaa | ccc | 4094 |
| Cys | Val | Gln | Lys | Ser | Thr | Ala | Leu | Thr | Gln | His | Arg | Gly | Lys | Pro |  |
|  | 1120 |  |  |  | 1125 |  |  |  | 1130 |  |  |  |  |  |  |
| ata | gaa | ctc | tca | gga | gaa | gcc | cta | gac | cca | ctt | ttc | atg | gat | cca | 4139 |
| Ile | Glu | Leu | Ser | Gly | Glu | Ala | Leu | Asp | Pro | Leu | Phe | Met | Asp | Pro |  |
|  | 1135 |  |  |  | 1140 |  |  |  | 1145 |  |  |  |  |  |  |
| gac | ttg | gca | tat | gga | act | tat | aca | gga | agc | tgt | ggt | cat | gta | atg | 4184 |
| Asp | Leu | Ala | Tyr | Gly | Thr | Tyr | Thr | Gly | Ser | Cys | Gly | His | Val | Met |  |
|  | 1150 |  |  |  | 1155 |  |  |  | 1160 |  |  |  |  |  |  |
| cac | gca | gtg | tgc | tgg | cag | aag | tat | ttt | gaa | gct | gta | cag | ctg | agc | 4229 |
| His | Ala | Val | Cys | Trp | Gln | Lys | Tyr | Phe | Glu | Ala | Val | Gln | Leu | Ser |  |
|  | 1165 |  |  |  | 1170 |  |  |  | 1175 |  |  |  |  |  |  |
| tct | cag | cag | cgc | att | cat | gtt | gac | ctt | ttt | gac | ttg | gaa | agt | gga | 4274 |
| Ser | Gln | Gln | Arg | Ile | His | Val | Asp | Leu | Phe | Asp | Leu | Glu | Ser | Gly |  |
|  | 1180 |  |  |  | 1185 |  |  |  | 1190 |  |  |  |  |  |  |
| gaa | tat | ctt | tgc | cct | ctt | tgc | aaa | tct | ctg | tgc | aat | act | gtg | atc | 4319 |
| Glu | Tyr | Leu | Cys | Pro | Leu | Cys | Lys | Ser | Leu | Cys | Asn | Thr | Val | Ile |  |
|  | 1195 |  |  |  | 1200 |  |  |  | 1205 |  |  |  |  |  |  |
| ccc | att | att | cct | ttg | caa | cct | caa | aag | ata | aac | agt | gag | aat | gca | 4364 |
| Pro | Ile | Ile | Pro | Leu | Gln | Pro | Gln | Lys | Ile | Asn | Ser | Glu | Asn | Ala |  |
|  | 1210 |  |  |  | 1215 |  |  |  | 1220 |  |  |  |  |  |  |
| gat | gct | ctt | gct | caa | ctt | ttg | acc | ctg | gca | cgg | tgg | ata | cag | act | 4409 |
| Asp | Ala | Leu | Ala | Gln | Leu | Leu | Thr | Leu | Ala | Arg | Trp | Ile | Gln | Thr |  |
|  | 1225 |  |  |  | 1230 |  |  |  | 1235 |  |  |  |  |  |  |
| gtt | ctg | gcc | aga | ata | tca | ggt | tat | aat | ata | aga | cat | gct | aaa | gga | 4454 |
| Val | Leu | Ala | Arg | Ile | Ser | Gly | Tyr | Asn | Ile | Arg | His | Ala | Lys | Gly |  |
|  | 1240 |  |  |  | 1245 |  |  |  | 1250 |  |  |  |  |  |  |
| gaa | aac | cca | att | cct | att | ttc | ttt | aat | caa | gga | atg | gga | gat | tct | 4499 |
| Glu | Asn | Pro | Ile | Pro | Ile | Phe | Phe | Asn | Gln | Gly | Met | Gly | Asp | Ser |  |
|  | 1255 |  |  |  | 1260 |  |  |  | 1265 |  |  |  |  |  |  |
| act | ttg | gag | ttc | cat | tcc | atc | ctg | agt | ttt | ggc | gtt | gag | tct | tcg | 4544 |
| Thr | Leu | Glu | Phe | His | Ser | Ile | Leu | Ser | Phe | Gly | Val | Glu | Ser | Ser |  |
|  | 1270 |  |  |  | 1275 |  |  |  | 1280 |  |  |  |  |  |  |
| att | aaa | tat | tca | aat | agc | atc | aag | gaa | atg | gtt | att | ctc | ttt | gcc | 4589 |
| Ile | Lys | Tyr | Ser | Asn | Ser | Ile | Lys | Glu | Met | Val | Ile | Leu | Phe | Ala |  |
|  | 1285 |  |  |  | 1290 |  |  |  | 1295 |  |  |  |  |  |  |
| aca | aca | att | tat | aga | att | gga | ttg | aaa | gtg | cca | cct | gat | gaa | agg | 4634 |
| Thr | Thr | Ile | Tyr | Arg | Ile | Gly | Leu | Lys | Val | Pro | Pro | Asp | Glu | Arg |  |
|  | 1300 |  |  |  | 1305 |  |  |  | 1310 |  |  |  |  |  |  |
| gat | cct | cga | gtc | ccc | atg | ctg | acc | tgg | agc | acc | tgc | gct | ttc | act | 4679 |
| Asp | Pro | Arg | Val | Pro | Met | Leu | Thr | Trp | Ser | Thr | Cys | Ala | Phe | Thr |  |
|  | 1315 |  |  |  | 1320 |  |  |  | 1325 |  |  |  |  |  |  |
| atc | cag | gca | att | gaa | aat | cta | ttg | gga | gat | gaa | gga | aaa | cct | ctg | 4724 |
| Ile | Gln | Ala | Ile | Glu | Asn | Leu | Leu | Gly | Asp | Glu | Gly | Lys | Pro | Leu |  |
|  | 1330 |  |  |  | 1335 |  |  |  | 1340 |  |  |  |  |  |  |
| ttt | gga | gca | ctt | caa | aat | agg | cag | cat | aat | ggt | ctg | aaa | gca | tta | 4769 |
| Phe | Gly | Ala | Leu | Gln | Asn | Arg | Gln | His | Asn | Gly | Leu | Lys | Ala | Leu |  |
|  | 1345 |  |  |  | 1350 |  |  |  | 1355 |  |  |  |  |  |  |
| atg | cag | ttt | gca | gtt | gca | cag | agg | att | acc | tgt | cct | cag | gtc | ctg | 4814 |

```
                Met Gln Phe Ala Val Ala Gln Arg Ile Thr Cys Pro Gln Val Leu
                    1360                1365                1370 ata cag aaa cat ctg gtt cgt ctt cta tca gtt gtt ctt cct aac             4859
Ile Gln Lys His Leu Val Arg Leu Leu Ser Val Val Leu Pro Asn
    1375                1380                1385 ata aaa tca gaa gat aca cca tgc ctt ctg tct ata gat ctg ttt             4904
Ile Lys Ser Glu Asp Thr Pro Cys Leu Leu Ser Ile Asp Leu Phe
    1390                1395                1400 cat gtt ttg gtg ggt gct gtg tta gca ttc cca tcc ttg tat tgg             4949
His Val Leu Val Gly Ala Val Leu Ala Phe Pro Ser Leu Tyr Trp
    1405                1410                1415 gat gac cct gtt gat ctg cag cct tct tca gtt agt tct tcc tat             4994
Asp Asp Pro Val Asp Leu Gln Pro Ser Ser Val Ser Ser Ser Tyr
    1420                1425                1430 aac cac ctt tat ctc ttc cat ttg atc acc atg gca cac atg ctt             5039
Asn His Leu Tyr Leu Phe His Leu Ile Thr Met Ala His Met Leu
    1435                1440                1445 cag ata cta ctt aca gta gac aca ggc cta ccc ctt gct cag gtt             5084
Gln Ile Leu Leu Thr Val Asp Thr Gly Leu Pro Leu Ala Gln Val
    1450                1455                1460 caa gaa gac agt gaa gag gct cat tcc gca tct tct ttc ttt gca             5129
Gln Glu Asp Ser Glu Glu Ala His Ser Ala Ser Ser Phe Phe Ala
    1465                1470                1475 gaa att tct caa tat aca agt ggc tcc att ggg tgt gat att cct             5174
Glu Ile Ser Gln Tyr Thr Ser Gly Ser Ile Gly Cys Asp Ile Pro
    1480                1485                1490 ggc tgg tat ttg tgg gtc tca ctg aag aat ggc atc acc cct tat             5219
Gly Trp Tyr Leu Trp Val Ser Leu Lys Asn Gly Ile Thr Pro Tyr
    1495                1500                1505 ctt cgc tgt gct gca ttg ttt ttc cac tat tta ctt ggg gta act             5264
Leu Arg Cys Ala Ala Leu Phe Phe His Tyr Leu Leu Gly Val Thr
    1510                1515                1520 ccg cct gag gaa ctg cat acc aat tct gca gaa gga gag tac agt             5309
Pro Pro Glu Glu Leu His Thr Asn Ser Ala Glu Gly Glu Tyr Ser
    1525                1530                1535 gca ctc tgt agc tat cta tct tta cct aca aat ttg ttc ctg ctc             5354
Ala Leu Cys Ser Tyr Leu Ser Leu Pro Thr Asn Leu Phe Leu Leu
    1540                1545                1550 ttc cag gaa tat tgg gat act gta agg ccc ttg ctc cag agg tgg             5399
Phe Gln Glu Tyr Trp Asp Thr Val Arg Pro Leu Leu Gln Arg Trp
    1555                1560                1565 tgt gca gat cct gcc tta cta aac tgt ttg aag caa aaa aac acc             5444
Cys Ala Asp Pro Ala Leu Leu Asn Cys Leu Lys Gln Lys Asn Thr
    1570                1575                1580 gtg gtc agg tac cct aga aaa aga aat agt ttg ata gag ctt cct             5489
Val Val Arg Tyr Pro Arg Lys Arg Asn Ser Leu Ile Glu Leu Pro
    1585                1590                1595 gat gac tat agc tgc ctc ctg aat caa gct tct cat ttc agg tgc             5534
Asp Asp Tyr Ser Cys Leu Leu Asn Gln Ala Ser His Phe Arg Cys
    1600                1605                1610 cca cgg tct gca gat gat gag cga aag cat cct gtc ctc tgc ctt             5579
Pro Arg Ser Ala Asp Asp Glu Arg Lys His Pro Val Leu Cys Leu
    1615                1620                1625 ttc tgt ggg gct ata cta tgt tct cag aac att tgc tgc cag gaa             5624
Phe Cys Gly Ala Ile Leu Cys Ser Gln Asn Ile Cys Cys Gln Glu
    1630                1635                1640 att gtg aac ggg gaa gag gtt gga gct tgc att ttt cac gca ctt             5669
Ile Val Asn Gly Glu Glu Val Gly Ala Cys Ile Phe His Ala Leu
    1645                1650                1655
```

-continued

```
cac tgt gga gcc gga gtc tgc att ttc cta aaa atc aga gaa tgc      5714
His Cys Gly Ala Gly Val Cys Ile Phe Leu Lys Ile Arg Glu Cys
    1660                1665                1670 cga gtg gtc ctg gtt gaa ggt aaa gcc aga ggc tgt gcc tat cca      5759
Arg Val Val Leu Val Glu Gly Lys Ala Arg Gly Cys Ala Tyr Pro
1675                1680                1685 gct cct tac ttg gat gaa tat gga gaa aca gac cct ggc ctg aag      5804
Ala Pro Tyr Leu Asp Glu Tyr Gly Glu Thr Asp Pro Gly Leu Lys
    1690                1695                1700 agg ggc aac ccc ctt cat tta tct cgt gag cgg tat cgg aag ctc      5849
Arg Gly Asn Pro Leu His Leu Ser Arg Glu Arg Tyr Arg Lys Leu
    1705                1710                1715 cat ttg gtc tgg caa caa cac tgc att ata gaa gag att gct agg      5894
His Leu Val Trp Gln Gln His Cys Ile Ile Glu Glu Ile Ala Arg
    1720                1725                1730 agc caa gag act aat cag atg tta ttt gga ttc aac tgg cag tta      5939
Ser Gln Glu Thr Asn Gln Met Leu Phe Gly Phe Asn Trp Gln Leu
    1735                1740                1745 ctg tgagctccaa ctctgcctca agacaatcac aaatgacgac agtagtaaag       5992
Leu gctgattcaa aattatggaa aactttctga gggctgggaa agtattggag ggtcttttgc 6052 tccatgtcca ggttcactta catcaataaa atatttctta atggagtatt gctttcaatt  6112
agcaaacata tgcttcacag gaaaaaagga catagatcaa tctgttttat gtgctagtat  6172
ttccaggaat ttattcccct tcataatttg tctcatttca ttttatttca tccacttggt  6232
agatgaagtc acgtcaaaca gttgtagaca ttttatgtgt tggttaactc ttctgcaatt  6292
ttgtatttgg tgtttt                                                 6308
```

<210> SEQ ID NO 2
<211> LENGTH: 1749
<212> TYPE: PRT
<213> ORGANISM: Homo sapiens

<400> SEQUENCE: 2

```
Met Ala Asp Glu Glu Ala Gly Gly Thr Glu Arg Met Glu Ile Ser Ala
1               5                   10                  15

Glu Leu Pro Gln Thr Pro Gln Arg Leu Ala Ser Trp Trp Asp Gln Gln
            20                  25                  30

Val Asp Phe Tyr Thr Ala Phe Leu His His Leu Ala Gln Leu Val Pro
        35                  40                  45

Glu Ile Tyr Phe Ala Glu Met Asp Pro Asp Leu Glu Lys Gln Glu Glu
    50                  55                  60

Ser Val Gln Met Ser Ile Phe Thr Pro Leu Glu Trp Tyr Leu Phe Gly
65                  70                  75                  80

Glu Asp Pro Asp Ile Cys Leu Glu Lys Leu Lys His Ser Gly Ala Phe
                85                  90                  95

Gln Leu Cys Gly Arg Val Phe Lys Ser Gly Glu Thr Thr Tyr Ser Cys
            100                 105                 110

Arg Asp Cys Ala Ile Asp Pro Thr Cys Val Leu Cys Met Asp Cys Phe
        115                 120                 125

Gln Asp Ser Val His Lys Asn His Arg Tyr Lys Met His Thr Ser Thr
    130                 135                 140

Gly Gly Gly Phe Cys Asp Cys Gly Asp Thr Glu Ala Trp Lys Thr Gly
145                 150                 155                 160

Pro Phe Cys Val Asn His Glu Pro Gly Arg Ala Gly Thr Ile Lys Glu
                165                 170                 175
```

```
Asn Ser Arg Cys Pro Leu Asn Glu Glu Val Ile Val Gln Ala Arg Lys
            180                 185                 190

Ile Phe Pro Ser Val Ile Lys Tyr Val Val Glu Met Thr Ile Trp Glu
            195                 200                 205

Glu Glu Lys Glu Leu Pro Pro Glu Leu Gln Ile Arg Glu Lys Asn Glu
            210                 215                 220

Arg Tyr Tyr Cys Val Leu Phe Asn Asp Glu His His Ser Tyr Asp His
225                 230                 235                 240

Val Ile Tyr Ser Leu Gln Arg Ala Leu Asp Cys Glu Leu Ala Glu Ala
            245                 250                 255

Gln Leu His Thr Thr Ala Ile Asp Lys Glu Gly Arg Arg Ala Val Lys
            260                 265                 270

Ala Gly Ala Tyr Ala Ala Cys Gln Glu Ala Lys Glu Asp Ile Lys Ser
            275                 280                 285

His Ser Glu Asn Val Ser Gln His Pro Leu His Val Glu Val Leu His
            290                 295                 300

Ser Glu Ile Met Ala His Gln Lys Phe Ala Leu Arg Leu Gly Ser Trp
305                 310                 315                 320

Met Asn Lys Ile Met Ser Tyr Ser Ser Asp Phe Arg Gln Ile Phe Cys
            325                 330                 335

Gln Ala Cys Leu Arg Glu Glu Pro Asp Ser Glu Asn Pro Cys Leu Ile
            340                 345                 350

Ser Arg Leu Met Leu Trp Asp Ala Lys Leu Tyr Lys Gly Ala Arg Lys
            355                 360                 365

Ile Leu His Glu Leu Ile Phe Ser Ser Phe Phe Met Glu Met Glu Tyr
            370                 375                 380

Lys Lys Leu Phe Ala Met Glu Phe Val Lys Tyr Lys Gln Leu Gln
385                 390                 395                 400

Lys Glu Tyr Ile Ser Asp Asp His Asp Arg Ser Ile Ser Ile Thr Ala
            405                 410                 415

Leu Ser Val Gln Met Phe Thr Val Pro Thr Leu Ala Arg His Leu Ile
            420                 425                 430

Glu Glu Gln Asn Val Ile Ser Val Ile Thr Glu Thr Leu Leu Glu Val
            435                 440                 445

Leu Pro Glu Tyr Leu Asp Arg Asn Asn Lys Phe Asn Phe Gln Gly Tyr
            450                 455                 460

Ser Gln Asp Lys Leu Gly Arg Val Tyr Ala Val Ile Cys Asp Leu Lys
465                 470                 475                 480

Tyr Ile Leu Ile Ser Lys Pro Thr Ile Trp Thr Glu Arg Leu Arg Met
            485                 490                 495

Gln Phe Leu Glu Gly Phe Arg Ser Phe Leu Lys Ile Leu Thr Cys Met
            500                 505                 510

Gln Gly Met Glu Glu Ile Arg Arg Gln Val Gly Gln His Ile Glu Val
            515                 520                 525

Asp Pro Asp Trp Glu Ala Ala Ile Ala Ile Gln Met Gln Leu Lys Asn
            530                 535                 540

Ile Leu Leu Met Phe Gln Glu Trp Cys Ala Cys Asp Glu Glu Leu Leu
545                 550                 555                 560

Leu Val Ala Tyr Lys Glu Cys His Lys Ala Val Met Arg Cys Ser Thr
            565                 570                 575

Ser Phe Ile Ser Ser Ser Lys Thr Val Val Gln Ser Cys Gly His Ser
            580                 585                 590
```

-continued

```
Leu Glu Thr Lys Ser Tyr Arg Val Ser Glu Asp Leu Val Ser Ile His
        595                 600                 605

Leu Pro Leu Ser Arg Thr Leu Ala Gly Leu His Val Arg Leu Ser Arg
        610                 615                 620

Leu Gly Ala Val Ser Arg Leu His Glu Phe Val Ser Phe Glu Asp Phe
625                 630                 635                 640

Gln Val Glu Val Leu Val Glu Tyr Pro Leu Arg Cys Leu Val Leu Val
                645                 650                 655

Ala Gln Val Val Ala Glu Met Trp Arg Arg Asn Gly Leu Ser Leu Ile
            660                 665                 670

Ser Gln Val Phe Tyr Tyr Gln Asp Val Lys Cys Arg Glu Glu Met Tyr
        675                 680                 685

Asp Lys Asp Ile Ile Met Leu Gln Ile Gly Ala Ser Leu Met Asp Pro
    690                 695                 700

Asn Lys Phe Leu Leu Leu Val Leu Gln Arg Tyr Glu Leu Ala Glu Ala
705                 710                 715                 720

Phe Asn Lys Thr Ile Ser Thr Lys Asp Gln Asp Leu Ile Lys Gln Tyr
                725                 730                 735

Asn Thr Leu Ile Glu Glu Met Leu Gln Val Leu Ile Tyr Ile Val Gly
            740                 745                 750

Glu Arg Tyr Val Pro Gly Val Gly Asn Val Thr Lys Glu Glu Val Thr
        755                 760                 765

Met Arg Glu Ile Ile His Leu Leu Cys Ile Glu Pro Met Pro His Ser
    770                 775                 780

Ala Ile Ala Lys Asn Leu Pro Glu Asn Glu Asn Glu Thr Gly Leu
785                 790                 795                 800

Glu Asn Val Ile Asn Lys Val Ala Thr Phe Lys Lys Pro Gly Val Ser
                805                 810                 815

Gly His Gly Val Tyr Glu Leu Lys Asp Glu Ser Leu Lys Asp Phe Asn
            820                 825                 830

Met Tyr Phe Tyr His Tyr Ser Lys Thr Gln His Ser Lys Ala Glu His
        835                 840                 845

Met Gln Lys Lys Arg Arg Lys Gln Glu Asn Lys Asp Glu Ala Leu Pro
    850                 855                 860

Pro Pro Pro Pro Glu Phe Cys Pro Ala Phe Ser Lys Val Ile Asn
865                 870                 875                 880

Leu Leu Asn Cys Asp Ile Met Met Tyr Ile Leu Arg Thr Val Phe Glu
                885                 890                 895

Arg Ala Ile Asp Thr Asp Ser Asn Leu Trp Thr Glu Gly Met Leu Gln
            900                 905                 910

Met Ala Phe His Ile Leu Ala Leu Gly Leu Leu Glu Glu Lys Gln Gln
        915                 920                 925

Leu Gln Lys Ala Pro Glu Glu Val Thr Phe Asp Phe Tyr His Lys
    930                 935                 940

Ala Ser Arg Leu Gly Ser Ser Ala Met Asn Ile Gln Met Leu Leu Glu
945                 950                 955                 960

Lys Leu Lys Gly Ile Pro Gln Leu Glu Gly Gln Lys Asp Met Ile Thr
                965                 970                 975

Trp Ile Leu Gln Met Phe Asp Thr Val Lys Arg Leu Arg Glu Lys Ser
            980                 985                 990

Cys Leu Ile Val Ala Thr Thr Ser  Gly Ser Glu Ser Ile  Lys Asn Asp
        995                 1000                 1005

Glu Ile  Thr His Asp Lys Glu  Lys Ala Glu Arg Lys  Arg Lys Ala
```

-continued

```
               1010                1015                1020

Glu Ala Ala Arg Leu His Arg Gln Lys Ile Met Ala Gln Met Ser
    1025                1030                1035

Ala Leu Gln Lys Asn Phe Ile Glu Thr His Lys Leu Met Tyr Asp
    1040                1045                1050

Asn Thr Ser Glu Met Pro Gly Lys Glu Asp Ser Ile Met Glu Glu
    1055                1060                1065

Glu Ser Thr Pro Ala Val Ser Asp Tyr Ser Arg Ile Ala Leu Gly
    1070                1075                1080

Pro Lys Arg Gly Pro Ser Val Thr Glu Lys Glu Val Leu Thr Cys
    1085                1090                1095

Ile Leu Cys Gln Glu Glu Gln Glu Val Lys Ile Glu Asn Asn Ala
    1100                1105                1110

Met Val Leu Ser Ala Cys Val Gln Lys Ser Thr Ala Leu Thr Gln
    1115                1120                1125

His Arg Gly Lys Pro Ile Glu Leu Ser Gly Glu Ala Leu Asp Pro
    1130                1135                1140

Leu Phe Met Asp Pro Asp Leu Ala Tyr Gly Thr Tyr Thr Gly Ser
    1145                1150                1155

Cys Gly His Val Met His Ala Val Cys Trp Gln Lys Tyr Phe Glu
    1160                1165                1170

Ala Val Gln Leu Ser Ser Gln Gln Arg Ile His Val Asp Leu Phe
    1175                1180                1185

Asp Leu Glu Ser Gly Glu Tyr Leu Cys Pro Leu Cys Lys Ser Leu
    1190                1195                1200

Cys Asn Thr Val Ile Pro Ile Pro Leu Gln Pro Gln Lys Ile
    1205                1210                1215

Asn Ser Glu Asn Ala Asp Ala Leu Ala Gln Leu Thr Leu Ala
    1220                1225                1230

Arg Trp Ile Gln Thr Val Leu Ala Arg Ile Ser Gly Tyr Asn Ile
    1235                1240                1245

Arg His Ala Lys Gly Glu Asn Pro Ile Pro Ile Phe Phe Asn Gln
    1250                1255                1260

Gly Met Gly Asp Ser Thr Leu Glu Phe His Ser Ile Leu Ser Phe
    1265                1270                1275

Gly Val Glu Ser Ser Ile Lys Tyr Ser Asn Ser Ile Lys Glu Met
    1280                1285                1290

Val Ile Leu Phe Ala Thr Thr Ile Tyr Arg Ile Gly Leu Lys Val
    1295                1300                1305

Pro Pro Asp Glu Arg Asp Pro Arg Val Pro Met Leu Thr Trp Ser
    1310                1315                1320

Thr Cys Ala Phe Thr Ile Gln Ala Ile Glu Asn Leu Leu Gly Asp
    1325                1330                1335

Glu Gly Lys Pro Leu Phe Gly Ala Leu Gln Asn Arg Gln His Asn
    1340                1345                1350

Gly Leu Lys Ala Leu Met Gln Phe Ala Val Ala Gln Arg Ile Thr
    1355                1360                1365

Cys Pro Gln Val Leu Ile Gln Lys His Leu Val Arg Leu Leu Ser
    1370                1375                1380

Val Val Leu Pro Asn Ile Lys Ser Glu Asp Thr Pro Cys Leu Leu
    1385                1390                1395

Ser Ile Asp Leu Phe His Val Leu Val Gly Ala Val Leu Ala Phe
    1400                1405                1410
```

```
Pro Ser Leu Tyr Trp Asp Asp Pro Val Asp Leu Gln Pro Ser Ser
    1415                1420                1425

Val Ser Ser Ser Tyr Asn His Leu Tyr Leu Phe His Leu Ile Thr
    1430                1435                1440

Met Ala His Met Leu Gln Ile Leu Leu Thr Val Asp Thr Gly Leu
    1445                1450                1455

Pro Leu Ala Gln Val Gln Glu Asp Ser Glu Glu Ala His Ser Ala
    1460                1465                1470

Ser Ser Phe Phe Ala Glu Ile Ser Gln Tyr Thr Ser Gly Ser Ile
    1475                1480                1485

Gly Cys Asp Ile Pro Gly Trp Tyr Leu Trp Val Ser Leu Lys Asn
    1490                1495                1500

Gly Ile Thr Pro Tyr Leu Arg Cys Ala Ala Leu Phe Phe His Tyr
    1505                1510                1515

Leu Leu Gly Val Thr Pro Pro Glu Glu Leu His Thr Asn Ser Ala
    1520                1525                1530

Glu Gly Glu Tyr Ser Ala Leu Cys Ser Tyr Leu Ser Leu Pro Thr
    1535                1540                1545

Asn Leu Phe Leu Leu Phe Gln Glu Tyr Trp Asp Thr Val Arg Pro
    1550                1555                1560

Leu Leu Gln Arg Trp Cys Ala Asp Pro Ala Leu Leu Asn Cys Leu
    1565                1570                1575

Lys Gln Lys Asn Thr Val Val Arg Tyr Pro Arg Lys Arg Asn Ser
    1580                1585                1590

Leu Ile Glu Leu Pro Asp Asp Tyr Ser Cys Leu Leu Asn Gln Ala
    1595                1600                1605

Ser His Phe Arg Cys Pro Arg Ser Ala Asp Asp Glu Arg Lys His
    1610                1615                1620

Pro Val Leu Cys Leu Phe Cys Gly Ala Ile Leu Cys Ser Gln Asn
    1625                1630                1635

Ile Cys Cys Gln Glu Ile Val Asn Gly Glu Glu Val Gly Ala Cys
    1640                1645                1650

Ile Phe His Ala Leu His Cys Gly Ala Gly Val Cys Ile Phe Leu
    1655                1660                1665

Lys Ile Arg Glu Cys Arg Val Val Leu Val Glu Gly Lys Ala Arg
    1670                1675                1680

Gly Cys Ala Tyr Pro Ala Pro Tyr Leu Asp Glu Tyr Gly Glu Thr
    1685                1690                1695

Asp Pro Gly Leu Lys Arg Gly Asn Pro Leu His Leu Ser Arg Glu
    1700                1705                1710

Arg Tyr Arg Lys Leu His Leu Val Trp Gln Gln His Cys Ile Ile
    1715                1720                1725

Glu Glu Ile Ala Arg Ser Gln Glu Thr Asn Gln Met Leu Phe Gly
    1730                1735                1740

Phe Asn Trp Gln Leu Leu
    1745

<210> SEQ ID NO 3
<211> LENGTH: 6300
<212> TYPE: DNA
<213> ORGANISM: Homo sapeins
<220> FEATURE:
<221> NAME/KEY: CDS
<222> LOCATION: (295)..(5559)
```

-continued

<400> SEQUENCE: 3

```
gccaagaatt cggcacgagg tgtcaggcct ggggttttct gtgtccttcc ctgggtcagg      60
gacgagccag tgacttgact cttgggcgct aagcttggga gggagcgcag gaggccgctg     120
tccttccttt ccggttcacg tcaccttcct ctccctctgt tgctccacct gcagccactt     180
ggacggctcc gggactgatt gcctggggca ggggtggcag tcgaggccgc cggggccgag     240
gtgaggctgc agctctccgg gcggcggtag cgctggggag gaggaggaga gaag atg      297
                                                              Met
                                                               1 gcg tcg gag cta gag cca gag gtg cag gcc atc gac cgg agt ttg ctg      345
Ala Ser Glu Leu Glu Pro Glu Val Gln Ala Ile Asp Arg Ser Leu Leu
         5                  10                  15 gaa tgt tcg gcc gag gag att gcg ggg aaa tgg ctg caa gca act gac      393
Glu Cys Ser Ala Glu Glu Ile Ala Gly Lys Trp Leu Gln Ala Thr Asp
             20                  25                  30 ctc act aga gaa gtg tac cag cat tta gcc cac tat gta ccc aaa atc      441
Leu Thr Arg Glu Val Tyr Gln His Leu Ala His Tyr Val Pro Lys Ile
         35                  40                  45 tac tgc agg ggt ccc aac cct ttt cca cag aaa gaa gac atg ctg gca      489
Tyr Cys Arg Gly Pro Asn Pro Phe Pro Gln Lys Glu Asp Met Leu Ala
 50                  55                  60                  65 cag cat gtt ttg ttg gga cca atg gaa tgg tac ctt tgt ggt gaa gat      537
Gln His Val Leu Leu Gly Pro Met Glu Trp Tyr Leu Cys Gly Glu Asp
                 70                  75                  80 cct gca ttt gga ttt cca aaa ctt gag caa gca aac aaa cct tct cat      585
Pro Ala Phe Gly Phe Pro Lys Leu Glu Gln Ala Asn Lys Pro Ser His
             85                  90                  95 ctt tgt ggt cgt gtt ttt aaa gta gga gag cct aca tat tct tgc aga      633
Leu Cys Gly Arg Val Phe Lys Val Gly Glu Pro Thr Tyr Ser Cys Arg
        100                 105                 110 gac tgt gca gtt gat cca act tgt gtt ttg tgc atg gag tgc ttt ttg      681
Asp Cys Ala Val Asp Pro Thr Cys Val Leu Cys Met Glu Cys Phe Leu
    115                 120                 125 gga agt att cac aga gat cat cga tat agg atg aca aca tca gga ggt      729
Gly Ser Ile His Arg Asp His Arg Tyr Arg Met Thr Thr Ser Gly Gly
130                 135                 140                 145 gga ggt ttc tgt gac tgt ggt gat act gaa gcc tgg aaa gag ggt cct      777
Gly Gly Phe Cys Asp Cys Gly Asp Thr Glu Ala Trp Lys Glu Gly Pro
                150                 155                 160 tac tgt caa aaa cat gaa ctt aac acc tct gaa att gag gaa gaa gag      825
Tyr Cys Gln Lys His Glu Leu Asn Thr Ser Glu Ile Glu Glu Glu Glu
            165                 170                 175 gat cct ctt gtt cat tta tca gaa gat gtg ata gca aga act tat aac      873
Asp Pro Leu Val His Leu Ser Glu Asp Val Ile Ala Arg Thr Tyr Asn
        180                 185                 190 att ttt gct att acg ttt cgg tat gca gta gaa ata tta acc tgg gaa      921
Ile Phe Ala Ile Thr Phe Arg Tyr Ala Val Glu Ile Leu Thr Trp Glu
    195                 200                 205 aaa gaa agt gaa ttg cca gca gat tta gag atg gta gag aag agt gac      969
Lys Glu Ser Glu Leu Pro Ala Asp Leu Glu Met Val Glu Lys Ser Asp
210                 215                 220                 225 acc tac tat tgc atg ctg ttt aat gat gag gtt cac acc tat gaa caa     1017
Thr Tyr Tyr Cys Met Leu Phe Asn Asp Glu Val His Thr Tyr Glu Gln
                230                 235                 240 gtt att tat act ctt cag aaa gct gtt aac tgt aca caa aaa gaa gct     1065
Val Ile Tyr Thr Leu Gln Lys Ala Val Asn Cys Thr Gln Lys Glu Ala
            245                 250                 255 att ggt ttt gca act aca gta gat cga gat ggg cgt agg tct gtt cga     1113
Ile Gly Phe Ala Thr Thr Val Asp Arg Asp Gly Arg Arg Ser Val Arg
```

```
Ile Gly Phe Ala Thr Thr Val Asp Arg Asp Gly Arg Arg Ser Val Arg
        260                 265                 270 tat gga gat ttt cag tat tgt gag caa gca aaa tca gta att gtg aga      1161
Tyr Gly Asp Phe Gln Tyr Cys Glu Gln Ala Lys Ser Val Ile Val Arg
        275                 280                 285 aat acc agt aga cag aca aag cca ctc aaa gtt caa gtt atg cat tcg      1209
Asn Thr Ser Arg Gln Thr Lys Pro Leu Lys Val Gln Val Met His Ser
290                 295                 300                 305 tct att gtc gca cat cag aat ttt ggt ttg aaa ctt ttg tct tgg ctg      1257
Ser Ile Val Ala His Gln Asn Phe Gly Leu Lys Leu Leu Ser Trp Leu
            310                 315                 320 gga agt att att gga tat tca gat ggc ctt cgc cgg att tta tgt caa      1305
Gly Ser Ile Ile Gly Tyr Ser Asp Gly Leu Arg Arg Ile Leu Cys Gln
            325                 330                 335 gtt ggt tta caa gaa ggg cca gat ggt gaa aac tct tct cta gtg gac      1353
Val Gly Leu Gln Glu Gly Pro Asp Gly Glu Asn Ser Ser Leu Val Asp
        340                 345                 350 aga ctg atg ctt agt gat tcc aaa tta tgg aaa ggt gct agg agt gta      1401
Arg Leu Met Leu Ser Asp Ser Lys Leu Trp Lys Gly Ala Arg Ser Val
355                 360                 365 tat cat cag ttg ttc atg agc agt ctg ctt atg gat ttg aaa tac aag      1449
Tyr His Gln Leu Phe Met Ser Ser Leu Leu Met Asp Leu Lys Tyr Lys
370                 375                 380                 385 aaa cta ttt gct gtt cga ttt gca aaa aat tac cag cag ttg cag aga      1497
Lys Leu Phe Ala Val Arg Phe Ala Lys Asn Tyr Gln Gln Leu Gln Arg
            390                 395                 400 gat ttt atg gag gat gat cac gag cga gca gtg tcg gtg act gct cta      1545
Asp Phe Met Glu Asp Asp His Glu Arg Ala Val Ser Val Thr Ala Leu
            405                 410                 415 tct gtc cag ttc ttc acc gca cct act ctg gct cga atg ctc atc aca      1593
Ser Val Gln Phe Phe Thr Ala Pro Thr Leu Ala Arg Met Leu Ile Thr
        420                 425                 430 gaa gaa aac ttg atg agc att atc att aag act ttt atg gat cat ttg      1641
Glu Glu Asn Leu Met Ser Ile Ile Ile Lys Thr Phe Met Asp His Leu
435                 440                 445 aga cat cga gat gcc cag ggc aga ttt cag ttt gaa cga tac act gct      1689
Arg His Arg Asp Ala Gln Gly Arg Phe Gln Phe Glu Arg Tyr Thr Ala
450                 455                 460                 465 tta caa gcc ttc aaa ttt agg aga gta cag agc ctt att tta gat ctc      1737
Leu Gln Ala Phe Lys Phe Arg Arg Val Gln Ser Leu Ile Leu Asp Leu
            470                 475                 480 aag tat gtg tta att agc aaa cca act gaa tgg tca gat gag ctg agg      1785
Lys Tyr Val Leu Ile Ser Lys Pro Thr Glu Trp Ser Asp Glu Leu Arg
            485                 490                 495 cag aag ttc cta gaa ggg ttt gat gcc ttt ttg gaa tta cta aaa tgt      1833
Gln Lys Phe Leu Glu Gly Phe Asp Ala Phe Leu Glu Leu Leu Lys Cys
        500                 505                 510 atg cag gga atg gat cca att aca cgt caa gta gga caa cat att gaa      1881
Met Gln Gly Met Asp Pro Ile Thr Arg Gln Val Gly Gln His Ile Glu
515                 520                 525 atg gaa cca gag tgg gaa gca gcc ttc aca cta caa atg aaa tta aca      1929
Met Glu Pro Glu Trp Glu Ala Ala Phe Thr Leu Gln Met Lys Leu Thr
530                 535                 540                 545 cat gtc att tca atg atg cag gac tgg tgt gct tca gat gaa aaa gtg      1977
His Val Ile Ser Met Met Gln Asp Trp Cys Ala Ser Asp Glu Lys Val
            550                 555                 560 tta atc gaa gct tac aag aaa tgt ctc gct gta ctg atg cag tgt cat      2025
Leu Ile Glu Ala Tyr Lys Lys Cys Leu Ala Val Leu Met Gln Cys His
            565                 570                 575
```

-continued

| | |
|---|---|
| ggt ggt tat act gat ggt gaa cag cca atc aca cta agc att tgt gga<br>Gly Gly Tyr Thr Asp Gly Glu Gln Pro Ile Thr Leu Ser Ile Cys Gly<br>580                          585                        590 | 2073 |
| cat tca gtg gaa act atc aga tac tgt gtt tcc caa gaa aaa gtt agc<br>His Ser Val Glu Thr Ile Arg Tyr Cys Val Ser Gln Glu Lys Val Ser<br>595                          600                        605 | 2121 |
| att cac ctc cca gtt tct cgc tta ctt gca ggt tta cat gta tta tta<br>Ile His Leu Pro Val Ser Arg Leu Leu Ala Gly Leu His Val Leu Leu<br>610                          615                        620                        625 | 2169 |
| agc aaa agt gaa gtg gca tat aaa ttt cca gag ctc cta cct cta agt<br>Ser Lys Ser Glu Val Ala Tyr Lys Phe Pro Glu Leu Leu Pro Leu Ser<br>                          630                        635                        640 | 2217 |
| gaa ctt agc cca ccc atg ttg ata gaa cac cct ctt aga tgt ctt gtt<br>Glu Leu Ser Pro Pro Met Leu Ile Glu His Pro Leu Arg Cys Leu Val<br>645                          650                        655 | 2265 |
| ctg tgt gcc caa gta cat gcc gga atg tgg aga aga aat ggg ttc tct<br>Leu Cys Ala Gln Val His Ala Gly Met Trp Arg Arg Asn Gly Phe Ser<br>                          660                        665                        670 | 2313 |
| cta gta aac cag att tat tac tac cat aat gtg aaa tgc aga cgt gag<br>Leu Val Asn Gln Ile Tyr Tyr Tyr His Asn Val Lys Cys Arg Arg Glu<br>675                          680                        685 | 2361 |
| atg ttt gac aag gat gta gta atg ctt cag aca ggt gtc tcc atg atg<br>Met Phe Asp Lys Asp Val Val Met Leu Gln Thr Gly Val Ser Met Met<br>690                          695                        700                        705 | 2409 |
| gat cca aat cat ttc ctg atg atc atg ctc agc cgc ttt gaa ctt tat<br>Asp Pro Asn His Phe Leu Met Ile Met Leu Ser Arg Phe Glu Leu Tyr<br>                          710                        715                        720 | 2457 |
| cag att ttc agt act cca gac tat gga aaa aga ttt agt tct gag att<br>Gln Ile Phe Ser Thr Pro Asp Tyr Gly Lys Arg Phe Ser Ser Glu Ile<br>725                          730                        735 | 2505 |
| acc cat aag gat gtt gtt cag cag aac aat act cta ata gaa gaa atg<br>Thr His Lys Asp Val Val Gln Gln Asn Asn Thr Leu Ile Glu Glu Met<br>                          740                        745                        750 | 2553 |
| cta tac ctc att ata atg ctt gtt gga gag aga ttt agt cct gga gtt<br>Leu Tyr Leu Ile Ile Met Leu Val Gly Glu Arg Phe Ser Pro Gly Val<br>755                          760                        765 | 2601 |
| gga cag gta aat gct aca gat gaa atc aag cga gag att atc cat cag<br>Gly Gln Val Asn Ala Thr Asp Glu Ile Lys Arg Glu Ile Ile His Gln<br>770                          775                        780                        785 | 2649 |
| ttg agt atc aag cct atg gct cat agt gaa ttg gta aag tct tta cct<br>Leu Ser Ile Lys Pro Met Ala His Ser Glu Leu Val Lys Ser Leu Pro<br>                          790                        795                        800 | 2697 |
| gaa gat gag aac aag gag act ggc atg gag agt gta atc gaa gca gtt<br>Glu Asp Glu Asn Lys Glu Thr Gly Met Glu Ser Val Ile Glu Ala Val<br>805                          810                        815 | 2745 |
| gcc cat ttc aag aaa cct gga tta aca gga cga ggc atg tat gaa ctg<br>Ala His Phe Lys Lys Pro Gly Leu Thr Gly Arg Gly Met Tyr Glu Leu<br>                          820                        825                        830 | 2793 |
| aaa cca gaa tgt gcc aaa gag ttc aac ttg tat ttc tat cac ttt tca<br>Lys Pro Glu Cys Ala Lys Glu Phe Asn Leu Tyr Phe Tyr His Phe Ser<br>835                          840                        845 | 2841 |
| agg gca gaa cag tcc aag gca gaa gaa gcg caa cgg aaa ttg aaa aga<br>Arg Ala Glu Gln Ser Lys Ala Glu Glu Ala Gln Arg Lys Leu Lys Arg<br>850                          855                        860                        865 | 2889 |
| caa aat aga gaa gat aca gca ctc cca cct ccg gtg ttg cct cca ttc<br>Gln Asn Arg Glu Asp Thr Ala Leu Pro Pro Pro Val Leu Pro Pro Phe<br>                          870                        875                        880 | 2937 |
| tgc cct ctg ttt gca agc ctg gtt aac att ttg cag tca gat gtc atg<br>Cys Pro Leu Phe Ala Ser Leu Val Asn Ile Leu Gln Ser Asp Val Met<br>                          885                        890                        895 | 2985 |

```
ttg tgc atc atg gga aca att ctg caa tgg gct gtg gaa cat aat gga    3033
Leu Cys Ile Met Gly Thr Ile Leu Gln Trp Ala Val Glu His Asn Gly
        900                 905                 910 tat gcc tgg tca gag tcc atg ctg caa agg gtg tta cat tta att ggc    3081
Tyr Ala Trp Ser Glu Ser Met Leu Gln Arg Val Leu His Leu Ile Gly
915                 920                 925 atg gca cta caa gaa gaa aaa caa cat tta gag aat gtc acg gaa gag    3129
Met Ala Leu Gln Glu Glu Lys Gln His Leu Glu Asn Val Thr Glu Glu
930                 935                 940                 945 cat gta gta aca ttt acc ttc act cag aag ata tca aaa cct ggt gaa    3177
His Val Val Thr Phe Thr Phe Thr Gln Lys Ile Ser Lys Pro Gly Glu
            950                 955                 960 gcg cca aaa aat tct cct agc ata cta gct atg ctg gaa aca cta caa    3225
Ala Pro Lys Asn Ser Pro Ser Ile Leu Ala Met Leu Glu Thr Leu Gln
        965                 970                 975 aat gct ccc tac cta gaa gtc cac aaa gac atg att cgg tgg ata ttg    3273
Asn Ala Pro Tyr Leu Glu Val His Lys Asp Met Ile Arg Trp Ile Leu
    980                 985                 990 aag act ttt aat gct gtt aaa aag atg agg gag agt tca cct acc agt    3321
Lys Thr Phe Asn Ala Val Lys Lys Met Arg Glu Ser Ser Pro Thr Ser
995                 1000                1005 ccc gtg gca gag aca gaa gga acc ata atg gaa gag agt tca agg        3366
Pro Val Ala Glu Thr Glu Gly Thr Ile Met Glu Glu Ser Ser Arg
1010                1015                1020 gac aaa gac aaa gct gag agg aag aga aaa gca gag att gcc aga        3411
Asp Lys Asp Lys Ala Glu Arg Lys Arg Lys Ala Glu Ile Ala Arg
1025                1030                1035 ctg cgc aga gaa aag atc atg gct cag atg tct gaa atg cag cgg        3456
Leu Arg Arg Glu Lys Ile Met Ala Gln Met Ser Glu Met Gln Arg
1040                1045                1050 cat ttt att gat gaa aac aaa gaa ctc ttt cag cag aca tta gaa        3501
His Phe Ile Asp Glu Asn Lys Glu Leu Phe Gln Gln Thr Leu Glu
1055                1060                1065 ctg gat gcc tca acc tct gct gtt ctt gat cat agc cct gtg gct        3546
Leu Asp Ala Ser Thr Ser Ala Val Leu Asp His Ser Pro Val Ala
1070                1075                1080 tca gat atg aca ctt aca gca ctg ggt ccc aca caa act cag gtt        3591
Ser Asp Met Thr Leu Thr Ala Leu Gly Pro Thr Gln Thr Gln Val
1085                1090                1095 cct gaa caa aga caa ttc gtt aca tgt ata ttg tgt caa gag gag        3636
Pro Glu Gln Arg Gln Phe Val Thr Cys Ile Leu Cys Gln Glu Glu
1100                1105                1110 caa gaa gtt aaa gtg gaa agc agg gca atg gtc ttg gca gca ttt        3681
Gln Glu Val Lys Val Glu Ser Arg Ala Met Val Leu Ala Ala Phe
1115                1120                1125 gtt cag aga tca act gta tta tca aaa aac aga agt aaa ttt att        3726
Val Gln Arg Ser Thr Val Leu Ser Lys Asn Arg Ser Lys Phe Ile
1130                1135                1140 caa gat cca gaa aaa tat gat cca tta ttc atg cac cct gat ctg        3771
Gln Asp Pro Glu Lys Tyr Asp Pro Leu Phe Met His Pro Asp Leu
1145                1150                1155 tct tgt gga aca cac act agt agc tgt ggg cac att atg cat gcc        3816
Ser Cys Gly Thr His Thr Ser Ser Cys Gly His Ile Met His Ala
1160                1165                1170 cat tgt tgg caa agg tat ttt gat tcc gtt caa gct aaa gaa cag        3861
His Cys Trp Gln Arg Tyr Phe Asp Ser Val Gln Ala Lys Glu Gln
1175                1180                1185 cga agg caa cag aga tta cgc tta cat acg agc tat gat gta gaa        3906
Arg Arg Gln Gln Arg Leu Arg Leu His Thr Ser Tyr Asp Val Glu
```

```
                                                                              1190                1195                1200
aac  gga  gaa  ttc  ctt  tgc  ccc  ctt  tgt  gaa  tgc  ttg  agt  aat  act    3951
Asn  Gly  Glu  Phe  Leu  Cys  Pro  Leu  Cys  Glu  Cys  Leu  Ser  Asn  Thr
1205                1210                1215 gtt  att  cct  ctg  ctg  ctt  cct  cca  aga  aat  att  ttt  aac  aac  agg    3996
Val  Ile  Pro  Leu  Leu  Leu  Pro  Pro  Arg  Asn  Ile  Phe  Asn  Asn  Arg
1220                1225                1230 tta  aat  ttt  tca  gac  caa  cca  aat  ctg  act  cag  tgg  att  aga  aca    4041
Leu  Asn  Phe  Ser  Asp  Gln  Pro  Asn  Leu  Thr  Gln  Trp  Ile  Arg  Thr
1235                1240                1245 ata  tct  cag  caa  ata  aaa  gca  tta  cag  ttt  ctt  agg  aaa  gaa  gaa    4086
Ile  Ser  Gln  Gln  Ile  Lys  Ala  Leu  Gln  Phe  Leu  Arg  Lys  Glu  Glu
1250                1255                1260 agt  act  cct  aat  aat  gcc  tct  aca  aag  aat  tca  gaa  aat  gtg  gat    4131
Ser  Thr  Pro  Asn  Asn  Ala  Ser  Thr  Lys  Asn  Ser  Glu  Asn  Val  Asp
1265                1270                1275 gaa  tta  cag  ctc  cct  gaa  ggg  ttc  agg  cct  gat  ttt  cgt  cct  aag    4176
Glu  Leu  Gln  Leu  Pro  Glu  Gly  Phe  Arg  Pro  Asp  Phe  Arg  Pro  Lys
1280                1285                1290 atc  cct  tat  tct  gag  agc  ata  aaa  gaa  atg  cta  acg  aca  ttt  gga    4221
Ile  Pro  Tyr  Ser  Glu  Ser  Ile  Lys  Glu  Met  Leu  Thr  Thr  Phe  Gly
1295                1300                1305 act  gct  acc  tac  aag  gtg  gga  cta  aag  gtt  cat  ccc  aat  gaa  gag    4266
Thr  Ala  Thr  Tyr  Lys  Val  Gly  Leu  Lys  Val  His  Pro  Asn  Glu  Glu
1310                1315                1320 gat  cct  cgt  gtt  ccc  ata  atg  tgt  tgg  ggt  agc  tgc  gcg  tac  acc    4311
Asp  Pro  Arg  Val  Pro  Ile  Met  Cys  Trp  Gly  Ser  Cys  Ala  Tyr  Thr
1325                1330                1335 atc  caa  agc  ata  gaa  aga  att  ttg  agt  gat  gaa  gat  aaa  cca  ttg    4356
Ile  Gln  Ser  Ile  Glu  Arg  Ile  Leu  Ser  Asp  Glu  Asp  Lys  Pro  Leu
1340                1345                1350 ttt  ggt  cct  tta  cct  tgc  aga  ctg  gat  gac  tgt  ctt  agg  tca  ttg    4401
Phe  Gly  Pro  Leu  Pro  Cys  Arg  Leu  Asp  Asp  Cys  Leu  Arg  Ser  Leu
1355                1360                1365 acg  aga  ttt  gcc  gca  gca  cac  tgg  aca  gtg  gca  tca  gtt  tca  gtg    4446
Thr  Arg  Phe  Ala  Ala  Ala  His  Trp  Thr  Val  Ala  Ser  Val  Ser  Val
1370                1375                1380 gtg  caa  gga  cat  ttt  tgt  aaa  ctt  ttt  gca  tca  ctg  gtg  cct  aat    4491
Val  Gln  Gly  His  Phe  Cys  Lys  Leu  Phe  Ala  Ser  Leu  Val  Pro  Asn
1385                1390                1395 gac  agc  cat  gag  gaa  ctt  cca  tgc  ata  tta  gat  att  gac  atg  ttt    4536
Asp  Ser  His  Glu  Glu  Leu  Pro  Cys  Ile  Leu  Asp  Ile  Asp  Met  Phe
1400                1405                1410 cat  tta  ttg  gtg  ggc  ttg  gtg  ctt  gca  ttt  cct  gcg  ttg  cag  tgt    4581
His  Leu  Leu  Val  Gly  Leu  Val  Leu  Ala  Phe  Pro  Ala  Leu  Gln  Cys
1415                1420                1425 cag  gat  ttt  tca  ggg  atc  agc  ctt  ggc  act  gga  gac  ctt  cac  att    4626
Gln  Asp  Phe  Ser  Gly  Ile  Ser  Leu  Gly  Thr  Gly  Asp  Leu  His  Ile
1430                1435                1440 ttc  cat  ctg  gtt  act  atg  gca  cac  atc  ata  cag  atc  tta  ctt  acc    4671
Phe  His  Leu  Val  Thr  Met  Ala  His  Ile  Ile  Gln  Ile  Leu  Leu  Thr
1445                1450                1455 tca  tgt  aca  gaa  gag  aat  ggc  atg  gat  caa  gaa  aat  ccc  cct  tgt    4716
Ser  Cys  Thr  Glu  Glu  Asn  Gly  Met  Asp  Gln  Glu  Asn  Pro  Pro  Cys
1460                1465                1470 gaa  gaa  gaa  tca  gca  gtt  ctt  gct  ttg  tat  aaa  aca  ctt  cac  cag    4761
Glu  Glu  Glu  Ser  Ala  Val  Leu  Ala  Leu  Tyr  Lys  Thr  Leu  His  Gln
1475                1480                1485 tat  acg  gga  agt  gcc  ttg  aaa  gaa  ata  cca  tcc  ggc  tgg  cat  ctg    4806
```

-continued

| | | | | | | | | | | |
|---|---|---|---|---|---|---|---|---|---|---|
| Tyr | Thr | Gly | Ser | Ala | Leu | Lys | Glu | Ile | Pro | Ser | Gly | Trp | His | Leu |
| 1490 | | | | | 1495 | | | | | 1500 | | | | |

```
tgg  agg  agt  gtc  aga  gct  gga  atc  atg  cct  ttc  ctg  aag  tgt  tct           4851
Trp  Arg  Ser  Val  Arg  Ala  Gly  Ile  Met  Pro  Phe  Leu  Lys  Cys  Ser
1505                1510                     1515 gct  tta  ttt  ttt  cat  tac  tta  aat  gga  gtt  cct  tcc  cca  ccc  gac           4896
Ala  Leu  Phe  Phe  His  Tyr  Leu  Asn  Gly  Val  Pro  Ser  Pro  Pro  Asp
1520                1525                     1530 att  caa  gtt  cct  gga  aca  agc  cat  ttt  gaa  cat  tta  tgt  agc  tat           4941
Ile  Gln  Val  Pro  Gly  Thr  Ser  His  Phe  Glu  His  Leu  Cys  Ser  Tyr
1535                1540                     1545 ctt  tcc  cta  cca  aac  aac  ctc  att  tgc  ctt  ttt  caa  gaa  aat  agt           4986
Leu  Ser  Leu  Pro  Asn  Asn  Leu  Ile  Cys  Leu  Phe  Gln  Glu  Asn  Ser
1550                1555                     1560 gag  ata  atg  aat  tca  ctg  att  gaa  agt  tgg  tgc  cgt  aac  agt  gaa           5031
Glu  Ile  Met  Asn  Ser  Leu  Ile  Glu  Ser  Trp  Cys  Arg  Asn  Ser  Glu
1565                1570                     1575 gtt  aaa  aga  tat  cta  gaa  ggt  gaa  aga  gat  gct  ata  aga  tat  cca           5076
Val  Lys  Arg  Tyr  Leu  Glu  Gly  Glu  Arg  Asp  Ala  Ile  Arg  Tyr  Pro
1580                1585                     1590 aga  gaa  tct  aac  aaa  tta  ata  aac  ctt  cca  gag  gat  tac  agc  agc           5121
Arg  Glu  Ser  Asn  Lys  Leu  Ile  Asn  Leu  Pro  Glu  Asp  Tyr  Ser  Ser
1595                1600                     1605 ctc  att  aat  caa  gca  tcc  aat  ttc  tcg  tgc  ccg  aaa  tca  ggt  ggt           5166
Leu  Ile  Asn  Gln  Ala  Ser  Asn  Phe  Ser  Cys  Pro  Lys  Ser  Gly  Gly
1610                1615                     1620 gat  aag  agc  aga  gcc  cca  act  ctg  tgc  ctt  gtg  tgc  gga  tct  ctg           5211
Asp  Lys  Ser  Arg  Ala  Pro  Thr  Leu  Cys  Leu  Val  Cys  Gly  Ser  Leu
1625                1630                     1635 ctg  tgc  tcc  cag  agt  tac  tgc  tgc  cag  act  gaa  ctg  gaa  ggg  gag           5256
Leu  Cys  Ser  Gln  Ser  Tyr  Cys  Cys  Gln  Thr  Glu  Leu  Glu  Gly  Glu
1640                1645                     1650 gat  gta  gga  gcc  tgc  aca  gct  cac  acc  tac  tcc  tgt  ggc  tct  gga           5301
Asp  Val  Gly  Ala  Cys  Thr  Ala  His  Thr  Tyr  Ser  Cys  Gly  Ser  Gly
1655                1660                     1665 gtg  ggc  atc  ttc  ctg  aga  gta  cgg  gaa  tgt  cag  gtg  cta  ttt  tta           5346
Val  Gly  Ile  Phe  Leu  Arg  Val  Arg  Glu  Cys  Gln  Val  Leu  Phe  Leu
1670                1675                     1680 gct  ggc  aaa  acc  aaa  ggc  tgt  ttt  tat  tct  cct  cct  tac  ctt  gat           5391
Ala  Gly  Lys  Thr  Lys  Gly  Cys  Phe  Tyr  Ser  Pro  Pro  Tyr  Leu  Asp
1685                1690                     1695 gac  tat  ggg  gag  acc  gac  cag  gga  ctc  aga  cgg  gga  aat  cct  tta           5436
Asp  Tyr  Gly  Glu  Thr  Asp  Gln  Gly  Leu  Arg  Arg  Gly  Asn  Pro  Leu
1700                1705                     1710 cat  tta  tgc  aaa  gag  cga  ttc  aag  aag  att  cag  aag  ctc  tgg  cac           5481
His  Leu  Cys  Lys  Glu  Arg  Phe  Lys  Lys  Ile  Gln  Lys  Leu  Trp  His
1715                1720                     1725 caa  cac  agt  gtc  aca  gag  gaa  att  gga  cat  gca  cag  gaa  gcc  aat           5526
Gln  His  Ser  Val  Thr  Glu  Glu  Ile  Gly  His  Ala  Gln  Glu  Ala  Asn
1730                1735                     1740 cag  aca  ctg  gtt  ggc  att  gac  tgg  caa  cat  tta  taattattgc                    5569
Gln  Thr  Leu  Val  Gly  Ile  Asp  Trp  Gln  His  Leu
1745                1750                     1755 accaccaaaa aacacaaact tggattttttt taacccagtt ggcttttaa gaaagaaaga                    5629 agttctgctg aatttggaaa taaattcttt atttaaactt tccttcccag ttttatagtt                    5689
tctggttctg aggactgatg aaaatcatct tccatcagca gatttttctt cactgtttgc                    5749
tgtgcccctc aaatataatg tcttgggttt taagatcgag caaggagctt ctcttcctag                    5809
```

-continued

```
attggatccc agcccctttg tggggtctg actgcatagt cccagccatt atgtgatatt    5869
tcacgttatt gatgatagtg aaccgtgggt ccgaagctga ctcaacggag gcagggaaca    5929
aagtctctgt ggtctgttgg gtcatacttc ctggttccac tgagtggccc aacactggga    5989
ctgggttggt gtccctctg ctgacaggac cctactccta ggagcaaagt ggttgatttt    6049
gaaggcagtg ttcccttctc tccattgact atgagagagt tggggacac acatgcagaa    6109 gaagcccgtg gggagaaggt ggattcctgg tgtgctggct ggttttcag ggctgttaga    6169 ggtttttttt ttcttttttt ttttatggc aagacttttg gctttgagaa aactcactta    6229
gagggctttc caaaaactta ggatggtcta aaaaattagg atattctttt agaattagga    6289
agaaaaatta g                                                         6300

<210> SEQ ID NO 4
<211> LENGTH: 1755
<212> TYPE: PRT
<213> ORGANISM: Homo sapeins

<400> SEQUENCE: 4
```

Met Ala Ser Glu Leu Glu Pro Glu Val Gln Ala Ile Asp Arg Ser Leu
1               5                   10                  15

Leu Glu Cys Ser Ala Glu Glu Ile Ala Gly Lys Trp Leu Gln Ala Thr
                20                  25                  30

Asp Leu Thr Arg Glu Val Tyr Gln His Leu Ala His Tyr Val Pro Lys
            35                  40                  45

Ile Tyr Cys Arg Gly Pro Asn Pro Phe Pro Gln Lys Glu Asp Met Leu
        50                  55                  60

Ala Gln His Val Leu Leu Gly Pro Met Glu Trp Tyr Leu Cys Gly Glu
65                  70                  75                  80

Asp Pro Ala Phe Gly Phe Pro Lys Leu Glu Gln Ala Asn Lys Pro Ser
                85                  90                  95

His Leu Cys Gly Arg Val Phe Lys Val Gly Glu Pro Thr Tyr Ser Cys
            100                 105                 110

Arg Asp Cys Ala Val Asp Pro Thr Cys Val Leu Cys Met Glu Cys Phe
        115                 120                 125

Leu Gly Ser Ile His Arg Asp His Arg Tyr Arg Met Thr Thr Ser Gly
    130                 135                 140

Gly Gly Gly Phe Cys Asp Cys Gly Asp Thr Glu Ala Trp Lys Glu Gly
145                 150                 155                 160

Pro Tyr Cys Gln Lys His Glu Leu Asn Thr Ser Glu Ile Glu Glu Glu
                165                 170                 175

Glu Asp Pro Leu Val His Leu Ser Glu Asp Val Ile Ala Arg Thr Tyr
            180                 185                 190

Asn Ile Phe Ala Ile Thr Phe Arg Tyr Ala Val Glu Ile Leu Thr Trp
        195                 200                 205

Glu Lys Glu Ser Glu Leu Pro Ala Asp Leu Glu Met Val Glu Lys Ser
    210                 215                 220

Asp Thr Tyr Tyr Cys Met Leu Phe Asn Asp Glu Val His Thr Tyr Glu
225                 230                 235                 240

Gln Val Ile Tyr Thr Leu Gln Lys Ala Val Asn Cys Thr Gln Lys Glu
                245                 250                 255

Ala Ile Gly Phe Ala Thr Thr Val Asp Arg Asp Gly Arg Arg Ser Val
            260                 265                 270

Arg Tyr Gly Asp Phe Gln Tyr Cys Glu Gln Ala Lys Ser Val Ile Val
        275                 280                 285

-continued

```
Arg Asn Thr Ser Arg Gln Thr Lys Pro Leu Lys Val Gln Val Met His
    290                 295                 300

Ser Ser Ile Val Ala His Gln Asn Phe Gly Leu Lys Leu Leu Ser Trp
305                 310                 315                 320

Leu Gly Ser Ile Ile Gly Tyr Ser Asp Gly Leu Arg Arg Ile Leu Cys
                325                 330                 335

Gln Val Gly Leu Gln Glu Gly Pro Asp Gly Glu Asn Ser Ser Leu Val
            340                 345                 350

Asp Arg Leu Met Leu Ser Asp Ser Lys Leu Trp Lys Gly Ala Arg Ser
        355                 360                 365

Val Tyr His Gln Leu Phe Met Ser Ser Leu Leu Met Asp Leu Lys Tyr
    370                 375                 380

Lys Lys Leu Phe Ala Val Arg Phe Ala Lys Asn Tyr Gln Gln Leu Gln
385                 390                 395                 400

Arg Asp Phe Met Glu Asp Asp His Glu Arg Ala Val Ser Val Thr Ala
                405                 410                 415

Leu Ser Val Gln Phe Phe Thr Ala Pro Thr Leu Ala Arg Met Leu Ile
            420                 425                 430

Thr Glu Glu Asn Leu Met Ser Ile Ile Ile Lys Thr Phe Met Asp His
        435                 440                 445

Leu Arg His Arg Asp Ala Gln Gly Arg Phe Gln Phe Glu Arg Tyr Thr
    450                 455                 460

Ala Leu Gln Ala Phe Lys Phe Arg Arg Val Gln Ser Leu Ile Leu Asp
465                 470                 475                 480

Leu Lys Tyr Val Leu Ile Ser Lys Pro Thr Glu Trp Ser Asp Glu Leu
                485                 490                 495

Arg Gln Lys Phe Leu Glu Gly Phe Asp Ala Phe Leu Glu Leu Leu Lys
            500                 505                 510

Cys Met Gln Gly Met Asp Pro Ile Thr Arg Gln Val Gly Gln His Ile
        515                 520                 525

Glu Met Glu Pro Glu Trp Glu Ala Ala Phe Thr Leu Gln Met Lys Leu
    530                 535                 540

Thr His Val Ile Ser Met Met Gln Asp Trp Cys Ala Ser Asp Glu Lys
545                 550                 555                 560

Val Leu Ile Glu Ala Tyr Lys Lys Cys Leu Ala Val Leu Met Gln Cys
                565                 570                 575

His Gly Gly Tyr Thr Asp Gly Glu Gln Pro Ile Thr Leu Ser Ile Cys
            580                 585                 590

Gly His Ser Val Glu Thr Ile Arg Tyr Cys Val Ser Gln Glu Lys Val
        595                 600                 605

Ser Ile His Leu Pro Val Ser Arg Leu Leu Ala Gly Leu His Val Leu
    610                 615                 620

Leu Ser Lys Ser Glu Val Ala Tyr Lys Phe Pro Glu Leu Leu Pro Leu
625                 630                 635                 640

Ser Glu Leu Ser Pro Pro Met Leu Ile Glu His Pro Leu Arg Cys Leu
                645                 650                 655

Val Leu Cys Ala Gln Val His Ala Gly Met Trp Arg Arg Asn Gly Phe
            660                 665                 670

Ser Leu Val Asn Gln Ile Tyr Tyr Tyr His Asn Val Lys Cys Arg Arg
        675                 680                 685

Glu Met Phe Asp Lys Asp Val Val Met Leu Gln Thr Gly Val Ser Met
    690                 695                 700
```

-continued

```
Met Asp Pro Asn His Phe Leu Met Ile Met Leu Ser Arg Phe Glu Leu
705                 710                 715                 720

Tyr Gln Ile Phe Ser Thr Pro Asp Tyr Gly Lys Arg Phe Ser Ser Glu
                725                 730                 735

Ile Thr His Lys Asp Val Val Gln Gln Asn Asn Thr Leu Ile Glu Glu
            740                 745                 750

Met Leu Tyr Leu Ile Ile Met Leu Val Gly Glu Arg Phe Ser Pro Gly
        755                 760                 765

Val Gly Gln Val Asn Ala Thr Asp Glu Ile Lys Arg Glu Ile Ile His
    770                 775                 780

Gln Leu Ser Ile Lys Pro Met Ala His Ser Glu Leu Val Lys Ser Leu
785                 790                 795                 800

Pro Glu Asp Glu Asn Lys Glu Thr Gly Met Glu Ser Val Ile Glu Ala
                805                 810                 815

Val Ala His Phe Lys Lys Pro Gly Leu Thr Gly Arg Gly Met Tyr Glu
            820                 825                 830

Leu Lys Pro Glu Cys Ala Lys Glu Phe Asn Leu Tyr Phe Tyr His Phe
        835                 840                 845

Ser Arg Ala Glu Gln Ser Lys Ala Glu Glu Ala Gln Arg Lys Leu Lys
    850                 855                 860

Arg Gln Asn Arg Glu Asp Thr Ala Leu Pro Pro Val Leu Pro Pro
865                 870                 875                 880

Phe Cys Pro Leu Phe Ala Ser Leu Val Asn Ile Leu Gln Ser Asp Val
                885                 890                 895

Met Leu Cys Ile Met Gly Thr Ile Leu Gln Trp Ala Val Glu His Asn
            900                 905                 910

Gly Tyr Ala Trp Ser Glu Ser Met Leu Gln Arg Val Leu His Leu Ile
        915                 920                 925

Gly Met Ala Leu Gln Glu Glu Lys Gln His Leu Glu Asn Val Thr Glu
    930                 935                 940

Glu His Val Val Thr Phe Thr Phe Thr Gln Lys Ile Ser Lys Pro Gly
945                 950                 955                 960

Glu Ala Pro Lys Asn Ser Pro Ser Ile Leu Ala Met Leu Glu Thr Leu
                965                 970                 975

Gln Asn Ala Pro Tyr Leu Glu Val His Lys Asp Met Ile Arg Trp Ile
            980                 985                 990

Leu Lys Thr Phe Asn Ala Val Lys  Lys Met Arg Glu Ser  Ser Pro Thr
        995                 1000                1005

Ser Pro  Val Ala Glu Thr Glu  Gly Thr Ile Met Glu  Glu Ser Ser
    1010                1015                1020

Arg Asp Lys Asp Lys Ala Glu  Arg Lys Arg Lys Ala  Glu Ile Ala
    1025                1030                1035

Arg Leu Arg Arg Glu Lys Ile  Met Ala Gln Met Ser  Glu Met Gln
    1040                1045                1050

Arg His  Phe Ile Asp Glu Asn  Lys Glu Leu Phe Gln  Gln Thr Leu
    1055                1060                1065

Glu Leu  Asp Ala Ser Thr Ser  Ala Val Leu Asp His  Ser Pro Val
    1070                1075                1080

Ala Ser  Asp Met Thr Leu Thr  Ala Leu Gly Pro Thr  Gln Thr Gln
    1085                1090                1095

Val Pro  Glu Gln Arg Gln Phe  Val Thr Cys Ile Leu  Cys Gln Glu
    1100                1105                1110

Glu Gln  Glu Val Lys Val Glu  Ser Arg Ala Met Val  Leu Ala Ala
```

|  |  |  | 1115 |  |  |  | 1120 |  |  |  | 1125 |
| --- | --- | --- | --- | --- | --- | --- | --- | --- | --- | --- | --- |

Phe Val Gln Arg Ser Thr Val Leu Ser Lys Asn Arg Ser Lys Phe
1130                     1135                    1140

Ile Gln Asp Pro Glu Lys Tyr Asp Pro Leu Phe Met His Pro Asp
1145                     1150                    1155

Leu Ser Cys Gly Thr His Thr Ser Ser Cys Gly His Ile Met His
1160                     1165                    1170

Ala His Cys Trp Gln Arg Tyr Phe Asp Ser Val Gln Ala Lys Glu
1175                     1180                    1185

Gln Arg Arg Gln Gln Arg Leu Arg Leu His Thr Ser Tyr Asp Val
1190                     1195                    1200

Glu Asn Gly Glu Phe Leu Cys Pro Leu Cys Glu Cys Leu Ser Asn
1205                     1210                    1215

Thr Val Ile Pro Leu Leu Pro Pro Arg Asn Ile Phe Asn Asn
1220                     1225                    1230

Arg Leu Asn Phe Ser Asp Gln Pro Asn Leu Thr Gln Trp Ile Arg
1235                     1240                    1245

Thr Ile Ser Gln Gln Ile Lys Ala Leu Gln Phe Leu Arg Lys Glu
1250                     1255                    1260

Glu Ser Thr Pro Asn Asn Ala Ser Thr Lys Asn Ser Glu Asn Val
1265                     1270                    1275

Asp Glu Leu Gln Leu Pro Glu Gly Phe Arg Pro Asp Phe Arg Pro
1280                     1285                    1290

Lys Ile Pro Tyr Ser Glu Ser Ile Lys Glu Met Leu Thr Thr Phe
1295                     1300                    1305

Gly Thr Ala Thr Tyr Lys Val Gly Leu Lys Val His Pro Asn Glu
1310                     1315                    1320

Glu Asp Pro Arg Val Pro Ile Met Cys Trp Gly Ser Cys Ala Tyr
1325                     1330                    1335

Thr Ile Gln Ser Ile Glu Arg Ile Leu Ser Asp Glu Asp Lys Pro
1340                     1345                    1350

Leu Phe Gly Pro Leu Pro Cys Arg Leu Asp Asp Cys Leu Arg Ser
1355                     1360                    1365

Leu Thr Arg Phe Ala Ala Ala His Trp Thr Val Ala Ser Val Ser
1370                     1375                    1380

Val Val Gln Gly His Phe Cys Lys Leu Phe Ala Ser Leu Val Pro
1385                     1390                    1395

Asn Asp Ser His Glu Glu Leu Pro Cys Ile Leu Asp Ile Asp Met
1400                     1405                    1410

Phe His Leu Leu Val Gly Leu Val Leu Ala Phe Pro Ala Leu Gln
1415                     1420                    1425

Cys Gln Asp Phe Ser Gly Ile Ser Leu Gly Thr Gly Asp Leu His
1430                     1435                    1440

Ile Phe His Leu Val Thr Met Ala His Ile Ile Gln Ile Leu Leu
1445                     1450                    1455

Thr Ser Cys Thr Glu Glu Asn Gly Met Asp Gln Glu Asn Pro Pro
1460                     1465                    1470

Cys Glu Glu Glu Ser Ala Val Leu Ala Leu Tyr Lys Thr Leu His
1475                     1480                    1485

Gln Tyr Thr Gly Ser Ala Leu Lys Glu Ile Pro Ser Gly Trp His
1490                     1495                    1500

Leu Trp Arg Ser Val Arg Ala Gly Ile Met Pro Phe Leu Lys Cys
1505                     1510                    1515

```
Ser Ala Leu Phe Phe His Tyr Leu Asn Gly Val Pro Ser Pro Pro
    1520                1525                1530
Asp Ile Gln Val Pro Gly Thr Ser His Phe Glu His Leu Cys Ser
    1535                1540                1545
Tyr Leu Ser Leu Pro Asn Asn Leu Ile Cys Leu Phe Gln Glu Asn
    1550                1555                1560
Ser Glu Ile Met Asn Ser Leu Ile Glu Ser Trp Cys Arg Asn Ser
    1565                1570                1575
Glu Val Lys Arg Tyr Leu Glu Gly Glu Arg Asp Ala Ile Arg Tyr
    1580                1585                1590
Pro Arg Glu Ser Asn Lys Leu Ile Asn Leu Pro Glu Asp Tyr Ser
    1595                1600                1605
Ser Leu Ile Asn Gln Ala Ser Asn Phe Ser Cys Pro Lys Ser Gly
    1610                1615                1620
Gly Asp Lys Ser Arg Ala Pro Thr Leu Cys Leu Val Cys Gly Ser
    1625                1630                1635
Leu Leu Cys Ser Gln Ser Tyr Cys Cys Gln Thr Glu Leu Glu Gly
    1640                1645                1650
Glu Asp Val Gly Ala Cys Thr Ala His Thr Tyr Ser Cys Gly Ser
    1655                1660                1665
Gly Val Gly Ile Phe Leu Arg Val Arg Glu Cys Gln Val Leu Phe
    1670                1675                1680
Leu Ala Gly Lys Thr Lys Gly Cys Phe Tyr Ser Pro Pro Tyr Leu
    1685                1690                1695
Asp Asp Tyr Gly Glu Thr Asp Gln Gly Leu Arg Arg Gly Asn Pro
    1700                1705                1710
Leu His Leu Cys Lys Glu Arg Phe Lys Lys Ile Gln Lys Leu Trp
    1715                1720                1725
His Gln His Ser Val Thr Glu Glu Ile Gly His Ala Gln Glu Ala
    1730                1735                1740
Asn Gln Thr Leu Val Gly Ile Asp Trp Gln His Leu
    1745                1750                1755

<210> SEQ ID NO 5
<211> LENGTH: 6089
<212> TYPE: DNA
<213> ORGANISM: Mus musculus
<220> FEATURE:
<221> NAME/KEY: CDS
<222> LOCATION: (766)..(6030)

<400> SEQUENCE: 5
caagtgtatc atatgccaag tacgccccct attgacgtca atgacggtaa atggcccgcc      60
tggcattatg cccagtacat gaccttatgg gactttccta cttggcagta catctacgta     120
ttagtcatcg ctattaccat ggtgatgcgg ttttggcagt acatcaatgg gcgtggatag     180
cggtttgact cacggggatt tccaagtctc cacccattg acgtcaatgg gagtttgttt     240
tggcaccaaa atcaacggga ctttccaaaa tgtcgtaaca actccgcccc attgacgcaa     300
atgggcggta ggcgtgtacg gtgggaggtc tatataagca gagctctctg gctaactaga     360
gaacccactg cttactggct tatcgaaatt aatacgactc actatagggg acccaagct      420 tggtaccgag ctcggatcca ctactcgacc cacgcgtccg cggtagtggc tgtccggagt     480
gccaggcctg gggttctcgg tgtccttccc ccggtcacgg gcgaggaggc gacttgactt     540
ctgggcgccg agcccgggcg cgcgcgcaag cggctgccgt ccccgctgca ggttcgcgtc     600
```

```
                                                    -continued ccgctttgct cctcgcgcat ctcggctcgg cggcagcccg dacggcccgg gactgacggc            660
cccaggacag gggtgaccgt cgcggctgcg ggagcagagg cgaagctgag gcccggggag            720
aggcgacagc ggcgagagca cccggggaga ggaggaggag agaag atg gcg tcg gag           777
                                                    Met Ala Ser Glu
                                                      1 atg gag ccc gag gtg cag gcc atc gac cgc agt ttg ctg gaa tgt tct             825
Met Glu Pro Glu Val Gln Ala Ile Asp Arg Ser Leu Leu Glu Cys Ser
  5              10                  15                  20 gcc gaa gag atc gca ggg aga tgg ctg caa gca acc gac ctc aac aga             873
Ala Glu Glu Ile Ala Gly Arg Trp Leu Gln Ala Thr Asp Leu Asn Arg
             25                  30                  35 gaa gtg tac cag cat tta gcc cac tgt gtg ccc aaa atc tac tgc cgg             921
Glu Val Tyr Gln His Leu Ala His Cys Val Pro Lys Ile Tyr Cys Arg
         40                  45                  50 ggc cct aac ccc ttc cct cag aag gaa gac acg ctg gca cag cac atc             969
Gly Pro Asn Pro Phe Pro Gln Lys Glu Asp Thr Leu Ala Gln His Ile
         55                  60                  65 ctg ctg gga ccg atg gag tgg tac atc tgc gct gaa gac cct gcg ctg            1017
Leu Leu Gly Pro Met Glu Trp Tyr Ile Cys Ala Glu Asp Pro Ala Leu
 70                  75                  80 gga ttt cca aag ctc gag cag gca aac aag cct tct cac ctc tgt ggc            1065
Gly Phe Pro Lys Leu Glu Gln Ala Asn Lys Pro Ser His Leu Cys Gly
 85                  90                  95                 100 cga gtg ttt aaa gtg ggg gaa cct aca tac tcc tgc aga gac tgt gca            1113
Arg Val Phe Lys Val Gly Glu Pro Thr Tyr Ser Cys Arg Asp Cys Ala
            105                 110                 115 gtt gac ccc acc tgt gtt tta tgc atg gag tgc ttc ctg gga agt atc            1161
Val Asp Pro Thr Cys Val Leu Cys Met Glu Cys Phe Leu Gly Ser Ile
            120                 125                 130 cat aga gac cat cga tat agg atg acc aca tcg gga gga ggg ggc ttc            1209
His Arg Asp His Arg Tyr Arg Met Thr Thr Ser Gly Gly Gly Gly Phe
            135                 140                 145 tgt gac tgt ggt gac act gag gcg tgg aaa gag gga cct tac tgc cag            1257
Cys Asp Cys Gly Asp Thr Glu Ala Trp Lys Glu Gly Pro Tyr Cys Gln
150                 155                 160 aag cac aag ctc agc agc tct gaa gtt gtg gag gag gag gat cct ctt            1305
Lys His Lys Leu Ser Ser Ser Glu Val Val Glu Glu Glu Asp Pro Leu
165                 170                 175                 180 gtg cat cta tca gaa gat gtg atc gcc aga act tac aac att ttt gct            1353
Val His Leu Ser Glu Asp Val Ile Ala Arg Thr Tyr Asn Ile Phe Ala
                185                 190                 195 att atg ttt cga tat gca gta gat ata ctg acc tgg gaa aaa gaa agt            1401
Ile Met Phe Arg Tyr Ala Val Asp Ile Leu Thr Trp Glu Lys Glu Ser
                200                 205                 210 gaa ttg cct gaa gac tta gaa gtg gca gag aag agt gac acc tac tac            1449
Glu Leu Pro Glu Asp Leu Glu Val Ala Glu Lys Ser Asp Thr Tyr Tyr
                215                 220                 225 tgc atg ctg ttt aat gat gag gtt cac acc tat gag caa gtc att tat            1497
Cys Met Leu Phe Asn Asp Glu Val His Thr Tyr Glu Gln Val Ile Tyr
230                 235                 240 acc ctt cag aaa gct gtg aac tgt aca cag aag gaa gcc att ggc ttt            1545
Thr Leu Gln Lys Ala Val Asn Cys Thr Gln Lys Glu Ala Ile Gly Phe
245                 250                 255                 260 gca act aca gtt gat cga gat ggc cgt agg cct gtc cga tat gga gat            1593
Ala Thr Thr Val Asp Arg Asp Gly Arg Arg Pro Val Arg Tyr Gly Asp
                265                 270                 275 ttc cag tac tgt gat caa gca aag aca gtc att gtg agg aac acc agc            1641
Phe Gln Tyr Cys Asp Gln Ala Lys Thr Val Ile Val Arg Asn Thr Ser
```

-continued

```
                  280                 285                 290
aga cag acc aag ccg ctc aaa gtt caa gtt atg cac tcc tcc gtg gct    1689
Arg Gln Thr Lys Pro Leu Lys Val Gln Val Met His Ser Ser Val Ala
            295                 300                 305 gct cat cag aat ttt ggt ttg aaa gct ctg tcg tgg ctg gga agt gtt    1737
Ala His Gln Asn Phe Gly Leu Lys Ala Leu Ser Trp Leu Gly Ser Val
        310                 315                 320 att gga tac tca gat ggc ctt cgc agg att ttg tgt caa gtt gga tta    1785
Ile Gly Tyr Ser Asp Gly Leu Arg Arg Ile Leu Cys Gln Val Gly Leu
325                 330                 335                 340 caa gaa ggt cca gat ggc gaa aac tct tct ctg gtc gac aga ctg atg    1833
Gln Glu Gly Pro Asp Gly Glu Asn Ser Ser Leu Val Asp Arg Leu Met
                345                 350                 355 ctt aat gat tcc aaa tta tgg aaa ggg gct agg agt gtg tat cac cag    1881
Leu Asn Asp Ser Lys Leu Trp Lys Gly Ala Arg Ser Val Tyr His Gln
            360                 365                 370 ttg ttc atg agc agc ctg ctc atg gac ctc aag tat aag aag ctg ttc    1929
Leu Phe Met Ser Ser Leu Leu Met Asp Leu Lys Tyr Lys Lys Leu Phe
        375                 380                 385 gcg ctt cga ttt gct aaa aat tac cgg cag ttg cag agg gat ttt atg    1977
Ala Leu Arg Phe Ala Lys Asn Tyr Arg Gln Leu Gln Arg Asp Phe Met
    390                 395                 400 gag gat gat cac gag cgg gca gtg tcg gtg act gct ctg tct gtc cag    2025
Glu Asp Asp His Glu Arg Ala Val Ser Val Thr Ala Leu Ser Val Gln
405                 410                 415                 420 ttc ttc acc gca ccg acg ctg gcg cga atg ctc ctc aca gaa gag aac    2073
Phe Phe Thr Ala Pro Thr Leu Ala Arg Met Leu Leu Thr Glu Glu Asn
                425                 430                 435 ctg atg acc gtt atc att aag gct ttc atg gac cat ttg aaa cac aga    2121
Leu Met Thr Val Ile Ile Lys Ala Phe Met Asp His Leu Lys His Arg
            440                 445                 450 gat gcc cag ggc aga ttc cag ttt gaa cgc tac act gcc ctc caa gcc    2169
Asp Ala Gln Gly Arg Phe Gln Phe Glu Arg Tyr Thr Ala Leu Gln Ala
        455                 460                 465 ttc aag ttc agg aga gtc cag agc ctc atc tta gat ctc aag tat gta    2217
Phe Lys Phe Arg Arg Val Gln Ser Leu Ile Leu Asp Leu Lys Tyr Val
    470                 475                 480 ttg att agc aaa cca acg gag tgg tca gat gag ctg agg cag aag ttc    2265
Leu Ile Ser Lys Pro Thr Glu Trp Ser Asp Glu Leu Arg Gln Lys Phe
485                 490                 495                 500 tta caa ggg ttc gat gcc ttc ttg gaa tta ctg aag tgc atg cag gga    2313
Leu Gln Gly Phe Asp Ala Phe Leu Glu Leu Leu Lys Cys Met Gln Gly
                505                 510                 515 atg gac ccg atc acg cgt cag gtg gga cag cac att gag atg gag cca    2361
Met Asp Pro Ile Thr Arg Gln Val Gly Gln His Ile Glu Met Glu Pro
            520                 525                 530 gag tgg gaa gca gcc ttc aca ctg cag atg aag ctg aca cac gtc atc    2409
Glu Trp Glu Ala Ala Phe Thr Leu Gln Met Lys Leu Thr His Val Ile
        535                 540                 545 tca atg gtg cag gac tgg tgt gct ctg gac gaa aaa gtg tta att gaa    2457
Ser Met Val Gln Asp Trp Cys Ala Leu Asp Glu Lys Val Leu Ile Glu
    550                 555                 560 gct tac aag aaa tgc ctg gct gtg ctg aca cag tgt cat ggc gga ttt    2505
Ala Tyr Lys Lys Cys Leu Ala Val Leu Thr Gln Cys His Gly Gly Phe
565                 570                 575                 580 act gat ggt gaa cag cca atc aca ctc agt att tgt gga cac tcg gtg    2553
Thr Asp Gly Glu Gln Pro Ile Thr Leu Ser Ile Cys Gly His Ser Val
                585                 590                 595 gaa acc atc aga tac tgt gtt tcc caa gaa aaa gtt agc att cac ctc    2601
```

```
                Glu Thr Ile Arg Tyr Cys Val Ser Gln Glu Lys Val Ser Ile His Leu
                            600                 605                 610 cca att tct cgc ttg ctt gca ggt ttg cat gta ttg tta agc aaa agt       2649
Pro Ile Ser Arg Leu Leu Ala Gly Leu His Val Leu Leu Ser Lys Ser
            615                 620                 625 gaa gtg gca tat aaa ttt cca gag ctc cta cct cta agt gaa ctg agc       2697
Glu Val Ala Tyr Lys Phe Pro Glu Leu Leu Pro Leu Ser Glu Leu Ser
        630                 635                 640 cca ccc atg ttg ata gaa cat cct ctt aga tgt ctt gtc tta tgt gct       2745
Pro Pro Met Leu Ile Glu His Pro Leu Arg Cys Leu Val Leu Cys Ala
645                 650                 655                 660 caa gtg cat gct ggg atg tgg aga aga aat ggc ttc tct cta gta aat       2793
Gln Val His Ala Gly Met Trp Arg Arg Asn Gly Phe Ser Leu Val Asn
                665                 670                 675 cag atc tat tac tac cat aat gtg aaa tgc agg cga gag atg ttc gac       2841
Gln Ile Tyr Tyr Tyr His Asn Val Lys Cys Arg Arg Glu Met Phe Asp
            680                 685                 690 aag gac ata gtg atg ctt cag aca ggt gtc tcc atg atg gac cca aac       2889
Lys Asp Ile Val Met Leu Gln Thr Gly Val Ser Met Met Asp Pro Asn
        695                 700                 705 cac ttc ctg atg atc atg ctc agc cgc ttt gaa ctc tat cag ctc ttc       2937
His Phe Leu Met Ile Met Leu Ser Arg Phe Glu Leu Tyr Gln Leu Phe
    710                 715                 720 agc acg cct gac tat ggg aag aga ttc agt tct gag gtt acc cat aag       2985
Ser Thr Pro Asp Tyr Gly Lys Arg Phe Ser Ser Glu Val Thr His Lys
725                 730                 735                 740 gac gtc gtt cag cag aac aac act ctg atc gaa gag atg ctc tac ctc       3033
Asp Val Val Gln Gln Asn Asn Thr Leu Ile Glu Glu Met Leu Tyr Leu
                745                 750                 755 atc atc atg ctt gtg gga gaa aga ttc aac cct ggg gtt gga cag gtg       3081
Ile Ile Met Leu Val Gly Glu Arg Phe Asn Pro Gly Val Gly Gln Val
            760                 765                 770 gct gcc aca gat gaa atc aag agg gag att atc cat cag ttg agc atc       3129
Ala Ala Thr Asp Glu Ile Lys Arg Glu Ile Ile His Gln Leu Ser Ile
        775                 780                 785 aag cct atg gct cac agt gag ctg gtg aag tct ctg cct gaa gat gag       3177
Lys Pro Met Ala His Ser Glu Leu Val Lys Ser Leu Pro Glu Asp Glu
    790                 795                 800 aac aag gag acc ggc atg gag agc gtc atc gag tcc gtt gca cat ttc       3225
Asn Lys Glu Thr Gly Met Glu Ser Val Ile Glu Ser Val Ala His Phe
805                 810                 815                 820 aag aaa cct ggg ctc aca ggg cga ggc atg tat gag ctg aag cca gag       3273
Lys Lys Pro Gly Leu Thr Gly Arg Gly Met Tyr Glu Leu Lys Pro Glu
                825                 830                 835 tgt gcc aaa gag ttc aac ctg tat ttt tat cat ttc tcc agg gca gag       3321
Cys Ala Lys Glu Phe Asn Leu Tyr Phe Tyr His Phe Ser Arg Ala Glu
            840                 845                 850 cag tcc aag gca gag gaa gct cag cgg aaa ttg aaa aga gaa aat aaa       3369
Gln Ser Lys Ala Glu Glu Ala Gln Arg Lys Leu Lys Arg Glu Asn Lys
        855                 860                 865 gaa gat aca gca ctc cct cct ccg gct ttg cca ccg ttc tgc cct ttg       3417
Glu Asp Thr Ala Leu Pro Pro Pro Ala Leu Pro Pro Phe Cys Pro Leu
    870                 875                 880 ttc gcg agt ctg gtt aac atc ttg cag tgt gac gtc atg ctg tac atc       3465
Phe Ala Ser Leu Val Asn Ile Leu Gln Cys Asp Val Met Leu Tyr Ile
885                 890                 895                 900 atg gga acg atc ctg cag tgg gct gta gag cat cac ggg tct gcc tgg       3513
Met Gly Thr Ile Leu Gln Trp Ala Val Glu His His Gly Ser Ala Trp
                905                 910                 915
```

```
                                                                -continued tca gag tcc atg cta cag agg gtg ctg cat ttg atc ggg atg gct ctc     3561
Ser Glu Ser Met Leu Gln Arg Val Leu His Leu Ile Gly Met Ala Leu
        920                 925                 930 cag gaa gag aag cac cac ttg gag aac gcc gtg gaa ggg cac gtg cag     3609
Gln Glu Glu Lys His His Leu Glu Asn Ala Val Glu Gly His Val Gln
        935                 940                 945 acc ttc acc ttc aca cag aag att tca aag cct ggt gat gca cca cat     3657
Thr Phe Thr Phe Thr Gln Lys Ile Ser Lys Pro Gly Asp Ala Pro His
        950                 955                 960 aac tcc ccg agc atc cta gct atg ctg gag acc ttg cag aac gcc ccc     3705
Asn Ser Pro Ser Ile Leu Ala Met Leu Glu Thr Leu Gln Asn Ala Pro
965                 970                 975                 980 tcc ctg gaa gcc cac aag gac atg atc agg tgg ttg cta aag atg ttt     3753
Ser Leu Glu Ala His Lys Asp Met Ile Arg Trp Leu Leu Lys Met Phe
                985                 990                 995 aat gca att aag aag ata aga gag tgt tca tcc agc agc cct gtg         3798
Asn Ala Ile Lys Lys Ile Arg Glu Cys Ser Ser Ser Ser Pro Val
            1000                1005                1010 gcc gag gcg gag gga acc ata atg gag gag agc tca aga gac aag         3843
Ala Glu Ala Glu Gly Thr Ile Met Glu Glu Ser Ser Arg Asp Lys
            1015                1020                1025 gac aaa gca gag agg aaa aga aaa gcc gag atc gcc aga ctg cgc         3888
Asp Lys Ala Glu Arg Lys Arg Lys Ala Glu Ile Ala Arg Leu Arg
            1030                1035                1040 cgg gag aag atc atg gcc cag atg tct gag atg cag cgg cac ttc         3933
Arg Glu Lys Ile Met Ala Gln Met Ser Glu Met Gln Arg His Phe
            1045                1050                1055 att gac gaa aac aaa gag ctc ttc cag cag acc cta gag ctg gac         3978
Ile Asp Glu Asn Lys Glu Leu Phe Gln Gln Thr Leu Glu Leu Asp
            1060                1065                1070 acc tct gcc tct gcc act ctt gac agc agc cct ccc gtt tca gac         4023
Thr Ser Ala Ser Ala Thr Leu Asp Ser Ser Pro Pro Val Ser Asp
            1075                1080                1085 gca gct ctt aca gca ctg ggc cca gca cag aca cag gtc cct gaa         4068
Ala Ala Leu Thr Ala Leu Gly Pro Ala Gln Thr Gln Val Pro Glu
            1090                1095                1100 ccg aga cag ttt gtc acc tgt ata tta tgt caa gag gag caa gag         4113
Pro Arg Gln Phe Val Thr Cys Ile Leu Cys Gln Glu Glu Gln Glu
            1105                1110                1115 gtg act gtg gga agc agg gcg atg gtc ttg gca gcg ttt gtt cag         4158
Val Thr Val Gly Ser Arg Ala Met Val Leu Ala Ala Phe Val Gln
            1120                1125                1130 agg tca acg gtt ctg tca aaa gac agg acg aaa acc atc gcg gac         4203
Arg Ser Thr Val Leu Ser Lys Asp Arg Thr Lys Thr Ile Ala Asp
            1135                1140                1145 cca gaa aaa tat gat cca tta ttc atg cac ccc gat ctg tct tgt         4248
Pro Glu Lys Tyr Asp Pro Leu Phe Met His Pro Asp Leu Ser Cys
            1150                1155                1160 ggg aca cac act ggc agc tgt ggg cac gtt atg cat gcc cat tgt         4293
Gly Thr His Thr Gly Ser Cys Gly His Val Met His Ala His Cys
            1165                1170                1175 tgg caa agg tat ttt gat tcc gtt caa gcc aag gag cag cga agg         4338
Trp Gln Arg Tyr Phe Asp Ser Val Gln Ala Lys Glu Gln Arg Arg
            1180                1185                1190 cag cag cgg ctg cgc ttg cac act agc tac gat gta gag aat ggc         4383
Gln Gln Arg Leu Arg Leu His Thr Ser Tyr Asp Val Glu Asn Gly
            1195                1200                1205 gag ttc ctc tgc ccg ctc tgt gag tgc ctg agc aac acg gtg atc         4428
Glu Phe Leu Cys Pro Leu Cys Glu Cys Leu Ser Asn Thr Val Ile
            1210                1215                1220
```

```
ccc ctg ctg ctt cct ccc agg agc atc ctc agc agg agg tta aat      4473
Pro Leu Leu Leu Pro Pro Arg Ser Ile Leu Ser Arg Arg Leu Asn
            1225                1230                1235 ttt tca gac caa cca gat ctg gca cag tgg acg aga gca gta aca      4518
Phe Ser Asp Gln Pro Asp Leu Ala Gln Trp Thr Arg Ala Val Thr
        1240                1245                1250 cag cag ata aag gtg gtc cag atg ctg agg aga aag cac aat gct      4563
Gln Gln Ile Lys Val Val Gln Met Leu Arg Arg Lys His Asn Ala
            1255                1260                1265 gct gac acg tct tct tca gag gac aca gaa gcc atg aat ata ata      4608
Ala Asp Thr Ser Ser Ser Glu Asp Thr Glu Ala Met Asn Ile Ile
        1270                1275                1280 ccg atc ccc gaa ggc ttc agg cct gat ttt tat cct agg aac cca      4653
Pro Ile Pro Glu Gly Phe Arg Pro Asp Phe Tyr Pro Arg Asn Pro
            1285                1290                1295 tat tct gat agc ata aaa gaa atg tta acg aca ttt gga acg gct      4698
Tyr Ser Asp Ser Ile Lys Glu Met Leu Thr Thr Phe Gly Thr Ala
        1300                1305                1310 gct tac aag gtg gga ctg aag gtt cat cct aat gaa ggt gac ccc      4743
Ala Tyr Lys Val Gly Leu Lys Val His Pro Asn Glu Gly Asp Pro
            1315                1320                1325 cgt gtg ccc atc ctg tgc tgg ggg acc tgt gca tac acc atc cag      4788
Arg Val Pro Ile Leu Cys Trp Gly Thr Cys Ala Tyr Thr Ile Gln
        1330                1335                1340 agc ata gaa aga att ttg agt gat gag gag aag cct gtt ttt gga      4833
Ser Ile Glu Arg Ile Leu Ser Asp Glu Glu Lys Pro Val Phe Gly
            1345                1350                1355 cct ctg cct tgt aga ctg gac gac tgt ctc agg tcg tta aca cgg      4878
Pro Leu Pro Cys Arg Leu Asp Asp Cys Leu Arg Ser Leu Thr Arg
        1360                1365                1370 ttt gca gca gca cat tgg aca gtg gcg tta ctt cct gtg gta caa      4923
Phe Ala Ala Ala His Trp Thr Val Ala Leu Leu Pro Val Val Gln
            1375                1380                1385 gga cac ttc tgt aaa ctc ttt gca tcc ttg gtg cct agt gac agc      4968
Gly His Phe Cys Lys Leu Phe Ala Ser Leu Val Pro Ser Asp Ser
        1390                1395                1400 tat gaa gac ctc ccg tgc ata cta gac atc gac atg ttt cac ttg      5013
Tyr Glu Asp Leu Pro Cys Ile Leu Asp Ile Asp Met Phe His Leu
            1405                1410                1415 ctg gtg ggc ctg gtg ctc gct ttc cca gct ctg cag tgt cag gat      5058
Leu Val Gly Leu Val Leu Ala Phe Pro Ala Leu Gln Cys Gln Asp
        1420                1425                1430 ttt tca gga agc agc ctg gcc act ggg gac ctg cac atc ttc cac      5103
Phe Ser Gly Ser Ser Leu Ala Thr Gly Asp Leu His Ile Phe His
            1435                1440                1445 ttg gtt acc atg gca cac atc gta cag atc tta ctt acc tca tgt      5148
Leu Val Thr Met Ala His Ile Val Gln Ile Leu Leu Thr Ser Cys
        1450                1455                1460 aca gaa gag aat ggc atg gat caa gag aat ccc act ggg gaa gaa      5193
Thr Glu Glu Asn Gly Met Asp Gln Glu Asn Pro Thr Gly Glu Glu
            1465                1470                1475 gaa ctg gcc att ctc tct ttg cac aaa aca ctt cac cag tat act      5238
Glu Leu Ala Ile Leu Ser Leu His Lys Thr Leu His Gln Tyr Thr
        1480                1485                1490 gga agt gcc ttg aaa gaa gcc ccc tcc ggc tgg cac ctg tgg agg      5283
Gly Ser Ala Leu Lys Glu Ala Pro Ser Gly Trp His Leu Trp Arg
            1495                1500                1505 agc gtc cgg gcc gcc atc atg cct ttc ctc aag tgc tct gct ttg      5328
Ser Val Arg Ala Ala Ile Met Pro Phe Leu Lys Cys Ser Ala Leu
```

|  |  |  |  |  |  |  |  |  |  |  |  |  |  |  |
|---|---|---|---|---|---|---|---|---|---|---|---|---|---|---|
|  |  | 1510 |  |  |  | 1515 |  |  |  | 1520 |  |  |  |  |
| ttt<br>Phe | ttc<br>Phe | cac<br>His | tat<br>Tyr<br>1525 | tta<br>Leu | aat<br>Asn | gga<br>Gly | gtc<br>Val | ccg<br>Pro<br>1530 | gcc<br>Ala | cct<br>Pro | cca<br>Pro | gac<br>Asp | ctt<br>Leu<br>1535 | caa<br>Gln | 5373 |
| gtt<br>Val | tct<br>Ser | gga<br>Gly | aca<br>Thr<br>1540 | agc<br>Ser | cat<br>His | ttt<br>Phe | gaa<br>Glu | cac<br>His<br>1545 | tta<br>Leu | tgt<br>Cys | aac<br>Asn | tac<br>Tyr | ctt<br>Leu<br>1550 | tcc<br>Ser | 5418 |
| cta<br>Leu | cca<br>Pro | acc<br>Thr | aac<br>Asn<br>1555 | ctc<br>Leu | att<br>Ile | cac<br>His | ctt<br>Leu | ttt<br>Phe<br>1560 | caa<br>Gln | gaa<br>Glu | aac<br>Asn | agt<br>Ser | gac<br>Asp<br>1565 | atc<br>Ile | 5463 |
| atg<br>Met | aac<br>Asn | tcc<br>Ser | ctg<br>Leu<br>1570 | att<br>Ile | gaa<br>Glu | agt<br>Ser | tgg<br>Trp | tgc<br>Cys<br>1575 | cag<br>Gln | aac<br>Asn | agt<br>Ser | gaa<br>Glu | gtt<br>Val<br>1580 | aaa<br>Lys | 5508 |
| cgg<br>Arg | tat<br>Tyr | cta<br>Leu | aat<br>Asn<br>1585 | ggc<br>Gly | gag<br>Glu | aga<br>Arg | gga<br>Gly | gcg<br>Ala<br>1590 | ata<br>Ile | agc<br>Ser | tac<br>Tyr | ccc<br>Pro | aga<br>Arg<br>1595 | gga<br>Gly | 5553 |
| gct<br>Ala | aac<br>Asn | aaa<br>Lys | ctg<br>Leu<br>1600 | ata<br>Ile | gac<br>Asp | ctt<br>Leu | cca<br>Pro | gag<br>Glu<br>1605 | gat<br>Asp | tac<br>Tyr | agc<br>Ser | agc<br>Ser | ctc<br>Leu<br>1610 | att<br>Ile | 5598 |
| aac<br>Asn | caa<br>Gln | gca<br>Ala | tcc<br>Ser<br>1615 | aat<br>Asn | ttc<br>Phe | tcg<br>Ser | tgc<br>Cys | ccc<br>Pro<br>1620 | aaa<br>Lys | tca<br>Ser | ggt<br>Gly | ggc<br>Gly | gac<br>Asp<br>1625 | aag<br>Lys | 5643 |
| agc<br>Ser | aga<br>Arg | gct<br>Ala | cct<br>Pro<br>1630 | act<br>Thr | ctg<br>Leu | tgc<br>Cys | ctc<br>Leu | gtg<br>Val<br>1635 | tgt<br>Cys | ggg<br>Gly | agt<br>Ser | ctc<br>Leu | ctc<br>Leu<br>1640 | tgc<br>Cys | 5688 |
| tct<br>Ser | cag<br>Gln | agt<br>Ser | tac<br>Tyr<br>1645 | tgc<br>Cys | tgc<br>Cys | caa<br>Gln | gct<br>Ala | gag<br>Glu<br>1650 | ctg<br>Leu | gag<br>Glu | ggt<br>Gly | gag<br>Glu | gac<br>Asp<br>1655 | gtc<br>Val | 5733 |
| gga<br>Gly | gcc<br>Ala | tgc<br>Cys | aca<br>Thr<br>1660 | gca<br>Ala | cac<br>His | acc<br>Thr | tac<br>Tyr | tcc<br>Ser<br>1665 | tgc<br>Cys | ggc<br>Gly | tcc<br>Ser | ggg<br>Gly | gcc<br>Ala<br>1670 | ggc<br>Gly | 5778 |
| atc<br>Ile | ttc<br>Phe | ctg<br>Leu | aga<br>Arg<br>1675 | gtg<br>Val | cgg<br>Arg | gaa<br>Glu | tgt<br>Cys | cag<br>Gln<br>1680 | gtg<br>Val | cta<br>Leu | ttt<br>Phe | tta<br>Leu | gct<br>Ala<br>1685 | ggc<br>Gly | 5823 |
| aaa<br>Lys | acc<br>Thr | aaa<br>Lys | gga<br>Gly<br>1690 | tgt<br>Cys | ttt<br>Phe | tat<br>Tyr | tct<br>Ser | cct<br>Pro<br>1695 | cct<br>Pro | tac<br>Tyr | ctt<br>Leu | gac<br>Asp | gac<br>Asp<br>1700 | tat<br>Tyr | 5868 |
| gga<br>Gly | gag<br>Glu | acc<br>Thr | gac<br>Asp<br>1705 | cag<br>Gln | gga<br>Gly | ctc<br>Leu | aga<br>Arg | cga<br>Arg<br>1710 | gga<br>Gly | aat<br>Asn | cct<br>Pro | tta<br>Leu | cat<br>His<br>1715 | tta<br>Leu | 5913 |
| tgc<br>Cys | caa<br>Gln | gag<br>Glu | cgg<br>Arg<br>1720 | ttt<br>Phe | cga<br>Arg | aag<br>Lys | atc<br>Ile | cag<br>Gln<br>1725 | aag<br>Lys | ctc<br>Leu | tgg<br>Trp | cag<br>Gln | cag<br>Gln<br>1730 | cat<br>His | 5958 |
| agt<br>Ser | atc<br>Ile | aca<br>Thr | gag<br>Glu<br>1735 | gag<br>Glu | atc<br>Ile | gga<br>Gly | cac<br>His | gcg<br>Ala<br>1740 | cag<br>Gln | gag<br>Glu | gct<br>Ala | aac<br>Asn | cag<br>Gln<br>1745 | acc<br>Thr | 6003 |
| ctg<br>Leu | gtc<br>Val | gga<br>Gly | att<br>Ile<br>1750 | gac<br>Asp | tgg<br>Trp | cag<br>Gln | cat<br>His | tta<br>Leu<br>1755 |  |  |  |  |  |  | 6050 | acttgacttg gagttttgta acacagctgg cttttccag                6089

<210> SEQ ID NO 6
<211> LENGTH: 1755
<212> TYPE: PRT
<213> ORGANISM: Mus musculus

<400> SEQUENCE: 6

Met Ala Ser Glu Met Glu Pro Glu Val Gln Ala Ile Asp Arg Ser Leu
1               5                   10                  15

-continued

```
Leu Glu Cys Ser Ala Glu Glu Ile Ala Gly Arg Trp Leu Gln Ala Thr
         20                  25                  30

Asp Leu Asn Arg Glu Val Tyr Gln His Leu Ala His Cys Val Pro Lys
             35                  40                  45

Ile Tyr Cys Arg Gly Pro Asn Pro Phe Pro Gln Lys Glu Asp Thr Leu
 50                  55                  60

Ala Gln His Ile Leu Leu Gly Pro Met Glu Trp Tyr Ile Cys Ala Glu
 65                  70                  75                  80

Asp Pro Ala Leu Gly Phe Pro Lys Leu Glu Gln Ala Asn Lys Pro Ser
                 85                  90                  95

His Leu Cys Gly Arg Val Phe Lys Val Gly Glu Pro Thr Tyr Ser Cys
            100                 105                 110

Arg Asp Cys Ala Val Asp Pro Thr Cys Val Leu Cys Met Glu Cys Phe
        115                 120                 125

Leu Gly Ser Ile His Arg Asp His Arg Tyr Arg Met Thr Thr Ser Gly
130                 135                 140

Gly Gly Gly Phe Cys Asp Cys Gly Asp Thr Glu Ala Trp Lys Glu Gly
145                 150                 155                 160

Pro Tyr Cys Gln Lys His Lys Leu Ser Ser Glu Val Val Glu Glu
                165                 170                 175

Glu Asp Pro Leu Val His Leu Ser Glu Asp Val Ile Ala Arg Thr Tyr
            180                 185                 190

Asn Ile Phe Ala Ile Met Phe Arg Tyr Ala Val Asp Ile Leu Thr Trp
        195                 200                 205

Glu Lys Glu Ser Glu Leu Pro Glu Asp Leu Glu Val Ala Glu Lys Ser
210                 215                 220

Asp Thr Tyr Tyr Cys Met Leu Phe Asn Asp Glu Val His Thr Tyr Glu
225                 230                 235                 240

Gln Val Ile Tyr Thr Leu Gln Lys Ala Val Asn Cys Thr Gln Lys Glu
                245                 250                 255

Ala Ile Gly Phe Ala Thr Thr Val Asp Arg Asp Gly Arg Arg Pro Val
            260                 265                 270

Arg Tyr Gly Asp Phe Gln Tyr Cys Asp Gln Ala Lys Thr Val Ile Val
        275                 280                 285

Arg Asn Thr Ser Arg Gln Thr Lys Pro Leu Lys Val Gln Val Met His
290                 295                 300

Ser Ser Val Ala Ala His Gln Asn Phe Gly Leu Lys Ala Leu Ser Trp
305                 310                 315                 320

Leu Gly Ser Val Ile Gly Tyr Ser Asp Gly Leu Arg Arg Ile Leu Cys
                325                 330                 335

Gln Val Gly Leu Gln Glu Gly Pro Asp Gly Glu Asn Ser Ser Leu Val
            340                 345                 350

Asp Arg Leu Met Leu Asn Asp Ser Lys Leu Trp Lys Gly Ala Arg Ser
        355                 360                 365

Val Tyr His Gln Leu Phe Met Ser Ser Leu Leu Met Asp Leu Lys Tyr
370                 375                 380

Lys Lys Leu Phe Ala Leu Arg Phe Ala Lys Asn Tyr Arg Gln Leu Gln
385                 390                 395                 400

Arg Asp Phe Met Glu Asp Asp His Glu Arg Ala Val Ser Val Thr Ala
                405                 410                 415

Leu Ser Val Gln Phe Phe Thr Ala Pro Thr Leu Ala Arg Met Leu Leu
            420                 425                 430

Thr Glu Glu Asn Leu Met Thr Val Ile Ile Lys Ala Phe Met Asp His
```

```
            435                 440                 445
Leu Lys His Arg Asp Ala Gln Gly Arg Phe Gln Phe Glu Arg Tyr Thr
    450                 455                 460
Ala Leu Gln Ala Phe Lys Phe Arg Arg Val Gln Ser Leu Ile Leu Asp
465                 470                 475                 480
Leu Lys Tyr Val Leu Ile Ser Lys Pro Thr Glu Trp Ser Asp Glu Leu
                485                 490                 495
Arg Gln Lys Phe Leu Gln Gly Phe Asp Ala Phe Leu Glu Leu Leu Lys
            500                 505                 510
Cys Met Gln Gly Met Asp Pro Ile Thr Arg Gln Val Gly Gln His Ile
            515                 520                 525
Glu Met Glu Pro Glu Trp Glu Ala Ala Phe Thr Leu Gln Met Lys Leu
    530                 535                 540
Thr His Val Ile Ser Met Val Gln Asp Trp Cys Ala Leu Asp Glu Lys
545                 550                 555                 560
Val Leu Ile Glu Ala Tyr Lys Lys Cys Leu Ala Val Leu Thr Gln Cys
                565                 570                 575
His Gly Gly Phe Thr Asp Gly Glu Gln Pro Ile Thr Leu Ser Ile Cys
            580                 585                 590
Gly His Ser Val Glu Thr Ile Arg Tyr Cys Val Ser Gln Glu Lys Val
        595                 600                 605
Ser Ile His Leu Pro Ile Ser Arg Leu Leu Ala Gly Leu His Val Leu
    610                 615                 620
Leu Ser Lys Ser Glu Val Ala Tyr Lys Phe Pro Glu Leu Leu Pro Leu
625                 630                 635                 640
Ser Glu Leu Ser Pro Pro Met Leu Ile Glu His Pro Leu Arg Cys Leu
                645                 650                 655
Val Leu Cys Ala Gln Val His Ala Gly Met Trp Arg Arg Asn Gly Phe
            660                 665                 670
Ser Leu Val Asn Gln Ile Tyr Tyr Tyr His Asn Val Lys Cys Arg Arg
            675                 680                 685
Glu Met Phe Asp Lys Asp Ile Val Met Leu Gln Thr Gly Val Ser Met
    690                 695                 700
Met Asp Pro Asn His Phe Leu Met Ile Met Leu Ser Arg Phe Glu Leu
705                 710                 715                 720
Tyr Gln Leu Phe Ser Thr Pro Asp Tyr Gly Lys Arg Phe Ser Ser Glu
                725                 730                 735
Val Thr His Lys Asp Val Val Gln Gln Asn Thr Leu Ile Glu Glu
            740                 745                 750
Met Leu Tyr Leu Ile Ile Met Leu Val Gly Glu Arg Phe Asn Pro Gly
            755                 760                 765
Val Gly Gln Val Ala Ala Thr Asp Glu Ile Lys Arg Glu Ile Ile His
    770                 775                 780
Gln Leu Ser Ile Lys Pro Met Ala His Ser Glu Leu Val Lys Ser Leu
785                 790                 795                 800
Pro Glu Asp Glu Asn Lys Glu Thr Gly Met Glu Ser Val Ile Glu Ser
                805                 810                 815
Val Ala His Phe Lys Lys Pro Gly Leu Thr Gly Arg Gly Met Tyr Glu
            820                 825                 830
Leu Lys Pro Glu Cys Ala Lys Glu Phe Asn Leu Tyr Phe Tyr His Phe
            835                 840                 845
Ser Arg Ala Glu Gln Ser Lys Ala Glu Glu Ala Gln Arg Lys Leu Lys
    850                 855                 860
```

-continued

```
Arg Glu Asn Lys Glu Asp Thr Ala Leu Pro Pro Ala Leu Pro Pro
865                 870                 875                 880

Phe Cys Pro Leu Phe Ala Ser Leu Val Asn Ile Leu Gln Cys Asp Val
            885                 890                 895

Met Leu Tyr Ile Met Gly Thr Ile Leu Gln Trp Ala Val Glu His His
            900                 905                 910

Gly Ser Ala Trp Ser Glu Ser Met Leu Gln Arg Val Leu His Leu Ile
            915                 920                 925

Gly Met Ala Leu Gln Glu Glu Lys His His Leu Glu Asn Ala Val Glu
930                 935                 940

Gly His Val Gln Thr Phe Thr Phe Thr Gln Lys Ile Ser Lys Pro Gly
945                 950                 955                 960

Asp Ala Pro His Asn Ser Pro Ser Ile Leu Ala Met Leu Glu Thr Leu
            965                 970                 975

Gln Asn Ala Pro Ser Leu Glu Ala His Lys Asp Met Ile Arg Trp Leu
            980                 985                 990

Leu Lys Met Phe Asn Ala Ile Lys Lys Ile Arg Glu Cys Ser Ser Ser
            995                 1000                1005

Ser Pro Val Ala Glu Ala Glu Gly Thr Ile Met Glu Glu Ser Ser
    1010            1015            1020

Arg Asp Lys Asp Lys Ala Glu Arg Lys Arg Lys Ala Glu Ile Ala
    1025            1030            1035

Arg Leu Arg Arg Glu Lys Ile Met Ala Gln Met Ser Glu Met Gln
    1040            1045            1050

Arg His Phe Ile Asp Glu Asn Lys Glu Leu Phe Gln Gln Thr Leu
    1055            1060            1065

Glu Leu Asp Thr Ser Ala Ser Ala Thr Leu Asp Ser Ser Pro Pro
    1070            1075            1080

Val Ser Asp Ala Ala Leu Thr Ala Leu Gly Pro Ala Gln Thr Gln
    1085            1090            1095

Val Pro Glu Pro Arg Gln Phe Val Thr Cys Ile Leu Cys Gln Glu
    1100            1105            1110

Glu Gln Glu Val Thr Val Gly Ser Arg Ala Met Val Leu Ala Ala
    1115            1120            1125

Phe Val Gln Arg Ser Thr Val Leu Ser Lys Asp Arg Thr Lys Thr
    1130            1135            1140

Ile Ala Asp Pro Glu Lys Tyr Asp Pro Leu Phe Met His Pro Asp
    1145            1150            1155

Leu Ser Cys Gly Thr His Thr Gly Ser Cys Gly His Val Met His
    1160            1165            1170

Ala His Cys Trp Gln Arg Tyr Phe Asp Ser Val Gln Ala Lys Glu
    1175            1180            1185

Gln Arg Arg Gln Gln Arg Leu Arg Leu His Thr Ser Tyr Asp Val
    1190            1195            1200

Glu Asn Gly Glu Phe Leu Cys Pro Leu Cys Glu Cys Leu Ser Asn
    1205            1210            1215

Thr Val Ile Pro Leu Leu Pro Pro Arg Ser Ile Leu Ser Arg
    1220            1225            1230

Arg Leu Asn Phe Ser Asp Gln Pro Asp Leu Ala Gln Trp Thr Arg
    1235            1240            1245

Ala Val Thr Gln Gln Ile Lys Val Val Gln Met Leu Arg Arg Lys
    1250            1255            1260
```

-continued

```
His Asn Ala Ala Asp Thr Ser Ser Ser Glu Asp Thr Glu Ala Met
1265                1270                1275

Asn Ile Ile Pro Ile Pro Glu Gly Phe Arg Pro Asp Phe Tyr Pro
    1280                1285                1290

Arg Asn Pro Tyr Ser Asp Ser Ile Lys Glu Met Leu Thr Thr Phe
    1295                1300                1305

Gly Thr Ala Ala Tyr Lys Val Gly Leu Lys Val His Pro Asn Glu
    1310                1315                1320

Gly Asp Pro Arg Val Pro Ile Leu Cys Trp Gly Thr Cys Ala Tyr
1325                1330                1335

Thr Ile Gln Ser Ile Glu Arg Ile Leu Ser Asp Glu Glu Lys Pro
    1340                1345                1350

Val Phe Gly Pro Leu Pro Cys Arg Leu Asp Asp Cys Leu Arg Ser
1355                1360                1365

Leu Thr Arg Phe Ala Ala Ala His Trp Thr Val Ala Leu Leu Pro
    1370                1375                1380

Val Val Gln Gly His Phe Cys Lys Leu Phe Ala Ser Leu Val Pro
    1385                1390                1395

Ser Asp Ser Tyr Glu Asp Leu Pro Cys Ile Leu Asp Ile Asp Met
    1400                1405                1410

Phe His Leu Leu Val Gly Leu Val Leu Ala Phe Pro Ala Leu Gln
    1415                1420                1425

Cys Gln Asp Phe Ser Gly Ser Ser Leu Ala Thr Gly Asp Leu His
    1430                1435                1440

Ile Phe His Leu Val Thr Met Ala His Ile Val Gln Ile Leu Leu
    1445                1450                1455

Thr Ser Cys Thr Glu Glu Asn Gly Met Asp Gln Glu Asn Pro Thr
    1460                1465                1470

Gly Glu Glu Glu Leu Ala Ile Leu Ser Leu His Lys Thr Leu His
1475                1480                1485

Gln Tyr Thr Gly Ser Ala Leu Lys Glu Ala Pro Ser Gly Trp His
    1490                1495                1500

Leu Trp Arg Ser Val Arg Ala Ala Ile Met Pro Phe Leu Lys Cys
1505                1510                1515

Ser Ala Leu Phe Phe His Tyr Leu Asn Gly Val Pro Ala Pro Pro
    1520                1525                1530

Asp Leu Gln Val Ser Gly Thr Ser His Phe Glu His Leu Cys Asn
    1535                1540                1545

Tyr Leu Ser Leu Pro Thr Asn Leu Ile His Leu Phe Gln Glu Asn
    1550                1555                1560

Ser Asp Ile Met Asn Ser Leu Ile Glu Ser Trp Cys Gln Asn Ser
    1565                1570                1575

Glu Val Lys Arg Tyr Leu Asn Gly Glu Arg Gly Ala Ile Ser Tyr
    1580                1585                1590

Pro Arg Gly Ala Asn Lys Leu Ile Asp Leu Pro Glu Asp Tyr Ser
    1595                1600                1605

Ser Leu Ile Asn Gln Ala Ser Asn Phe Ser Cys Pro Lys Ser Gly
    1610                1615                1620

Gly Asp Lys Ser Arg Ala Pro Thr Leu Cys Leu Val Cys Gly Ser
1625                1630                1635

Leu Leu Cys Ser Gln Ser Tyr Cys Cys Gln Ala Glu Leu Glu Gly
    1640                1645                1650

Glu Asp Val Gly Ala Cys Thr Ala His Thr Tyr Ser Cys Gly Ser
```

```
                    1655              1660              1665

Gly  Ala  Gly  Ile  Phe  Leu  Arg  Val  Arg  Glu  Cys  Gln  Val  Leu  Phe
          1670                    1675                    1680

Leu  Ala  Gly  Lys  Thr  Lys  Gly  Cys  Phe  Tyr  Ser  Pro  Pro  Tyr  Leu
     1685                    1690                    1695

Asp  Asp  Tyr  Gly  Glu  Thr  Asp  Gln  Gly  Leu  Arg  Arg  Gly  Asn  Pro
1700                    1705                    1710

Leu  His  Leu  Cys  Gln  Glu  Arg  Phe  Arg  Lys  Ile  Gln  Lys  Leu  Trp
     1715                    1720                    1725

Gln  Gln  His  Ser  Ile  Thr  Glu  Glu  Ile  Gly  His  Ala  Gln  Glu  Ala
1730                    1735                    1740

Asn  Gln  Thr  Leu  Val  Gly  Ile  Asp  Trp  Gln  His  Leu
     1745                    1750                    1755
```

<210> SEQ ID NO 7
<211> LENGTH: 21
<212> TYPE: DNA
<213> ORGANISM: Artificial sequence
<220> FEATURE:
<223> OTHER INFORMATION: Synthetic primer

<400> SEQUENCE: 7
ctgctcgagt ctgcgtcaaa c                                     21

<210> SEQ ID NO 8
<211> LENGTH: 24
<212> TYPE: DNA
<213> ORGANISM: Artificial sequence
<220> FEATURE:
<223> OTHER INFORMATION: Synthetic primer

<400> SEQUENCE: 8
tctcgatatg ttgcagcctt gcta                                  24

<210> SEQ ID NO 9
<211> LENGTH: 23
<212> TYPE: DNA
<213> ORGANISM: Artificial sequence
<220> FEATURE:
<223> OTHER INFORMATION: Synthetic primer

<400> SEQUENCE: 9
gtatgaactt gccgaggctt tta                                   23

<210> SEQ ID NO 10
<211> LENGTH: 23
<212> TYPE: DNA
<213> ORGANISM: Artificial sequence
<220> FEATURE:
<223> OTHER INFORMATION: Synthetic primer

<400> SEQUENCE: 10
caatactttc ccagccctca gaa                                   23

<210> SEQ ID NO 11
<211> LENGTH: 18
<212> TYPE: DNA
<213> ORGANISM: Artificial sequence
<220> FEATURE:
<223> OTHER INFORMATION: Synthetic primer

<400> SEQUENCE: 11
atggcgtcgc tagagcca                                         18

```
<210> SEQ ID NO 12
<211> LENGTH: 23
<212> TYPE: DNA
<213> ORGANISM: Artificial sequence
<220> FEATURE:
<223> OTHER INFORMATION: Synthetic primer

<400> SEQUENCE: 12
caaagcggct gagcatgatc atc                                              23

<210> SEQ ID NO 13
<211> LENGTH: 23
<212> TYPE: DNA
<213> ORGANISM: Artificial sequence
<220> FEATURE:
<223> OTHER INFORMATION: Synthetic primer

<400> SEQUENCE: 13
tgaacagcca atcacactaa gca                                              23

<210> SEQ ID NO 14
<211> LENGTH: 20
<212> TYPE: DNA
<213> ORGANISM: Artificial sequence
<220> FEATURE:
<223> OTHER INFORMATION: Synthetic primer

<400> SEQUENCE: 14
ttataaatgc caaatgccaa                                                  20

<210> SEQ ID NO 15
<211> LENGTH: 1757
<212> TYPE: PRT
<213> ORGANISM: Mus musculus

<400> SEQUENCE: 15
```

Met Ala Asp Glu Glu Met Asp Gly Ala Glu Arg Met Asp Val Ser Pro
1               5                   10                  15

Glu Pro Pro Leu Ala Pro Gln Arg Pro Ala Ser Trp Trp Asp Gln Gln
            20                  25                  30

Val Asp Phe Tyr Thr Ala Phe Leu His His Leu Ala Gln Leu Val Pro
        35                  40                  45

Glu Ile Tyr Phe Ala Glu Met Asp Pro Asp Leu Glu Lys Gln Glu Glu
    50                  55                  60

Ser Val Gln Met Ser Ile Leu Thr Pro Leu Glu Trp Tyr Leu Phe Gly
65                  70                  75                  80

Glu Asp Pro Asp Ile Cys Leu Gly Lys Leu Lys His Ser Gly Ala Phe
                85                  90                  95

Gln Leu Cys Gly Lys Val Phe Lys Ser Gly Glu Thr Thr Tyr Ser Cys
            100                 105                 110

Arg Asp Cys Ala Ile Asp Pro Thr Cys Val Leu Cys Met Asp Cys Phe
        115                 120                 125

Gln Ser Ser Val His Lys Asn His Arg Tyr Lys Met His Thr Ser Thr
    130                 135                 140

Gly Gly Gly Phe Cys Asp Cys Gly Asp Thr Glu Ala Trp Lys Thr Gly
145                 150                 155                 160

Pro Phe Cys Val Asp His Glu Pro Gly Arg Ala Gly Thr Thr Lys Glu
                165                 170                 175

Ser Leu His Cys Pro Leu Asn Glu Glu Val Ile Ala Gln Ala Arg Arg

```
                180             185             190
Ile Phe Pro Ser Val Ile Lys Tyr Ile Val Glu Met Thr Ile Trp Glu
            195             200             205
Glu Glu Lys Glu Leu Pro Pro Glu Leu Gln Ile Arg Glu Lys Asn Glu
        210             215             220
Arg Tyr Tyr Cys Val Leu Phe Asn Asp Glu His His Ser Tyr Asp His
225             230             235             240
Val Ile Tyr Ser Leu Gln Arg Ala Leu Asp Cys Glu Leu Ala Glu Ala
            245             250             255
Gln Leu His Thr Thr Ala Ile Asp Lys Glu Gly Arg Arg Ala Val Lys
        260             265             270
Ala Gly Val Tyr Ala Thr Cys Gln Glu Ala Lys Glu Asp Ile Lys Ser
        275             280             285
His Ser Glu Asn Val Ser Gln His Pro Leu His Val Glu Val Leu His
        290             295             300
Ser Val Val Met Ala His Gln Lys Phe Ala Leu Arg Leu Gly Ser Trp
305             310             315             320
Met Asn Lys Ile Met Ser Tyr Ser Ser Asp Phe Arg Gln Ile Phe Cys
            325             330             335
Gln Ala Cys Leu Val Glu Glu Pro Gly Ser Glu Asn Pro Cys Leu Ile
        340             345             350
Ser Arg Leu Met Leu Trp Asp Ala Lys Leu Tyr Lys Gly Ala Arg Lys
        355             360             365
Ile Leu His Glu Leu Ile Phe Ser Ser Phe Met Glu Met Glu Tyr
370             375             380
Lys Lys Leu Phe Ala Met Glu Phe Val Lys Tyr Tyr Lys Gln Leu Gln
385             390             395             400
Lys Glu Tyr Ile Ser Asp Asp His Glu Arg Ser Ile Ser Ile Thr Ala
            405             410             415
Leu Ser Val Gln Met Leu Thr Val Pro Thr Leu Ala Arg His Leu Ile
        420             425             430
Glu Glu Gln Asn Val Ile Ser Val Ile Thr Glu Thr Leu Leu Glu Val
        435             440             445
Leu Pro Glu Tyr Leu Asp Arg Asn Asn Lys Phe Asn Phe Gln Gly Tyr
    450             455             460
Ser Gln Asp Lys Leu Gly Arg Val Tyr Ala Val Ile Cys Asp Leu Lys
465             470             475             480
Tyr Ile Leu Ile Ser Lys Pro Val Ile Trp Thr Glu Arg Leu Arg Ala
            485             490             495
Gln Phe Leu Glu Gly Phe Arg Ser Phe Leu Lys Ile Leu Thr Cys Met
        500             505             510
Gln Gly Met Glu Glu Ile Arg Arg Gln Val Gly Gln His Ile Glu Val
        515             520             525
Asp Pro Asp Trp Glu Ala Ala Ile Ala Ile Gln Met Gln Leu Lys Asn
    530             535             540
Ile Leu Leu Met Phe Gln Glu Trp Cys Ala Cys Asp Glu Asp Leu Leu
545             550             555             560
Leu Val Ala Tyr Lys Glu Cys His Lys Ala Val Met Arg Cys Ser Thr
            565             570             575
Asn Phe Met Ser Ser Thr Lys Thr Val Val Gln Leu Cys Gly His Ser
        580             585             590
Leu Glu Thr Lys Ser Tyr Lys Val Ser Glu Asp Leu Val Ser Ile His
    595             600             605
```

-continued

```
Leu Pro Leu Ser Arg Thr Leu Ala Gly Leu His Val Arg Leu Ser Arg
    610                 615                 620
Leu Gly Ala Ile Ser Arg Leu His Glu Phe Val Pro Phe Asp Ser Phe
625                 630                 635                 640
Gln Val Glu Val Leu Val Glu Tyr Pro Leu Arg Cys Leu Val Leu Val
                645                 650                 655
Ala Gln Val Val Ala Glu Met Trp Arg Arg Asn Gly Leu Ser Leu Ile
                660                 665                 670
Ser Gln Val Phe Tyr Tyr Gln Asp Val Lys Cys Arg Glu Glu Met Tyr
            675                 680                 685
Asp Lys Asp Ile Ile Met Leu Gln Ile Gly Ala Ser Ile Met Asp Pro
    690                 695                 700
Asn Lys Phe Leu Leu Leu Val Leu Gln Arg Tyr Glu Leu Thr Asp Ala
705                 710                 715                 720
Phe Asn Lys Thr Ile Ser Thr Lys Asp Gln Asp Leu Ile Lys Gln Tyr
                725                 730                 735
Asn Thr Leu Ile Glu Glu Met Leu Gln Val Leu Ile Tyr Ile Val Gly
                740                 745                 750
Glu Arg Tyr Val Pro Gly Val Gly Asn Val Thr Arg Glu Glu Val Ile
            755                 760                 765
Met Arg Glu Ile Thr His Leu Leu Cys Ile Glu Pro Met Pro His Ser
    770                 775                 780
Ala Ile Ala Arg Asn Leu Pro Glu Asn Glu Asn Asn Glu Thr Gly Leu
785                 790                 795                 800
Glu Asn Val Ile Asn Lys Val Ala Thr Phe Lys Lys Pro Gly Val Ser
                805                 810                 815
Gly His Gly Val Tyr Glu Leu Lys Asp Glu Ser Leu Lys Asp Phe Asn
                820                 825                 830
Met Tyr Phe Tyr His Tyr Ser Lys Thr Gln His Ser Lys Ala Glu His
            835                 840                 845
Met Gln Lys Lys Arg Arg Lys Gln Glu Asn Lys Asp Glu Ala Leu Pro
    850                 855                 860
Pro Pro Pro Pro Glu Phe Cys Pro Ala Phe Ser Lys Val Val Asn
865                 870                 875                 880
Leu Leu Ser Cys Asp Val Met Ile Tyr Ile Leu Arg Thr Ile Phe Glu
                885                 890                 895
Arg Ala Val Asp Thr Glu Ser Asn Leu Trp Thr Glu Gly Met Leu Gln
            900                 905                 910
Met Ala Phe His Ile Leu Ala Leu Gly Leu Leu Glu Glu Lys Gln Gln
    915                 920                 925
Leu Gln Lys Ala Pro Glu Glu Glu Val Ala Phe Asp Phe Tyr His Lys
    930                 935                 940
Ala Ser Arg Leu Gly Ser Ser Ala Met Asn Ala Gln Asn Ile Gln Met
945                 950                 955                 960
Leu Leu Glu Arg Leu Lys Gly Ile Pro Gln Leu Glu Gly Gln Lys Asp
                965                 970                 975
Met Ile Thr Trp Ile Leu Gln Met Phe Asp Thr Val Lys Arg Leu Arg
            980                 985                 990
Glu Lys Ser Cys Leu Val Val Ala  Thr Thr Ser Gly Leu  Glu Cys Ile
        995                 1000                1005
Lys Ser  Glu Glu Ile Thr His  Asp Lys Glu Lys Ala  Glu Arg Lys
   1010                1015                1020
```

```
Arg Lys Ala Glu Ala Ala Arg Leu His Arg Gln Lys Ile Met Ala
    1025            1030                1035
Gln Met Ser Ala Leu Gln Lys Asn Phe Ile Glu Thr His Lys Leu
    1040            1045                1050
Met Tyr Asp Asn Thr Ser Glu Val Thr Gly Lys Glu Asp Ser Ile
    1055            1060                1065
Met Glu Glu Glu Ser Thr Ser Ala Val Ser Glu Ala Ser Arg Ile
    1070            1075                1080
Ala Leu Gly Pro Lys Arg Gly Pro Ala Val Thr Glu Lys Glu Val
    1085            1090                1095
Leu Thr Cys Ile Leu Cys Gln Glu Gln Glu Val Lys Leu Glu
    1100            1105                1110
Asn Asn Ala Met Val Leu Ser Ala Cys Val Gln Lys Ser Thr Ala
    1115            1120                1125
Leu Thr Gln His Arg Gly Lys Pro Val Asp His Leu Gly Glu Thr
    1130            1135                1140
Leu Asp Pro Leu Phe Met Asp Pro Asp Leu Ala His Gly Thr Tyr
    1145            1150                1155
Thr Gly Ser Cys Gly His Val Met His Ala Val Cys Trp Gln Lys
    1160            1165                1170
Tyr Phe Glu Ala Val Gln Leu Ser Ser Gln Gln Arg Ile His Val
    1175            1180                1185
Asp Leu Phe Asp Leu Glu Ser Gly Glu Tyr Leu Cys Pro Leu Cys
    1190            1195                1200
Lys Ser Leu Cys Asn Thr Val Ile Pro Ile Ile Pro Leu Gln Pro
    1205            1210                1215
Gln Lys Ile Asn Ser Glu Asn Ala Glu Ala Leu Ala Gln Leu Leu
    1220            1225                1230
Thr Leu Ala Arg Trp Ile Gln Thr Val Leu Ala Arg Ile Ser Gly
    1235            1240                1245
Tyr Asn Ile Lys His Ala Lys Gly Glu Ala Pro Ala Val Pro Val
    1250            1255                1260
Leu Phe Asn Gln Gly Met Gly Asp Ser Thr Phe Glu Phe His Ser
    1265            1270                1275
Ile Leu Ser Phe Gly Val Gln Ser Ser Val Lys Tyr Ser Asn Ser
    1280            1285                1290
Ile Lys Glu Met Val Ile Leu Phe Ala Thr Thr Ile Tyr Arg Ile
    1295            1300                1305
Gly Leu Lys Val Pro Pro Asp Glu Leu Asp Pro Arg Val Pro Met
    1310            1315                1320
Met Thr Trp Ser Thr Cys Ala Phe Thr Ile Gln Ala Ile Glu Asn
    1325            1330                1335
Leu Leu Gly Asp Glu Gly Lys Pro Leu Phe Gly Ala Leu Gln Asn
    1340            1345                1350
Arg Gln His Ser Gly Leu Lys Ala Leu Met Gln Phe Ala Val Ala
    1355            1360                1365
Gln Arg Ala Thr Cys Pro Gln Val Leu Ile His Lys His Leu Ala
    1370            1375                1380
Arg Leu Leu Ser Val Ile Leu Pro Asn Leu Gln Ser Glu Asn Thr
    1385            1390                1395
Pro Gly Leu Leu Ser Val Asp Leu Phe His Val Leu Val Gly Ala
    1400            1405                1410
Val Leu Ala Phe Pro Ser Leu Tyr Trp Asp Asp Thr Val Asp Leu
```

```
                1415                1420                1425

Gln Pro Ser Pro Leu Ser Ser Ser Tyr Asn His Leu Tyr Leu Phe
    1430                1435                1440

His Leu Ile Thr Met Ala His Met Leu Gln Ile Leu Leu Thr Thr
    1445                1450                1455

Asp Thr Asp Leu Ser Pro Gly Pro Pro Leu Ala Glu Gly Glu Glu
    1460                1465                1470

Asp Ser Glu Glu Ala Arg Cys Ala Ser Ala Phe Phe Val Glu Val
    1475                1480                1485

Ser Gln His Thr Asp Gly Leu Thr Gly Cys Gly Ala Pro Gly Trp
    1490                1495                1500

Tyr Leu Trp Leu Ser Leu Arg Asn Gly Ile Thr Pro Tyr Leu Arg
    1505                1510                1515

Cys Ala Ala Leu Leu Phe His Tyr Leu Leu Gly Val Ala Pro Pro
    1520                1525                1530

Glu Glu Leu Phe Ala Asn Ser Ala Glu Gly Glu Phe Ser Ala Leu
    1535                1540                1545

Cys Ser Tyr Leu Ser Leu Pro Thr Asn Leu Phe Leu Leu Phe Gln
    1550                1555                1560

Glu Tyr Trp Asp Thr Ile Arg Pro Leu Leu Gln Arg Trp Cys Gly
    1565                1570                1575

Asp Pro Ala Leu Leu Lys Ser Leu Lys Gln Lys Ser Ala Val Val
    1580                1585                1590

Arg Tyr Pro Arg Lys Arg Asn Ser Leu Ile Glu Leu Pro Glu Asp
    1595                1600                1605

Tyr Ser Cys Leu Leu Asn Gln Ala Ser His Phe Arg Cys Pro Arg
    1610                1615                1620

Ser Ala Asp Asp Glu Arg Lys His Pro Val Leu Cys Leu Phe Cys
    1625                1630                1635

Gly Ala Ile Leu Cys Ser Gln Asn Ile Cys Cys Gln Glu Ile Val
    1640                1645                1650

Asn Gly Glu Glu Val Gly Ala Cys Val Phe His Ala Leu His Cys
    1655                1660                1665

Gly Ala Gly Val Cys Ile Phe Leu Lys Ile Arg Glu Cys Arg Val
    1670                1675                1680

Val Leu Val Glu Gly Lys Ala Arg Gly Cys Ala Tyr Pro Ala Pro
    1685                1690                1695

Tyr Leu Asp Glu Tyr Gly Glu Thr Asp Pro Gly Leu Lys Arg Gly
    1700                1705                1710

Asn Pro Leu His Leu Ser Arg Glu Arg Tyr Arg Lys Leu His Leu
    1715                1720                1725

Val Trp Gln Gln His Cys Ile Ile Glu Glu Ile Ala Arg Ser Gln
    1730                1735                1740

Glu Thr Asn Gln Met Leu Phe Gly Phe Asn Trp Gln Leu Leu
    1745                1750                1755

<210> SEQ ID NO 16
<211> LENGTH: 11
<212> TYPE: PRT
<213> ORGANISM: Artificial sequence
<220> FEATURE:
<223> OTHER INFORMATION: Synthetic peptide

<400> SEQUENCE: 16

Tyr Gly Arg Lys Lys Arg Arg Gln Arg Arg Arg
```

<210> SEQ ID NO 17
<211> LENGTH: 15
<212> TYPE: PRT
<213> ORGANISM: Artificial sequence
<220> FEATURE:
<223> OTHER INFORMATION: Synthetic peptide

<400> SEQUENCE: 17

Gly Gly Gly Gly Tyr Gly Arg Lys Lys Arg Arg Gln Arg Arg Arg
 1               5                  10                  15

<210> SEQ ID NO 18
<211> LENGTH: 5205
<212> TYPE: DNA
<213> ORGANISM: Homo sapiens
<220> FEATURE:
<221> NAME/KEY: misc_feature
<222> LOCATION: (662)..(662)
<223> OTHER INFORMATION: n = a, c, g, or t
<220> FEATURE:
<221> NAME/KEY: misc_feature
<222> LOCATION: (668)..(668)
<223> OTHER INFORMATION: n = a, c, g, or t

<400> SEQUENCE: 18

| | | |
|---|---|---|
| atggcggacg aggaggctgg aggtactgag aggatggaaa tcagcgcgga gttaccccag | 60 |
| accccctcagc gtctggcatc ttggtgggat cagcaagttg attttttatac tgctttcttg | 120 |
| catcatttgg cacaattggt gccagaaatt tactttgctg aaatggaccc agacttggaa | 180 |
| aagcaggagg aaagtgtaca aatgtcaata ttcactccac tggaatggta cttatttgga | 240 |
| gaagatccag atatttgctt agagaaattg aagcacagtg gagcatttca gctttgtggg | 300 |
| agggttttca aaagtggaga gacaacctat tcttgcaggg attgtgcaat tgatccaaca | 360 |
| tgtgtactct gtatggactg cttccaggac agtgttcata aaaatcatcg ttacaagatg | 420 |
| catacttcta ctggaggagg ttctgtgac tgtggagaca cagaggcatg gaaaactggc | 480 |
| cctttttgtg taaatcatga acctggaaga gcaggtacta aaaagagaaa ttcacgctgt | 540 |
| ccgttgaatg aagaggtaat tgtccaagcc aggaaaatat ttccttcagt gataaaatat | 600 |
| gtcgtagaaa tgactatatg ggaagaggaa aagaactgc ctcctgaact ccagataagg | 660 |
| knryycvndh hsydhgtcat atacagccta caaagagctc ttgactgtga gctcgcagag | 720 |
| gcccagttgc ataccactgc cattgacaaa gagggtcgtc gggctgttaa gcgggagct | 780 |
| tatgctgctt gccaggaagc aaaggaagat ataaagagtc attcagaaaa tgtctctcaa | 840 |
| catccacttc atgtagaagt attacactca gagattatgg ctcatcagaa atttgctttg | 900 |
| cgtcttggtt cctggatgaa caaaattatg agctattcaa gtgactttag gcagatcttt | 960 |
| tgccaagcat gccttagaga gaacctgac tcggagaatc cctgtctcat aagcaggtta | 1020 |
| atgctttggg atgcaaagct ttataaaggt gcccgtaaga tccttcatga attgatcttc | 1080 |
| agcagttttt ttatggagat ggaatacaaa aaactctttg ctatgaatt tgtgaagtat | 1140 |
| tataaacaac tgcagaaaga atatatcagt gatgatcatg acagaagtat ctctataact | 1200 |
| gcactttcag ttcagatgtt tactgttcct actctggctc acatcttat tgaagagcag | 1260 |
| aatgttatct ctgtcattac tgaaactctg ctagaagttt tacctgagta cttggacagg | 1320 |
| aacaataaat tcaacttcca gggttatagc caggacaaat tgggaagagt atatgcagta | 1380 |
| atatgtgacc taaagtatat cctgatcagc aaacccacaa tatggacaga agattaaga | 1440 |

```
atgcagttcc ttgaaggttt tcgatctttt ttgaagattc ttacctgtat gcagggaatg    1500
gaagaaatcc gaagacaggt tgggcaacac attgaagtgg atcctgattg ggaggctgcc    1560
attgctatac agatgcaatt gaagaatatt ttactcatgt tccaagagtg gtgtgcttgt    1620
gatgaagaac tcttacttgt ggcttataaa gaatgtcaca aagctgtgat gaggtgcagt    1680
accagtttca tatctagtag caagacagta gtacaatcgt gtggacatag tttggaaaca    1740
aagtcctaca gagtatctga ggatcttgta agcatacatc tgccactctc taggacccct    1800
gctggtcttc atgtacgttt aagcaggctg ggtgctgttt caagactgca tgaatttgtg    1860
tcttttgagg actttcaagt agaggtacta gtggaatatc ctttacgttg tctggtgttg    1920
gttgcccagg ttgttgctga gatgtggcga agaaatggac tgtctcttat tagccaggtg    1980
ttttattacc aagatgttaa gtgcagagaa gaaatgtatg ataaagatat catcatgctt    2040
cagattggtg catctttaat ggatcccaat aagttcttgt tactggtact tcagaggtat    2100
gaacttgccg aggcttttaa caagaccata tctacaaaag accaggattt gattaaacaa    2160
tataatacac taatagaaga aatgcttcag gtcctcatct atattgtggg tgagcgttat    2220
gtacctggag tgggaaatgt gaccaaagaa gaggtcacaa tgagagaaat cattcacttg    2280
ctttgcattg aacccatgcc acacagtgcc attgccaaaa atttacctga gaatgaaaat    2340
aatgaaactg gcttagagaa tgtcataaac aaagtggcca catttaagaa accaggtgta    2400
tcaggccatg gagtttatga actaaaagat gaatcactga aagacttcaa tatgtacttt    2460
tatcattact ccaaaaccca gcatagcaag gctgaacata tgcagaagaa aaggagaaaa    2520
caagaaaaca aagatgaagc attgccgcca ccaccacctc ctgaattctg ccctgctttc    2580
agcaaagtga ttaaccttct caactgtgat atcatgatgt acattctcag gaccgtattt    2640
gagcgggcaa tagacacaga ttctaacttg tggaccgaag ggatgctcca aatggctttt    2700
catattctgg cattgggttt actagaagag aagcaacagc ttcaaaaagc tcctgaagaa    2760
gaagtaacat ttgactttta tcataaggct tcaagattgg gaagttcagc catgaatata    2820
caaatgcttt tggaaaaact caaaggaatt ccccagttag aaggccagaa ggacatgata    2880
acgtggatac ttcagatgtt tgacacagtg aagcgattaa gagaaaaatc ttgtttaatt    2940
gtagcaacca catcaggatc ggaatctatt aagaatgatg agattactca tgataaagaa    3000
aaagcagaac gaaaaagaaa agctgaagct gctaggctac atcgccagaa gatcatggct    3060
cagatgtctg ccttacagaa aaacttcatt gaaactcata aactcatgta tgacaataca    3120
tcagaaatgc ctgggaaaga agattccatt atggaggaag agagcacccc agcagtcagt    3180
gactactcta gaattgcttt gggtcctaaa cggggtccat ctgttactga aaaggaggtg    3240
ctgacgtgca tcctttgcca agaagaacag gaggtgaaaa tagaaaataa tgccatggta    3300
ttatcggcct gtgtccagaa atctactgcc ttaacccagc acaggggaaa acccatagaa    3360
ctctcaggag aagcccctaga cccacttttc atggatccag acttggcata tggaacttat    3420
acaggaagct gtggtcatgt aatgcacgca gtgtgctggc agaagtattt tgaagctgta    3480
cagctgagct ctcagcagcg cattcatgtt gacctttttg acttggaaag tggagaatat    3540 cttttgccctc tttgcaaatc tctgtgcaat actgtgatcc ccattattcc tttgcaacct    3600
caaaagataa acagtgagaa tgcagatgct cttgctcaac ttttgaccct ggcacggtgg    3660
atacagactg ttctggccag aatatcaggt tataatataa gacatgctaa aggagaaaac    3720
ccaattccta ttttctcttaa tcaaggaatg ggagattcta ctttggagtt ccattccatc    3780
ctgagttttg gcgttgagtc ttcgattaaa tattcaaata gcatcaagga aatggttatt    3840
```

| | |
|---|---|
| ctctttgcca caacaattta tagaattgga ttgaaagtgc cacctgatga aagggatcct | 3900 |
| cgagtcccca tgctgacctg gagcacctgc gctttcacta tccaggcaat tgaaaatcta | 3960 |
| ttgggagatg aaggaaaacc tctgtttgga gcacttcaaa ataggcagca taatggtctg | 4020 |
| aaagcattaa tgcagtttgc agttgcacag aggattacct gtcctcaggt cctgatacag | 4080 |
| aaacatctgg ttcgtcttct atcagttgtt cttcctaaca taaaatcaga agatacacca | 4140 |
| tgccttctgt ctatagatct gtttcatgtt ttggtgggtg ctgtgttagc attcccatcc | 4200 |
| ttgtattggg atgaccctgt tgatctgcag ccttcttcag ttagttcttc ctataaccac | 4260 |
| ctttatctct tccatttgat caccatggca cacatgcttc agatactact tacagtagac | 4320 |
| acaggcctac cccttgctca ggttcaagaa gacagtgaag aggctcattc cgcatcttct | 4380 |
| ttctttgcag aaatttctca atatacaagt ggctccattg ggtgtgatat tcctggctgg | 4440 |
| tatttgtggg tctcactgaa gaatggcatc accccttatc ttcgctgtgc tgcattgttt | 4500 |
| ttccactatt tacttggggt aactccgcct gaggaactgc ataccaattc tgcagaagga | 4560 |
| gagtacagtg cactctgtag ctatctatct ttacctacaa atttgttcct gctcttccag | 4620 |
| gaatattggg atactgtaag gcccttgctc cagaggcggt gtgcagatcc tgccttacta | 4680 |
| aactgtttga agcaaaaaaa caccgtggtc aggtacccta gaaaaagaaa tagtttgata | 4740 |
| gagcttcctg atgactatag ctgcctcctg aatcaagctt ctcatttcag gtgcccacgg | 4800 |
| tctgcagatg atgagcgaaa gcatcctgtc ctctgccttt tctgtggggc tatactatgt | 4860 |
| tctcagaaca tttgctgcca ggaaattgtg aacggggaag aggttggagc ttgcattttt | 4920 |
| cacgcacttc actgtggagc cggagtctgc attttcctaa aaatcagaga atgccgagtg | 4980 |
| gtcctggttg aaggtaaagc cagaggctgt gcctatccag ctccttactt ggatgaatat | 5040 |
| ggagaaacag accctggcct gaagaggggc aaccccttc atttatctcg tgagcggtat | 5100 |
| cggaagctcc atttggtctg gcaacaacac tgcattatag aagagattgc taggagccaa | 5160 |
| gagactaatc agatgttatt tggattcaac tggcagttac tgtga | 5205 |

```
<210> SEQ ID NO 19
<211> LENGTH: 1734
<212> TYPE: PRT
<213> ORGANISM: Homo sapiens

<400> SEQUENCE: 19
```

| Ala | Met | Glu | Gly | Asn | Met | Ala | Asp | Glu | Glu | Ala | Gly | Gly | Thr | Glu | Arg |
|---|---|---|---|---|---|---|---|---|---|---|---|---|---|---|---|
| 1 | | | | 5 | | | | | 10 | | | | | 15 | |

| Met | Glu | Ile | Ser | Ala | Glu | Leu | Pro | Gln | Thr | Pro | Gln | Arg | Leu | Ala | Ser |
|---|---|---|---|---|---|---|---|---|---|---|---|---|---|---|---|
| | | | 20 | | | | | 25 | | | | | 30 | | |

| Trp | Trp | Asp | Gln | Gln | Val | Asp | Phe | Tyr | Thr | Ala | Phe | Leu | His | His | Leu |
|---|---|---|---|---|---|---|---|---|---|---|---|---|---|---|---|
| | 35 | | | | | 40 | | | | | 45 | | | | |

| Ala | Gln | Leu | Val | Pro | Glu | Ile | Tyr | Phe | Ala | Glu | Met | Asp | Pro | Asp | Leu |
|---|---|---|---|---|---|---|---|---|---|---|---|---|---|---|---|
| | | 50 | | | | | 55 | | | | | 60 | | | |

| Glu | Lys | Gln | Glu | Glu | Ser | Val | Gln | Met | Ser | Ile | Phe | Thr | Pro | Leu | Glu |
|---|---|---|---|---|---|---|---|---|---|---|---|---|---|---|---|
| 65 | | | | | 70 | | | | | 75 | | | | | 80 |

| Trp | Tyr | Leu | Phe | Gly | Glu | Asp | Pro | Asp | Ile | Cys | Leu | Glu | Lys | Leu | Lys |
|---|---|---|---|---|---|---|---|---|---|---|---|---|---|---|---|
| | | | | 85 | | | | | 90 | | | | | 95 | |

| His | Ser | Gly | Ala | Phe | Gln | Leu | Cys | Gly | Arg | Val | Phe | Lys | Ser | Gly | Glu |
|---|---|---|---|---|---|---|---|---|---|---|---|---|---|---|---|
| | | | 100 | | | | | 105 | | | | | 110 | | |

| Thr | Thr | Tyr | Ser | Cys | Arg | Asp | Cys | Ala | Ile | Asp | Pro | Thr | Cys | Val | Leu |
|---|---|---|---|---|---|---|---|---|---|---|---|---|---|---|---|
| | | 115 | | | | | 120 | | | | | 125 | | | |

-continued

```
Cys Met Asp Cys Phe Gln Asp Ser Val His Lys Asn His Arg Tyr Lys
    130                 135                 140
Met His Thr Ser Thr Gly Gly Gly Phe Cys Asp Cys Gly Asp Thr Glu
145                 150                 155                 160
Ala Trp Lys Thr Gly Pro Phe Cys Val Asn His Glu Pro Gly Arg Ala
                165                 170                 175
Gly Thr Ile Lys Glu Asn Ser Arg Cys Pro Leu Asn Glu Glu Val Ile
            180                 185                 190
Val Gln Ala Arg Lys Ile Phe Pro Ser Val Ile Lys Tyr Val Val Glu
        195                 200                 205
Met Thr Ile Trp Glu Glu Lys Glu Leu Pro Pro Glu Leu Gln Ile
    210                 215                 220
Arg Glu Lys Asn Glu Arg Tyr Tyr Cys Val Leu Phe Asn Asp Glu His
225                 230                 235                 240
His Ser Tyr Asp His Val Ile Tyr Ser Leu Gln Arg Ala Leu Asp Cys
                245                 250                 255
Glu Leu Ala Glu Ala Gln Leu His Thr Thr Ala Ile Asp Lys Glu Gly
            260                 265                 270
Arg Arg Ala Val Lys Ala Gly Tyr Ala Ala Cys Gln Glu Ala Lys
        275                 280                 285
Glu Asp Ile Lys Ser His Ser Glu Asn Val Ser Gln His Pro Leu His
    290                 295                 300
Val Glu Val Leu His Ser Glu Ile Met Ala His Gln Lys Phe Ala Leu
305                 310                 315                 320
Arg Leu Gly Ser Trp Met Asn Lys Ile Met Ser Tyr Ser Ser Asp Phe
                325                 330                 335
Arg Gln Ile Phe Cys Gln Ala Cys Leu Arg Glu Glu Pro Asp Ser Glu
            340                 345                 350
Asn Pro Cys Leu Ile Ser Arg Leu Met Leu Trp Asp Ala Lys Leu Tyr
        355                 360                 365
Lys Gly Ala Arg Lys Ile Leu His Glu Leu Ile Phe Ser Ser Phe Phe
    370                 375                 380
Met Glu Met Glu Tyr Lys Lys Leu Phe Ala Met Glu Phe Val Lys Tyr
385                 390                 395                 400
Tyr Lys Gln Leu Gln Lys Glu Tyr Ile Ser Asp Asp His Asp Arg Ser
                405                 410                 415
Ile Ser Ile Thr Ala Leu Ser Val Gln Met Phe Thr Val Pro Thr Leu
            420                 425                 430
Ala Arg His Leu Ile Glu Glu Gln Asn Val Ile Ser Val Ile Thr Glu
        435                 440                 445
Thr Leu Leu Glu Val Leu Pro Glu Tyr Leu Asp Arg Asn Asn Lys Phe
    450                 455                 460
Asn Phe Gln Gly Tyr Ser Gln Asp Lys Leu Gly Arg Val Tyr Ala Val
465                 470                 475                 480
Ile Cys Asp Leu Lys Tyr Ile Leu Ile Ser Lys Pro Thr Ile Trp Thr
                485                 490                 495
Glu Arg Leu Arg Met Gln Phe Leu Glu Gly Phe Arg Ser Phe Leu Lys
            500                 505                 510
Ile Leu Thr Cys Met Gln Gly Met Glu Glu Ile Arg Arg Gln Val Gly
        515                 520                 525
Gln His Ile Glu Val Asp Pro Asp Trp Glu Ala Ala Ile Ala Ile Gln
    530                 535                 540
Met Gln Leu Lys Asn Ile Leu Leu Met Phe Gln Glu Trp Cys Ala Cys
```

```
                    545                 550                 555                 560

Asp Glu Glu Leu Leu Leu Val Ala Tyr Lys Glu Cys His Lys Ala Val
                565                 570                 575

Met Arg Cys Ser Thr Ser Phe Ile Ser Ser Lys Thr Val Val Gln
            580                 585                 590

Ser Cys Gly His Ser Leu Glu Thr Lys Ser Tyr Arg Val Ser Glu Asp
            595                 600                 605

Leu Val Ser Ile His Leu Pro Leu Ser Arg Thr Leu Ala Gly Leu His
            610                 615                 620

Val Arg Leu Ser Arg Leu Gly Ala Val Ser Arg Leu His Glu Phe Val
625                 630                 635                 640

Ser Phe Glu Asp Phe Gln Val Glu Val Leu Val Glu Tyr Pro Leu Arg
                645                 650                 655

Cys Leu Val Leu Val Ala Gln Val Val Ala Glu Met Trp Arg Arg Asn
                660                 665                 670

Gly Leu Ser Leu Ile Ser Gln Val Phe Tyr Tyr Gln Asp Val Lys Cys
                675                 680                 685

Arg Glu Glu Met Tyr Asp Lys Asp Ile Ile Met Leu Gln Ile Gly Ala
            690                 695                 700

Ser Leu Met Asp Pro Asn Lys Phe Leu Leu Val Leu Gln Arg Tyr
705                 710                 715                 720

Glu Leu Ala Glu Ala Phe Asn Lys Thr Ile Ser Thr Lys Asp Gln Asp
                725                 730                 735

Leu Ile Lys Gln Tyr Asn Thr Leu Ile Glu Glu Met Leu Gln Val Leu
            740                 745                 750

Ile Tyr Ile Val Gly Glu Arg Tyr Val Pro Gly Val Gly Asn Val Thr
            755                 760                 765

Lys Glu Glu Val Thr Met Arg Glu Ile Ile His Leu Leu Cys Ile Glu
            770                 775                 780

Pro Met Pro His Ser Ala Ile Ala Lys Asn Leu Pro Glu Asn Glu Asn
785                 790                 795                 800

Asn Glu Thr Gly Leu Glu Asn Val Ile Asn Lys Val Ala Thr Phe Lys
                805                 810                 815

Lys Pro Gly Val Ser Gly His Gly Val Tyr Glu Leu Lys Asp Glu Ser
                820                 825                 830

Leu Lys Asp Phe Asn Met Tyr Phe Tyr His Tyr Ser Lys Thr Gln His
            835                 840                 845

Ser Lys Ala Glu His Met Gln Lys Lys Arg Arg Lys Gln Glu Asn Lys
            850                 855                 860

Asp Glu Ala Leu Pro Pro Pro Pro Glu Phe Cys Pro Ala Phe
865                 870                 875                 880

Ser Lys Val Ile Asn Leu Leu Asn Cys Asp Ile Met Met Tyr Ile Leu
                885                 890                 895

Arg Thr Val Phe Glu Arg Ala Ile Asp Thr Asp Ser Asn Leu Trp Thr
            900                 905                 910

Glu Gly Met Leu Gln Met Ala Phe His Ile Leu Ala Leu Gly Leu Leu
            915                 920                 925

Glu Glu Lys Gln Gln Leu Gln Lys Ala Pro Glu Glu Val Thr Phe
            930                 935                 940

Asp Phe Tyr His Lys Ala Ser Arg Leu Gly Ser Ser Ala Met Asn Ile
945                 950                 955                 960

Gln Met Leu Leu Glu Lys Leu Lys Gly Ile Pro Gln Leu Glu Gly Gln
                965                 970                 975
```

```
Lys Asp Met Ile Thr Trp Ile Leu Gln Met Phe Asp Thr Val Lys Arg
            980                 985                 990

Leu Arg Glu Lys Ser Cys Leu Ile Val Ala Thr Thr Ser Gly Ser Glu
        995                 1000                1005

Ser Ile Lys Asn Asp Glu Ile Thr His Asp Lys Glu Lys Ala Glu
    1010                1015                1020

Arg Lys Arg Lys Ala Glu Ala Ala Arg Leu His Arg Gln Lys Ile
    1025                1030                1035

Met Ala Gln Met Ser Ala Leu Gln Lys Asn Phe Ile Glu Thr His
    1040                1045                1050

Lys Leu Met Tyr Asp Asn Thr Ser Glu Met Pro Gly Lys Glu Asp
    1055                1060                1065

Ser Ile Met Glu Glu Glu Ser Thr Pro Ala Val Ser Asp Tyr Ser
    1070                1075                1080

Arg Ile Ala Leu Gly Pro Lys Arg Gly Pro Ser Val Thr Glu Lys
    1085                1090                1095

Glu Val Leu Thr Cys Ile Leu Cys Gln Glu Gln Glu Val Lys
    1100                1105                1110

Ile Glu Asn Asn Ala Met Val Leu Ser Ala Cys Val Gln Lys Ser
    1115                1120                1125

Thr Ala Leu Thr Gln His Arg Gly Lys Pro Ile Glu Leu Ser Gly
    1130                1135                1140

Glu Ala Leu Asp Pro Leu Phe Met Asp Pro Asp Leu Ala Tyr Gly
    1145                1150                1155

Thr Tyr Thr Gly Ser Cys Gly His Val Met His Ala Val Cys Trp
    1160                1165                1170

Gln Lys Tyr Phe Glu Ala Val Gln Leu Ser Ser Gln Gln Arg Ile
    1175                1180                1185

His Val Asp Leu Phe Asp Leu Glu Ser Gly Glu Tyr Leu Cys Pro
    1190                1195                1200

Leu Cys Lys Ser Leu Cys Asn Thr Val Ile Pro Ile Ile Pro Leu
    1205                1210                1215

Gln Pro Gln Lys Ile Asn Ser Glu Asn Ala Asp Ala Leu Ala Gln
    1220                1225                1230

Leu Leu Thr Leu Ala Arg Trp Ile Gln Thr Val Leu Ala Arg Ile
    1235                1240                1245

Ser Gly Tyr Asn Ile Arg His Ala Lys Gly Glu Asn Pro Ile Pro
    1250                1255                1260

Ile Phe Phe Asn Gln Gly Met Gly Asp Ser Thr Leu Glu Phe His
    1265                1270                1275

Ser Ile Leu Ser Phe Gly Val Glu Ser Ser Ile Lys Tyr Ser Asn
    1280                1285                1290

Ser Ile Lys Glu Met Val Ile Leu Phe Ala Thr Thr Ile Tyr Arg
    1295                1300                1305

Ile Gly Leu Lys Val Pro Pro Asp Glu Arg Asp Pro Arg Val Pro
    1310                1315                1320

Met Leu Thr Trp Ser Thr Cys Ala Phe Thr Ile Gln Ala Ile Glu
    1325                1330                1335

Asn Leu Leu Gly Asp Glu Gly Lys Pro Leu Phe Gly Ala Leu Gln
    1340                1345                1350

Asn Arg Gln His Asn Gly Leu Lys Ala Leu Met Gln Phe Ala Val
    1355                1360                1365
```

-continued

```
Ala Gln Arg Ile Thr Cys Pro Gln Val Leu Ile Gln Lys His Leu
    1370            1375                1380

Val Arg Leu Leu Ser Val Val Leu Pro Asn Ile Lys Ser Glu Asp
    1385            1390                1395

Thr Pro Cys Leu Leu Ser Ile Asp Leu Phe His Val Leu Val Gly
    1400            1405                1410

Ala Val Leu Ala Phe Pro Ser Leu Tyr Trp Asp Asp Pro Val Asp
    1415            1420                1425

Leu Gln Pro Ser Ser Val Ser Ser Ser Tyr Asn His Leu Tyr Leu
    1430            1435                1440

Phe His Leu Ile Thr Met Ala His Met Leu Gln Ile Leu Leu Thr
    1445            1450                1455

Val Asp Thr Gly Leu Pro Leu Ala Gln Val Gln Glu Asp Ser Glu
    1460            1465                1470

Glu Ala His Ser Ala Ser Ser Phe Phe Ala Glu Ile Ser Gln Tyr
    1475            1480                1485

Thr Ser Gly Ser Ile Gly Cys Asp Ile Pro Gly Trp Tyr Leu Trp
    1490            1495                1500

Val Ser Leu Lys Asn Gly Ile Thr Pro Tyr Leu Arg Cys Ala Ala
    1505            1510                1515

Leu Phe Phe His Tyr Leu Leu Gly Val Thr Pro Pro Glu Glu Leu
    1520            1525                1530

His Thr Asn Ser Ala Glu Gly Glu Tyr Ser Ala Leu Cys Ser Tyr
    1535            1540                1545

Leu Ser Leu Pro Thr Asn Leu Phe Leu Leu Phe Gln Glu Tyr Trp
    1550            1555                1560

Asp Thr Val Arg Pro Leu Leu Gln Arg Arg Cys Ala Asp Pro Ala
    1565            1570                1575

Leu Leu Asn Cys Leu Lys Gln Lys Asn Thr Val Val Arg Tyr Pro
    1580            1585                1590

Arg Lys Arg Asn Ser Leu Ile Glu Leu Pro Asp Asp Tyr Ser Cys
    1595            1600                1605

Leu Leu Asn Gln Ala Ser His Phe Arg Cys Pro Arg Ser Ala Asp
    1610            1615                1620

Asp Glu Arg Lys His Pro Val Leu Cys Leu Phe Cys Gly Ala Ile
    1625            1630                1635

Leu Cys Ser Gln Asn Ile Cys Cys Gln Glu Ile Val Asn Gly Glu
    1640            1645                1650

Glu Val Gly Ala Cys Ile Phe His Ala Leu His Cys Lys Ala Arg
    1655            1660                1665

Gly Cys Ala Tyr Pro Ala Pro Tyr Leu Asp Glu Tyr Gly Glu Thr
    1670            1675                1680

Asp Pro Gly Leu Lys Arg Gly Asn Pro Leu His Leu Ser Arg Glu
    1685            1690                1695

Arg Tyr Arg Lys Leu His Leu Val Trp Gln Gln His Cys Ile Ile
    1700            1705                1710

Glu Glu Ile Ala Arg Ser Gln Glu Thr Asn Gln Met Leu Phe Gly
    1715            1720                1725

Phe Asn Trp Gln Leu Leu
    1730

<210> SEQ ID NO 20
<211> LENGTH: 22
<212> TYPE: DNA
```

```
<213> ORGANISM: Artificial sequence
<220> FEATURE:
<223> OTHER INFORMATION: Synthetic primer

<400> SEQUENCE: 20
agaaggagag tacagtgcac tc                                              22

<210> SEQ ID NO 21
<211> LENGTH: 20
<212> TYPE: DNA
<213> ORGANISM: Artificial sequence
<220> FEATURE:
<223> OTHER INFORMATION: Synthetic primer

<400> SEQUENCE: 21
cgaaagcatc ctgtcctctg                                                 20

<210> SEQ ID NO 22
<211> LENGTH: 18
<212> TYPE: DNA
<213> ORGANISM: Artificial sequence
<220> FEATURE:
<223> OTHER INFORMATION: Synthetic primer

<400> SEQUENCE: 22
aggaagctgt ggtcatgt                                                   18

<210> SEQ ID NO 23
<211> LENGTH: 14
<212> TYPE: DNA
<213> ORGANISM: Artificial sequence
<220> FEATURE:
<223> OTHER INFORMATION: Synthetic primer

<400> SEQUENCE: 23
gttaggaaga actg                                                       14

<210> SEQ ID NO 24
<211> LENGTH: 20
<212> TYPE: DNA
<213> ORGANISM: Artificial sequence
<220> FEATURE:
<223> OTHER INFORMATION: Synthetic primer

<400> SEQUENCE: 24
aagaacagcg aaggcaacag                                                 20

<210> SEQ ID NO 25
<211> LENGTH: 22
<212> TYPE: DNA
<213> ORGANISM: Artificial sequence
<220> FEATURE:
<223> OTHER INFORMATION: Synthetic primer

<400> SEQUENCE: 25
cgcagctacc ccaacacatt ct                                              22

<210> SEQ ID NO 26
<211> LENGTH: 22
<212> TYPE: DNA
```

-continued

```
<213> ORGANISM: Artificial sequence
<220> FEATURE:
<223> OTHER INFORMATION: Synthetic primer

<400> SEQUENCE: 26
tttcttccat tccctgcata ca                                                22

<210> SEQ ID NO 27
<211> LENGTH: 25
<212> TYPE: DNA
<213> ORGANISM: Artificial sequence
<220> FEATURE:
<223> OTHER INFORMATION: Synthetic primer

<400> SEQUENCE: 27
caaaacttta taaaggtgcc cgtaa                                             25

<210> SEQ ID NO 28
<211> LENGTH: 23
<212> TYPE: DNA
<213> ORGANISM: Artificial sequence
<220> FEATURE:
<223> OTHER INFORMATION: Synthetic primer

<400> SEQUENCE: 28
attccctgca tgcacttcag taa                                               23

<210> SEQ ID NO 29
<211> LENGTH: 21
<212> TYPE: DNA
<213> ORGANISM: Artificial sequence
<220> FEATURE:
<223> OTHER INFORMATION: Synthetic primer

<400> SEQUENCE: 29
cattccctgc atgcacttca g                                                 21
```

HUMAN E3α UBIQUITIN LIGASE FAMILY

RELATED APPLICATIONS

This application is a divisional U.S. Ser. No. 11/789,408, now issued U.S. Pat. No. 7,422,847, which was filed Apr. 24, 2007, which in turn is a divisional of U.S. Ser. No. 10/758,636, now issued U.S. Pat. No. 7,220,547, which was filed Jan. 15, 2004, which in turn is a divisional application of U.S. Ser. No. 09/724,126, now issued U.S. Pat. No. 6,706,505, which was filed Nov. 28, 2000, which in turn claims priority under 35 U.S.C. §119 from U.S. provisional patent application Ser. No. 60/187,911, which was filed Mar. 8, 2000, which is incorporated herein by reference in its entirety.

FIELD OF THE INVENTION

The present invention includes novel human E3α ubiquitin ligase polypeptides (huE3αI and huE3αII) and nucleic acid molecules encoding the same. The invention also relates to vectors, host cells, selective binding agents, such as antibodies, and methods for producing huE3α polypeptides. Also provided for are methods for the diagnosis, treatment, amelioration and/or prevention of diseases associated with huE3α polypeptides, as well as methods for identifying modulators of huE3α ligase activity.

BACKGROUND OF THE INVENTION

Technical advances in the identification, cloning, expression and manipulation of nucleic acid molecules and deciphering of the human genome have greatly accelerated the discovery of novel therapeutics based upon deciphering of the human genome. Rapid nucleic acid sequencing techniques can now generate sequence information at unprecedented rates and, coupled with computational analyses, allow the assembly of overlapping sequences into the partial and entire genomes as well as the identification of polypeptide-encoding regions. A comparison of a predicted amino acid sequence against a database compilation of known amino acid sequences can allow one to determine the extent of homology to previously identified sequences and/or structural landmarks. The cloning and expression of a polypeptide-encoding region of a nucleic acid molecule provides a polypeptide product for structural and functional analyses. The manipulation of nucleic acid molecules and encoded polypeptides to create variants and derivatives thereof may confer advantageous properties on a product for use as a therapeutic.

In spite of significant technical advances in genome research over the past decade, the potential for the development of novel therapeutics based on the human genome is still largely unrealized. Many genes encoding potentially beneficial polypeptide therapeutics, or those encoding polypeptides which may act as "targets" for therapeutic molecules, have still not been identified. In addition, structural and functional analyses of polypeptide products from many human genes have not been undertaken.

Accordingly, it is an object of the invention to identify novel polypeptides and nucleic acid molecules encoding the same which have diagnostic or therapeutic benefit.

Most types of intracellular proteins are degraded through the ubiquitin-proteosome pathway. In this system, proteins are marked for protesomal degradation by the conjugation of ubiquitin molecules to the protein. Conjugation of the ubiquitin molecule initially involves activation by the E1 enzyme. Upon activation the ubiquitin molecule is transferred to the E2 enzyme which serves as a carrier-protein. The E2 enzyme interacts with a specific E3 ligase family member. The E3 ligase binds to proteins targeted for degradation and catalyzes the transfer of ubiquitin from the E2 carrier enzyme to the target protein. Since the target protein binds to the ligase prior to conjugatin, E3 ligase is the rate limiting step for ubiquitin conjugation and determines the specificity of the system. The ubiquitin chain serves as a degradation marker for the 26S proteosome (See Ciechanover, *EMBO J.*, 17: 7151-7160, 1998).

There are only a few known E3 ligases and the sequence homology between them is low. The E3α family is the main family of intracellular ubiquitin ligases and is involved in N-end rule pathway of protein degradation. The N-end rule states that there is a strong relation between the in vivo half-life of a protein and the identity of its N-terminal amino acids. Accordingly, E3α enzyme binds directly to the primary destabilizing N-terminal amino acid and catalyzes ubiquitin conjugation thereby targeting the protein for degradation. E3α family members also recognize non-N-end rule substrates (See Ciechanover, *EMBO J.*, 17: 7151-7160, 1998).

The E3α enzyme family currently consists of intracellular enzymes isolated from rabbit (Reiss and Hershiko, *J. Biol. Chem.* 265: 3685-3690, 1990), mouse (Kwon et al, *Proc. Natl. Acad. Sci., U.S.A* 95: 7898-7903, 1999), yeast (Bartel et al., *EMBO J.*, 9: 3179-3189, 1990) and the *C. elegans* (Wilson et al., *Nature*, 368: 32-38, 1994; Genebank Accession No. U88308) counterparts termed UBR-1. Comparison of these known sequences indicates regions of high similarity regions (I-V) which suggest the existence of a distinct family. The regions of similarity contain essential residues for the recognition of N-end rule substrates. In region I, the residues Cys-145, Val-146, Gly-173, and Asp-176 are known to be necessary for type-1 substrate binding in yeast and are conserved in the mouse. In regions II and III, residues Asp-318, His-321, and Glu-560 are essential for type-2 substrate binding in yeast and are also conserved in the mouse. In addition, there is a conserved zinc-finger domain in region I and a conserved RING-H2 domain in region IV (Kwon et al., *Proc. Natl. Acad. Sci., U.S.A*, 95: 7898-7903, 1999).

The full length mouse E3α cDNA sequence and a partial human E3α nucleotide sequence (≈1 kb) have recently been cloned and characterized as described in U.S. Pat. No. 5,861,312 and Kwon et al. (*Proc. Natl. Acad. U.S.A.*, 95: 7898-7908, 1999). The full length mouse E3α cDNA sequence is 5271 bp in length and encodes a 1757 amino acid polypeptide. The mouse E3α gene is localized to the central region of chromosome 2 and is highly expressed in skeletal muscle, heart and brain. The partial human E3α sequence was used to characterize tissue expression and chromosomal localization. This analysis indicated that the human E3α gene is located on chromosome 15q and exhibits a similar expression pattern as mouse E3α with high expression in skeletal muscle, heart and brain. As described herein, the present invention discloses two novel, full length, human E3α sequences (huE3αI and huE3αII) and a novel, full length mouse E3α sequence (muE3αII). Expression of huE3αI and huE3αII mRNA is highly enriched in skeletal muscle tissues. Functionally, huE3α polypeptides are intracellular enzymes that control protein conjugation and degradation.

Increased proteolysis through the ubiquitin-proteosome pathway has been determined to be a major cause of rapid muscle wasting in many pathological states including but not limited to fasting, metabolic acidosis, muscle denervation, kidney failure, renal cachexia, uremia, diabetes mellitus, sepsis, AIDS wasting syndrome, cancer cachexia, negative nitrogen balance cachexia, burns and Cushing's syndrome (See Mitch and Goldberg, *New England J. Med*, 335:1897-1905, 1996). Studies in animal models have shown that muscle wasting disorders are associated with increased ubiquitin content in muscles, increased levels of mRNA transcripts encoding ubiquitin, E2 enzyme and proteosome subunit mRNA, and increased ubiquitin-conjugation to muscle-proteins (See Lecker et al., *J. Nutr.*, 129: 227S-237S, 1999). In this context, the N-end rule pathway has been shown to play a role in muscle atrophy. E3α inhibitors, such as dipeptides and methyl ester, reduce the level of ubiquitin conjugation in atrophying rat muscles caused by sepsis, fasting and cancer cachexia (Soloman et al., *Proc. Natl. Acad. Sci. U.S.A.* 95: 12602-12607, 1999). These observations indicate that E3α plays a role in the overall increase in ubiquitination that is associated with and may mediate muscle atrophy in catabolic and other disease states.

Thus, identification of members of the N-end rule protein degradation pathway has led to a better understanding of protein degradation in human cells and the mechanisms of protein degradation in pathological condition which involve muscle atrophy. Identification of the two novel human E3α ubiquitin ligase genes and polypeptides, as described herein, will further clarify the understanding of these processes and facilitate the development of therapies for pathological conditions which involve abnormal or excessive protein degradation including conditions which involve atrophy of muscle.

SUMMARY OF THE INVENTION

The present invention relates to novel human E3α nucleic acid molecules and polypeptides encoded by these nucleic acid molecules.

The invention provides isolated nucleic acid molecules comprising or consisting of a nucleotide sequence selected from the group consisting of:

a) the nucleotide sequence as set forth in SEQ ID NOS: 1 or 3 b) a nucleotide sequence encoding the polypeptide set forth in SEQ ID NOS: 2 and 4;

c) a nucleotide sequence which hybridizes under moderate or highly stringent conditions to the compliments of (a) or (b); and d) a nucleotide complementary to (a)-(c)

The invention also provides isolated nucleic acid molecules comprising a nucleotide sequence selected from the group consisting of:

a) a nucleotide sequence encoding a polypeptide that is at least about 70, 75, 80, 85, 90, 95, 96, 97, 98, or 99 percent identical to the polypeptide set forth in SEQ ID NOS: 2 or 4, wherein the polypeptide has an activity of the polypeptide set forth in SEQ ID NOS: 2 or 4 and the percent identity for these nucleic acid sequences are determined using a computer program selected from the group consisting of GAP, BLASTP, BLASTN, FASTA, BLASTA, BLASTX, BestFit, and the Smith-Waterman algorithm;

b) a nucleotide sequence encoding an allelic variant or splice variant of the nucleotide sequence as set forth in SEQ ID NOS: 1 or 3;

c) the nucleotide sequence of the DNA insert in ATCC Deposit No. PTA-1489 or PTA-1490;

d) a nucleotide sequence of SEQ ID NOS: 1; 3; (a); or (b) encoding a polypeptide fragment of at least about 25 amino acid residues, wherein the polypeptide has an activity of the polypeptide set forth in SEQ ID NOS: 2 or 4;

e) a nucleotide sequence of SEQ ID NOS: 1, 3, or (a)-(c) comprising a fragment of at least about 16 nucleotides;

f) a nucleotide sequence which hybridizes under moderately or highly stringent conditions to the complement of any of (a)-(e); and g) a nucleotide sequence complementary to any of (a)-(d).

The invention also provides isolated nucleic acid molecules comprising a nucleotide sequence selected from the group consisting of:

a) a nucleotide sequence encoding a polypeptide set forth in SEQ ID NOS: 2 or 4 with at least one conservative amino acid substitution, wherein the polypeptide has an activity of the polypeptide set forth in SEQ ID NOS: 2 or 4;

b) a nucleotide sequence encoding a polypeptide set forth in SEQ ID NOS: 2 or 4 with at least one amino acid insertion, wherein the polypeptide has an activity of the polypeptide set forth in SEQ ID NOS: 2 or 4;

c) a nucleotide sequence encoding a polypeptide set forth in SEQ ID NOS: 2 or 4 with at least one amino acid deletion, wherein the polypeptide has an activity of the polypeptide set forth in SEQ ID NOS: 2 or 4;

d) a nucleotide sequence encoding a polypeptide set forth in SEQ ID NOS: 2 or 4 which has a C- and/or N-terminal truncation, wherein the polypeptide has an activity of the polypeptide set forth in SEQ ID NOS: 2 or 4;

e) a nucleotide sequence encoding a polypeptide set forth in SEQ ID NOS: 2 or 4 with at least one modification selected from the group consisting of amino acid substitutions, amino acid insertions, amino acid deletions, C-terminal truncation, and N-terminal truncation, wherein the polypeptide has an activity of the polypeptide set forth in SEQ ID NOS: 2 or 4;

f) a nucleotide sequence of (a)-(e) comprising a fragment of at least about 16 nucleotides;

g) a nucleotide sequence which hybridizes under moderately or highly stringent conditions to the complement of any of (a)-(f); and h) a nucleotide sequence complementary to any of (a)-(e).

The invention also provides isolated polypeptides comprising the amino acid sequence selected from the group consisting of:

a) the amino acid sequence as set forth in SEQ ID NOS: 2 or 4;

b) the mature amino acid sequence as set forth in SEQ ID NOS: 2 or 4 comprising a mature amino terminus at residues 1, and optionally further comprising an amino terminal methionine;

c) an amino acid sequence that is at least about 70, 75, 80, 85, 90, 95, 96, 97, 98, or 99 percent identical to the amino acid sequence of the polypeptide of SEQ ID NOS: 2 or 4 wherein the polypeptide has an activity of the polypeptide set forth in SEQ ID NOS: 2 or 4 and the percent identity for these amino acid sequences are determined using a computer program selected from the group consisting of GAP, BLASTP, BLASTN, FASTA, BLASTA, BLASTX, BestFit, and the Smith-Waterman algorithm.

d) a fragment of the amino acid sequence set forth in SEQ ID NOS: 2 or 4 comprising at least about 25, 50, 75, 100, or greater than 100 amino acid residues, wherein the fragment has an activity of the polypeptide set forth in SEQ ID NOS: 2 or 4;

e) the amino acid sequence encoded by the DNA insert of ATCC Deposit No. PTA-1489 or PTA-1490;

f) an amino acid sequence for an ortholog of SEQ ID NOS: 2 or 4; including the murine ortholog set out as SEQ ID NO: 6.

g) an allelic variant or splice variant of (a), (b), (e) or (f);

The present invention also provides isolated polypeptides comprising the amino acid sequence selected from the group consisting of:

a) the amino acid as sequence set forth in SEQ ID NOS: 2 or 4 with at least one conservative amino acid substitution, wherein the polypeptide has an activity of the polypeptide set forth in SEQ ID NOS: 2 or 4;

b) the amino acid sequence as set forth in SEQ ID NOS: 2 or 4 with at least one amino acid insertion, wherein the polypeptide has an activity of the polypeptide set forth in SEQ ID NOS: 2 or 4;

c) the amino acid sequence as set forth in SEQ ID NOS: 2 or 4 with at least one amino acid deletion, wherein the polypeptide has an activity of the polypeptide set forth in SEQ ID NOS: 2 or 4;

d) the amino acid sequence as set forth in SEQ ID NOS: 2 or 4 which has a C- and/or N-terminal truncation, wherein the polypeptide has an activity of the polypeptide set forth in SEQ ID NOS: 2 or 4; and e) the amino acid sequence as set forth in SEQ ID NOS: 2 or 4, with at least one modification selected from the group consisting of amino acid substitutions, amino acid insertions, amino acid deletions, C-terminal truncation, and N-terminal truncation, wherein the polypeptide has an activity of the polypeptide set forth in SEQ ID NOS: 2 or 4.

The present invention provides expression vectors comprising the nucleic acid molecules set forth herein, host cells comprising the expression vectors of the invention, and a method of producing a human E3α polypeptide comprising culturing the host cells and optionally isolating the polypeptide so produced. An another embodiment provides for viral vectors comprising the nucleic acid molecules of the inventions. Further provided is a process for determining whether a compound inhibits huE3α polypeptide activity or production comprising exposing a host cell expressing huE3α polypeptide to the compound, and measuring huE3α polypeptide activity or production in said cell.

A transgenic non-human animal comprising a nucleic acid molecule encoding a huE3α polypeptide is also encompassed by the invention. The huE3α nucleic acid molecules are introduced into the animal in a manner that allows expression and increased levels of a huE3α polypeptide, which may include increased circulating levels. The transgenic non-human animal is preferably a mammal, and more preferably a rodent, such as a rat or a mouse.

Also provided are derivatives of the huE3α polypeptides of the present invention, fusion polypeptides comprising the huE3α polypeptides of the invention, and selective binding agents such as antibodies capable of specifically binding the polypeptides of the invention.

Pharmaceutical compositions comprising the nucleotides, polypeptides, or selective binding agents of the present invention and a carrier, adjuvant, solubilizer, stabilizer, anti-oxidant, or other pharmaceutically acceptable formulation agent are also encompassed by the invention. The pharmaceutical compositions include therapeutically effective amounts of the nucleotides or polypeptides of the present invention, and involve methods of using the polypeptides and nucleic acid molecules.

The huE3α polypeptides and nucleic acid molecules of the present invention may be used for therapeutic or diagnostic purposes to treat, prevent, and/or detect diseases or disorders, including those recited herein.

Methods of regulating expression and modulating (i.e., increasing or decreasing) levels of a huE3α polypeptide are also encompassed by the invention. One method comprises administering to an animal a nucleic acid molecule encoding a huE3α polypeptide. In another method, a nucleic acid molecule comprising elements that regulate or modulate the expression of a huE3α polypeptide may be administered. Examples of these methods include gene therapy, cell therapy and antisense therapy as further described herein. Further provided is a method of identifying a compound which binds to a huE3α polypeptide comprising.

A device, comprising a membrane suitable for implantation and host cells expressing a huE3α polypeptide encapsulated within said membrane, wherein said membrane is permeable to said protein product and impermeable to materials detrimental to said cells is also encompassed by the present invention.

BRIEF DESCRIPTION OF THE FIGURES

FIG. 1 shows the alignment of the amino acid sequences for huE3αI, huE3αII, muE3αI and muE3αII (SEQ ID NOS: 2, 4, 15 and 6, respectively).

DETAILED DESCRIPTION OF THE INVENTION

Figure 2:
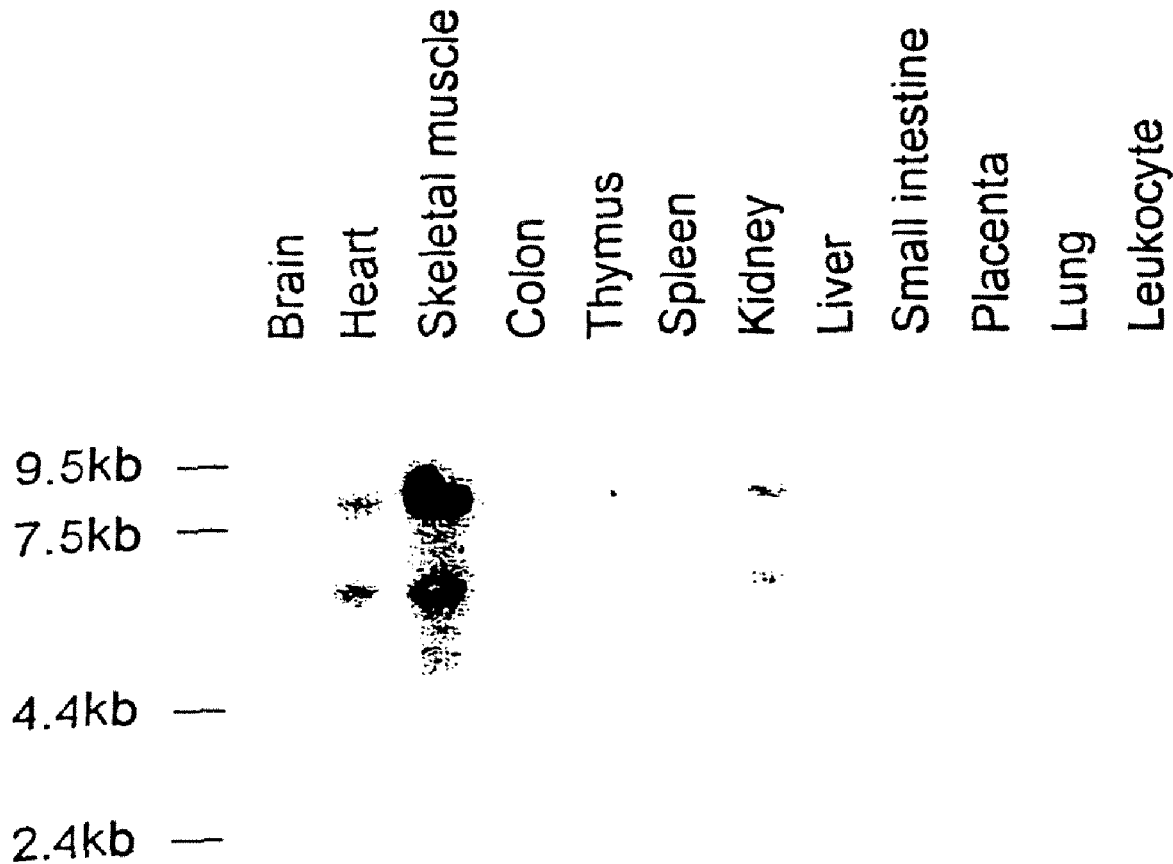
FIG. 2 shows the results of a human multiple tissue Northern blot detecting huE3αII expression.

The section headings used herein are for organizational purposes only and are not to be construed as limiting the subject matter described therein. All references cited in this application are expressly incorporated by reference herein.

Definitions

The term "huE3α" encompasses two novel orthologs of human E3α ubiquitin ligase described herein including huE3αI polynucleotide and polypeptide (SEQ ID NOS: 1 and 2, respectively) and huE3αII polynucleotide and polypeptide (SEQ ID NOS: 3 and 4, respectively).

The term "huE3α nucleic acid molecule" or "polynucleotide" refers to a nucleic acid molecules including a nucleotide sequence as set forth in SEQ ID NOS: 1 or 3, a nucleotide sequence encoding the polypeptide set forth in SEQ ID NOS: 2 or 4, a nucleotide sequence of the DNA insert in ATCC deposit nos. PTA-1489 or PTA-1490, or nucleic acid molecule related thereto. Related nucleic acid molecules include a nucleotide sequence that is at least about 70 percent identical to the nucleotide sequence as shown in SEQ ID NOS: 1 or 3, or comprise or consist essentially of a nucleotide sequence encoding a polypeptide that is at least about 70 percent identical to the polypeptide set forth in SEQ ID NOS: 2 or 4. In preferred embodiments, these nucleotide sequences are about 75 percent, or about 80 percent, or about 85 percent, or about 90 percent, or about 95, 96, 97, 98, or 99 percent identical to the nucleotide sequence as shown in SEQ ID NOS: 1 or 3, or the nucleotide sequences encode a polypeptide that is about 75 percent, or about 80 percent, or about 85 percent, or about 90 percent, or about 95, 96, 97, 98, or 99 percent identical to the polypeptide sequence as set forth in SEQ ID NOS: 2 or 4.

Related nucleic acid molecules also include fragments of the huE3αI or hu E3αII nucleic acid molecules which fragments contain at least about 10 contiguous nucleotides, or about 15, or about 20, or about 25, or about 50, or about 75, or about 100, or greater than about 100 contiguous nucleotides of a huE3α nucleic acid molecule of SEQ ID NOS: 1 or 3. Related nucleic acid molecules also include fragments of the above huE3α nucleic acid molecules which encode a polypeptide of at least about 25 amino acid residues, or about 50, or about 75, or about 100, or greater than about 100 amino acid residues of the huE3α polypeptide of SEQ ID NOS: 2 or 4. Related nucleic acid molecules also include a nucleotide sequence encoding a polypeptide comprising or consisting essentially of a substitution, modification, addition and/or a deletion of one or more amino acid residues compared to the polypeptide set forth in SEQ ID NOS: 2 or 4. In addition, related huE3α nucleic acid molecules include those molecules which comprise nucleotide sequences which hybridize under moderately or highly stringent conditions as defined herein with the fully complementary sequence of any of the hu3α nucleic acid molecules of SEQ ID NOS: 1 or 3.

In preferred embodiments, the related nucleic acid molecules comprise sequences which hybridize under moderately or highly stringent conditions with a molecule having a sequence as shown in SEQ ID NOS: 1 or 3, or of a molecule encoding a polypeptide, which polypeptide comprises the sequence as shown in SEQ ID NOS: 2 or 4, or of a nucleic acid fragment as defined herein, or of a nucleic acid fragment encoding a polypeptide as defined herein or the complement of any or the forgoing molecules. It is also understood that related nucleic acid molecules include allelic or splice variants of a huE3α nucleic acid molecule of SEQ ID NOS: 1 or 3, and include sequences which are complementary to any of the above nucleotide sequences. The related encoded polypeptides possess at least one activity of the polypeptide depicted in SEQ ID NOS: 2 or 4.

The term "isolated nucleic acid molecule" refers to a nucleic acid molecule of the invention that is free from at least one contaminating nucleic acid molecule with which it is naturally associated. Preferably, the isolated nucleic acid molecule of the present invention is substantially free from any other contaminating mammalian nucleic acid molecule(s) which would interfere with its use in polypeptide production or its therapeutic, diagnostic, or preventative use.

A "nucleic acid sequence" or "nucleic acid molecule" as used herein refer to a DNA or RNA sequence. The terms encompasses molecules formed from any of the known base analogs of DNA and RNA such as, but not limited to 4-acetylcytosine, 8-hydroxy-N-6-methyladenosine, aziridinyl-cytosine, pseudoisocytosine, 5-(carboxyhydroxylmethyl) uracil, 5-fluorouracil, 5-bromouracil, 5-carboxymethylaminomethyl-2-thiouracil, 5-carboxy-methylamino-methyluracil, dihydrouracil, inosine, N6-iso-pentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonyl-methyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "operably linked" is used as recognized in the art to refer to an arrangement of flanking sequences wherein the flanking sequences so described are configured or assembled so as to perform their usual function. Thus, a flanking sequence operably linked to a coding sequence may be capable of effecting the replication, transcription and/or translation of the coding sequence. For example, a coding sequence is operably linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence and the promoter sequence can still be considered "operably linked" to the coding sequence.

The term "pharmaceutically acceptable carrier" or "physiologically acceptable carrier" as used herein refer to one or more formulation materials suitable for accomplishing or enhancing delivery of the huE3α polypeptide, huE3α nucleic acid molecule, or huE3α selective binding agent as a pharmaceutical composition.

The term "allelic variant" refers to one of several possible naturally occurring alternate forms of a gene occupying a given locus on a chromosome of an organism or a population of organisms.

The term "splice variant" refers to a nucleic acid molecule, usually RNA, which is generated by alternative processing of intron sequences in an RNA transcript of huE3α polypeptide amino acid sequence.

The term "expression vector" refers to a vector which is suitable for transformation of a host cell and contains nucleic acid sequences which direct and/or control the expression of inserted heterologous nucleic acid sequences. Expression includes, but is not limited to, processes such as transcription, translation, and RNA splicing, if introns are present.

The term "vector" is used as recognized in the art to refer to any molecule (e.g., nucleic acid, plasmid, or virus) used to transfer coding information to a host cell.

The term "transformation" as used herein refers to a change in a cell's genetic characteristics, and a cell has been transformed when it has been modified to contain a new DNA. For example, a cell is transformed where it is genetically modified from its native state. Following transfection or transduction, the transforming DNA may recombine with that of the cell by physically integrating into a chromosome of the cell, may be maintained transiently as an episomal element without being replicated, or may replicate independently as a plasmid. A cell is considered to have been stably transformed when the DNA is replicated with the division of the cell.

The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, for example, Graham et al., *Virology*, 52: 456, 1973; Sambrook et al., *Molecular Cloning, A Laboratory Manual*, Cold Spring Harbor Laboratories, New York, 1989; Davis et al., *Basic Methods in Molecular Biology*, Elsevier, 1986; and Chu et al., *Gene*, 13: 197, 1981. Such techniques can be used to introduce one or more exogenous DNA moieties into suitable host cells.

The term "transduction" is used to refer to the transfer of genes from one bacterium to another, usually by a phage. "Transduction" also refers to the acquisition and transfer of eukaryotic cellular sequences by retroviruses.

The term "host cell" is used to refer to a cell which has been transformed, or is capable of being transformed, by a vector bearing a selected gene of interest which is then expressed by the cell. The term includes the progeny of the parent cell, whether or not the progeny is identical in morphology or in genetic make-up to the original parent, so long as the selected gene is present.

The term "highly stringent conditions" refers to those conditions that are designed to permit hybridization of DNA strands whose sequences are highly complementary, and to exclude hybridization of significantly mismatched DNAs. Hybridization stringency is principally determined by temperature, ionic strength, and the concentration of denaturing agents such as formamide. Examples of "highly stringent conditions" for hybridization and washing are 0.015 M sodium chloride, 0.0015 M sodium citrate at 65-68° C. or 0.015 M sodium chloride, 0.0015M sodium citrate, and 50% formamide at 42° C. See Sambrook, Fritsch & Maniatis, Molecular Cloning: A Laboratory Manual, 2$^{nd}$ Ed., Cold Spring Harbor Laboratory, (Cold Spring Harbor, N.Y. 1989); Anderson et al., Nucleic Acid Hybridisation: A Practical Approach, Ch. 4, IRL Press Limited (Oxford, England).

More stringent conditions (such as higher temperature, lower ionic strength, higher formamide, or other denaturing agent) may also be used, however, the rate of hybridization will be affected. Other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate, $NaDodSO_4$, or SDS, ficoll, Denhardt's solution, sonicated salmon sperm DNA (or other non-complementary DNA), and dextran sulfate, although another suitable agents can also be used. The concentration and types of these additives can be changed without substantially affecting the stringency of the hybridization conditions. Hybridization experiments are usually carried out at pH 6.8-7.4, however, at typical ionic strength conditions, the rate of hybridization is nearly independent of pH. (See Anderson et al., *Nucleic Acid Hybridisation: a Practical Approach*, Ch. 4, IRL Press Limited (Oxford, England)).

Factors affecting the stability of DNA duplex include base composition, length, and degree of base pair mismatch. Hybridization conditions can be adjusted by one skilled in the art in order to accommodate these variables and allow DNAs of different sequence relatedness to form hybrids. The melting temperature of a perfectly matched DNA duplex can be estimated by the following equation:

$$T_m(°C.)=81.5+16.6(\log[Na+])+0.41(\% G+C)-600/N-0.72(\% \text{ formamide})$$

where N is the length of the duplex formed, [Na+] is the molar concentration of the sodium ion in the hybridization or washing solution, % G+C is the percentage of (guanine+cytosine) bases in the hybrid. For imperfectly matched hybrids, the melting temperature is reduced by approximately 1° C. for each 1% mismatch.

The term "moderately stringent conditions" refers to conditions under which a DNA duplex with a greater degree of base pair mismatching than could occur under "highly stringent conditions" is able to form. Examples of typical "moderately stringent conditions" are 0.01 5M sodium chloride, 0.0015 M sodium citrate at 50-65° C. or 0.015 M sodium chloride, 0.0015 M sodium citrate, and 20% formamide at 37-50° C. By way of example, a "moderately stringent" condition of 50° C. in 0.015 M sodium ion will allow about a 21% mismatch.

It will be appreciated by those skilled in the art that there is no absolute distinction between "highly" and "moderately" stringent conditions. For example, at 0.015M sodium ion (no formamide), the melting temperature of perfectly matched long DNA is about 71° C. With a wash at 65° C. (at the same ionic strength), this would allow for approximately a 6% mismatch. To capture more distantly related sequences, one skilled in the art can simply lower the temperature or raise the ionic strength.

A good estimate of the melting temperature in 1 M NaCl* for oligonucleotide probes up to about 20 nt is given by:

$$Tm=2°\text{ C. per }A\text{-}T\text{ base pair}+4°\text{ C. per }G\text{-}C\text{ base pair}$$

*The sodium ion concentration in 6× salt sodium citrate (SSC) is 1M. See Suggs et al., *Developmental Biology Using Purified Genes*, p. 683, Brown and Fox (eds.) (1981).

High stringency washing conditions for oligonucleotides are usually at a temperature of 0-5° C. below the Tm of the oligonucleotide in 6×SSC, 0.1% SDS for longer nucleotides.

The term "huE3α polypeptide" refers to a polypeptide comprising the amino acid sequence of huE3αI or huE3αII (SEQ ID NOS: 2 or 4, respectively), and related polypeptides having a natural sequence or mutated sequence. Related polypeptides include: allelic variants; splice variants; fragments; derivatives; substitution, deletion, and insertion variants; fusion polypeptides; and orthologs of the huE3α polypeptides of SEQ ID NOS: 2 or 4, which possess at least one activity of the polypeptide depicted in SEQ ID NOS: 2 or 4. Human E3α polypeptides may be mature polypeptides, as defined herein, and may or may not have an amino terminal methionine residue, depending on the method by which they are prepared.

The term "huE3α polypeptide fragment" refers to a polypeptide that comprises less than the full length amino acid sequence of a huE3αI or huE3αII polypeptide set forth in SEQ ID NOS: 2 or 4, respectively. Such huE3α fragments can be 6 amino acids or more in length, and may arise, for example, from a truncation at the amino terminus (with or without a leader sequence), a truncation at the carboxy terminus, and/or an internal deletion of one or more residues from the amino acid sequence. Human E3α fragments may result from alternative RNA splicing or from in vivo protease activity. Membrane-bound forms of huE3α are also contemplated by the present invention. In preferred embodiments, truncations and/or deletions comprise about 10 amino acids, or about 20 amino acids, or about 50 amino acids, or about 75 amino acids, or about 100 amino acids, or more than about 100 amino acids. The polypeptide fragments so produced will comprise about 25 contiguous amino acids, or about 50 amino acids, or about 75 amino acids, or about 100 amino acids, or about 150 amino acids, or about 200 amino acids. Such huE3α polypeptide fragments may optionally comprise an amino terminal methionine residue. It will be appreciated that such fragments can also be used, for example, to generate antibodies to huE3α polypeptides.

The term "huE3α polypeptide variants" refers to huE3α polypeptides which contain one or more amino acid sequence substitutions, deletions, and/or additions as compared to the huE3α polypeptide amino acid sequence set forth as huE3αI or huE3αII (SEQ ID NOS: 2 or 4, respectively). Variants may be naturally occurring or artificially constructed. Such huE3α polypeptide variants may be prepared from the corresponding nucleic acid molecules encoding said variants, which have a DNA sequence that varies accordingly from the DNA sequences for wild type huE3α polypeptides as set forth in SEQ ID NOS: 1 or 3. In preferred embodiments, the variants have from 1 to 3, or from 1 to 5, or from 1 to 10, or from 1 to 20, or from 1 to 25, or from 1 to 50, or from 1 to 75, or from 1 to 100, or more than 100 amino acid substitutions, insertions, additions and/or deletions, wherein the substitutions may be conservative, or non-conservative, or any combination thereof.

One skilled in the art will be able to determine suitable variants of the native huE3α polypeptide using well known techniques. For example, one may predict suitable areas of the molecule that may be changed without destroying biological activity. Also, one skilled in the art will realize that even areas that may be important for biological activity or for structure may be subject to conservative amino acid substitutions without destroying the biological activity or without adversely affecting the polypeptide structure.

For predicting suitable areas of the molecule that may be changed without destroying activity, one skilled in the art may target areas not believed to be important for activity. For example, when similar polypeptides with similar activities from the same species or from other species are known, one skilled in the art may compare the amino acid sequence of huE3α polypeptide to such similar polypeptides. After making such a comparison, one skilled in the art can determine residues and portions of the molecules that are conserved among similar polypeptides. One skilled in the art would know that changes in areas of the huE3α molecule that are not conserved would be less likely to adversely affect the biological activity and/or structure of a huE3α polypeptide. One skilled in the art would also know that, even in relatively conserved regions, one may substitute chemically similar amino acids for the naturally occurring residues while retaining activity (conservative amino acid residue substitutions).

Additionally, one skilled in the art can review structure-function studies identifying residues in similar polypeptides that are important for activity or structure. In view of such a comparison, one skilled in the art can predict the importance of amino acid residues in a huE3α polypeptide that correspond to amino acid residues that are important for activity or structure in similar polypeptides. One skilled in the art may opt for chemically similar amino acid substitutions for such predicted important amino acid residues of huE3α polypeptides.

If available, one skilled in the art can also analyze the three-dimensional structure and amino acid sequence in relation to that structure in similar polypeptides. In view of that information, one skilled in the art may predict the alignment of amino acid residues of huE3α polypeptide with respect to its three dimensional structure. One skilled in the art may choose not to make radical changes to amino acid residues predicted to be on the surface of the protein, since such residues may be involved in important interactions with other molecules.

Additional methods of predicting secondary structure include "threading" (Jones et al., *Current Opin. Struct. Biol.*, 7(3):377-87 (1997); Sippl et al., *Structure*, 4(1):15-9 (1996)), "profile analysis" (Bowie et al., *Science*, 253:164-170 (1991); Gribskov et al., *Meth. Enzym.*, 183:146-159 (1990); Gribskov et al., *Proc. Nat. Acad. Sci.*, 84(13):4355-4358 (1987)), and "evolutionary linkage" (See Home, supra, and Brenner, supra 1997).

Moreover, one skilled in the art may generate test variants containing a single amino acid substitution at each amino acid residue. The variants could be screened using activity assays described herein. Such variants could be used to gather information about suitable variants. For example, if one discovered that a change to a particular amino acid residue resulted in destroyed, undesirably reduced, or unsuitable activity, variants with such a change would be avoided. In other words, based on information gathered from such routine experiments, one skilled in the art can readily determine the amino acids where further substitutions should be avoided either alone or in combination with other mutations.

In making such changes, the hydropathic index of amino acids may be considered. Each amino acid has been assigned a its hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte et al., *J. Mol. Biol.,* 157: 105-131, 1982). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity, particularly where the biologically functionally equivalent protein or peptide thereby created is intended for use in immunological embodiments, as in the present case.

The U.S. Pat. No. 4,554,101 states that the greatest local average hydrophilicity of a protein, as governed by the hydrophilicity of its adjacent amino acids, correlates with its immunogenicity and antigenicity, i.e., with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred. One may also identify epitopes from primary amino acid sequences on the basis of hydrophilicity. Through the methods disclosed in U.S. Pat. No. 4,554,101 one of skill in the art is able to identify epitopes from within a given amino acid sequence. These regions are also referred to as "epitopic core regions".

Numerous scientific publications have been devoted to the prediction of secondary structure, and to the identification of epitopes, from analyses of amino acid sequences. See Chou et al., *Biochemistry,* 13(2): 222-245, 1974; Chou et al., *Biochemistry,* 113(2): 211-222, 1974; Chou et al., *Adv. Enzymol. Relat. Areas Mol. Biol.,* 47: 45-148, 1978; Chou et al., *Ann. Rev. Biochem.,* 47: 251-276 and Chou et al., *Biophys. J.,* 26: 367-384, 1979. Moreover, computer programs are currently available to assist with predicting antigenic portions and epitopic core regions of proteins. Examples include those programs based upon the Jameson-Wolf analysis (Jameson et al., *Comput. Appl. Biosci.,* 4(1): 181-186, 1998 and Wolf et al., *Comput. Appl. Biosci.,* 4(1): 187-191, 1988, the program PepPlot® (Brutlag et al., *CABS,* 6: 237-245 1990, and Weinberger et al., *Science,* 228: 740-742, 1985) and other new programs for protein tertiary structure prediction (Fetrow et al., *Biotechnology,* 11: 479-483 1993).

In preferred embodiments, the variants have from 1 to 3, or from 1 to 5, or from 1 to 10, or from 1 to 15, or from 1 to 20, or from 1 to 25, or from 1 to 50, or from 1 to 75, or from 1 to 100, or more than 100 amino acid substitutions, insertions, additions and/or deletions, wherein the substitutions may be conservative, as described herein, or non-conservative, or any combination thereof. In addition, the variants can have additions of amino acid residues either at the carboxy terminus or at the amino terminus (with or without a leader sequence).

Preferred huE3α polypeptide variants include glycosylation variants wherein the number and/or type of glycosylation sites has been altered compared to native huE3α polypeptide. In one embodiment, huE3α polypeptide variants comprise a greater or a lesser number of N-linked glycosylation sites. An N-linked glycosylation site is characterized by the sequence: Asn-X-Ser or Asn-X-Thr, wherein the amino acid residue designated as X may be any amino acid residue except proline. The substitution(s) of amino acid residues to create this sequence provides a potential new site for the addition of an N-linked carbohydrate chain. Alternatively, substitutions which eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred huE3α variants include cysteine variants, wherein one or more cysteine residues are deleted or substituted with another amino acid (e.g., serine). Cysteine variants are useful when huE3α polypeptides must be refolded into a biologically active conformation such as after the isolation of insoluble inclusion bodies. Cysteine variants generally have fewer cysteine residues than the native protein, and typically have an even number to minimize interactions resulting from unpaired cysteines.

The term "huE3α fusion polypeptide" refers to a fusion of huE3αI or huE3αII polypeptide, fragment, and/or variant thereof, with a heterologous peptide or polypeptide. IN addition, the polypeptide comprising the amino acid sequence of SEQ ID NO: 2 or 4 or huE3α polypeptide variant many be fused to a homologous polypeptide to form a homodimer or to a heterologous polypeptide to form a heterodimer. Heterologous peptides and polypeptides include, but are not limited to: an epitope to allow for the detection and/or isolation of a huE3α fusion polypeptide; a transmembrane receptor protein or a portion thereof, such as an extracellular domain, or a transmembrane and intracellular domain; a ligand or a portion thereof which binds to a transmembrane receptor protein; an enzyme or portion thereof which is catalytically active; a polypeptide or peptide which promotes oligomerization, such as a leucine zipper domain; a polypeptide or peptide which increases stability, such as an immunoglobulin constant region, and a polypeptide which has a therapeutic activity different from the huE3α polypeptide.

In addition, a huE3α polypeptide may be fused to itself or to a fragment, variant, or derivative thereof. Fusions can be made either at the amino terminus or at the carboxy terminus of a huE3α polypeptide. Fusions may be direct with no linker or adapter molecule or indirect using through a linker or adapter molecule. A linker or adapater molecule may be one or more amino acid residues, typically from 20 amino acids residues, or up to about 50 amino acid residues. A linker or adapter molecule may also be designed with a cleavage site for a DNA restriction endonuclease or for a protease to allow for the separation of the fused moieties. It will be appreciated that once constructed, the fusion polypeptides can be derivatized according to the methods described herein.

In a further embodiment of the invention, a huE3α polypeptide, including a fragment, variant, and/or derivative, is fused to an Fc region of human IgG. Antibodies comprise two functionally independent parts, a variable domain known as "Fab", which binds antigens, and a constant domain known as "Fc", which is involved in effector functions such as complement activation and attack by phagocytic cells. An Fc has a long serum half-life, whereas an Fab is short-lived (Capon et al., *Nature,* 337: 525-31, 1989). When constructed together with a therapeutic protein, an Fc domain can provide longer half-life or incorporate such functions as Fc receptor binding, protein A binding, complement fixation and perhaps even placental transfer (Capon et al., *Nature,* 337: 525-31. 1989). Table I summarizes the use of certain Fc fusions known in the art, including materials and methods applicable to the production of fused huE3α polypeptides.

TABLE I

Fc Fusion with Therapeutic Proteins

| Form of Fc | Fusion partner | Therapeutic implications | Reference |
|---|---|---|---|
| IgG1 | N-terminus of CD30-L | Hodgkin's disease; anaplastic lymphoma; T-cell leukemia | U.S. Pat. No. 5,480,981 |
| Murine Fc 2a | IL-10 | anti-inflammatory; transplant rejection | Zheng et al., J. Immunol., 154: 5590-600, 1995 |
| IgG1 | TNF receptor | septic shock | Fisher et al., N. Engl. J. Med., 334: 1697-1702, 1996; Van Zee et al.,, J. Immunol., 156: 2221-30, 1996 |
| IgG, IgA, IgM, or IgE (excluding the first domain) | TNF receptor | inflammation, autoimmune disorders | U.S. Pat. No. 5,808,029, issued Sep. 15, 1998 |
| IgG1 | CD4 receptor | AIDS | Capon et al., Nature 337: 525-31, 1989 |
| IgG1, IgG3 | N-terminus of IL-2 | anti-cancer, antiviral | Harvill et al., Immunotech., 1: 95-105 1995 |
| IgG1 | C-terminus of OPG | osteoarthritis; bone density | WO 97/23614, published Jul. 3, 1997 |
| IgG1 | N-terminus of leptin | anti-obesity | PCT/US 97/23183, filed Dec. 11, 1997 |
| Human Ig Cγ1 | CTLA-4 | autoimmune disorders | Linsley, J. Exp. Med., 174: 561-9, 1991 |

In one example, all or portion of the human IgG hinge, CH2 and CH3 regions may be fused at either the N-terminus or C-terminus of the huE3α polypeptides using methods known to the skilled artisan. In another example, a portion of a hinge regions and CH2 and CH3 regions may be fused. The resulting huE3α Fc-fusion polypeptide may be purified by use of a Protein A affinity column. Peptides and proteins fused to an Fc region have been found to exhibit a substantially greater half-life in vivo than the unfused counterpart. Also, a fusion to an Fc region allows for dimerization/multimerization of the fusion polypeptide. The Fc region may be a naturally occurring Fc region, or may be altered to improve certain qualities, such as therapeutic qualities, circulation time, reduce aggregation, etc.

The term "huE3α polypeptide derivatives" refers to huE3αI or huE3αII polypeptides, fragments, or variants, as defined herein, that have been chemically modified. The derivatives are modified in a manner that is different from naturally occurring huE3α, polypeptides either in the type or location of the molecules attached to the polypeptide. Derivatives may further include molecules formed by the deletion of one or more chemical groups which are naturally attached to the huE3α polypeptide.

For example, the polypeptides may be modified by the covalent attachment of one or more polymers, including, but not limited to, water soluble polymers, N-linked or O-linked carbohydrates, sugars, phosphates, and/or other such molecules. For example, the polymer selected is typically water soluble so that the protein to which it is attached does not precipitate in an aqueous environment, such as a physiological environment. The polymer may be of any molecular weight, and may be branched or unbranched. Included within the scope of suitable polymers is a mixture of polymers. Preferably, for therapeutic use of the end-product preparation, the polymer will be pharmaceutically acceptable.

Suitable water soluble polymers or mixtures thereof include, but are not limited to, polyethylene glycol (PEG), monomethoxy-polyethylene glycol, dextran (such as low molecular weight dextran, of, for example about 6 kD), cellulose, or other carbohydrate based polymers, poly-(N-vinyl pyrrolidone) polyethylene glycol, propylene glycol homopolymers, a polypropylene oxide/ethylene oxide co-polymer, polyoxyethylated polyols (e.g., glycerol) and polyvinyl alcohol. Also encompassed by the present invention are bifunctional PEG crosslinking molecules which may be used to prepare covalently attached huE3α multimers.

For the acylation reactions, the polymer(s) selected should have a single reactive ester group. For reductive alkylation, the polymer(s) selected should have a single reactive aldehyde group. A reactive aldehyde is, for example, polyethylene glycol propionaldehyde, which is water stable, or mono $C_1$-$C_{10}$ alkoxy or aryloxy derivatives thereof (see U.S. Pat. No. 5,252,714).

The pegylation of huE3α polypeptides may be carried out by any of the pegylation reactions known in the art, as described for example in the following references: Francis et al., *Focus on Growth Factors,* 3: 4-10, 1992; EP 0154316; EP 0401384 and U.S. Pat. No. 4,179,337. Pegylation may be carried out via an acylation reaction or an alkylation reaction with a reactive polyethylene glycol molecule (or an analogous reactive water-soluble polymer) as described herein.

Polyethylene glycol (PEG) is a water-soluble polymer suitable for use herein. As used herein, the terms "polyethylene glycol" and "PEG" are meant to encompass any of the forms of PEG that have been used to derivatize proteins, including mono-($C_1$-$C_{10}$) alkoxy- or aryloxy-polyethylene glycol.

In general, chemical derivatization may be performed under any suitable conditions used to react a biologically active substance with an activated polymer molecule. Methods for preparing pegylated huE3α polypeptides will generally comprise the steps of (a) reacting the polypeptide with polyethylene glycol (such as a reactive ester or aldehyde derivative of PEG) under conditions whereby huE3α polypeptide becomes attached to one or more PEG groups, and (b) obtaining the reaction product(s). In general, the optimal reaction conditions for the acylation reactions will be determined based on known parameters and the desired result. For example, the larger the ratio of PEG:protein, the greater the percentage of poly-pegylated product. In one embodiment, the huE3α polypeptide derivative may have a single PEG moiety at the amino terminus. See, for example, U.S. Pat. No. 5,234,784.

Generally, conditions which may be alleviated or modulated by the administration of the present huE3α polypeptide derivative include those described herein for huE3α polypeptides. However, the huE3α polypeptide derivative disclosed herein may have additional activities, enhanced or reduced biological activity, or other characteristics, such as increased or decreased half-life, as compared to the non-derivatized molecules.

The terms "biologically active huE3α polypeptides", "biologically active huE3α polypeptide fragments", "biologically active huE3α polypeptide variants", and "biologically active huE3α polypeptide derivatives" refer to huE3αI or huE3αII polypeptides having at least one activity characteristic of a human E3α ubiquitin ligase, such as the activity of the polynucleotide set forth in SEQ ID NOS: 2 or 4. In general, huE3α polypeptides, fragments, variants, and derivatives thereof, will have at least one activity characteristic of a huE3α polypeptide such as depicted in SEQ ID NOS: 2 or 4. In addition, a huE3α polypeptide may be active as an immunogen, that is, the polypeptide contains at least one epitope to which antibodies may be raised.

"Naturally occurring" or "native" when used in connection with biological materials such as nucleic acid molecules, polypeptides, host cells, and the like, refers to materials which are found in nature and are not manipulated by man. Similarly, "non-naturally occurring" or "non-native" as used herein refers to a material that is not found in nature or that has been structurally modified or synthesized by man.

The term "isolated polypeptide" refers to a polypeptide of the present invention that is free from at least one contaminating polypeptide that is found in its natural environment. Preferably, the isolated polypeptide is substantially free from any other contaminating mammalian polypeptides which would interfere with its therapeutic, preventative, or diagnostic use.

The term "ortholog" refers to a polypeptide that corresponds to a polypeptide identified from a different species that corresponds to huE3αpolypeptide amino acid sequence. For example, mouse and human E3α polypeptides are considered orthologs.

The term "mature huE3α polypeptide" refers to a polypeptide lacking a leader sequence. A mature polypeptide may also include other modifications such as proteolytic processing of the amino terminus (with or without a leader sequence) and/or the carboxy terminus, cleavage of a smaller polypeptide from a larger precursor, N-linked and/or O-linked glycosylation, and the like. An exemplary mature huE3α polypeptide is depicted by SEQ ID NOS: 2 or 4.

The terms "effective amount" and "therapeutically effective amount" refer to the amount of a huE3α polypeptide or huE3α nucleic acid molecule used to support an observable level of one or more biological activities of the huE3α polypeptides as set forth herein.

The term "selective binding agent" refers to a molecule or molecules having specificity for huE3α molecules. Selective binding agents include antibodies, such as polyclonal antibodies, monoclonal antibodies (mAbs), chimeric antibodies, CDR-grafted antibodies, anti-idiotypic (anti-Id) antibodies to antibodies that can be labeled in soluble or bound form, as well as fragments, regions, or derivatives thereof which are provided by known techniques, including, but not limited to enzymatic cleavage, peptide synthesis, or recombinant techniques.

As used herein, the terms, "specific" and "specificity" refer to the ability of the selective binding agents to bind to human huE3α polypeptides. It will be appreciated, however, that the selective binding agents may also bind orthologs of huE3α, polypeptides, that is, interspecies versions of E3α, such as mouse and rat E3α polypeptides. A preferred embodiment relates to antibodies that are highly specific to huE3α polypeptides yet do not cross-react (that is, they fail to bind) with specificity to non-huE3α polypeptides.

The term "antigen" refers to a molecule or a portion of a molecule capable of being bound by a selective binding agent, such as an antibody, which is additionally capable of inducing an animal to produce antibodies capable of binding to an epitope of that antigen. An antigen can have one or more epitopes. The specific binding reaction referred to above is meant to indicate that the antigen will react, in a highly selective manner, with its corresponding antibody and not with the multitude of other antibodies which can be evoked by other antigens.

Human E3α polypeptides, fragments, variants, and derivatives may be used to prepare huE3α selective binding agents using methods known in the art. Thus, antibodies and antibody fragments that bind huE3α polypeptides are within the scope of the present invention. Antibody fragments include those portions of the antibody which bind to an epitope on the huE3α polypeptide. Examples of such fragments include Fab and F(ab') fragments generated by enzymatic cleavage of full-length antibodies. Other binding fragments include those generated by recombinant DNA techniques, such as the expression of recombinant plasmids containing nucleic acid sequences encoding antibody variable regions. These antibodies may be, for example, polyclonal monospecific polyclonal, monoclonal, recombinant, chimeric, humanized, human, single chain, and/or bispecific.

Relatedness of Nucleic Acid Molecules and/or Polypeptides

The term "identity", as known in the art, refers to a relationship between the sequences of two or more polypeptide molecules or two or more nucleic acid molecules, as determined by comparing the sequences. In the art, "identity" also means the degree of sequence relatedness between nucleic acid molecule or polypeptide sequences, as the case may be, as determined by the match between strings of two or more nucleotide or two or more amino acid sequences. "Identity" measures the percent of identical matches between two or more sequences with gap alignments (if any) addressed by a particular mathematical model or computer programs (i.e., "algorithms").

The term "similarity" is a related concept, but in contrast to "identity", refers to a measure of similarity which includes both identical matches and conservative substitution matches. If two polypeptide sequences have, for example, 10/20 identical amino acids, and the remainder are all non-conservative substitutions, then the percent identity and similarity would both be 50%. If in the same example, there are 5 more positions where there are conservative substitutions, then the percent identity remains 50%, but the percent similarity would be 75% (15/20). Therefore, in cases where there are conservative substitutions, the degree of similarity between two polypeptide sequences will be higher than the percent identity between those two sequences.

The term "isolated nucleic acid molecule" refers to a nucleic acid molecule of the invention that (1) has been separated from at least about 50 percent of proteins, lipids, carbohydrates or other materials with which it is naturally found when total DNA is isolated from the source cells, (2) is not linked to all or a portion of a polynucleotide to which the "isolated nucleic acid molecule" is linked in nature, (3) is operably linked to a polynucleotide which it is not linked to in nature, or (4) does not occur in nature as part of a larger polynucleotide sequence. Preferably, the isolated nucleic acid molecule of the present invention is substantially free from any other contaminating nucleic acid molecule(s) or other contaminants that are found in its natural environment that would interfere with its use in polypeptide production or its therapeutic, diagnostic, phophylactic or research use.

The term "isolated polypeptide" refers to a polypeptide of the present invention that (1) has been separated from at least about 50 percent of polynucleotides, lipids, carbohydrates or other materials with which it is naturally found when isolated from the source cell, (2) is not linked (by covalent or noncovalent interaction) to all or a portion of a polypeptide to which the "isolated polypeptide" is linked in nature, (3) is operably linked (by covalent or noncovalent interaction) to a polypeptide with which it is not linked in nature, or (4) does not occur in nature. Preferably, the isolated polypeptide is substantially free from any other contaminating polypeptides or other contaminants that are found in its natural environment that would interfere with its therapeutic, diagnostic, prophylactic or research use.

The term "conservative amino acid substitution" refers to a substitution of a native amino acid residue with a normative residue such that there is little or no effect on the polarity or charge of the amino acid residue at that position. For example, a conservative substitution results from the replacement of a non-polar residue in a polypeptide with any other non-polar residue. Furthermore, any native residue in the polypeptide may also be substituted with alanine, as has been previously described for "alanine scanning mutagenesis." General rules for conservative amino acid substitutions are set forth in Table II.

TABLE II

Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

Conservative amino acid substitutions also encompass non-naturally occurring amino acid residues which are typically incorporated by chemical peptide synthesis rather than by synthesis in biological systems. These include peptidomimetics, and other reversed or inverted forms of amino acid moieties. It will be appreciated by those skilled in the art the nucleic acid and polypeptide molecules described herein may be chemically synthesized as well as produced by recombinant means.

Conservative modifications to the amino acid sequence (and the corresponding modifications to the encoding nucleotides) will produce huE3α polypeptides having functional and chemical characteristics similar to those of naturally occurring huE3α polypeptides. In contrast, substantial modifications in the functional and/or chemical characteristics of huE3α polypeptides may be accomplished by selecting substitutions that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain. Naturally occurring residues may be divided into classes based on common side chain properties:

1) hydrophobic: norleucine, Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

Non-conservative substitutions may involve the exchange of a member of one of these classes for a member from another class. Such substituted residues may be introduced into regions of the human E3α polypeptide that are homologous with non-human E3α polypeptides, or into the non-homologous regions of the molecule.

Identity and similarity of related nucleic acid molecules and polypeptides can be readily calculated by known methods. Such methods include, but are not limited to, those described in *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part 1, Griffin, A. M., and Griffin, H. G., eds., Humana Press, New Jersey, 1994; *Sequence Analysis in Molecular Biology*, von Heinje, G., Academic Press, 1987; *Sequence Analysis Primer*, Gribskov, M. and Devereux, J., eds., M. Stockton Press, New York, 1991; and Carillo et al., *SIAM J. Applied Math.*, 48: 1073, 1988.

Preferred methods to determine identity and/or similarity are designed to give the largest match between the sequences tested. Methods to determine identity and similarity are described in publicly available computer programs. Preferred computer program methods to determine identity and similarity between two sequences include, but are not limited to, the GCG program package, including GAP (Devereux et al, *Nucl. Acid. Res.*, 12: 387, 1984; Genetics Computer Group, University of Wisconsin, Madison, Wis.), BLASTP, BLASTN, and FASTA (Altschul et al., *J. Mol. Biol.*, 215: 403-410, 1990). The BLASTX program is publicly available from the National Center for Biotechnology Information (NCBI) and other sources (*BLAST Manual*, Altschul et al. NCB/NLM/NIH Bethesda, Md. 20894; Altschul et al., supra). The well known Smith Waterman algorithm may also be used to determine identity.

Certain alignment schemes for aligning two amino acid sequences may result in the matching of only a short region of the two sequences, and this small aligned region may have very high sequence identity even though there is no significant relationship between the two full length sequences. Accordingly, in a preferred embodiment, the selected alignment method (GAP program) will result in an alignment that spans at least 50 contiguous amino acids of the target polypeptide.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). A gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually $1/10$ times the gap opening penalty), as well as a comparison matrix such as PAM 250 or BLOSUM 62 are used in conjunction with the algorithm. A standard comparison matrix (see Dayhoff et al., *Atlas of Protein Sequence and Structure*, vol. 5, supp. 3 (1978) for the PAM 250 comparison matrix; Henikoff et al., *Proc. Natl. Acad. Sci.* USA, 89: 10915-10919, 1992 for the BLOSUM 62 comparison matrix) is also used by the algorithm.

Preferred parameters for a polypeptide sequence comparison include the following:

Algorithm: Needleman et al., *J. Mol. Biol.*, 48, 443-453, 1970;

Comparison matrix: BLOSUM 62 from Henikoff et al., *Proc. Natl. Acad. Sci. USA*, 89: 10915-10919, 1992)

Gap Penalty: 12

Gap Length Penalty: 4

Threshold of Similarity: 0

The GAP program is useful with the above parameters. The aforementioned parameters are the default parameters for polypeptide comparisons (along with no penalty for end gaps) using the GAP algorithm.

Preferred parameters for nucleic acid molecule sequence comparisons include the following:

Algorithm: Needleman et al., *J. Mol. Biol.*, 48: 443-453, 1970;

Comparison matrix: matches=+10, mismatch=0

Gap Penalty: 50

Gap Length Penalty: 3

The GAP program is also useful with the above parameters. The aforementioned parameters are the default parameters for nucleic acid molecule comparisons.

Other exemplary algorithms, gap opening penalties, gap extension penalties, comparison matrices, thresholds of similarity, etc. may be used by those of skill in the art, including those set forth in the Program Manual, Wisconsin Package, Version 9, September, 1997. The particular choices to be made will be apparent to those of skill in the art and will depend on the specific comparison to be made, such as DNA to DNA, protein to protein, protein to DNA; and additionally, whether the comparison is between given pairs of sequences (in which case GAP or BestFit are generally preferred) or between one sequence and a large database of sequences (in which case FASTA or BLASTA are preferred).

Synthesis

It will be appreciated by those skilled in the art the nucleic acid and polypeptide molecules described herein may be produced by recombinant and other means.

Nucleic Acid Molecules

Recombinant DNA methods used herein are generally those set forth in Sambrook et al., *Molecular Cloning: A Laboratory Manual*, Cold Spring Harbor Laboratory Press, Cold Spring Harbor, N.Y. (1989), and/or Ausubel et al., eds., *Current Protocols in Molecular Biology*, Green Publishers Inc. and Wiley and Sons, NY (1994). The present invention provides for nucleic acid molecules as described herein and methods for obtaining the molecules. Human E3α (huE3α) refers to the nucleotide sequence of either huE3αI or huE3αII. A gene or cDNA encoding a huE3α polypeptide or fragment thereof may be obtained by hybridization screening of a genomic or cDNA library, or by PCR amplification. Where a gene encoding a huE3α polypeptide has been identified from one species, all or a portion of that gene may be used as a probe to identify corresponding genes from other species (orthologs) or related genes from the same species (homologs). The probes or primers may be used to screen cDNA libraries from various tissue sources believed to express the huE3α gene. In addition, part or all of a nucleic acid molecule having the sequence as set forth in SEQ ID NOS: 1 or 3 may be used to screen a genomic library to identify and isolate a gene encoding a huE3α polypeptide. Typically, conditions of moderate or high stringency will be employed for screening to minimize the number of false positives obtained from the screen.

Nucleic acid molecules encoding huE3α polypeptides may also be identified by expression cloning which employs the detection of positive clones based upon a property of the expressed protein. Typically, nucleic acid libraries are screened by the binding of an antibody or other binding partner (e.g., receptor or ligand) to cloned proteins which are expressed and displayed on a host cell surface. The antibody or binding partner is modified with a detectable label to identify those cells expressing the desired clone.

Additional methods of predicting secondary structure include "threading" (Jones et al., *Current Opin. Struct. Biol.*, 7(3):377-87 (1997); Sippl et al., *Structure*, 4(1):15-9 (1996)), "profile analysis" (Bowie et al., *Science*, 253:164-170 (1991); Gribskov et al., *Meth. Enzym.*, 183:146-159 (1990); Gribskov et al., *Proc. Nat. Acad. Sci.*, 84(13):4355-4358 (1987)), and "evolutionary linkage" (See Home, supra, and Brenner, supra 1997).

Another means of preparing a nucleic acid molecule encoding a huE3α polypeptide, including a fragment or variant, is chemical synthesis using methods well known to the skilled artisan such as those described by Engels et al., *Angew. Chem. Intl. Ed.*, 28: 716-734, 1989. These methods include, inter alia, the phosphotriester, phosphoramidite, and H-phosphonate methods for nucleic acid synthesis. A preferred method for such chemical synthesis is polymer-supported synthesis using standard phosphoramidite chemistry. Typically, the DNA encoding the huE3α polypeptide will be several hundred nucleotides in length. Nucleic acids larger than about 100 nucleotides can be synthesized as several fragments using these methods. The fragments can then be ligated together to form the full length huE3α polypeptide. Usually, the DNA fragment encoding the amino terminus of the polypeptide will have an ATG, which encodes a methionine residue. This methionine may or may not be present on the mature form of the huE3α polypeptide, depending on whether the polypeptide produced in the host cell is designed to be secreted from that cell.

In some cases, it may be desirable to prepare nucleic acid molecules encoding huE3α polypeptide variants. Nucleic acid molecules encoding variants may be produced using site directed mutagenesis, PCR amplification, or other appropriate methods, where the primer(s) have the desired point mutations (see Sambrook et al., supra, and Ausubel et al., supra, for descriptions of mutagenesis techniques). Chemical synthesis using methods described by Engels et al., supra, may also be used to prepare such variants. Other methods known to the skilled artisan may be used as well.

In certain embodiments, nucleic acid variants contain codons which have been altered for the optimal expression of a huE3α polypeptide in a given host cell. Particular codon alterations will depend upon the huE3α polypeptide(s) and host cell(s) selected for expression. Such "codon optimization" can be carried out by a variety of methods, for example, by selecting codons which are preferred for use in highly expressed genes in a given host cell. Computer algorithms which incorporate codon frequency tables such as "Ecohigh.cod" for codon preference of highly expressed bacterial genes may be used and are provided by the University of Wisconsin Package Version 9.0, Genetics Computer Group, Madison, Wis. Other useful codon frequency tables include "Celegans_high.cod", "Celegans_low.cod", "*Drosophila*_high.cod", "Human_high.cod", "Maize_high.cod", and "Yeast_high.cod".

In other embodiments, nucleic acid molecules encode huE3α variants with conservative amino acid substitutions as described herein, huE3α variants comprising an addition and/or a deletion of one or more N-linked or O-linked glycosylation sites, huE3α variants having deletions and/or substitutions of one or more cysteine residues, or huE3α polypeptide fragments as described herein. In addition, nucleic acid molecules may encode any combination of huE3α variants, fragments, and fusion polypeptides described herein.\

Vectors and Host Cells

A nucleic acid molecule encoding a huE3α polypeptide is inserted into an appropriate expression vector using standard ligation techniques wherein huE3α refers to either the polypeptide sequence of huE3αI or huE3αII. The vector is typically selected to be functional in the particular host cell employed (i.e., the vector is compatible with the host cell machinery such that amplification of the gene and/or expression of the gene can occur). A nucleic acid molecule encoding a huE3α polypeptide may be amplified/expressed in prokaryotic, yeast, insect (baculovirus systems), and/or eukaryotic host cells. Selection of the host cell will depend in part on whether a huE3α polypeptide is to be post-translationally modified (e.g., glycosylated and/or phosphorylated). If so, yeast, insect, or mammalian host cells are preferable. For a review of expression vectors, see *Meth. Enz.*, v.185, D. V. Goeddel, ed. Academic Press Inc., San Diego, Calif. (1990).

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotides: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide sequence located at the 5' or 3' end of the huE3α polypeptide coding sequence; the oligonucleotide molecule encodes polyHis (such as hexaHis), or another "tag" such as FLAG, HA (hemaglutinin influenza virus) or myc for which commercially available antibodies exist. This tag is typically fused to the polypeptide upon expression of the polypeptide, and can serve as a means for affinity purification of the huE3α polypeptide from the host cell. Affinity purification can be accomplished, for example, by column chromatography using antibodies against the tag as an affinity matrix. Optionally, the tag can subsequently be removed from the purified huE3α polypeptide by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), or synthetic, or the flanking sequences may be native sequences which normally function to regulate huE3α polypeptide expression. As such, the source of a flanking sequence may be any prokaryotic or eukaryotic organism, any vertebrate or invertebrate organism, or any plant, provided that the flanking sequences is functional in, and can be activated by, the host cell machinery.

The flanking sequences useful in the vectors of this invention may be obtained by any of several methods well known in the art. Typically, flanking sequences useful herein other than endogenous huE3α gene flanking sequences will have been previously identified by mapping and/or by restriction endonuclease digestion and can thus be isolated from the proper tissue source using the appropriate restriction endonucleases. In some cases, the full nucleotide sequence of one or more flanking sequence may be known. Here, the flanking sequence may be synthesized using the methods described herein for nucleic acid synthesis or cloning.

Where all or only a portion of the flanking sequence is known, it may be obtained using PCR and/or by screening a genomic library with suitable oligonucleotide and/or flanking sequence fragments from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. Amplification of the vector to a certain copy number can, in some cases, be important for the optimal expression of the huE3α polypeptide. If the vector of choice does not contain an origin of replication site, one may be chemically synthesized based on a known sequence, and ligated into the vector. For example, the origin of replication from the plasmid pBR322 (Product No. 303-3s, New England Biolabs, Beverly, Mass.) is suitable for most gram-negative bacteria and various origins (e.g., SV40, polyoma, adenovirus, vesicular stomatitus virus (VSV) or papillomaviruses such as HPV or BPV) are useful for cloning vectors in mammalian cells. Generally, the origin of replication component is not needed for mammalian expression vectors (for example, the SV40 origin is often used only because it contains the early promoter).

A transcription termination sequence is typically located 3' of the end of a polypeptide coding region and serves to terminate transcription. Usually, a transcription termination sequence in prokaryotic cells is a G-C rich fragment followed by a poly T sequence. While the sequence is easily cloned from a library or even purchased commercially as part of a vector, it can also be readily synthesized using methods for nucleic acid synthesis such as those described herein.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells, (b) complement auxotrophic deficiencies of the cell; or (c) supply critical nutrients not available from complex media. Preferred selectable markers are the kanamycin resistance gene, the ampicillin resistance gene, and the tetracycline resistance gene. A neomycin resistance gene may also be used for selection in prokaryotic and eukaryotic host cells.

Other selection genes may be used to amplify the gene which will be expressed. Amplification is the process wherein genes which are in greater demand for the production of a protein critical for growth are reiterated in tandem within the chromosomes of successive generations of recombinant cells. Examples of suitable selectable markers for mammalian cells include dihydrofolate reductase (DHFR) and thymidine kinase. The mammalian cell transformants are placed under selection pressure which only the transformants are uniquely adapted to survive by virtue of the selection gene present in the vector. Selection pressure is imposed by culturing the transformed cells under conditions in which the concentration of selection agent in the medium is successively changed, thereby leading to the amplification of both the selection gene and the DNA that encodes huE3α polypeptides. As a result, increased quantities of huE3α polypeptides are synthesized from the amplified DNA.

A ribosome binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the huE3α polypeptide to be expressed. The Shine-Dalgarno sequence is varied but is typically a polypurine (i.e., having a high A-G content). Many Shine-Dalgarno sequences have been identified, each of which can be readily synthesized using methods set forth above and used in a prokaryotic vector.

A leader, or signal, sequence may be used to direct a huE3α polypeptide out of the host cell. Typically, a nucleotide sequence encoding the signal sequence is positioned in the coding region of the huE3α nucleic acid molecule, or directly at the 5' end of the huE3α polypeptide coding region. Many signal sequences have been identified, and any of those that are functional in the selected host cell may be used in conjunction with the huE3α nucleic acid molecule. Therefore, a signal sequence may be homologous (naturally occurring) or heterologous to the huE3α gene or cDNA. Additionally, a signal sequence may be chemically synthesized using methods described herein. In most cases, the secretion of a huE3α polypeptide from the host cell via the presence of a signal peptide will result in the removal of the signal peptide from the huE3α polypeptide. The signal sequence may be a component of the vector, or it may be a part of huE3α DNA that is inserted into the vector.

Included within the scope of this invention is the use of either a nucleotide sequence encoding a native huE3α signal sequence joined to a huE3α polypeptide coding region or a nucleotide sequence encoding a heterologous signal sequence joined to a huE3α polypeptide coding region. The heterologous signal sequence selected should be one that is recognized and processed, i.e., cleaved by a signal peptidase, by the host cell. For prokaryotic host cells that do not recognize and process the native huE3α signal sequence, the signal sequence is substituted by a prokaryotic signal sequence selected, for example, from the group of the alkaline phosphatase, penicillinase, or heat-stable enterotoxin II leaders. For yeast secretion, the native huE3α signal sequence may be substituted by the yeast invertase, alpha factor, or acid phosphatase leaders. In mammalian cell expression the native signal sequence is satisfactory, although other mammalian signal sequences may be suitable.

In some cases, such as where glycosylation is desired in a eukaryotic host cell expression system, one may manipulate the various presequences to improve glycosylation or yield. For example, one may alter the peptidase cleavage site of a particular signal peptide, or add presequences, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the N-terminus. Alternatively, use of some enzyme cleavage sites may result in a slightly truncated form of the desired huE3α polypeptide, if the enzyme cuts at such area within the mature polypeptide.

In many cases, transcription of a nucleic acid molecule is increased by the presence of one or more introns in the vector; this is particularly true where a polypeptide is produced in eukaryotic host cells, especially mammalian host cells. The introns used may be naturally occurring within the huE3α gene, especially where the gene used is a full length genomic sequence or a fragment thereof. Where the intron is not naturally occurring within the gene (as for most cDNAs), the intron(s) may be obtained from another source. The position of the intron with respect to flanking sequences and the huE3α gene is generally important, as the intron must be expressed to be effective. Thus, when a huE3α cDNA molecule is being expressed, the preferred position for the intron is 3' to the transcription start site, and 5' to the polyA transcription termination sequence. Preferably, the intron or introns will be located on one side or the other (i.e., 5' or 3') of the cDNA such that it does not interrupt the coding sequence. Any intron from any source, including any viral, prokaryotic and eukaryotic (plant or animal) organisms, may be used to practice this invention, provided that it is compatible with the host cell(s) into which it is inserted. Also included herein are synthetic introns. Optionally, more than one intron may be used in the vector.

The expression and cloning vectors of the present invention will each typically contain a promoter that is recognized by the host organism and operably linked to the molecule encoding a huE3α polypeptide. Promoters are untranscribed sequences located upstream (5') to the start codon of a structural gene (generally within about 100 to 1000 bp) that control the transcription and translation of the structural gene. Promoters are conventionally grouped into one of two classes, inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continual gene product production; that is, there is little or no control over gene expression. A large number of promoters, recognized by a variety of potential host cells, are well known. A suitable promoter is operably linked to the DNA encoding a huE3α polypeptide by removing the promoter from the source DNA by restriction enzyme digestion and inserting the desired promoter sequence into the vector. The native huE3α promoter sequence may be used to direct amplification and/or expression of huE3α DNA. A heterologous promoter is preferred, however, if it permits greater transcription and higher yields of the expressed protein as compared to the native promoter, and if it is compatible with the host cell system that has been selected for use.

Promoters suitable for use with prokaryotic hosts include the beta-lactamase and lactose promoter systems; alkaline phosphatase, a tryptophan (trp) promoter system; and hybrid promoters such as the tac promoter. Other known bacterial promoters are also suitable. Their sequences have been published, thereby enabling one skilled in the art to ligate them to the desired DNA sequence(s), using linkers or adapters as needed to supply any useful restriction sites.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowl pox virus, adenovirus (such as Adenovirus 2), bovine papilloma virus, avian sarcoma virus, cytomegalovirus (CMV), a retrovirus, hepatitis-B virus and most preferably Simian Virus 40 (SV40). Other suitable mammalian promoters include heterologous mammalian promoters, e.g., heat-shock promoters and the actin promoter.

Additional promoters which may be of interest in controlling huE3α gene transcription include, but are not limited to: the SV40 early promoter region (Bernoist and Chambon, Nature, 290: 304-310, 1981); the CMV promoter; the promoter contained in the 3' long terminal repeat of Rous sarcoma virus (Yamamoto et al., Cell, 22: 787-797, 1980); the herpes thymidine kinase promoter (Wagner et al., Proc. Natl. Acad. Sci. USA, 78: 144-1445, 1981); the regulatory sequences of the metallothionine gene (Brinster et al., Nature, 296: 39-42, 1982); prokaryotic expression vectors such as the beta-lactamase promoter (Villa-Kamaroff, et al, Proc. Natl. Acad. Sci. USA, 75: 3727-3731, 1978); or the tac promoter (DeBoer, et al., Proc. Natl. Acad. Sci. USA, 80: 21-25, 1983). Also of interest are the following animal transcriptional control regions, which exhibit tissue specificity and have been utilized in transgenic animals: the elastase I gene control region which is active in pancreatic acinar cells (Swift et al., Cell, 38: 639-646, 1984; Ornitz et al., Cold Spring Harbor Symp. Quant. Biol., 50: 399-409, 1986; MacDonald, Hepatology, 7: 425-515, 1987); the insulin gene control region which is active in pancreatic beta cells (Hanahan, Nature, 315: 115-122, 1985); the immunoglobulin gene control region which is active in lymphoid cells (Grosschedl et al., Cell, 38: 647-658 (1984); Adames et al., Nature, 318: 533-538 (1985); Alexander et al., Mol. Cell. Biol., 7: 1436-1444, 1987); the mouse mammary tumor virus control region which is active in testicular, breast, lymphoid and mast cells (Leder et al., Cell, 45: 485-495, 1986); the albumin gene control region which is active in liver (Pinkert et al., Genes and Devel., 1: 268-276, 1987); the alphafetoprotein gene control region which is active in liver (Krumlauf et al., Mol. Cell. Biol., 5: 1639-1648, 1985; Hammer et al, Science, 235: 53-58, 1987); the alpha 1-antitrypsin gene control region which is active in the liver (Kelsey et al., Genes and Devel., 1: 161-171, 1987); the beta-globin gene control region which is active in myeloid cells (Mogram et al., Nature, 315: 338-340, 1985; Kollias et al./, Cell, 46: 89-94, 1986); the myelin basic protein gene control region which is active in oligodendrocyte cells in the brain (Readhead et al., Cell, 48: 703-712, 1987); the myosin light chain-2 gene control region which is active in skeletal muscle (Sani, Nature, 314: 283-286, 1985); and the gonadotropic releasing hormone gene control region which is active in the hypothalamus (Mason et al., Science, 234: 1372-1378, 1986).

An enhancer sequence may be inserted into the vector to increase the transcription of a DNA encoding a huE3α polypeptide of the present invention by higher eukaryotes. Enhancers are cis-acting elements of DNA, usually about 10-300 bp in length, that act on the promoter to increase its transcription. Enhancers are relatively orientation and position independent. They have been found 5' and 3' to the transcription unit. Several enhancer sequences available from mammalian genes are known (e.g., globin, elastase, albumin, alpha-feto-protein and insulin). Typically, however, an enhancer from a virus will be used. The SV40 enhancer, the cytomegalovirus early promoter enhancer, the polyoma enhancer, and adenovirus enhancers are exemplary enhancing elements for the activation of eukaryotic promoters. While an enhancer may be spliced into the vector at a position 5' or 3' to huE3α DNA, it is typically located at a site 5' from the promoter.

Expression vectors of the invention may be constructed from a starting vector such as a commercially available vector. Such vectors may or may not contain all of the desired flanking sequences. Where one or more of the desired flanking sequences are not already present in the vector, they may be individually obtained and ligated into the vector. Methods used for obtaining each of the flanking sequences are well known to one skilled in the art.

Preferred vectors for practicing this invention are those which are compatible with bacterial, insect, and mammalian host cells. Such vectors include, inter alia, pCRII, pCR3, and pcDNA3.1 (Invitrogen Company, Carlsbad, Calif.), pBSII (Stratagene Company, La Jolla, Calif.), pET15 (Novagen, Madison, Wis.), pGEX (Pharmacia Biotech, Piscataway, N.J.), pEGFP-N2 (Clontech, Palo Alto, Calif.), pETL (Blue-BacII; Invitrogen), pDSR-alpha (PCT Publication No. WO90/14363) and pFastBacDual (Gibco/BRL, Grand Island, N.Y.).

Additional suitable vectors include, but are not limited to, cosmids, plasmids, or modified viruses, but it will be appreciated that the vector system must be compatible with the selected host cell. Such vectors include, but are not limited to plasmids such as Bluescript® plasmid derivatives (a high copy number ColE1-based phagemid, Stratagene Cloning Systems Inc., La Jolla Calif.), PCR cloning plasmids designed for cloning Taq-amplified PCR products (e.g., TOPO™ TA Cloning® Kit, PCR2.1® plasmid derivatives, Invitrogen, Carlsbad, Calif.), and mammalian, yeast, or virus vectors such as a baculovirus expression system (pBacPAK plasmid derivatives, Clontech, Palo Alto, Calif.). The recombinant molecules can be introduced into host cells via transformation, transfection, infection, electroporation, or other known techniques.

After the vector has been constructed and a nucleic acid molecule encoding a huE3α polypeptide has been inserted into the proper site of the vector, the completed vector may be inserted into a suitable host cell for amplification and/or polypeptide expression. Host cells may be prokaryotic host cells (such as E. coli) or eukaryotic host cells (such as a yeast cell, an insect cell, or a vertebrate cell). The host cell, when cultured under appropriate conditions, synthesizes a huE3α polypeptide which can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity, such as glycosylation or phosphorylation, and ease of folding into a biologically active molecule.

A number of suitable host cells are known in the art and many are available from the American Type Culture Collection (ATCC), 10801 University Boulevard, Manassas, Va. 20110-2209. Examples include, but are not limited to, mammalian cells, such as Chinese hamster ovary cells (CHO) (ATCC No. CCL61) CHO DHFR-cells (Urlaub et al., Proc. Natl. Acad. Sci. USA, 97: 4216-4220, 1980), human embryonic kidney (HEK) 293 or 293T cells (ATCC No. CRL1573), or 3T3 cells (ATCC No. CCL92). The selection of suitable mammalian host cells and methods for transformation, culture, amplification, screening and product production and purification are known in the art. Other suitable mammalian cell lines, are the monkey COS-1 (ATCC No. CRL1650) and COS-7 cell lines (ATCC No. CRL1651), and the CV-1 cell line (ATCC No. CCL70). Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, mouse neuroblastoma N2A cells, HeLa, mouse L-929 cells, 3T3 lines derived from Swiss, Balb-c or NIH mice, BHK or HaK hamster cell lines, which are available from the American Type Culture Collection, Manassas, Va. Each of these cell lines is known by and available to those skilled in the art of protein expression.

Similarly useful as host cells suitable for the present invention are bacterial cells. For example, the various strains of *E. coli* (e.g., HB101, (ATCC No. 33694) DH5, DH10, and MC1061 (ATCC No. 53338)) are well-known as host cells in the field of biotechnology. Various strains of *B. subtilis, Pseudomonas* spp., other *Bacillus* spp., *Streptomyces* spp., and the like may also be employed in this method.

Many strains of yeast cells known to those skilled in the art are also available as host cells for the expression of the polypeptides of the present invention. Preferred yeast cells include, for example, *Saccharomyces cerivisae* and *Pichia pastoris*.

Additionally, where desired, insect cell systems may be utilized in the methods of the present invention. Such systems are described for example in Kitts et al, *Biotechniques,* 14: 810-817 (1993); Lucklow, *Curr. Opin. Biotechnol.,* 4: 564-572, 1993; and Lucklow et al. *J. Virol.,* 67: 4566-4579, 1993. Preferred insect cells are Sf-9 and Hi5 (Invitrogen, Carlsbad, Calif.).

The transformation of an expression vector for a huE3α polypeptide into a selected host cell may be accomplished by well known methods including methods such as transfection, infection, calcium chloride, electroporation, microinjection, lipofection or the DEAE-dextran method or other known techniques. The method selected will in part be a function of the type of host cell to be used. These methods and other suitable methods are well known to the skilled artisan, and are set forth, for example, in Sambrook et al., supra.

One may also use transgenic animals to express glycosylated huE3α polypeptides. For example, one may use a transgenic milk-producing animal (a cow or goat, for example) and obtain the present glycosylated polypeptide in the animal milk. One may also use plants to produce huE3α polypeptides, however, in general, the glycosylation occurring in plants is different from that produced in mammalian cells, and may result in a glycosylated product which is not suitable for human therapeutic use.

Polypeptide Production

Host cells comprising a huE3α expression vector may be cultured using standard media well known to the skilled artisan. The huE3α expression vector refers a vector which expresses either huE3αI or huE3αII. The media will usually contain all nutrients necessary for the growth and survival of the cells. Suitable media for culturing *E. coli* cells include, for example, Luria Broth (LB) and/or Terrific Broth (TB). Suitable media for culturing eukaryotic cells are, Roswell Park Memorial Institute medium 1640 (RPMI 1640), Minimal Essential Medium (MEM), and/or Dulbecco's Modified Eagle Medium (DMEM), all of which may be supplemented with serum and/or growth factors as indicated by the particular cell line being cultured. A suitable medium for insect cultures is Grace's medium supplemented with yeastolate, lactalbumin hydrolysate, and/or fetal calf serum as necessary.

Typically, an antibiotic or other compound useful for selective growth of transformed cells is added as a supplement to the media. The compound to be used will be dictated by the selectable marker element present on the plasmid with which the host cell was transformed. For example, where the selectable marker element is kanamycin resistance, the compound added to the culture medium will be kanamycin. Other compounds for selective growth include ampicillin, tetracycline, and neomycin.

The amount of a huE3α polypeptide produced by a host cell can be evaluated using standard methods known in the art. Such methods include, without limitation, Western blot analysis, SDS-polyacrylamide gel electrophoresis, non-denaturing gel electrophoresis, High Performance Liquid Chromatography (HPLC) separation, immunoprecipitation, and/or activity assays such as DNA binding gel shift assays.

If a huE3α polypeptide has been designed to be secreted from the host cells, the majority of polypeptide may be found in the cell culture medium. If however, the huE3α polypeptide is not secreted from the host cells, it will be present in the cytoplasm and/or the nucleus (for eukaryotic host cells) or in the cytosol (for bacterial host cells).

For a huE3α polypeptide situated in the host cell cytoplasm and/or nucleus, the host cells are typically first disrupted mechanically or with a detergent to release the intracellular contents into a buffered solution. Human E3α polypeptide can then be isolated from this solution.

The purification of a huE3α polypeptide from solution can be accomplished using a variety of techniques. If the polypeptide has been synthesized such that it contains a tag such as Hexahistidine (huE3α polypeptide/hexaHis) or other small peptide such as FLAG (Eastman Kodak Co., New Haven, Conn.) or myc (Invitrogen, Carlsbad, Calif.) at either its carboxyl or amino terminus, it may essentially be purified in a one-step process by passing the solution through an affinity column where the column matrix has a high affinity for the tag or for the polypeptide directly (i.e., a monoclonal antibody specifically recognizing and binding to the huE3α polypeptide). For example, polyhistidine binds with great affinity and specificity to nickel, thus an affinity column of nickel (such as the Qiagen® nickel columns) can be used for purification of huE3α polypeptide/polyHis. See for example, Ausubel et al., eds., *Current Protocols in Molecular Biology*, Section 10.11.8, John Wiley & Sons, New York (1993).

Where a huE3α polypeptide is prepared without a tag attached, and no antibodies are available, other well known procedures for purification can be used. Such procedures include, without limitation, ion exchange chromatography, molecular sieve chromatography, High Performance Liquid Chromatography (HPLC), native gel electrophoresis in combination with gel elution, and preparative isoelectric focusing ("Isoprime" machine/technique, Hoefer Scientific, San Francisco, Calif.). In some cases, two or more of these techniques may be combined to achieve increased purity.

If a huE3α polypeptide is produced intracellularly, the intracellular material (including inclusion bodies for gram-negative bacteria) can be extracted from the host cell using any standard technique known to the skilled artisan. For example, the host cells can be lysed to release the contents of the periplasm/cytoplasm by French press, homogenization, and/or sonication followed by centrifugation.

If a huE3α polypeptide has formed inclusion bodies in the cytosol, the inclusion bodies can often bind to the inner and/or outer cellular membranes and thus will be found primarily in the pellet material after centrifugation. The pellet material can then be treated at pH extremes or with chaotropic agent such as a detergent, guanidine, guanidine derivatives, urea, or urea derivatives in the presence of a reducing agent such as dithiothreitol at alkaline pH or tris carboxyethyl phosphine at acid pH to release, break apart, and solubilize the inclusion bodies. The solubilized huE3α polypeptide can then be analyzed using gel electrophoresis, immunoprecipitation or the like. If it is desired to isolate the huE3α polypeptide, isolation may be accomplished using standard methods such as those described herein and in Marston et al., *Meth. Enz.,* 182: 264-275 1990.

In some cases, a huE3α polypeptide may not be biologically active upon isolation. Various methods for "refolding" or converting the polypeptide to its tertiary structure and generating disulfide linkages, can be used to restore biological activity. Such methods include exposing the solubilized polypeptide to a pH usually above 7 and in the presence of a particular concentration of a chaotrope. The selection of chaotrope is very similar to the choices used for inclusion body solubilization, but usually the chaotrope is used at a lower concentration and is not necessarily the same as chaotropes used for the solubilization. In most cases the refolding/oxidation solution will also contain a reducing agent or the reducing agent plus its oxidized form in a specific ratio to generate a particular redox potential allowing for disulfide shuffling to occur in the formation of the protein's cysteine bridge(s). Some of the commonly used redox couples include cysteine/cystamine, glutathione (GSH)/dithiobis GSH, cupric chloride, dithiothreitol (DTT)/dithiane DTT, and 2-2mercaptoethanol(βME)/dithi(βME). A cosolvent may be used to increase the efficiency of the refolding, and the more common reagents used for this purpose include glycerol, polyethylene glycol of various molecular weights, arginine and the like.

If inclusion bodies are not formed to a significant degree upon expression of a huE3α polypeptide, then the polypeptide will be found primarily in the supernatant after centrifugation of the cell homogenate. The polypeptide may be further isolated from the supernatant using methods such as those described herein.

In situations where it is preferable to partially or completely purify a huE3α polypeptide such that it is partially or substantially free of contaminants, standard methods known to those skilled in the art may be used. Such methods include, without limitation, separation by electrophoresis followed by electroelution, various types of chromatography (affinity, immunoaffinity, molecular sieve, and/or ion exchange), and/or high pressure liquid chromatography. In some cases, it may be preferable to use more than one of these methods for complete purification.

Human E3α polypeptides, including fragments, variants, and/or derivatives thereof may also be prepared by chemical synthesis methods (such as solid phase peptide synthesis) using techniques known in the art, such as those set forth by Merrifield et al., *J. Am. Chem. Soc.,* 85: 2149, 1963, Houghten et al., *Proc Natl Acad. Sci. USA,* 82: 5132 1985, and Stewart and Young, *Solid Phase Peptide Synthesis,* Pierce Chemical Co., Rockford, Ill. (1984). Such polypeptides may be synthesized with or without a methionine on the amino terminus. Chemically synthesized huE3α polypeptides may be oxidized using methods set forth in these references to form disulfide bridges. Chemically synthesized huE3α polypeptides are expected to have comparable biological activity to the corresponding huE3α polypeptides produced recombinantly or purified from natural sources, and thus may be used interchangeably with a recombinant or natural huE3α polypeptide.

Another means of obtaining a huE3α polypeptide is via purification from biological samples such as source tissues and/or fluids in which the huE3α polypeptide is naturally found. Such purification can be conducted using methods for protein purification as described herein. The presence of the huE3α polypeptide during purification may be monitored using, for example, using an antibody prepared against recombinantly produced huE3α polypeptide or peptide fragments thereof.

A number of additional methods for producing nucleic acids and polypeptides are known in the art. See for example, Roberts et al., *Proc. Natl. Acad. Sci. U.S.A.,* 94:12297-12303, 1997, which describes the production of fusion proteins between an mRNA and its encoded peptide. See also Roberts, R., *Curr. Opin. Chem. Biol.,* 3:268-273, 1999. Additionally, U.S. Pat. No. 5,824,469 describes methods of obtaining oligonucleotides capable of carrying out a specific biological function. The procedure involves generating a heterogeneous pool of oligonucleotides, each having a 5' randomized sequence, a central preselected sequence, and a 3' randomized sequence. The resulting heterogeneous pool is introduced into a population of cells that do not exhibit the desired biological function. Subpopulations of the cells are then screened for those which exhibit a predetermined biological function. From that subpopulation, oligonucleotides capable of carrying out the desired biological function are isolated.

U.S. Pat. Nos. 5,763,192; 5,814,476; 5,723,323; and 5,817,483 describe processes for producing peptides or polypeptides. This is done by producing stochastic genes or fragments thereof, and then introducing these genes into host cells which produce one or more proteins encoded by the stochastic genes. The host cells are then screened to identify those clones producing peptides or polypeptides having the desired activity.

Another method for producing peptides or polypeptides is described in PCT/US98/20094 (WO99/15650) filed by Athersys, Inc. Known as "Random Activation of Gene Expression for Gene Discovery" (RAGE-GD), the process involves the activation of endogenous gene expression or over-expression of a gene by in situ recombination methods. For example, expression of an endogenous gene is activated or increased by integrating a regulatory sequence into the target cell which is capable of activating expression of the gene by non-homologous or illegitimate recombination. The target DNA is first subjected to radiation, and a genetic promoter inserted. The promoter eventually locates a break at the front of a gene, initiating transcription of the gene. This results in expression of the desired peptide or polypeptide.

It will be appreciated that these methods can also be used to create comprehensive IL-17 like protein expression libraries, which can subsequently be used for high throughput phenotypic screening in a variety of assays, such as biochemical assays, cellular assays, and whole organism assays (e.g., plant, mouse, etc.).

Chemical Derivatives

Chemically modified derivatives of polypeptides may be prepared by one skilled in the art, given the disclosures set forth herein below. Polypeptide derivatives are modified in a manner that is different, either in the type or location of the molecules naturally attached to the polypeptide. Derivatives may include molecules formed by the deletion of one or more naturally-attached chemical groups. The polypeptide comprising the amino acid sequence of SEQ ID NO: 2, or a polypeptide variant, may be modified by the covalent attachment of one or more polymers. For example, the polymer selected is typically water soluble so that the protein to which it is attached does not precipitate in an aqueous environment, such as a physiological environment. Included within the scope of suitable polymers is a mixture of polymers. Preferably, for therapeutic use of the end-product preparation, the polymer will be pharmaceutically acceptable.

The polymers each may be of any molecular weight and may be branched or unbranched. The polymers each typically have an average molecular weight of between about 2 kDa to about 100 kDa (the term "about" indicating that in preparations of a water soluble polymer, some molecules will weigh more, some less, than the stated molecular weight). The average molecular weight of each polymer is preferably between about 5 kDa and about 50 kDa, more preferably between about 12 kDa and about 40 kDa and most preferably between about 20 kDa to about 35 kDa. Suitable water soluble polymers or mixtures thereof include, but are not limited to, N-linked or O-linked carbohydrates; sugars; phosphates; polyethylene glycol (PEG) (including the forms of PEG that have been used to derivatize proteins, including mono-(C1-C10) alkoxy- or aryloxy-polyethylene glycol), monomethoxy-polyethylene glycol; dextran (such as low molecular weight dextran of, for example about 6 kD; cellulose, or other carbohydrate-based polymers, poly-(N-vinyl pyrrolidone) polyethylene glycol, propylene glycol homopolymers, a polypropylene oxide/ethylene oxide co-polymer, polyoxyethylated polyols (e.g., glycerol) and polyvinyl alcohol. Also encompassed by the present invention are bifunctional crosslinking molecules which may be used to prepare covalently attached multimers of the polypeptide comprising the amino acid sequence of SEQ ID NO: 2 or a polypeptide variant.

In general, chemical derivatization may be performed under any suitable condition used to react a protein with an activated polymer molecule. Methods for preparing chemical derivatives of polypeptides will generally comprise the steps of (a) reacting the polypeptide with the activated polymer molecule (such as a reactive ester or aldehyde derivative of the polymer molecule) under conditions whereby the polypeptide comprising the amino acid sequence of SEQ ID NO: 2, or a polypeptide variant becomes attached to one or more polymer molecules, and (b) obtaining the reaction product(s). The optimal reaction conditions will be determined based on known parameters and the desired result. For example, the larger the ratio of polymer molecules:protein, the greater the percentage of attached polymer molecule. In one embodiment, the polypeptide derivative may have a single polymer molecule moiety at the amino terminus. (See, for example, U.S. Pat. No. 5,234,784). The pegylation of the polypeptide may be specifically carried out by any of the pegylation reactions known in the art, as described for example in the following references: Francis et al., *Focus on Growth Factors*, 3:4-10 (1992); EP 0154316; EP 0401384 and U.S. Pat. No. 4,179,337. For example, pegylation may be carried out via an acylation reaction or an alkylation reaction with a reactive polyethylene glycol molecule (or an analogous reactive water-soluble polymer) as described herein. For the acylation reactions, the polymer(s) selected should have a single reactive ester group. For reductive alkylation, the polymer(s) selected should have a single reactive aldehyde group. A reactive aldehyde is, for example, polyethylene glycol propionaldehyde, which is water stable, or mono $C_1$-$C_{10}$ alkoxy or aryloxy derivatives thereof (see U.S. Pat. No. 5,252,714).

In another embodiment, polypeptides may be chemically coupled to biotin, and the biotin polypeptide molecules which are conjugated are then allowed to bind to avidin, resulting in tetravalent avidin/biotin polypeptide molecules. Polypeptides may also be covalently coupled to dinitrophenol (DNP) or trinitrophenol (TNP) and the resulting conjugates precipitated with anti-DNP or anti-TNP-IgM to form decameric conjugates with a valency of 10.

Generally, conditions which may be alleviated or modulated by the administration of the present polypeptide derivatives include those described herein for polypeptides. However, the polypeptide derivatives disclosed herein may have additional activities, enhanced or reduced biological activity, or other characteristics, such as increased or decreased half-life, as compared to the non-derivatized molecules.

Selective Binding Agents

As used herein, the term "selective binding agent" refers to a molecule which has specificity for one or more huE3α polypeptides. Suitable selective binding agents include, but are not limited to, antibodies and derivatives thereof, polypeptides, and small molecules. Suitable selective binding agents may be prepared using methods known in the art. An exemplary huE3α polypeptide selective binding agent of the present invention is capable of binding a certain portion of the huE3α polypeptide thereby inhibiting the binding of a cofactor to the huE3α polypeptide.

Human E3α polypeptides, fragments, variants, and derivatives may be used to prepare selective binding agents (such as antibodies) using methods known in the art; wherein huE3α polypeptide refers to either huE3αI or huE3αII polypeptide. Thus, selective binding agents such as antibodies and antibody fragments that bind huE3α polypeptides are within the scope of the present invention. The antibodies may be polyclonal, monospecific polyclonal, monoclonal, recombinant, chimeric, humanized, human, single chain, and/or bispecific.

Polyclonal antibodies directed toward a huE3α polypeptide generally are raised in animals (e.g., rabbits or mice) by multiple subcutaneous or intraperitoneal injections of huE3α polypeptide and an adjuvant. It may be useful to conjugate a huE3α polypeptide, or a variant, fragment, or derivative thereof to a carrier protein that is immunogenic in the species to be immunized, such as keyhole limpet heocyanin, serum, albumin, bovine thyroglobulin, or soybean trypsin inhibitor. Also, aggregating agents such as alum are used to enhance the immune response. After immunization, the animals are bled and the serum is assayed for anti-huE3α antibody titer.

Monoclonal antibodies directed toward huE3α polypeptides are produced using any method which provides for the production of antibody molecules by continuous cell lines in culture. Examples of suitable methods for preparing monoclonal antibodies include the hybridoma methods of Kohler et al., *Nature*, 256: 495-497, 1975 and the human B-cell hybridoma method, Kozbor, *J. Immunol.*, 133: 3001, 1984; Brodeur et al., *Monoclonal Antibody Production Techniques and Applications*, pp. 51-63 (Marcel Dekker, Inc., New York, 1987). Also provided by the invention are hybridoma cell lines which produce monoclonal antibodies reactive with huE3α polypeptides.

Monoclonal antibodies of the invention may be modified for use as therapeutics. One embodiment is a "chimeric" antibody in which a portion of the heavy and/or light chain is identical with or homologous to a corresponding sequence in antibodies derived from a particular species or belonging to a particular antibody class or subclass, while the remainder of the chain(s) is identical with or homologous to a corresponding sequence in antibodies derived from another species or belonging to another antibody class or subclass. Also included are fragments of such antibodies, so long as they exhibit the desired biological activity. See, U.S. Pat. No. 4,816,567; Morrison et al., *Proc. Natl. Acad. Sci.*, 81: 6851-6855 (1985).

In another embodiment, a monoclonal antibody of the invention is a "humanized" antibody. Methods for humanizing non-human antibodies are well known in the art. Generally, a humanized antibody has one or more amino acid residues introduced into it from a source which is non-human.

Humanization can be performed following methods known in the art (Jones et al., *Nature* 321: 522-525, 1986; Riechmann et al., *Nature*, 332: 323-327 (1988); Verhoeyen et al., *Science* 239:1534-1536, 1988), by substituting rodent complementarity-determining regions (CDRs) for the corresponding regions of a human antibody.

Also encompassed by the invention are human antibodies which bind huE3α polypeptides, fragments, variants and/or derivatives. Such antibodies are produced by immunization with a huE3α antigen (i.e., having at least 6 contiguous amino acids), optionally conjugated to a carrier, of transgenic animals (e.g., mice) that are capable of producing a repertoire of human antibodies in the absence of endogenous immunoglobulin production. See, for example, Jakobovits et al., *Proc. Natl. Acad. Sci.,* 90: 2551-2555, 1993; Jakobovits et al., *Nature* 362: 255-258, 1993; Bruggermann et al., *Year in Immuno.*, 7: 33 (1993). In one method, such transgenic animals are produced by incapacitating the endogenous loci encoding the heavy and light immunoglobulin chains therein, and inserting loci encoding human heavy and light chain proteins into the genome thereof. Partially modified animals, that is those having less than the full complement of modifications, are then cross-bred to obtain an animal having all of the desired immune system modifications. When administered an immunogen, these transgenic animals produce antibodies with human variable regions, including human (rather than e.g., murine) antibodies which are immunospecific for these antigens. See PCT application Nos. PCT/US96/05928 and PCT/US93/06926. Additional methods are described in U.S. Pat. No. 5,545,807, PCT application Nos. PCT/US91/245, PCT/GB89/01207, and in EP 546073B1 and EP 546073A1.

Human antibodies can also be produced from phage-display libraries (Hoogenboom et al., *J. Mol. Biol.* 227: 381 1991; Marks et al., *J. Mol. Biol.* 222: 581, 1991). These processes mimic immune selection through the display of antibody repertoires on the surface of filamentous bacteriophage, and subsequent selection of phage by their binding to an antigen of choice. One such technique is described in PCT Application WO99/10494, filed in the name of Adams et al., which describes the isolation of high affinity and functional agonistic antibodies for MPL- and msk-receptors using such an approach.

Chimeric, CDR grafted, and humanized antibodies are typically produced by recombinant methods. Nucleic acids encoding the antibodies are introduced into host cells and expressed using materials and procedures described herein. In a preferred embodiment, the antibodies are produced in mammalian host cells, such as CHO cells. Human antibodies may be produced by the expression of recombinant DNA in host cells or by expression in hybridoma cells as described herein.

For diagnostic applications, in certain embodiments, anti-huE3α antibodies typically will be labeled with a detectable moiety. The detectable moiety can be any one which is capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin; or an enzyme, such as alkaline phosphatase, β-galactosidase, or horseradish peroxidase (Bayer et al, *Meth. Enz.,* 184: 138-163 1990).

The anti-huE3α antibodies of the invention may be employed in any known assay method, such as competitive binding assays, direct and indirect sandwich assays, and immunoprecipitation assays (Sola, *Monoclonal Antibodies: A Manual of Techniques*, pp. 147-158 (CRC Press, Inc., 1987)) for the detection and quantitation of huE3α polypeptides. The antibodies will bind huE3α polypeptides with an affinity which is appropriate for the assay method being employed.

Competitive binding assays rely on the ability of a labeled standard (e.g., a huE3α polypeptide, or an immunologically reactive portion thereof) to compete with the test sample analyte (a huE3α polypeptide) for binding with a limited amount of antihuE3α antibody. The amount of a huE3α polypeptide in the test sample is inversely proportional to the amount of standard that becomes bound to the antibodies. To facilitate determining the amount of standard that becomes bound, the antibodies typically are insolubilized before or after the competition, so that the standard and analyte that are bound to the antibodies may conveniently be separated from the standard and analyte which remain unbound.

Sandwich assays typically involve the use of two antibodies, each capable of binding to a different immunogenic portion, or epitope, of the protein to be detected and/or quantitated. In a sandwich assay, the test sample analyte is typically bound by a first antibody which is immobilized on a solid support, and thereafter a second antibody binds to the analyte, thus forming an insoluble three part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assays). For example, one type of sandwich assay is an enzyme-linked immunosorbent assay (ELISA), in which case the detectable moiety is an enzyme.

The selective binding agents, including antibodies, are also useful for in vivo imaging. An antibody labeled with a detectable moiety may be administered to an animal, preferably into the bloodstream, and the presence and location of the labeled antibody in the host is assayed. The antibody may be labeled with any moiety that is detectable in an animal, whether by nuclear magnetic resonance, radiology, or other detection means known in the art.

Selective binding agents of the invention, including antibodies, may be used as therapeutics. These therapeutic agents are generally agonists or antagonists, in that they either enhance or reduce, respectively, at least one of the biological activities of a polypeptide. In one embodiment, antagonist antibodies of the invention are antibodies or binding fragments thereof which are capable of specifically binding to a polypeptide and which are capable of inhibiting or eliminating the functional activity of a polypeptide in vivo or in vitro. In preferred embodiments, the selective binding agent, e.g., an antagonist antibody will inhibit the functional activity of a polypeptide by at least about 50%, and preferably by at least about 80%. In another embodiment, the selective binding agent may be an antibody that is capable of interacting with a binding partner (a ligand, co-factor, or receptor) thereby inhibiting or eliminating activity in vitro or in vivo. Selective binding agents, including agonist and antagonist antibodies are identified by screening assays which are well known in the art.

The invention also relates to a kit comprising huE3α selective binding agents (such as antibodies) and other reagents useful for detecting huE3α levels in biological samples. Such reagents may include a secondary activity, a detectable label, blocking serum, positive and negative control samples, and detection reagents.

Genetically Engineered Non-Human Animals

Additionally included within the scope of the present invention are non-human animals such as mice, rats, or other rodents, rabbits, goats, or sheep, or other farm animals, in which the gene (or genes) encoding a native E3α ubiquitin ligase polypeptide (such as E3αI or E3αII) has (have) been disrupted ("knocked out") such that the level of expression of this gene or genes is (are) significantly decreased or completely abolished. Such animals may be prepared using techniques and methods such as those described in U.S. Pat. No. 5,557,032.

The present invention further includes non-human animals such as mice, rats, or other rodents, rabbits, goats, or sheep, or other farm animals, in which either the native form of the E3α ubiquitin ligase polypeptide gene(s) for that animal or a heterologous E3α ubiquitin ligase polypeptide gene(s) is (are) over expressed by the animal, thereby creating a "transgenic" animal. Such transgenic animals may be prepared using well known methods such as those described in U.S. Pat. No. 5,489,743 and PCT application No. WO94/28122.

The present invention further includes non-human animals in which the promoter for one or more of the E3α ubiquitin ligase polypeptides of the present invention is either activated or inactivated (e.g., by using homologous recombination methods) to alter the level of expression of one or more of the native E3α ubiquitin ligase polypeptides.

These non-human animals may be used for drug candidate screening. In such screening, the impact of a drug candidate on the animal may be measured. For example, drug candidates may decrease or increase the expression of the E3α ubiquitin ligase polypeptide gene. In certain embodiments, the amount of E3α ubiquitin ligase polypeptide, or a fragment (s), that is produced may be measured after the exposure of the animal to the drug candidate. Additionally, in certain embodiments, one may detect the actual impact of the drug candidate on the animal. For example, the overexpression of a particular gene may result in, or be associated with, a disease or pathological condition. In such cases, one may test a drug candidate's ability to decrease expression of the gene or its ability to prevent or inhibit a pathological condition. In other examples, the production of a particular metabolic product such as a fragment of a polypeptide, may result in, or be associated with, a disease or pathological condition. In such cases, one may test a drug candidate's ability to decrease the production of such a metabolic product or its ability to prevent or inhibit a pathological condition.

Microarray

It will be appreciated that DNA microarray technology can be utilized in accordance with the present invention. DNA microarrays are miniature, high density arrays of nucleic acids positioned on a solid support, such as glass. Each cell or element within the array has numerous copies of a single species of DNA which acts as a target for hybridization for its cognate mRNA. In expression profiling using DNA microarray technology, mRNA is first extracted from a cell or tissue sample and then converted enzymatically to fluorescently labeled cDNA. This material is hybridized to the microarray and unbound cDNA is removed by washing. The expression of discrete genes represented on the array is then visualized by quantitating the amount of labeled cDNA which is specifically bound to each target DNA. In this way, the expression of thousands of genes can be quantitated in a high throughput, parallel manner from a single sample of biological material.

This high throughput expression profiling has a broad range of applications with respect to the molecules of the invention, including, but not limited to: the identification and validation of disease-related genes as targets for therapeutics; molecular toxicology of molecules and inhibitors thereof; stratification of populations and generation of surrogate markers for clinical trials; and the enhancement of a related small molecule drug discovery by aiding in the identification of selective compounds in high throughput screens (HTS).

Assaying for Other Modulators of huE3α Polypeptide Activity

In some situations, it may be desirable to identify molecules that are modulators, i.e., antagonists and agonists, of the activity of huE3α polypeptide.

Natural or synthetic molecules that modulate huE3α polypeptides can be identified using one or more screening assays, such as those described herein. Such molecules may be administered either in an ex vivo manner, or in an in vivo manner by injection, or by oral delivery, implantation device, or the like.

The following definition is used herein for describing the assays. "Test molecule(s)" refers to the molecule(s) that is/are under evaluation for the ability to modulate (i.e., increase or decrease) the activity of a huE3α polypeptide. Most commonly, a test molecule will interact directly with a huE3α polypeptide. However, it is also contemplated that a test molecule may also modulate huE3α polypeptide activity indirectly, such as by affecting huE3α gene expression, or by binding to a huE3α binding partner (e.g., receptor, co-factor or ligand). In one embodiment, a test molecule will bind to a huE3α polypeptide with an affinity constant of at least about $10^{-6}$ M, preferably about $10^{-8}$ M, more preferably about $10^{-9}$ M, and even more preferably about $10^{-10}$ M.

Methods for identifying compounds which interact with huE3α polypeptides are encompassed by the present invention. In certain embodiments, a huE3α polypeptide is incubated with a test molecule under conditions which permit the interaction of the test molecule with a huE3α polypeptide, and the extent of the interaction can be measured. The test molecule(s) can be screened in a substantially purified form or in a crude mixture. Test molecule(s) can be nucleic acid molecules, proteins, peptides, carbohydrates, lipids, or small molecular weight organic or inorganic compounds. Once a set of has been identified as interacting with a huE3α polypeptide, the molecules may be further evaluated for their ability to increase or decrease huE3α activity.

The measurement of the interaction of test molecules with huE3α polypeptides may be carried out in several formats, including cell-based binding assays, membrane binding assays, solution-phase assays and immunoassays. In general, test molecules are incubated with a huE3α polypeptide for a specified period of time, and huE3α activity is determined by one or more assays described herein for measuring biological activity.

The interaction of test molecules with huE3α polypeptides may also be assayed directly using polyclonal or monoclonal antibodies in an immunoassay. Alternatively, modified forms of huE3α polypeptides containing epitope tags as described herein may be used in solution and immunoassays.

In certain embodiments, a huE3α polypeptide agonist or antagonist may be a protein, peptide, carbohydrate, lipid, or small molecular weight molecule which interacts with huE3α polypeptide to regulate its activity. Molecules which regulate huE3α polypeptide expression include nucleic acids which are complementary to nucleic acids encoding a huE3α polypeptide, or are complementary to nucleic acids sequences which direct or control the expression of huE3α polypeptide, and which act as antisense regulators of expression.

Once a set of test molecules has been identified as interacting with a polypeptide, the molecules may be further evaluated for their ability to increase or decrease polypeptide activity. The measurement of the interaction of test molecules with polypeptides may be carried out in several formats, including cell-based binding assays, membrane binding assays, solution-phase assays and immunoassays. In general, test molecules are incubated with a polypeptide for a specified period of time, and polypeptide activity is determined by one or more assays for measuring biological activity.

The interaction of test molecules with polypeptides may also be assayed directly using polyclonal or monoclonal antibodies in an immunoassay. Alternatively, modified forms of polypeptides containing epitope tags as described herein may be used in immunoassays.

In the event that polypeptides display biological activity through an interaction with a binding partner (e.g., a receptor, a ligand or a co-factor), a variety of in vitro assays may be used to measure the binding of a polypeptide to the corresponding binding partner (such as a selective binding agent, receptor, ligand, or co-factor). These assays may be used to screen test molecules for their ability to increase or decrease the rate and/or the extent of binding of a polypeptide to its binding partner. In one assay, a polypeptide is immobilized in the wells of a microtiter plate. Radiolabeled binding partner (for example, iodinated binding partner) and the test molecule(s) can then be added either one at a time (in either order) or simultaneously to the wells. After incubation, the wells can be washed and counted using a scintillation counter, for radioactivity to determine the extent to which the binding partner bound to polypeptide. Typically, the molecules will be tested over a range of concentrations, and a series of control wells lacking one or more elements of the test assays can be used for accuracy in the evaluation of the results. An alternative to this method involves reversing the "positions" of the proteins, i.e., immobilizing binding partner to the microtiter plate wells, incubating with the test molecule and radiolabeled polypeptide, and determining the extent of polypeptide binding. See, for example, chapter 18, *Current Protocols in Molecular Biology*, Ausubel et al., eds., John Wiley & Sons, New York, N.Y. (1995).

As an alternative to radiolabelling, a polypeptide or its binding partner may be conjugated to biotin and the presence of biotinylated protein can then be detected using streptavidin linked to an enzyme, such as horseradish peroxidase (HRP) or alkaline phosphatase (AP), that can be detected colorometrically, or by fluorescent tagging of streptavidin. An antibody directed to a polypeptide or to a binding partner and conjugated to biotin may also be used and can be detected after incubation with enzyme-linked streptavidin linked to AP or HRP.

A polypeptide or a like binding partner can also be immobilized by attachment to agarose beads, acrylic beads or other types of such inert solid phase substrates. The substrate-protein complex can be placed in a solution containing the complementary protein and the test compound. After incubation, the beads can be precipitated by centrifugation, and the amount of binding between a polypeptide and its binding partner can be assessed using the methods described herein. Alternatively, the substrate-protein complex can be immobilized in a column, and the test molecule and complementary protein are passed through the column. The formation of a complex between a polypeptide and its binding partner can then be assessed using any of the techniques set forth herein, i.e., radiolabelling, antibody binding or the like.

Another in vitro assay that is useful for identifying a test molecule which increases or decreases the formation of a complex between a polypeptide and a binding partner is a surface plasmon resonance detector system such as the BIAcore assay system (Pharmacia, Piscataway, N.J.). The BIAcore system may be carried out using the manufacturer's protocol. This assay essentially involves the covalent binding of either polypeptide or a binding partner to a dextran-coated sensor chip which is located in a detector. The test compound and the other complementary protein can then be injected, either simultaneously or sequentially, into the chamber containing the sensor chip. The amount of complementary protein that binds can be assessed based on the change in molecular mass which is physically associated with the dextran-coated side of the sensor chip; the change in molecular mass can be measured by the detector system.

In some cases, it may be desirable to evaluate two or more test compounds together for their ability to increase or decrease the formation of a complex between a polypeptide and a binding partner. In these cases, the assays set forth herein can be readily modified by adding such additional test compound(s) either simultaneous with, or subsequent to, the first test compound. The remainder of the steps in the assay are set forth herein.

In vitro assays such as those described herein may be used advantageously to screen large numbers of compounds for effects on complex formation by polypeptide and binding partner. The assays may be automated to screen compounds generated in phage display, synthetic peptide, and chemical synthesis libraries.

Compounds which increase or decrease the formation of a complex between a polypeptide and a binding partner may also be screened in cell culture using cells and cell lines expressing either polypeptide or binding partner. Cells and cell lines may be obtained from any mammal, but preferably will be from human or other primate, canine, or rodent sources. The binding of a polypeptide to cells expressing binding partner at the surface is evaluated in the presence or absence of test molecules, and the extent of binding may be determined by, for example, flow cytometry using a biotinylated antibody to a binding partner. Cell culture assays can be used advantageously to further evaluate compounds that score positive in protein binding assays described herein Cell cultures can be used to screen the impact of a drug candidate. For example, drug candidates may decrease or increase the expression of the huE3α polypeptide gene. In certain embodiments, the amount of huE3α polypeptide or a fragment(s) that is produced may be measured after exposure of the cell culture to the drug candidate. In certain embodiments, one may detect the actual impact of the drug candidate on the cell culture. For example, the overexpression of a particular gene may have a particular impact on the cell culture. In such cases, one may test a drug candidate's ability to increase or decrease the expression of the gene or its ability to prevent or inhibit a particular impact on the cell culture. In other examples, the production of a particular metabolic product such as a fragment of a polypeptide, may result in, or be associated with, a disease or pathological condition. In such cases, one may test a drug candidate's ability to decrease the production of such a metabolic product in a cell culture.

A yeast two hybrid system (Chien et al., *Proc. Natl. Acad. Sci. USA*, 88: 9578-9583, 1991) can be used to identify novel polypeptides that bind to a yeast-two hybrid bait construct can be generated in a vector (such as the pAS2-1 form Clontech) which encodes a yeast-two hybrid domain fused to the huE3α polynucleotide. This bait construct may be used to screen human cDNA libraries wherein the cDNA library sequences are fused to GAL4 activation domains. Positive interactions will result in the activation of a reporter gene such as β-gal. Positive clones emerging from the screening may be characterized further to identify interacting proteins.

Internalizing Proteins

The TAT protein sequence (from HIV) can be used to internalize proteins into a cell by targeting the lipid bi-layer component of the cell membrane. See e.g., Falwell et al., *Proc. Natl. Acad. Sci.*, 91: 664-668, 1994. For example, an 11 amino acid sequence (YGRKKRRQRRR; SEQ ID NO: 16) of the HIV TAT protein (termed the "protein transduction domain", or TAT PDT) has been shown to mediate delivery of large bioactive proteins such as β-galactosidase and p27Kip across the cytoplasmic membrane and the nuclear membrane of a cell. See Schwarze et al., *Science*, 285: 1569-1572, 1999; and Nagahara et al., *Nature Medicine*, 4: 1449-1452, 1998. Schwartze et al. (Science, 285:1569-72, 1999) demonstrated that cultured cells acquired β-gal activity when exposed to a fusion of the TAT PDT and β-galactosidase. Injection of mice with the TAT-β-gal fusion proteins resulted in β-gal expression in a number of tissues, including liver, kidney, lung, heart, and brain tissue.

It will thus be appreciated that the TAT protein sequence may be used to internalize a desired protein or polypeptide into a cell. In the context of the present invention, the TAT protein sequence can be fused to another molecule such as a huE3α antagonist (i.e.: anti-huE3α selective binding agent or small molecule) and administered intracellularly to inhibit the activity of the huE3α molecule. Where desired, the huE3α protein itself, or a peptide fragment or modified form of huE3α, may be fused to such a protein transducer for administrating to cells using the procedures, described above.

Therapeutic Uses

The huE3α nucleic acid molecules, polypeptides, and antagonists thereof (including, but not limited to, anti-huE3α selective binding agents) can be used to treat, diagnose, and/or prevent a number of diseases, conditions, and disorders, including but not limited to cachexia, muscle wasting diseases and other catabolic disorders such as cancer cachexia, renal cachexia, inflammatory cachexia, muscle wasting disorders associated with metabolic acidosis, uremia, burns, hyperthyroidism, Cushing's syndrome and fasting, and denervation atrophy, diabetes mellitus, sepsis and AIDS wasting syndrome.

Those skilled in the art will recognize that many combinations of deletions, insertions, and substitutions (individually or collectively "variant(s)" herein) can be made within the amino acid sequences of the huE3α polypeptide, provided that the resulting molecule is biologically active (e.g., possesses the ability to affect one or more of the diseases and disorders such as those recited herein).

As contemplated by the present invention, a polypeptide, or antagonist thereof (including, but not limited to, anti-huE3α selective binding agents) may be administered as an adjunct to other therapy and also with other pharmaceutical compositions suitable for the indication being treated. A polypeptide and any of one or more additional therapies or pharmaceutical formulations may be administered separately, sequentially, or simultaneously.

In a specific embodiment, the present invention is directed to the use of a huE3α polypeptide, or antagonist (including, but not limited to, anti-huE3α selective binding agents) thereof in combination (pretreatment, post-treatment, or concurrent treatment) with secreted or soluble human fas antigen or recombinant versions thereof (WO96/20206 and Mountz et al., *J. Immunology*, 155: 4829-4837; and EP 510 691. WO96/20206 discloses secreted human fas antigen (native and recombinant, including an Ig fusion protein), methods for isolating the genes responsible for coding the soluble recombinant human fas antigen, methods for cloning the gene in suitable vectors and cell types, and methods for expressing the gene to produce the inhibitors. EP 510 691 teaches DNAs coding for human fas antigen, including soluble fas antigen, vectors expressing for said DNAs and transformants transfected with the vector. When administered parenterally, doses of a secreted or soluble fas antigen fusion protein each are generally from about 1 microgram/kg to about 100 micrograms/kg.

Treatment of the diseases and disorders recited herein can include the use of first line drugs for control of pain and inflammation; these drugs are classified as non-steroidal, anti-inflammatory drugs (NSAIDs). Secondary treatments include corticosteroids, slow acting antirheumatic drugs (SAARDs), or disease modifying (DM) drugs. Information regarding the following compounds can be found in The Merck Manual of Diagnosis and Therapy, Sixteenth Edition, Merck, Sharp & Dohme Research Laboratories, Merck & Co., Rahway, N.J. (1992) and in Pharmaprojects, PJB Publications Ltd.

In a specific embodiment, the present invention is directed to the use of a huE3α, or antagonist (including, but not limited to, anti-huE3α selective binding agents) and any of one or more NSAIDs for the treatment of the diseases and disorders recited herein. NSAIDs owe their anti-inflammatory action, at least in part, to the inhibition of prostaglandin synthesis (Goodman and Gilman in "The Pharmacological Basis of Therapeutics," MacMillan 7th Edition (1985)). NSAIDs can be characterized into at least nine groups: (1) salicylic acid derivatives; (2) propionic acid derivatives; (3) acetic acid derivatives; (4) fenamic acid derivatives; (5) carboxylic acid derivatives; (6) butyric acid derivatives; (7) oxicams; (8) pyrazoles and (9) pyrazolones.

In another specific embodiment, the present invention is directed to the use of an huE3α polypeptide, or antagonist (including, but not limited to, anti-huE3α selective binding agents) in combination (pretreatment, post-treatment, or concurrent treatment) with any of one or more salicylic acid derivatives, prodrug esters or pharmaceutically acceptable salts thereof. Such salicylic acid derivatives, prodrug esters and pharmaceutically acceptable salts thereof comprise: acetaminosalol, aloxiprin, aspirin, benorylate, bromosaligenin, calcium acetylsalicylate, choline magnesium trisalicylate, magnesium salicylate, choline salicylate, diflusinal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide O-acetic acid, salsalate, sodium salicylate and sulfasalazine. Structurally related salicylic acid derivatives having similar analgesic and anti-inflammatory properties are also intended to be encompassed by this group.

In an additional specific embodiment, the present invention is directed to the use of an huE3α polypeptide, or antagonist (including, but not limited to, anti-huE3α selective binding agents) in combination (pretreatment, post-treatment, or concurrent treatment) with any of one or more propionic acid derivatives, prodrug esters or pharmaceutically acceptable salts thereof. The propionic acid derivatives, prodrug esters, and pharmaceutically acceptable salts thereof comprise: alminoprofen, benoxaprofen, bucloxic acid, carprofen, dexindoprofen, fenoprofen, flunoxaprofen, fluprofen, flurbiprofen, furcloprofen, ibuprofen, ibuprofen aluminum, ibuproxam, indoprofen, isoprofen, ketoprofen, loxoprofen, miroprofen, naproxen, naproxen sodium, oxaprozin, piketoprofen, pimeprofen, pirprofen, pranoprofen, protizinic acid, pyridoxiprofen, suprofen, tiaprofenic acid and tioxaprofen. Structurally related propionic acid derivatives having similar analgesic and anti-inflammatory properties are also intended to be encompassed by this group.

In yet another specific embodiment, the present invention is directed to the use of a huE3α polypeptide, or antagonist (including, but not limited to, anti-huE3α selective binding agents) in combination (pretreatment, post-treatment, or concurrent treatment) with any of one or more acetic acid derivatives, prodrug esters or pharmaceutically acceptable salts thereof. The acetic acid derivatives, prodrug esters, and pharmaceutically acceptable salts thereof comprise: acemetacin, aldlofenac, amfenac, bufexamac, cinmetacin, clopirac, delmetacin, diclofenac potassium, diclofenac sodium, etodolac, felbinac, fenclofenac, fenclorac, fenclozic acid, fentiazac, furofenac, glucametacin, ibufenac, indomethacin, isofezolac, isoxepac, lonazolac, metiazinic acid, oxametacin, oxpinac, pimetacin, proglumetacin, sulindac, talmetacin, tiaramide, tiopinac, tolmetin, tolmetin sodium, zidometacin and zomepirac. Structurally related acetic acid derivatives having similar analgesic and anti-inflammatory properties are also intended to be encompassed by this group.

In another specific embodiment, the present invention is directed to the use of a huE3α polypeptide, or antagonist (including, but not limited to, anti-huE3α selective binding agents) in combination (pretreatment, post-treatment, or concurrent treatment) with any of one or more fenamic acid derivatives, prodrug esters or pharmaceutically acceptable salts thereof. The fenamic acid derivatives, prodrug esters and pharmaceutically acceptable salts thereof comprise: enfenamic acid, etofenamate, flufenamic acid, isonixin, meclofenamic acid, meclofenamate sodium, medofenamic acid, mefenamic acid, niflumic acid, talniflumate, terofenamate, tolfenamic acid and ufenamate. Structurally related fenamic acid derivatives having similar analgesic and anti-inflammatory properties are also intended to be encompassed by this group.

In an additional specific embodiment, the present invention is directed to the use of a huE3α polypeptide, or antagonist (including, but not limited to, anti-huE3α selective binding agents) in combination (pretreatment, post-treatment, or concurrent treatment) with any of one or more carboxylic acid derivatives, prodrug esters or pharmaceutically acceptable salts thereof. The carboxylic acid derivatives, prodrug esters, and pharmaceutically acceptable salts thereof which can be used comprise: clidanac, diflunisal, flufenisal, inoridine, ketorolac and tinoridine. Structurally related carboxylic acid derivatives having similar analgesic and anti-inflammatory properties are also intended to be encompassed by this group.

In yet another specific embodiment, the present invention is directed to the use of a huE3α polypeptide, or antagonist (including, but not limited to, anti-huE3α selective binding agents) in combination (pretreatment, post-treatment, or concurrent treatment) with any of one or more butyric acid derivatives, prodrug esters or pharmaceutically acceptable salts thereof. The butyric acid derivatives, prodrug esters, and pharmaceutically acceptable salts thereof comprise: bumadizon, butibufen, fenbufen and xenbucin. Structurally related butyric acid derivatives having similar analgesic and anti-inflammatory properties are also intended to be encompassed by this group.

In another specific embodiment, the present invention is directed to the use of a huE3α polypeptide, or antagonist (including, but not limited to, anti-huE3α selective binding agents) in combination (pretreatment, post-treatment, or concurrent treatment) with any of one or more oxicams, prodrug esters, or pharmaceutically acceptable salts thereof. The oxicams, prodrug esters, and pharmaceutically acceptable salts thereof comprise: droxicam, enolicam, isoxicam, piroxicam, sudoxicam, tenoxicam and 4-hydroxyl-1,2-benzothiazine 1,1-dioxide 4-(N-phenyl)-carboxamide. Structurally related oxicams having similar analgesic and anti-inflammatory properties are also intended to be encompassed by this group.

In still another specific embodiment, the present invention is directed to the use of a huE3α polypeptide, or antagonist (including, but not limited to, anti-huE3α selective binding agents) in combination (pretreatment, post-treatment, or concurrent treatment) with any of one or more pyrazoles, prodrug esters, or pharmaceutically acceptable salts thereof. The pyrazoles, prodrug esters, and pharmaceutically acceptable salts thereof which may be used comprise: difenamizole and epirizole. Structurally related pyrazoles having similar analgesic and anti-inflammatory properties are also intended to be encompassed by this group.

In an additional specific embodiment, the present invention is directed to the use of a huE3α polypeptide, or antagonist (including, but not limited to, anti-huE3α selective binding agents) in combination (pretreatment, post-treatment or, concurrent treatment) with any of one or more pyrazolones, prodrug esters, or pharmaceutically acceptable salts thereof. The pyrazolones, prodrug esters and pharmaceutically acceptable salts thereof which may be used comprise: apazone, azapropazone, benzpiperylon, feprazone, mofebutazone, morazone, oxyphenbutazone, phenylbutazone, pipebuzone, propylphenazone, ramifenazone, suxibuzone and thiazolinobutazone. Structurally related pyrazalones having similar analgesic and anti-inflammatory properties are also intended to be encompassed by this group.

In another specific embodiment, the present invention is directed to the use of a huE3α polypeptide, or antagonist (including, but not limited to, anti-huE3α selective binding agents) in combination (pretreatment, post-treatment, or concurrent treatment) with any of one or more of the following NSAIDs: -acetamidocaproic acid, S-adenosyl-methionine, 3-amino-4-hydroxybutyric acid, amixetrine, anitrazafen, antrafenine, bendazac, bendazac lysinate, benzydamine, beprozin, broperamole, bucolome, bufezolac, ciproquazone, cloximate, dazidamine, deboxamet, detomidine, difenpiramide, difenpyramide, difisalamine, ditazol, emorfazone, fanetizole mesylate, fenflumizole, floctafenine, flumizole, flunixin, fluproquazone, fopirtoline, fosfosal, guaimesal, guaiazolene, isonixim, lefetamine HCl, leflunomide, lofemizole, lotifazole, lysin clonixinate, meseclazone, nabumetone, nictindole, nimesulide, orgotein, orpanoxin, oxaceprol, oxapadol, paranyline, perisoxal, perisoxal citrate, pifoxime, piproxen, pirazolac, pirfenidone, proquazone, proxazole, thielavin B, tiflamizole, timegadine, tolectin, tolpadol, tryptamid and those designated by company code number such as 480156S, AA861, AD1590, AFP802, AFP860, AI77B, AP504, AU8001, BPPC, BW540C, CHINOIN 127, CN100, EB382, EL508, F1044, FK-506, GV3658, ITF182, KCNTEI6090, KME4, LA2851, MR714, MR897, MY309, ONO3144, PR823, PV102, PV108, R830, RS2131, SCR152, SH440, SIR133, SPAS510, SQ27239, ST281, SY6001, TA60, TAI-901 (4-benzoyl-1-indancarboxylic acid), TVX2706, U60257, UR2301 and WY41770. Structurally related NSAIDs having similar analgesic and anti-inflammatory properties to the NSAIDs are also intended to be encompassed by this group.

In still another specific embodiment, the present invention is directed to the use of a huE3α polypeptide, or antagonist (including, but not limited to, anti-huE3α selective binding agents) in combination (pretreatment, post-treatment or concurrent treatment) with any of one or more corticosteroids, prodrug esters or pharmaceutically acceptable salts thereof for the treatment of the diseases and disorders recited herein, including acute and chronic inflammation such as rheumatic diseases, graft versus host disease and multiple sclerosis. Corticosteroids, prodrug esters and pharmaceutically acceptable salts thereof include hydrocortisone and compounds which are derived from hydrocortisone, such as 21-acetoxypregnenolone, alclomerasone, algestone, amcinonide, beclomethasone, betamethasone, betamethasone valerate, budesonide, chloroprednisone, clobetasol, clobetasol propionate, clobetasone, clobetasone butyrate, clocortolone, cloprednol, corticosterone, cortisone, cortivazol, deflazacon, desonide, desoximerasone, dexamethasone, diflorasone, diflucortolone, difluprednate, enoxolone, fluazacort, flucloronide, flumethasone, flumethasone pivalate, flucinolone acetonide, flunisolide, fluocinonide, fluorocinolone acetonide, fluocortin butyl, fluocortolone, fluocortolone hexanoate, diflucortolone valerate, fluoromethalone, fluperolone acetate, fluprednidene acetate, fluprednisolone, flurandenolide, formocortal, halcinonide, halometasone, halopredone acetate, hydro-cortamate, hydrocortisone, hydrocortisone acetate, hydro-cortisone butyrate, hydrocortisone phosphate, hydrocortisone 21-sodium succinate, hydrocortisone tebutate, mazipredone, medrysone, meprednisone, methylprednisolone, mometasone furoate, paramethasone, prednicarbate, prednisolone, prednisolone 21-diedryaminoacetate, prednisolone sodium phosphate, prednisolone sodium succinate, prednisolone sodium 21-m-sulfobenzoate, prednisolone sodium 21-stearoglycolate, prednisolone tebutate, prednisolone 21-trimethylacetate, prednisone, prednival, prednylidene, prednylidene 21-diethylaminoacetate, tixocortol, triamcinolone, triamcinolone acetonide, triamcinolone benetonide and triamcinolone hexacetonide. Structurally related corticosteroids having similar analgesic and anti-inflammatory properties are also intended to be encompassed by this group.

In another specific embodiment, the present invention is directed to the use of an huE3α polypeptide, or antagonist (including, but not limited to, anti-huE3α selective binding agents) in combination (pretreatment, post-treatment, or concurrent treatment) with any of one or more slow-acting antirheumatic drugs (SAARDs) or disease modifying antirheumatic drugs (DMARDS), prodrug esters, or pharmaceutically acceptable salts thereof for the treatment of the diseases and disorders recited herein, including acute and chronic inflammation such as rheumatic diseases, graft versus host disease and multiple sclerosis. SAARDs or DMARDS, prodrug esters and pharmaceutically acceptable salts thereof comprise: allocupreide sodium, auranofin, aurothioglucose, aurothioglycanide, azathioprine, brequinar sodium, bucillamine, calcium 3-aurothio-2-propanol-1-sulfonate, chlorambucil, chloroquine, clobuzarit, cuproxoline, cyclophosphamide, cyclosporin, dapsone, 15-deoxyspergualin, diacerein, glucosamine, gold salts (e.g., cycloquine gold salt, gold sodium thiomalate, gold sodium thiosulfate), hydroxychloroquine, hydroxychloroquine sulfate, hydroxyurea, kebuzone, levamisole, lobenzarit, melittin, 6-mercaptopurine, methotrexate, mizoribine, mycophenolate mofetil, myoral, nitrogen mustard, D-penicillamine, pyridinol imidazoles such as SKNF86002 and SB203580, rapamycin, thiols, thymopoietin and vincristine. Structurally related SAARDs or DMARDs having similar analgesic and anti-inflammatory properties are also intended to be encompassed by this group.

In another specific embodiment, the present invention is directed to the use of a huE3α polypeptide, or antagonist (including, but not limited to, anti-huE3α selective binding agents) in combination (pretreatment, post-treatment, or concurrent treatment) with any of one or more COX2 inhibitors, prodrug esters or pharmaceutically acceptable salts thereof for the treatment of the diseases and disorders recited herein, including acute and chronic inflammation. Examples of COX2 inhibitors, prodrug esters or pharmaceutically acceptable salts thereof include, for example, celecoxib. Structurally related COX2 inhibitors having similar analgesic and anti-inflammatory properties are also intended to be encompassed by this group.

In still another specific embodiment, the present invention is directed to the use of a huE3α polypeptide, or antagonist (including, but not limited to, anti-huE3α selective binding agents) in combination (pretreatment, post-treatment, or concurrent treatment) with any of one or more antimicrobials, prodrug esters or pharmaceutically acceptable salts thereof for the treatment of the diseases and disorders recited herein, including cachexia, muscle wasting diseases and other catabolic disorders. Antimicrobials include, for example, the broad classes of penicillins, cephalosporins and other beta-lactams, aminoglycosides, azoles, quinolones, macrolides, rifamycins, tetracyclines, sulfonamides, lincosamides and polymyxins. The penicillins include, but are not limited to penicillin G, penicillin V, methicillin, nafcillin, oxacillin, cloxacillin, dicloxacillin, floxacillin, ampicillin, ampicillin/sulbactam, amoxicillin, amoxicillin/clavulanate, hetacillin, cyclacillin, bacampicillin, carbenicillin, carbenicillin indanyl, ticarcillin, ticarcillin/clavulanate, azlocillin, mezlocillin, peperacillin, and mecillinam. The cephalosporins and other beta-lactams include, but are not limited to cephalothin, cephapirin, cephalexin, cephradine, cefazolin, cefadroxil, cefaclor, cefamandole, cefotetan, cefoxitin, ceruroxime, cefonicid, ceforadine, cefixime, cefotaxime, moxalactam, ceftizoxime, cetriaxone, cephoperazone, ceftazidime, imipenem and aztreonam. The aminoglycosides include, but are not limited to streptomycin, gentamicin, tobramycin, amikacin, netilmicin, kanamycin and neomycin. The azoles include, but are not limited to fluconazole. The quinolones include, but are not limited to nalidixic acid, norfloxacin, enoxacin, ciprofloxacin, ofloxacin, sparfloxacin and temafloxacin. The macrolides include, but are not limited to erythomycin, spiramycin and azithromycin. The rifamycins include, but are not limited to rifampin. The tetracyclines include, but are not limited to spicycline, chlortetracycline, clomocycline, demeclocycline, deoxycycline, guamecycline, lymecycline, meclocycline, methacycline, minocycline, oxytetracycline, penimepicycline, pipacycline, rolitetracycline, sancycline, senociclin and tetracycline. The sulfonamides include, but are not limited to sulfanilamide, sulfamethoxazole, sulfacetamide, sulfadiazine, sulfisoxazole and co-trimoxazole (trimethoprim/sulfamethoxazole). The lincosamides include, but are not limited to clindamycin and lincomycin. The polymyxins (polypeptides) include, but are not limited to polymyxin B and colistin.

Human E3α Compositions and Administration

Therapeutic compositions are within the scope of the present invention. Such compositions may comprise a therapeutically effective amount of a huE3α polypeptide, including a fragment, variant, derivative, or one or more selective binding agents which either inhibit or stimulate an activity of huE3α in admixture with a pharmaceutically acceptable agent such as a pharmaceutically acceptable formulation agent; wherein huE3α refers to the polypeptide sequence of huE3αI or huE3αII.

Human E3α pharmaceutical compositions typically include a therapeutically or prophylactically effective amount of huE3α polypeptide, (an inhibitor of huE3α action) nucleic acid molecule or selective binding agent in a mixture with one or more pharmaceutically and physiologically acceptable formulation agents selected for suitability with the mode of administration. Suitable formulation materials or pharmaceutically acceptable agents include, but are not limited to, antioxidants, preservatives, coloring, flavoring and diluting agents, emulsifying agents, suspending agents, solvents, fillers, bulking agents, buffers, delivery vehicles, diluents, excipients and/or pharmaceutical adjuvants. For example, a suitable vehicle or carrier may be water for injection, physiological saline solution, or artificial cerebrospinal fluid, possibly supplemented with other materials common in compositions for parenteral administration. Neutral buffered saline or saline mixed with serum albumin are further exemplary vehicles. The term "pharmaceutically acceptable carrier" or "physiologically acceptable carrier" as used herein refers to one or more formulation agents suitable for accomplishing or enhancing the delivery of the huE3α polypeptide, nucleic acid molecule or selective binding agent as a pharmaceutical composition.

Acceptable formulation materials preferably are nontoxic to recipients and are preferably inert at the dosages and concentrations employed. The materials may include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as ethylenediamine tetraacetic acid (EDTA); sugar alcohols such as mannitol or sorbitol; salt-forming counterions such as sodium; and/or nonionic surfactants such as tween, pluronics, or polyethylene glycol (PEG).

Typically, a huE3α molecule pharmaceutical composition will be administered in the form of a composition comprising a purified polypeptide, in conjunction with one or more physiologically acceptable agents. It will be appreciated that when used herein, the term "huE3α molecule pharmaceutical composition" also encompasses compositions containing a nucleic acid molecule or selective binding agent of the present invention.

Neutral buffered saline or saline mixed with serum albumin are exemplary appropriate carriers. Other standard pharmaceutically acceptable agents such as diluents and excipients may be included as desired. For example, the huE3α polypeptide product may be formulated as a lyophilizate using appropriate excipients such as sucrose. Other exemplary pharmaceutical compositions comprise Tris buffer of about pH 7.0-8.5, or acetate buffer of about pH 4.0-5.5, which may further include sorbitol or a suitable substitute therefor.

The primary vehicle or carrier in a pharmaceutical composition may be either aqueous or non-aqueous in nature. In addition, the composition may contain other formulation materials for modifying or maintaining the pH, osmolarity, viscosity, clarity, color, sterility, stability, rate of dissolution, or odor of the formulation. Similarly, the composition may contain additional formulation materials for modifying or maintaining the rate of release of huE3α polypeptide, nucleic acid molecule or selective binding agent, or for promoting the absorption or penetration of huE3α such molecules.

The huE3α molecule pharmaceutical compositions can be administered parenterally. Alternatively, the compositions may be administered through the digestive tract, such as orally, or by inhalation. When parenterally administered, the therapeutic compositions for use in this invention may be in the form of a pyrogen-free, parenterally acceptable aqueous solution. The preparation of such pharmaceutically acceptable compositions, with due regard to pH, isotonicity, stability and the like, is within the skill of the art.

A particularly suitable vehicle for parenteral injection is sterile distilled water in which a huE3α polypeptide is formulated as a sterile, isotonic solution, properly preserved. Yet another preparation can involve the formulation of the desired molecule with an agent, such as injectable microspheres, bio-erodible particles or beads, or liposomes, that provides for the controlled or sustained release of the product which may then be delivered as a depot injection. Other suitable means for the introduction of the desired molecule include implantable drug delivery devices.

The pharmaceutical compositions of the present invention may include other components, for example parenterally acceptable preservatives, tonicity agents, cosolvents, wetting agents, complexing agents, buffering agents, antimicrobials, antioxidants and surfactants, as are well known in the art. For example, suitable tonicity enhancing agents include alkali metal halides (preferably sodium or potassium chloride), mannitol, sorbitol, and the like. Suitable preservatives include, but are not limited to, benzalkonium chloride, thimerosal, phenethyl alcohol, methylparaben, propylparaben, chlorhexidine, sorbic acid, and the like. Hydrogen peroxide may also be used as preservative. Suitable cosolvents are for example glycerin, propylene glycol and polyethylene glycol. Suitable complexing agents are for example caffeine, polyvinylpyrrolidone, beta-cyclodextrin or hydroxypropyl-beta-cyclodextrin. Suitable surfactants or wetting agents include sorbitan esters, polysorbates such as polysorbate 80, tromethamine, lecithin, cholesterol, tyloxapal, and the like. The buffers can be conventional buffers such as borate, citrate, phosphate, bicarbonate, or Tris-HCl.

The formulation components are present in concentrations that are acceptable to the site of administration. For example, buffers are used to maintain the composition at physiological pH or at slightly lower pH, typically within a pH range of from about 5 to about 8.

In one embodiment of the present invention, huE3α polypeptide compositions may be prepared for storage by mixing the selected composition having the desired degree of purity with optional physiologically acceptable carriers, excipients, or stabilizers (*Remington's pharmaceutical sciences*, 18$^{th}$ edition, A. R. Gennaro, ed., Mack Publishing Company (1990)) in the form of a lyophilized cake or an aqueous solution.

The optimal pharmaceutical formulation will be determined by one skilled in the art depending upon, for example, the intended route of administration, delivery format, and desired dosage. See for example, *Remington's Pharmaceutical Sciences*, pp. 1435-1712. Such compositions may influence the physical state, stability, rate of in vivo release, and rate of in vivo clearance of the present huE3α polypeptides.

An effective amount of a huE3α polypeptide composition to be employed therapeutically will depend, for example, upon the therapeutic objectives such as the indication for which the huE3α polypeptide is being used, the route of administration, and the condition of the patient. Accordingly, the clinician may titer the dosage and modify the route of administration to obtain the optimal therapeutic effect. A typical dosage may range from about 0.1 µg/kg to up to about 100 mg/kg or more, depending on the factors mentioned above. In other embodiments, the dosage may range from 1 µg/kg up to about 100 mg/kg; or 5 µg/kg up to about 100 mg/kg; or 0.1 µg/kg up to about 100 mg/kg; or 1 µg/kg up to about 100 mg/kg.

Typically, a clinician will administer the composition until a dosage is reached that achieves the desired effect. The composition may therefore be administered as a single dose, or as two or more doses (which may or may not contain the same amount of the desired molecule) over time, or as a continuous infusion via implantation device or catheter.

One skilled in the art will appreciate that the appropriate dosage levels for treatment will thus vary depending, in part, upon the molecule delivered, the therapeutic context, type of disorder under treatment, the age, and general health of the recipient.

The huE3α molecule pharmaceutical composition to be used for in vivo administration typically must be sterile. This may be accomplished by filtration through sterile filtration membranes. Where the composition is lyophilized, sterilization using these methods may be conducted either prior to, or following, lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or a dehydrated or lyophilized powder. Such formulations may be stored either in a ready-to-use form or in a form (e.g., lyophilized) requiring reconstitution prior to administration.

In a specific embodiment, the present invention is directed to kits for producing a single-dose administration unit. The kits may each contain both a first container having a dried protein and a second container having an aqueous formulation. Also included within the scope of this invention are kits containing single and multi-chambered pre-filled syringes (e.g., liquid syringes and lyosyringes).

An effective amount of a pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the molecule is being used, the route of administration, and the size (body weight, body surface or organ size) and condition (the age and general health) of the patient. Accordingly, the clinician may titer the dosage and modify the route of administration to obtain the optimal therapeutic effect. A typical dosage may range from about 0.1 mg/kg to up to about 100 mg/kg or more, depending on the factors mentioned above. In other embodiments, the dosage may range from 0.1 mg/kg up to about 100 mg/kg; or 1 mg/kg up to about 100 mg/kg; or 5 mg/kg up to about 100 mg/kg.

The frequency of dosing will depend upon the pharmacokinetic parameters of the molecule in the formulation used. Typically, a clinician will administer the composition until a dosage is reached that achieves the desired effect. The composition may therefore be administered as a single dose, or as two or more doses (which may or may not contain the same amount of the desired molecule) over time, or as a continuous infusion via implantation device or catheter.

Pharmaceutical compositions such as (1) slow-release formulations, (2) inhalant mists, or (3) orally active formulations are also envisioned. The huE3α molecule pharmaceutical composition generally is formulated for parenteral administration. Such parenterally administered therapeutic compositions are typically in the form of a pyrogen-free, parenterally acceptable aqueous solution comprising the desired huE3α molecule in a pharmaceutically acceptable vehicle. The huE3α molecule pharmaceutical compositions also may include particulate preparations of polymeric compounds such as polylactic acid, polyglycolic acid, etc. or the introduction of the molecule into liposomes. Hyaluronic acid may also be used, and this may have the effect of promoting sustained duration in the circulation.

In one embodiment, a pharmaceutical composition may be formulated for inhalation. For example, huE3α polypeptide may be formulated as a dry powder for inhalation. Human E3α polypeptide or nucleic acid molecule inhalation solutions may also be formulated in a liquefied propellant for aerosol delivery, with or without a liquified propellant. In yet another embodiment, solutions may be nebulized. Pulmonary administration is further described in PCT WO94/20069, which describes pulmonary delivery of chemically modified proteins.

It is also contemplated that certain formulations may be administered orally. In one embodiment of the present invention, huE3α polypeptides which are administered in this fashion can be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents can be included to facilitate absorption of the huE3α polypeptide. Diluents, flavorings, low melting point waxes, vegetable oils, lubricants, suspending agents, tablet disintegrating agents, and binders may also be employed.

Another pharmaceutical composition may involve an effective quantity of huE3α polypeptides in a mixture with non-toxic excipients which are suitable for the manufacture of tablets. By dissolving the tablets in sterile water, or other appropriate vehicle, solutions can be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional huE3α molecule formulations will be evident to those skilled in the art, including formulations involving huE3α molecules in combination with one or more other therapeutic agents. Techniques for formulating a variety of other sustained- or controlled-delivery means, such as liposome carriers, bio-erodible microparticles or porous beads and depot injections, are also known to those skilled in the art. See for example, PCT/US93/00829 which describes controlled release of porous polymeric microparticles for the delivery of pharmaceutical compositions.

Additional examples of sustained-release preparations include semipermeable polymer matrices in the form of shaped articles, e.g. films, or microcapsules. Sustained release matrices may include polyesters, hydrogels, polylactides (U.S. Pat. No. 3,773,919, EP 58,481), copolymers of L-glutamic acid and gamma ethyl-L-glutamate (Sidman et al., *Biopolymers,* 22: 547-556, 1983), poly (2-hydroxyethyl-methacrylate) (Langer et al., *J. Biomed. Mater. Res.,* 15: 167-27, 1981; and Langer, *Chem. Tech.,* 12: 98-105, 1982), ethylene vinyl acetate (Langer et al, supra) or poly-D(−)-3-hydroxybutyric acid (EP 133,988). Sustained-release compositions also may include liposomes, which can be prepared by any of several methods known in the art. (See e.g., Eppstein et al., *Proc. Natl. Acad. Sci. USA,* 82: 3688-3692, 1985; EP 36,676; EP 88,046; EP 143,949.)

Regardless of the manner of administration, the specific dose may be calculated according to body weight, body surface area or organ size. Further refinement of the appropriate dosage is routinely made by those of ordinary skill in the art and is within the ambit of tasks routinely performed by them.

Appropriate dosages may be ascertained through use of appropriate dose-response data.

The route of administration of the pharmaceutical composition is in accord with known methods, e.g. oral, inhalation, injection or infusion by intravenous, intraperitoneal, intracerebral (intra-parenchymal), intracerebroventricular, intramuscular, intra-ocular, intraarterial, intraportal, or intralesional routes, or by sustained release systems or implantation device. Where desired, the compositions may be administered continuously by infusion, by bolus injection devices or by implantation device.

Alternatively or additionally, the composition may be administered locally via implantation into the affected area of a membrane, sponge, or other appropriate material on to which the desired molecule has been absorbed or encapsulated. Where an implantation device is used, the device may be implanted into any suitable tissue or organ, and delivery of the desired molecule may be directly through the device via diffusion, time-released bolus, or via continuous administration, or via catheter using continuous infusion.

It will further be appreciated that the huE3α polypeptides, including fragments, variants, and derivatives, may be employed alone, together, or in combination with other polypeptides and pharmaceutical compositions. For example, the huE3α polypeptides may be used in combination with cytokines, growth factors, antibiotics, anti-inflammatories, and/or chemotherapeutic agents as is appropriate for the indication being treated.

In some cases, it may be desirable to use huE3α pharmaceutical compositions in an ex vivo manner. In such instances, cells, tissues, or organs that have been removed from the patient are exposed to huE3α pharmaceutical compositions after which the cells, tissues and/or organs are subsequently implanted back into the patient.

In other cases, a huE3α polypeptide can be delivered by implanting certain cells that have been genetically engineered, using methods such as those described herein, to express and secrete the polypeptides. Such cells may be animal or human cells, and may be autologous, heterologous, or xenogeneic. Optionally, the cells may be immortalized. However, in order to decrease the chance of an immunological response, the cells may be encapsulated to avoid infiltration of surrounding tissues. The encapsulation materials are typically biocompatible, semi-permeable polymeric enclosures or membranes that allow the release of the protein product(s) but prevent the destruction of the cells by the patient's immune system or by other detrimental factors from the surrounding tissues.

Additional embodiments of the present invention relate to cells and methods (e.g., homologous recombination and/or other recombinant production methods) for both the in vitro production of therapeutic polypeptides by means of homologous recombination and for the production and delivery of therapeutic polypeptides by gene therapy or cell therapy.

It is further envisioned that huE3α polypeptides can be produced by homologous recombination, or with recombinant production methods utilizing control elements introduced into cells already containing DNA encoding huE3α polypeptides. For example, homologous recombination methods may be used to modify a cell that contains a normally transcriptionally silent huE3α gene, or an under expressed gene, and thereby produce a cell which expresses therapeutically efficacious amounts of huE3α polypeptides. Homologous recombination is a technique originally developed for targeting genes to induce or correct mutations in transcriptionally active genes. Kucherlapati, *Prog. in Nucl. Acid Res. & Mol. Biol.*, 36:301, 1989. The basic technique was developed as a method for introducing specific mutations into specific regions of the mammalian genome (Thomas et al., *Cell*, 44: 419-428, 1986; Thomas and Capecchi, *Cell*, 51:503-512, 1987; Doetschman et al, *Proc. Natl. Acad. Sci.*, 85: 8583-8587, 1988) or to correct specific mutations within defective genes (Doetschman et al., *Nature*, 330: 576-578, 1987). Exemplary homologous recombination techniques are described in U.S. Pat. No. 5,272,071 (EP 9193051, EP Publication No. 505500; PCT/US90/07642, International Publication No. WO 91/09955).

Through homologous recombination, the DNA sequence to be inserted into the genome can be directed to a specific region of the gene of interest by attaching it to targeting DNA. The targeting DNA is a nucleotide sequence that is complementary (homologous) to a region of the genomic DNA. Small pieces of targeting DNA that are complementary to a specific region of the genome are put in contact with the parental strand during the DNA replication process. It is a general property of DNA that has been inserted into a cell to hybridize, and therefore, recombine with other pieces of endogenous DNA through shared homologous regions. If this complementary strand is attached to an oligonucleotide that contains a mutation or a different sequence or an additional nucleotide, it too is incorporated into the newly synthesized strand as a result of the recombination. As a result of the proofreading function, it is possible for the new sequence of DNA to serve as the template. Thus, the transferred DNA is incorporated into the genome.

Attached to these pieces of targeting DNA are regions of DNA which may interact with or control the expression of a huE3α polypeptide, e.g., flanking sequences. For example, a promoter/enhancer element, a suppressor, or an exogenous transcription modulatory element is inserted in the genome of the intended host cell in proximity and orientation sufficient to influence the transcription of DNA encoding the desired huE3α polypeptide. The control element controls a portion of the DNA present in the host cell genome. Thus, the expression of huE3α polypeptide may be achieved not by transfection of DNA that encodes the huE3α gene itself, but rather by the use of targeting DNA (containing regions of homology with the endogenous gene of interest) coupled with DNA regulatory segments that provide the endogenous gene sequence with recognizable signals for transcription of a huE3α polypeptide.

In an exemplary method, the expression of a desired targeted gene in a cell (i.e., a desired endogenous cellular gene) is altered by the introduction, by homologous recombination into the cellular genome at a preselected site, by the introduction of DNA which includes at least a regulatory sequence, an exon and a splice donor site. These components are introduced into the chromosomal (genomic) DNA in such a manner that this, in effect, results in the production of a new transcription unit (in which the regulatory sequence, the exon and the splice donor site present in the DNA construct are operatively linked to the endogenous gene). As a result of the introduction of these components into the chromosomal DNA, the expression of the desired endogenous gene is altered.

Altered gene expression, as described herein, encompasses activating (or causing to be expressed) a gene which is normally silent (unexpressed) in the cell as obtained, as well as increasing the expression of a gene which is not expressed at physiologically significant levels in the cell as obtained. The embodiments further encompass changing the pattern of regulation or induction such that it is different from the pattern of regulation or induction that occurs in the cell as obtained, and reducing (including eliminating) the expression of a gene which is expressed in the cell as obtained.

One method by which homologous recombination can be used to increase, or cause, huE3α polypeptide production from a cell's endogenous huE3α gene involves first using homologous recombination to place a recombination sequence from a site-specific recombination system (e.g., Cre/loxP, FLP/FRT) (Sauer, *Current Opinion In Biotechnology*, 5: 521-527, 1994; Sauer, *Methods In Enzymology*, 225: 890-900, 1993) upstream (that is, 5' to) of the cell's endogenous genomic huE3α coding region. A plasmid containing a recombination site homologous to the site that was placed just upstream of the genomic huE3α coding region is introduced into the modified cell line along with the appropriate recombinase enzyme. This recombinase causes the plasmid to integrate, via the plasmid's recombination site, into the recombination site located just upstream of the genomic huE3α coding region in the cell line (Baubonis and Sauer, *Nucleic Acids Res.*, 21: 2025-2029, 1993; O'Gorman et al., *Science*, 251: 1351-1355, 1991). Any flanking sequences known to increase transcription (e.g., enhancer/promoter, intron, translational enhancer), if properly positioned in this plasmid, would integrate in such a manner as to create a new or modified transcriptional unit resulting in de novo or increased huE3α polypeptide production from the cell's endogenous huE3α gene.

A further method to use the cell line in which the site specific recombination sequence had been placed just upstream of the cell's endogenous genomic huE3α coding region is to use homologous recombination to introduce a second recombination site elsewhere in the cell line's genome. The appropriate recombinase enzyme is then introduced into the two-recombination-site cell line, causing a recombination event (deletion, inversion, translocation) (Sauer, *Current Opinion In Biotechnology*, 5: 521-527, 1994; Sauer, *Methods In Enzymology*, 225: 890-900, 1993) that would create a new or modified transcriptional unit resulting in de novo or increased huE3α polypeptide production from the cell's endogenous huE3α gene.

An additional approach for increasing, or causing, the expression of huE3α polypeptide from a cell's endogenous huE3α gene involves increasing, or causing, the expression of a gene or genes (e.g., transcription factors) and/or decreasing the expression of a gene or genes (e.g., transcriptional repressors) in a manner which results in de novo or increased huE3α polypeptide production from the cell's endogenous huE3α gene. This method includes the introduction of a non-naturally occurring polypeptide (e.g., a polypeptide comprising a site specific DNA binding domain fused to a transcriptional factor domain) into the cell such that de novo or increased huE3α polypeptide production from the cell's endogenous huE3α gene results.

The present invention further relates to DNA constructs useful in the method of altering expression of a target gene. In certain embodiments, the exemplary DNA constructs comprise: (a) one or more targeting sequences; (b) a regulatory sequence; (c) an exon; and (d) an unpaired splice-donor site. The targeting sequence in the DNA construct directs the integration of elements (a)-(d) into a target gene in a cell such that the elements (b)-(d) are operatively linked to sequences of the endogenous target gene. In another embodiment, the DNA constructs comprise: (a) one or more targeting sequences, (b) a regulatory sequence, (c) an exon, (d) a splice-donor site, (e) an intron, and (f) a splice-acceptor site, wherein the targeting sequence directs the integration of elements (a)-(f) such that the elements of (b)-(f) are operatively linked to the endogenous gene. The targeting sequence is homologous to the preselected site in the cellular chromosomal DNA with which homologous recombination is to occur. In the construct, the exon is generally 3' of the regulatory sequence and the splice-donor site is 3' of the exon.

If the sequence of a particular gene is known, such as the nucleic acid sequence encoding a huE3α polypeptide presented herein, a piece of DNA that is complementary to a selected region of the gene can be synthesized or otherwise obtained, such as by appropriate restriction of the native DNA at specific recognition sites bounding the region of interest. This piece serves as a targeting sequence upon insertion into the cell and will hybridize to its homologous region within the genome. If this hybridization occurs during DNA replication, this piece of DNA, and any additional sequence attached thereto, will act as an Okazaki fragment and will be incorporated into the newly synthesized daughter strand of DNA. The present invention, therefore, includes nucleotides encoding a huE3α polypeptide, which nucleotides may be used as targeting sequences.

Human E3α polypeptide cell therapy, e.g., the implantation of cells producing huE3α polypeptides, is also contemplated. This embodiment involves implanting cells capable of synthesizing and secreting a biologically active form of huE3α polypeptide. Such huE3α polypeptide-producing cells can be cells that are natural producers of huE3α polypeptides or may be recombinant cells whose ability to produce huE3α polypeptides has been augmented by transformation with a gene encoding the desired huE3α polypeptide or with a gene augmenting the expression of huE3α polypeptide. Such a modification may be accomplished by means of a vector suitable for delivering the gene as well as promoting its expression and secretion. In order to minimize a potential immunological reaction in patients being administered a huE3α polypeptide, as may occur with the administration of a polypeptide of a foreign species, it is preferred that the natural cells producing huE3α polypeptide be of human origin and produce huE3α polypeptide. Likewise, it is preferred that the recombinant cells producing huE3α polypeptide be transformed with an expression vector containing a gene encoding a human huE3α polypeptide.

Implanted cells may be encapsulated to avoid the infiltration of surrounding tissue. Human or non-human animal cells may be implanted in patients in biocompatible, semipermeable polymeric enclosures or membranes that allow the release of huE3α polypeptide, but that prevent the destruction of the cells by the patient's immune system or by other detrimental factors from the surrounding tissue. Alternatively, the patient's own cells, transformed to produce huE3α polypeptides ex vivo, may be implanted directly into the patient without such encapsulation.

Techniques for the encapsulation of living cells are known in the art, and the preparation of the encapsulated cells and their implantation in patients may be routinely accomplished. For example, Baetge et al. (WO95/05452; PCT/US94/09299) describe membrane capsules containing genetically engineered cells for the effective delivery of biologically active molecules. The capsules are biocompatible and are easily retrievable. The capsules encapsulate cells transfected with recombinant DNA molecules comprising DNA sequences coding for biologically active molecules operatively linked to promoters that are not subject to down regulation in vivo upon implantation into a mammalian host. The devices provide for the delivery of the molecules from living cells to specific sites within a recipient. In addition, see U.S. Pat. Nos. 4,892,538, 5,011,472, and 5,106,627. A system for encapsulating living cells is described in PCT Application WO91/10425 of Aebischer et al. See also, PCT Application WO91/10470 of Aebischer et al., Winn et al., *Exper. Neurol.*, 113: 322-329, 1991, Aebischer et al., *Exper. Neurol.*, 111: 269-275, 1991; and Tresco et al., *ASAIO*, 38:17-23, 1992.

In vivo and in vitro gene therapy delivery of huE3α polypeptides is also envisioned. In vivo gene therapy may be accomplished by introducing the gene encoding huE3α polypeptide into cells via local injection of a huE3α nucleic acid molecule or by other appropriate viral or non-viral delivery vectors (Hefti, *Neurobiology*, 25: 1418-1435, 1994). For example, a nucleic acid molecule encoding a huE3α polypeptide may be contained in an adeno-associated virus vector for delivery to the targeted cells (e.g., Johnson, International Publication No. WO95/34670; International Application No. PCT/US95/07178). The recombinant adeno-associated virus (AAV) genome typically contains AAV inverted terminal repeats flanking a DNA sequence encoding a huE3α polypeptide operably linked to functional promoter and polyadenylation sequences.

Alternative suitable viral vectors include, but are not limited to, retrovirus, adenovirus, herpes simplex virus, lentivirus, hepatitis virus, parvovirus, papovavirus, poxvirus, alphavirus, coronavirus, rhabdovirus, paramyxovirus, and papilloma virus vectors. U.S. Pat. No. 5,672,344 describes an in vivo viral-mediated gene transfer system involving a recombinant neurotrophic HSV-1 vector. U.S. Pat. No. 5,399,346 provides examples of a process for providing a patient with a therapeutic protein by the delivery of human cells which have been treated in vitro to insert a DNA segment encoding a therapeutic protein. Additional methods and materials for the practice of gene therapy techniques are described in U.S. Pat. No. 5,631,236 involving adenoviral vectors; U.S. Pat. No. 5,672,510 involving retroviral vectors; and U.S. Pat. No. 5,635,399 involving retroviral vectors expressing cytokines.

Nonviral delivery methods include, but are not limited to, liposome-mediated transfer, naked DNA delivery (direct injection), receptor-mediated transfer (ligand-DNA complex), electroporation, calcium phosphate precipitation, and microparticle bombardment (e.g., gene gun). Gene therapy materials and methods may also include the use of inducible promoters, tissue-specific enhancer-promoters, DNA sequences designed for site-specific integration, DNA sequences capable of providing a selective advantage over the parent cell, labels to identify transformed cells, negative selection systems and expression control systems (safety measures), cell-specific binding agents (for cell targeting), cell-specific internalization factors, and transcription factors to enhance expression by a vector as well as methods of vector manufacture. Such additional methods and materials for the practice of gene therapy techniques are described in U.S. Pat. No. 4,970,154 involving electroporation techniques; WO96/40958 involving nuclear ligands; U.S. Pat. No. 5,679,559 describing a lipoprotein-containing system for gene delivery; U.S. Pat. No. 5,676,954 involving liposome carriers; U.S. Pat. No. 5,593,875 concerning methods for calcium phosphate transfection; and U.S. Pat. No. 4,945,050 wherein biologically active particles are propelled at cells at a speed whereby the particles penetrate the surface of the cells and become incorporated into the interior of the cells.

In yet other embodiments, regulatory elements can be included for the controlled expression of the huE3α gene in the target cell. Such elements are turned on in response to an appropriate effector. In this way, a therapeutic polypeptide can be expressed when desired. One conventional control means involves the use of small molecule dimerizers or rapalogs (as described in WO9641865 (PCT/US96/099486); WO9731898 (PCT/US97/03137) and WO9731899 (PCT/US95/03157)) used to dimerize chimeric proteins which contain a small molecule-binding domain and a domain capable of initiating biological process, such as a DNA-binding protein or transcriptional activation protein. The dimerization of the proteins can be used to initiate transcription of the huE3α gene.

Other suitable control means or gene switches include, but are not limited to, the following systems. Mifepristone (RU486) is used as a progesterone antagonist. The binding of a modified progesterone receptor ligand-binding domain to the progesterone antagonist activates transcription by forming a dimer of two transcription factors which then pass into the nucleus to bind DNA. The ligand binding domain is modified to eliminate the ability of the receptor to bind to the natural ligand. The modified steroid hormone receptor system is further described in U.S. Pat. No. 5,364,791; WO9640911, and WO9710337.

Yet another control system uses ecdysone (a fruit fly steroid hormone) which binds to and activates an ecdysone receptor (cytoplasmic receptor). The receptor then translocates to the nucleus to bind a specific DNA response element (promoter from ecdysone-responsive gene). The ecdysone receptor includes a transactivation domain/DNA-binding domain/ligand-binding domain to initiate transcription. The ecdysone system is further described in U.S. Pat. No. 5,514,578; WO9738117; WO9637609; and WO9303162.

Another control means uses a positive tetracycline-controllable transactivator. This system involves a mutated tet repressor protein DNA-binding domain (mutated tet R-4 amino acid changes which resulted in a reverse tetracycline-regulated transactivator protein, i.e., it binds to a tet operator in the presence of tetracycline) linked to a polypeptide which activates transcription. Such systems are described in U.S. Pat. Nos. 5,464,758; 5,650,298 and 5,654,168.

Additional expression control systems and nucleic acid constructs are described in U.S. Pat. Nos. 5,741,679 and 5,834,186 to Innovir Laboratories Inc.

One example of a gene therapy technique is to use the huE3α gene (either genomic DNA, cDNA, and/or synthetic DNA encoding a huE3α polypeptide which may be operably linked to a constitutive or inducible promoter to form a "gene therapy DNA construct". The promoter may be homologous or heterologous to the endogenous huE3α gene, provided that it is active in the cell or tissue type into which the construct will be inserted. Other components of the gene therapy DNA construct may optionally include, DNA molecules designed for site-specific integration (e.g., endogenous sequences useful for homologous recombination), tissue-specific promoter, enhancer(s) or silencer(s), DNA molecules capable of providing a selective advantage over the parent cell, DNA molecules useful as labels to identify transformed cells, negative selection systems, cell specific binding agents (as, for example, for cell targeting), cell-specific internalization factors, and transcription factors to enhance expression by a vector as well as factors to enable vector manufacture.

This gene therapy DNA construct can then be introduced into cells (either ex vivo or in vivo). One means for introducing the gene therapy DNA construct is by means of viral vectors as described herein. Certain vectors, such as retroviral vectors, will deliver the gene therapy DNA construct to the chromosomal DNA of the cells, and the gene therapy DNA construct can integrate into the chromosomal DNA. Other vectors will function as episomes, and the gene therapy DNA construct will remain in the cytoplasm.

Another means to increase endogenous huE3α polypeptide expression in a cell via gene therapy is to insert one or more enhancer elements into the huE3α polypeptide promoter, where the enhancer element(s) can serve to increase transcriptional activity of the huE3α gene. The enhancer element(s) used will be selected based on the tissue in which one desires to activate the gene(s); enhancer elements known to confer promoter activation in that tissue will be selected. For example, if a gene encoding a huE3α polypeptide is to be "turned on" in T-cells, the lck promoter enhancer element may be used. Here, the functional portion of the transcriptional element to be added may be inserted into a fragment of DNA containing the huE3α polypeptide promoter (and optionally, inserted into a vector and/or 5' and/or 3' flanking sequence(s), etc.) using standard cloning techniques. This construct, known as a "homologous recombination construct", can then be introduced into the desired cells either ex vivo or in vivo.

Gene therapy can be used to decrease huE3α polypeptide expression by modifying the nucleotide sequence of the endogenous promoter(s). Such modification is typically accomplished via homologous recombination methods. For example, a DNA molecule containing all or a portion of the promoter of the huE3α gene(s) selected for inactivation can be engineered to remove and/or replace pieces of the promoter that regulate transcription. For example the TATA box and/or the binding site of a transcriptional activator of the promoter may be deleted using standard molecular biology techniques; such deletion can inhibit promoter activity thereby repressing the transcription of the corresponding huE3α gene. The deletion of the TATA box or the transcription activator binding site in the promoter may be accomplished by generating a DNA construct comprising all or the relevant portion of the huE3α polypeptide promoter(s) (from the same or a related species as the huE3α gene(s) to be regulated) in which one or more of the TATA box and/or transcriptional activator binding site nucleotides are mutated via substitution, deletion and/or insertion of one or more nucleotides. As a result, the TATA box and/or activator binding site has decreased activity or is rendered completely inactive. This construct, which also will typically contain at least about 500 bases of DNA that correspond to the native (endogenous) 5' and 3' DNA sequences adjacent to the promoter segment that has been modified, may be introduced into the appropriate cells (either ex vivo or in vivo) either directly or via a viral vector as described herein. Typically, the integration of the construct into the genomic DNA of the cells will be via homologous recombination, where the 5' and 3' DNA sequences in the promoter construct can serve to help integrate the modified promoter region via hybridization to the endogenous chromosomal DNA.

Other gene therapy methods may also be employed where it is desirable to inhibit the activity of one or more huE3α polypeptides. For example, antisense DNA or RNA molecules, which have a sequence that is complementary to at least a portion of the selected huE3α gene(s) can be introduced into the cell. Typically, each such antisense molecule will be complementary to the start site (5' end) of each selected huE3α gene. When the antisense molecule then hybridizes to the corresponding huE3α mRNA, translation of this mRNA is prevented or reduced. It will also be appreciated by those skilled in the art that antisense and ribozyme molecules may also be administered directly.

Alternatively, gene therapy may be employed to create a dominant-negative inhibitor of one or more huE3α polypeptides. In this situation, the DNA encoding a mutant full length or truncated polypeptide of each selected huE3α polypeptide can be prepared and introduced into the cells of a patient using either viral or non-viral methods as described herein. Each such mutant is typically designed to compete with endogenous polypeptide in its biological role.

Additional Uses of huE3α Nucleic Acids and Polypeptides

Nucleic acid molecules of the present invention may be used to map the locations of the huE3α gene and related genes on chromosomes. Mapping may be done by techniques known in the art, such as PCR amplification and in situ hybridization.

The nucleic acid molecules are also used as antisense inhibitors of huE3α polypeptide expression. Such inhibition may be effected by nucleic acid molecules which are complementary to and hybridize to expression control sequences (triple helix formation) or to huE3α mRNA. Antisense probes may be designed by available techniques using the sequence of huE3α nucleic acid molecules disclosed herein. Antisense inhibitors provide information relating to the decrease or absence of a huE3α polypeptide in a cell or organism.

Hybridization probes may be prepared using the huE3α nucleic acid sequences provided herein to screen cDNA, genomic or synthetic DNA libraries for related sequences. Regions of the DNA and/or amino acid sequence of huE3α polypeptide that exhibit significant identity to known sequences are readily determined using sequence alignment algorithms as described herein and those regions may be used to design probes for screening.

Human E3α nucleic acid molecules, as well as fragments, variants, and/or derivatives that do not themselves encode biologically active polypeptides, may be useful as hybridization probes in diagnostic assays to test, either qualitatively or quantitatively, for the presence of huE3α DNA or corresponding RNA in mammalian tissue or bodily fluid samples.

Human E3α polypeptide fragments, variants, and/or derivatives, whether biologically active or not, are also useful for preparing antibodies that bind to a huE3α polypeptide. The antibodies may be used for in vitro diagnostic purposes, including, but not limited to, use in labeled form to detect the presence of huE3α polypeptide in a body fluid or cell sample.

The full length cDNAs encoding huE3αI was subcloned into pCR 2.1 vector (Invitrogen, Cat.#K030-40). The full length cDNA encoding huE3αII was subcloned into pcDNA 3.1/His A vector (Invitrogen Cat.#V38-20). The full length cDNA encoding muE3αII was subcloned into pCR 2.1 vector (Invitrogen). The above plasmids were deposited on Mar. 15, 2000 to the American Type Culture Collection, 10801 University Boulevard, Manassas, Va. 20110-2209. The plasmid containing huE3αI is designated PTA-1489, the plasmid containing huE3αII is designated PTA-1490 and the plasmid containing muE3αII is designated PTA-1488.

The following examples are intended for illustration purposes only, and should not be construed as limiting the scope of the invention in any way.

EXAMPLE 1

Cloning of cDNA Encoding Human E3αI

Materials and methods for cDNA cloning and analysis are described in Sambrook et al., supra. which is incorporated herein by reference.

BLAST analysis of the Genebank dbEST database with the full length murine E3α ubiquitin ligase nucleotide sequence (muE3I; Genebank Accession No.: AF061555; SEQ ID NO: 15), revealed 4 human EST sequences (Genebank accession numbers AI187306, AI92195, AI87306, and AI400279) which potentially encode different regions of a novel human E3α ubiquitin ligase ortholog (huE3αI) gene. Based on these EST sequences, two sets of PCR primers (#2282-91/2282-93 and #2282-94/2282-97) were designed. These sequences are set out below in Table III.

TABLE III

| Primer   | Sequence                    | SEQ ID NO: |
|----------|-----------------------------|------------|
| 2282-91  | CTC CTC GAG TCT GCG TCA AAC | 7          |
| 2385-35  | TCT GCA TAT GTT CAG CCT TGC TA | 8       |
| 2282-94  | GTA TGA ACT TGC CGA GGC TTT TA | 9       |
| 2294-37  | CAA TAC TTT CCC AGC CCT CAG AA | 10      |

The primer sets #2282-91/2282-93 (SEQ ID NOS: 7 and 8) and #2282-94/2294-37 (SEQ ID NOS: 9 and 10) were used to generate two PCR products which span the whole huE3αI gene including the 5' and 3' untranslated regions. Polymerase chain reactions (PCR) were performed using a Perkin-Elmer 9600 thermocycler. In general, 50 µl PCR reactions contained 24 µl of $H_2O$, 5 µl of 10× cDNA PCR Reaction Buffer (Clontech), 2 µl of 10 mM dNTP mix (dATP, dCTP, dGTP, dTTP), 1 µl of Primer 2282-91 or 2282-94 (20 µl), 1 µl of Primer 2285-35 or 2294-37 (20 µl), 2 µl of 50× Advantage 2 Polymerase Mix (Clontech) and 15 µl of Marathon Ready cDNA from a human heart library (Clontech cat.# 7404-1) or a human muscle library (Clontech cat. # 7413-1). The reaction mixture was incubated at 94° C. for 30 seconds, followed by 40 cycles of 94° C. for 30 seconds, 60° C. for 30 seconds, and 72° C. for 5 minutes.

The PCR products were electrophoresed on a 1% agarose gel as described by Sambrook et al., supra. The appropriate sized bands (14 kB and 3 kB) were excised from the agarose gel and purified with the QIAquick Gel Extraction kit (Qiagen, cat#28704). The two purified DNA fragments were subcloned into pCR2.1 vectors and transformed into E. coli (Strain INVαF) utilizing the Invitrogen Original TA Cloning kit (cat.#K2000-40).

After subcloning, DNA plasmids were purified with the QIAprep Spin Miniprep kit (cat#27104). The sequence of the PCR products were verified by automated sequencing with the Prism 377 Sequencer and the BIg Dye Terminator Ready Reaction mix with AmpliTaq DNA polymerase (Perkin Elmer Applied Biosystems). Each sequencing reaction was performed in a Perkin Elmer 9600 thermocycler with 25 cycles of 96° C. for 10 seconds, 50° C. for 5 seconds and 60° C. for 2 minutes. The samples were purified using Centriflex Gel Filtration cartridges (Edge Biosystems). The samples were heated to 85° C. for 2 minutes and inserted into the Prism 377 Sequencer. The sequences were analyzed using the Sequencher™ Sequence Analysis software (Gene Codes Corp.). The sequences of the PCR product generated from human heart and human muscle were identical. The full length huE3αI clone was obtained by ligating the two PCR products together at their XbaI site.

The nucleic acid sequence of huE3αI (SEQ ID NO: 1), consists of an open reading frame of 5247 nucleotides which encodes a 1749 amino acid polypeptide, in addition to 695 bp in the 5' untranslated region and 362 bp in the 3' untranslated region. Alignment of the human and mouse amino acid sequence, as shown in FIG. 1 (SEQ ID NOS: 2 and 15, respectively), exhibited 92.5% overall sequence identity.

In the present invention, a novel full length human E3α cDNA (huE3αI; SEQ ID NO: 1) was isolated and cloned and the full length polypeptide sequence (SEQ ID NO: 2) was disclosed. A partial sequence of the human E3α gene had been previously reported. (See U.S. Pat. No. 5,861,312; Kwon et al., Proc. Natl. Acad. of Sci. USA, 95: 7898-7903, 1998). The reported partial sequence is encompassed in SEQ ID NO: 1; but only represents a small portion of the entire full length gene (nucleotides 702 to 1066).

EXAMPLE 2

Cloning of cDNA Encoding Human E3α Ortholog, huE3αII

BLAST analysis of the Amgenesis database (Amgen internal EST database) with the human E3αI amino acid sequences revealed 4 Amgenesis EST sequences (amgi-039645, smop2-0079fl2 and zhgb-aa693825 and Genebank accession no.: AA002347) which encode potential regions of the human and mouse E3α ubiquitin ligase ortholog nucleotide sequences which are denoted as E3αII. Based on the zhgb-aa693825 and AA002347 sequences, two PCR primer sets (#2380-88/2378-32 and #2381-48/2385-94) were designed. These sequences are set out below in Table IV.

TABLE IV

| Primer   | Sequence                    | SEQ ID NO: |
|----------|-----------------------------|------------|
| 2380-88  | ATG GCG TCG CTA GAG CCA     | 11         |
| 2378-32  | CAA AGC GGC TGA GCA TGA TCA TC | 12      |
| 2381-48  | TGA ACA GCC AAT CAC ACT AAG CA | 13      |
| 2385-94  | TTA TAA ATG CCA GTC AAT GCC AA | 14      |

The primer sets #2380-88/2378-32 (SEQ ID NOS: 11 and 12) and #2381-48/2385-94 (SEQ ID NOS: 13 and 14) were used to generate two PCR products which encode the coding region of a novel ortholog of human E3α ligase (huE3αII). The 5' and 3' untranslated regions of huE3 µl were determined based on the EST sequences amgi-03645 and smop2-0079fl2 in order to obtain the full length huE3αII cDNA. PCR was performed as described above utilizing Marathon-Ready cDNA from human heart and human muscle libraries. The two PCR products were electrophoresed on a 1% gel as described by Sambrook et al., supra. The appropriate sized bands (2.2 kB and 3.5 kB) were excised from the agarose and purified by QIAquick Gel Extraction kit (cat.# 28704). The PCR products were subcloned into the pcDNA3.1-HisA vector (Invitrogen cat.#V385-20) and transformed into E. coli (Strain INVαF) using the Invitrogen Original TA Cloning kit. The insert DNA was purified with the QIAprep Spin Miniprep kit (QIAGEN cat.#27104) and subsequenly digested with NotI/SacI for the 2 kB product and SacI/XhoI for the 3.3 kB product. The PCR products were sequenced as described in Example 1 and the products generated from human heart and human muscle cDNA libraries were identical. The full length huE3αII gene was generated by ligating these two PCR products at their SacI sites.

The nucleic acid sequence of huE3αII (SEQ ID NO: 3), consists of an open reading frame of 5265 nucleotides which encodes a 1755 amino acid polypeptide, in addition to 294 bp in the 5' untranslated region and 740 bp in the 3' untranslated region. Alignment of the human and mouse amino acid E3αII sequences, as shown in FIG. 1 (SEQ ID NOS: 4 and 6, respectively), exhibited 90.4% overall sequence identity. There is a 48.1% overall amino acid sequence identity between human E3αI and human E3αII (SEQ ID NOS:2 and 4, respectively).

In the present invention, a novel full length cDNA sequence encoding huE3 μl (SEQ ID NO: 3) was cloned and isolated, and the full length polypeptide sequence was disclosed (SEQ ID NO: 4). A partial sequence of huE3αII was identified in WO9904265 as one of many partial sequences with unknown identities that were speculated to be cancer markers.

EXAMPLE 3

Cloning of the Murine E3αII Ortholog

BLAST analysis of the Amgen internal database, Amgensis, with human E3αII amino acid sequences identified the mouse cDNA clone (Smop2-00079-fl2) as a potential mouse ortholog of E3αII ubiquitin ligase. The Amgenesis database contained the entire coding region of the mouse E3αII ubiquitin ligase (muE3αII) gene. The cDNA clone of was obtained from the Amgen sequencing group. The sequence of the clone was confirmed to be the full cDNA of muE3αII as described in Example 1. The nucleic acid sequence of muE3αII (SEQ ID NO: 5), consists of an open reading frame of 5265 nucleotides which encodes a 1755 amino acid polypeptide, in addition to 765 bp in the 5' untranslated region and 56 bp in the 3' untranslated region.

EXAMPLE 4

Human E3αII Tissue Expression

Tissue expression patterns of huE3αI and huE3αII mRNA were analyzed by Northern blot analysis. To detect the presence of huE3αII transcript in various tissues, a $^{32}$P-labeled fragment of huE3αII, which was 452 bp and corresponded to nucleotides 3557-4009 of SEQ ID NO: 3, was used as a probe. For detection of huE3αI transcript in various tissues, a $^{32}$P-labeled fragment of huE3αI, which was 696 bp and corresponded to nucleotides 3468-4164 of SEQ ID NO: 1, was used as a probe. The probes were labeled by random priming method using Prime-it RMT labeling kit (Stratagene, Cat#300392). The specific activities was $1.436 \times 10^6$ cpm/μl for the huE3αII probe and $1.207 \times 10^6$ cpm/μl for the huE3αI probe. Human multiple tissue poly A+ RNA blots (Clontech cat.#7780-1) were prehybridized in Church hybridization solution (1% BSA, 7% SDS, 0.5 M sodium phosphate, pH 7.0, 1 mM EDTA) for 4 hour at 65° C. The blots are then hybridized in Church hybridization solution with $3.0 \times 10^6$ cpm/ml $^{32}$P labeled probe for overnight at 65° C. The blots are then washed 3 times in Wash B buffer (1% SDS, 0.04 M sodium phosphate, 1 mM EDTA) for 5 minutes each at room temperature, followed by two times at 65° C. The blots were exposed to X-ray film at room temperature overnight (for huE3αII detection) or one week (for huE3αI detection).

Figure 3:
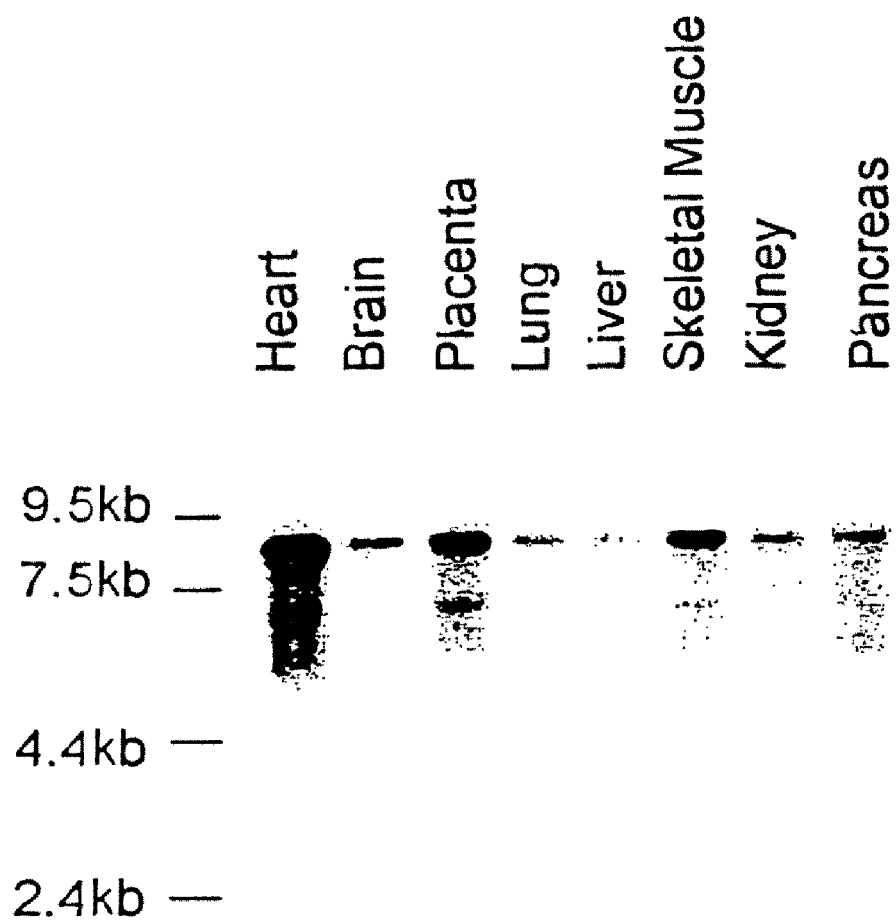
FIG. 3 shows the results of a human multiple tissue Northern blot detecting huE3αI expression.

The Northern blot analysis revealed that huE3αII (FIG. 2) is predominantly expressed in skeletal muscle, with moderate expression in heart and kidney tissue and minimal or no expression in other tissues examined including brain, colon, thymus, spleen, liver, small intestines, placenta, lung and peripheral white blood cells. In contrast, the expression of huE3αI (FIG. 3) is less muscle-specific. Although heart and skeletal muscle had relative high levels of huE3αI transcripts, moderate levels of huE3αI was found to spread through the various tissues examined. The results indicate that huE3αII is the more muscle-specific form of huE3α which is predominantly expressed in skeletal muscle tissue.

EXAMPLE 5

Production of huE3α Polypeptides

A. Bacterial Expression of huE3α Polypeptides

PCR is used to amplify template DNA sequences encoding a huE3α polypeptide using primers corresponding to the 5' and 3' ends of the sequence. The amplified DNA products may be modified to contain restriction enzyme sites to allow for insertion into expression vectors. PCR products are gel purified and inserted into expression vectors using standard recombinant DNA methodology. An exemplary vector, such as pAMG21 (ATCC No. 98113) containing the lux promoter and a gene encoding kanamycin resistance is digested with BamHI and NdeI for directional cloning of inserted DNA. The ligated mixture is transformed into an *E. coli* host strain by electroporation and transformants are selected for kanamycin resistance. Plasmid DNA from selected colonies is isolated and subjected to DNA sequencing to confirm the presence of the insert.

Transformed host cells are incubated in 2×YT medium containing 30 μg/ml kanamycin at 30° C. prior to induction. Gene expression is induced by the addition of N-(3-oxohexanoyl)-dl-homoserine lactone to a final concentration of 30 ng/ml followed by incubation at either 30° C. or 37° C. for six hours. The expression of huE3α polypeptide is evaluated by centrifugation of the culture, resuspension and lysis of the bacterial pellets, and analysis of host cell proteins by SDS-polyacrylamide gel electrophoresis.

Inclusion bodies containing huE3α polypeptide are purified as follows. Bacterial cells are pelleted by centrifugation and resuspended in water. The cell suspension is lysed by sonication and pelleted by centrifugation at 195,000×g for 5 to 10 minutes. The supernatant is discarded, and the pellet is washed and transferred to a homogenizer. The pellet is homogenized in 5 ml of a Percoll solution (75% liquid Percoll/0.15 M NaCl) until uniformly suspended and then diluted and centrifuged at 21,600×g for 30 minutes. Gradient fractions containing the inclusion bodies are recovered and pooled. The isolated inclusion bodies are analyzed by SDS-PAGE. A single band on an SDS polyacrylamide gel corresponding to *E. coli-produced* huE3α polypeptide is excised from the gel, and the N-terminal amino acid sequence is determined essentially as described by Matsudaira et al., J. Biol. Chem., 262: 10-35 (1987).

B. Mammalian Cell Production of huE3α Polypeptides

The huE3α DNA was subcloned into a mammalian expression vector as described above using standard DNA technology. An exemplary expression vector, pCEP4 (Invitrogen, Carlsbad, Calif.), which contains an Epstein-Barr virus origin of replication, may be used for the expression of huE3α in 293-EBNA-1 cells. Amplified and gel purified PCR products are ligated into pCEP4 vector and lipofected into 293-EBNA cells. The transfected cells are selected in 100 μg/ml hygromycin and the resulting drug-resistant cultures are grown to confluence. The cells are then cultured in serum-free media for 72 hours. The conditioned media is removed and, huE3α protein polypeptide expression is analyzed by SDS-PAGE. Human E3α polypeptide expression may be detected by silver staining. Alternatively, huE3α polypeptide is produced as a fusion protein with an epitope tag, such as an IgG constant domain or a FLAG epitope, which may be detected by Western blot analysis using antibodies to the tag peptide.

Human E3α polypeptides may be excised from an SDS-polyacrylamide gel, or huE3α fusion proteins are purified by affinity chromatography to the epitope tag, and subjected to N-terminal amino acid sequence analysis as described herein.

EXAMPLE 6

Production of Anti-huE3α Polypeptide Antibodies

Antibodies to huE3α polypeptides may be obtained by immunization with purified protein or with huE3α peptides produced by biological or chemical synthesis. Suitable procedures for generating antibodies include those described in Hudson and Bay, *Practical Immunology, Second Edition"*, Edition, Blackwell Scientific Publications.

In one procedure for the production of antibodies, animals (typically mice or rabbits) are injected with a huE3α antigen (such as an recombinant truncated forms of huE3α polypeptide), and those with sufficient serum titer levels as determined by ELISA are selected for hybridoma production. Spleens of immunized animals are collected and prepared as single cell suspensions from which splenocytes are recovered. The splenocytes are fused to mouse myeloma cells (such as Sp2/0-Ag14 cells), allowed to incubate in DMEM with 200 U/ml penicillin, 200 μg/ml streptomycin sulfate, and 4 mM glutamine, then incubated in HAT selection medium (Hypoxanthine; Aminopterin; Thymidine). After selection, the tissue culture supernatants are taken from each fusion well and tested for anti-huE3α antibody production by ELISA.

Alternative procedures for obtaining anti-huE3α antibodies may also be employed, such as the immunization of transgenic mice harboring human Ig loci for production of human antibodies, and the screening of synthetic antibody libraries, such as those generated by mutagenesis of an antibody variable domain.

EXAMPLE 7

Biological Activity of huE3α Polypeptides

Human E3α family members are known to catalyze the ubiquitin conjugation reaction which ultimately results in protein degradation. To determine the biological activity of huE3α polypeptide, the rate of ubiquitin conjugation and the rate of protein degradation are measured. The following are examples of assays to measure these biological activities.

A. Ubiquitin Conjugation Assay:

The enzymatic activity of E3α family members is thought to be the rate limiting step in ubiquitin conjugation. Rat skeletal muscles are dissected, homogenized, and centrifuged at 100,000×g to remove proteosomes. The soluble extract is incubated with $^{125}$I-ubiquitin (Amersham, Arlington Heights, Ill.) (0.15 mg/ml) in 20 mM Tris (pH 7.4), 1 mM DTT, 5 mM MgCl$_2$, and 2 mM ATPγS at 37° C. in the presence and absence of huE3α polypeptide. At various time points, the reactions are terminated by the addition of sample buffer and SDS-PAGE is performed on a 12% gel. The gel is then dried and autoradiographed. If huE3α acts as an E3α family member, the level of ubiquitination should increase in extracts treated with the huE3α polypeptide (Soloman et al., *Proc. Natl. Acad. of Sci. U.S.A.*, 95:12602-07, 1998).

B. Protein Degradation Assays:

Measurement of tyrosine release is a preferred method for determining the rate of protein turnover in skeletal muscles. Rat skeletal muscles are dissected and homogenated. The extracts are incubated at 37° C. for 2 hours in 20 mM Tris (pH 7.6), 5 mM MgCl$_2$, 2 mM DTT, ATP-regenerating system (10 μg creatine phosphokinase and 10 mM creatine phosphate), 1 mM ATP, and 25 mg of ubiquitin in the presence and absence of huE3α polypeptide. Subsequently, the reactions are terminated with 20% TCA. After centrifugation, the concentrations of tyrosine in the supernatant is measured by fluorescence spectroscopy according to the method of Waakkes and Udenfriend (*J. Lab. Clin. Med.*, 50: 733-736, 1957).

Measurement of radiolabeled proteins will also indicate if huE3α polypeptide exhibits E3α family biological activity. Rat skeletal muscle homogenates are incubated at 37° C. for 2 hours with $^{125}$I-labeled N-end pathway substrates, such as $^{125}$I-lyzozyme and $^{125}$I-lactalbumin, in the presence and absence of huE3α polypeptide. Following the incubation, 20% TCA is added to precipitate the radioactivity. The release of TCA-soluble radioactivity is measured using a gamma counter and correlates the rate of protein degradation. The addition of huE3α polypeptide should increase the rate of protein degradation in both of these assays.

EXAMPLE 8

Identification of Modulators of the Biological Activity of huE3α Polypeptides

The assays described in Example 7 demonstrate preferred methods to measure the biological activity of huE3α as an ubiquitin ligase. These methods are also useful for identifying modulators of huE3α ubiquitin ligase activity.

The rate limiting step of ubiquitin conjugation consists of E3α catalyzing the transfer of the activated ubiquitin molecule to the target protein. The rate of ubiquitination modulated by huE3α can be measured in dissected rat skeletal muscles as described in Example 7. The addition of potential huE3α modulators (inhibitors or stimulators) to this system will allow for the identification of E3α stimulators and inhibitors by virtue of their ability to modulate the level or rate of ubiquitin conjugation to the target protein. If the addition of the modulator decreases the rate of huE3α-modulated ubiquitin conjugation, it is considered a huE3α inhibitor. If the modulator increases the rate of ubiquitin conjugation it is considered a stimulator.

The effect of huE3α modulators can also be determined by measuring their effect on the rate of protein turnover as described in Example 7. If huE3α exhibits the biological activity of an ubiquitin ligase, it will induce protein degradation. Protein turnover is measured by quantitating tyrosine release or the degradation of radioactively labeled N-end pathway substrates in the presence of E3α modulators. The addition of effective huE3α modulators will either increase or decrease the rate of protein degradation.

EXAMPLE 9

Identification of huE3αI Single Nucleotide Polymorphisms (SNP)

A BLAST search of the Celera Human Genome database was conducted using the huE3αI cDNA sequence (SEQ ID NO: 1) as a probe. The sequences identified in the search were used to manually assemble a polynucleotide sequence (SEQ ID NO: 18) which was discovered to have a single nucleotide mismatch at nucleotide 5397 of the huE3αI cDNA sequence (SEQ ID NO: 1). The polynucleotide sequence of SEQ ID NO: 18 contains a huE3αI SNP with a change of a cytosine to a thymidine at position 4702, which caused the predicted amino acid sequence of SEQ ID NO: 2 to change from an Arg residue to a W (Trp) residue at position 1508.

PCR was carried out to confirm the polynucleotide sequence of huE3αI cDNA. Primers were designed to flank the mismatch as follows: 5' AGAAGGAGAGTACAGTG-CACTC3' (SEQ ID NO: 20) and 5'CGAAAGCATCCTGTC-CTCTG (SEQ ID NO: 21). PCR was carried out as described in Example 1 with the Marathon-Ready cDNA library (Clontech cat no. 7413-1) from which huE3αI cDNA was cloned. The PCR reactions resulted in 8 individual PCR products which had identical sequences to the huE3αI SNP (SEQ ID NO: 18).

These experiments have confirmed the sequence of a huE3αI SNP set out in SEQ ID NO: 18 wherein the nucleotide at position 4657 is a cytosine. Accordingly, the correct predicted amino acid sequence is set out as SEQ ID NO: 19, wherein the residue at position 1573 is R (Arg).

EXAMPLE 10

Human E3αI and E3αII Stimulate Ubiquitination

To confirm that huE3αI and huE3αII have the predicted enzymatic activity of stimulating ubiquitin conjugation, ubiquitination reactions were carried out in 293 cells. Cultures of 293T cells (ATCC accession no. CRL1573) were transfected with huE3α I or huE3αII full length cDNA (SEQ ID NOS: 1 or 3, respectively) that had been subcloned into pcDNA3.1 vector (Invitrogen) under the control of the CMV promoter using Lipofectamine reagent 2000 (Gibco, cat no. 11668-027) according to the manufacture's instructions. As a control, 293T cultures were transfected with pcDNA3.1 vector without the cDNA insert. The transfected cells were lysed in ice-cold lysis buffer (50 mM Tris-HCl (pH 8.0), 2 mM DTT, 5 mM $MgCl_2$) in the presence of Sigma P8340 protease inhibitor cocktail (containing 4-(2-aminoethyl)benzenesulfonyl fluoride, pepstatin A, E-64, bestatin, leupeptin and aprotinin) at 100 μl/$10^7$ cells. The crude lysates were then centrifuged at 10,000 g for 10 minutes.

The supernatants prepared from vector- (Control), human E3α-1- (hu-E3α-I) or human E3-αII- (hu-E3α-II) transfected cells were subjected to ubiquitination reactions. To measure ubiquitination of endogenous proteins, 30 μg of cell lysate was incubated with $^{125}$I-ubiquitin (0.15 mg/ml, approximately $10^7$ cpm) in a total volume of 40 μl in a buffer containing 50 mM Tris, pH 8.0, 2 mM DTT, 5 mM $MgCl_2$, 2 mM adenosine 5'-[-thio]triphosphate (ATP S), 50 μg/ml ubiquitin aldehyde, MG132 20 μg/ml and protease inhibitor cocktail (Sigma P8340) at 37° C. for 30 minutes. Reactions were stopped by adding sample buffer and were subjected to 12% SDS PAGE. The gels were then dried and autoradiographed.

Figure 4:
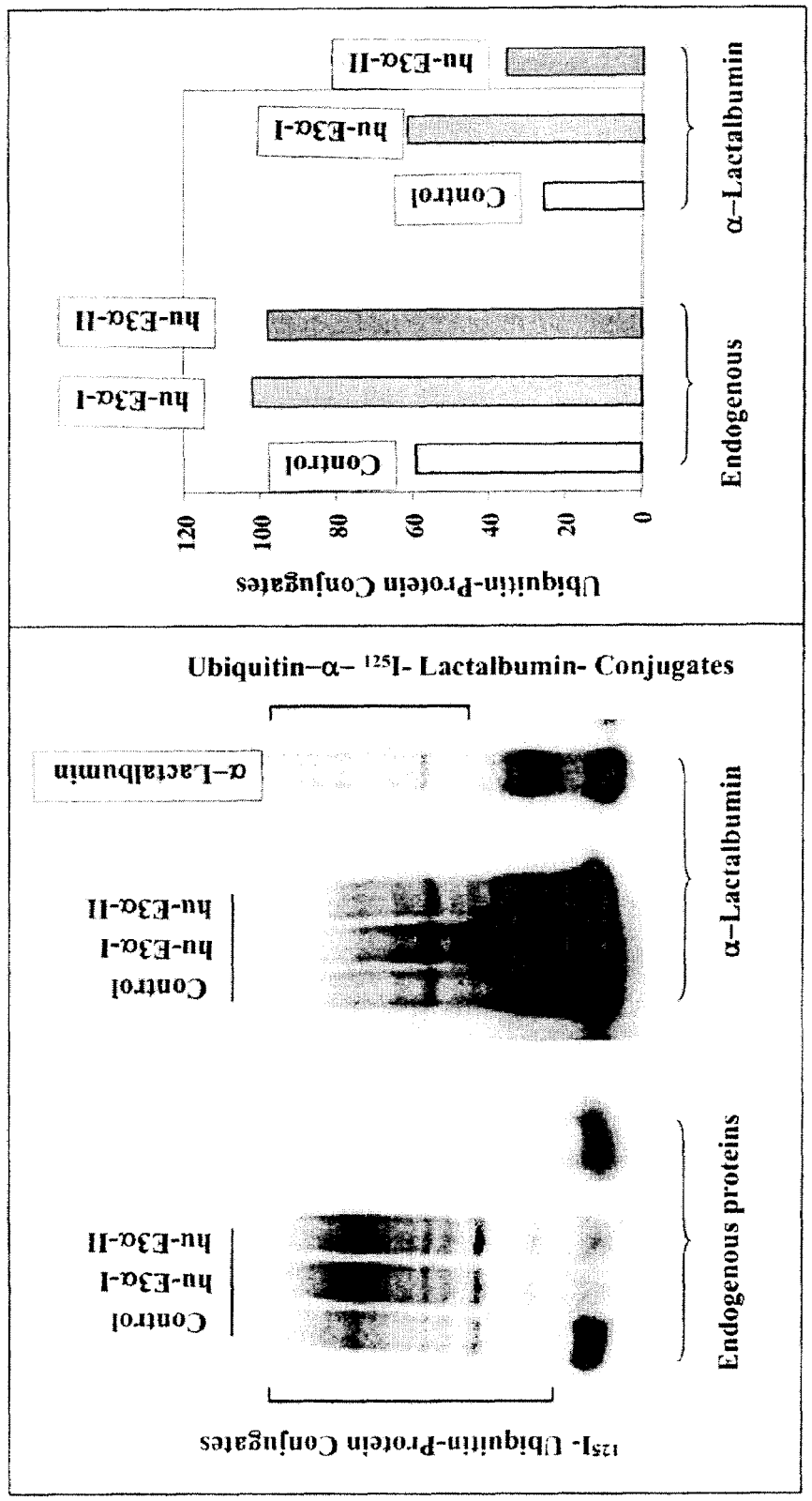
FIG. 4 shows that transfection of 293T cells with huE3αI and huE3II cDNA stimulates the ubiquitination of endogenous proteins and exogenously added α-lactalbumin in cell lysates. The left panel shows the results of gel-shift assays of ubiquitinated proteins. The high molecular weight bands (above 18 kDa for endogenous proteins and above 33 kDa for α-lactalbumin) are identified as "$^{125}$I Ubiquitin-protein conjugates". The left panel plots the quantitative measurement of ubiquinated proteins measured by a PhosphoImager.

The ubiquitination of α-lactalbumin, a known substrate for N-end Rule Ubiquitination was also measured with the 239T transfected cells. For these reactions, 30 μg of cell lysate proteins was incubated with 0.15 mg/ml $^{125}$I-α-Lactalbumin and 0.25 mg/ml unlabeled ubiquitin in a total volume of 40 μl in a buffer containing 50 mM Tris (pH 8.0) 2 mM DTT, 5 mM $MgCl_2$, 2 mM adenosine 5'-[-thio]triphosphate (ATP S), ubiquitin aldehyde 50 ug/ml, 20 μg/ml MG132 and protease inhibitor cocktail (Sigma P8340) at 37° C. for 30 minutes. Reactions were stopped by adding sample buffer and each reaction was run of a 8% SDS PAGE was performed. The gels were then dried and autoradiographed The amount of radioactivity incorporated into high molecular weight bands denoted as "ubiquitin-protein conjugates" in FIG. 4 (above 18 kDa for endogenous proteins and above 35 kDa for α-Lactalbumin) were quantitated by using PhosphaImager and plotted (right panel). These reactions indicated that recombinant expression of huE3αI or huE3αII in 293 cells lead to accelerated ubiquitination of endogenous cellular proteins and ubiquitin conjugation to α-lactobumin, a bona fide N-end rule substrate.

To further substantiate the enzymatic activity of huE3αI and huE3 μl, ubiquitin conjugation to endogenous cellular proteins were measured in cultured muscle cell lines. Cultures of murine $C_2C_{12}$ or rat L6 myotube cells (ATCC accession nos. CRL-1772 and CRL-1458, respectively) were transfected with huE3αI or huE3αII full length cDNA under control of the CMV promoter using Lipofectamine 2000 Reagent (Gibco). Mock transfection with the pcDNA3.1 vector without a cDNA insert was performed as a control. Cell lysates were prepared as described above for the 293T cells and the resulting supernatants were used in ubiquitin conjugation reactions. For each reaction, 30 μg of $C_2C_{12}$ or L6 myotube cell lysate was incubated with $^{125}$I-ubiquitin (0.15 mg/ml, approximately ×$10^7$ cpm) in a total volume of 25-30 μl in a buffer containing 50 mM Tris, pH 8.0, 2 mM DTT, 5 mM MgCl2, 2 mM adenosine 5'-[-thio]triphosphate (ATP S), 50 μg/ml ubiquitin aldehyde, 20 μg/ml MG132 and protease inhibitor cocktail (Sigma P8340) at 37° C. for 30 minutes. Reactions were stopped by adding sample buffer and were subjected to 12% SDS PAGE. The gels were then dried and autoradiographed.

Figure 5:
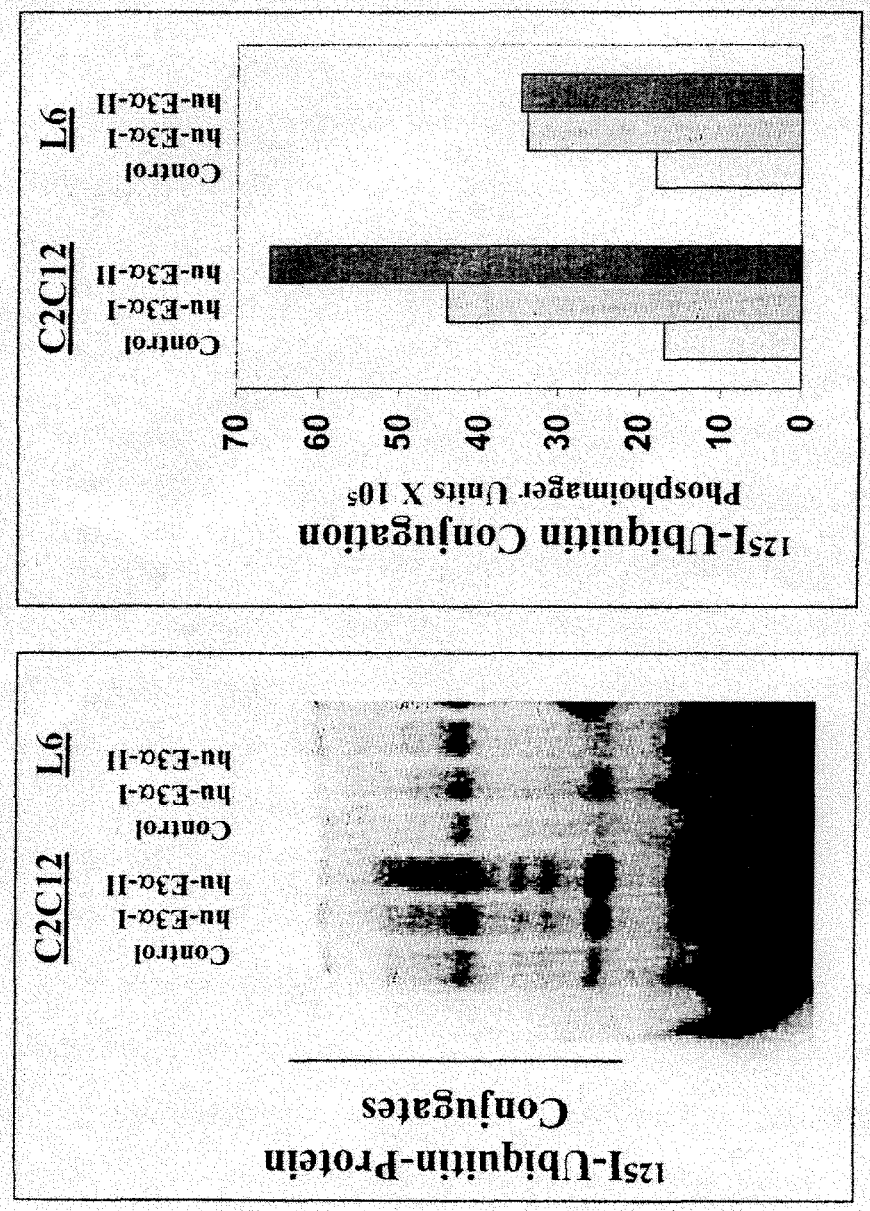
FIG. 5 shows that transfection of $C_2C_{12}$ and L6 myotube cells with huE3αI and huE3II cDNA stimulates the ubiquitination of endogenous proteins cell lysates. The left panel shows the ubiquitinated high molecular weight bands (above 18 kDa for endogenous proteins) as "$^{125}$I-Ubiquitin-protein conjugates". The left panel plots the quantitative measurement of ubiquinated proteins measured by a PhosphoImager.

The amount of ubiquitinated muscle proteins ($^{125}$I-Ubiquitin protein conjugates) were quantitated as the total radioactivity incorporated into high molecular weight bands (above 18 kDa) using a Phsophoimager as shown in FIG. 5 (left panel). These reactions indicated that transfection of huE3αI and huE3αII increased ubiquitination of cellular proteins 2-3 fold (see FIG. 5, right panel) in murine $C_2C_{12}$ and rat myotube cultures.

EXAMPLE 11

Expression of Human E3αI and Human E3αII is Unregulated During Cachexia Disease States The Yoshida Hepatoma-130 (YAH) cachexia rat model as described in Baracos et al. (*Am. J. Physiol.*, 268(5 Pt 1): E996-1006, 1995) was used to determine if huE3αI and huE3αII are upregulated in cachexia disease states. For tumor implantation, female Sprague-Dawley rats of the Buffalo strain from a colony maintained at the University of Alberta were used as the host for the YAH tumor cells. Tumor cell stocks were maintained in liquid nitrogen and used after two passages in recipient female animals of the same strain. Rats were housed in individual wire mesh cages in a temperature (24° C.)- and humidity (80%)-controlled room on a 12:12-h light-dark cycle. Rats were fed ground laboratory chow (Continental Grain, Chicago, Ill.) containing 24% crude protein.

Rats were allocated by initial body weight to three groups such that the sizes (mean±SE) of the animals receiving each treatment were similar (~200 g). Two different treatments were compared: YAH-bearing and pair-fed control rats. The pair-fed rats, which received one meal per every day at 9.00 am, were fed on the basis of their body weights, the same amount of food consumed by the tumor-bearing rats. On days 1, 2, 3, 4 and 5 after tumor-implantation, food intake was determined in preliminary experiments to be 9, 7.5, 5.3, 1.5, and 0.9% respectively, of initial body weight per day. Rats were implanted with 100 ml of ascites fluid containing YAH cells from a single donor animal. The control rats were implanted with an equal volume of saline buffer. Rats were sacrificed by $CO_2$ asphyxiation after 3 and 5 days, and epitrochelaris, EDL, soleus, medial gastrocnemius muscles were rapidly dissected and the gastrocnemius muscles were weighed. Tissues were frozen immediately in liquid nitrogen and stored at −70° C. until use.

The gastrocnemius skeletal muscle weights in YAH-130 tumor bearing rats were significantly lower than those measured from the pair-fed control rats. As indicated in the Table V below, the YAH-130 tumor bearing rats underwent muscle wasting by day 3 after tumor implantation which was more apparent at day 5 after implantation. The muscle weights are calculated (in grams) as the mean±standard error.

| Days after Tumor Implantation | n | Pair Fed Control (in grams) | Tumor-Bearing (in grams) | Percent Change |
|---|---|---|---|---|
| 3 days | 8 | 530 ± 14.6 | 508 ± 7.3 | −4.3% |
| 5 days | 8 | 593 ± 8.1 | 443 ± 9.4 | −25.3% | n = number of animals

The rate of ubiquitin conjugation of the endogenous muscle proteins were carried out as described in Example 10 using the skeletal muscles from the YAH tumor-bearing rats. The frozen gastrocnemius muscles collected (via dissection at sacrifice) from 6 tumor-bearing rats were combined. The muscle extracts (20% weight/volume) were prepared by homogenizing the muscles in a buffer containing 50 mM Tris HCl (pH 8.00), 5 mM $MgCl_2$, 2 mM DTT, protease inhibitor cocktail (Sigma P8340) and 10% glycerol. The homogenates were then centrifuged at 40,000 g for 1 hr and the resulting supernatants were used as crude muscle extracts.

For some assays, the crude muscle extracts were fractionated further by chromatography on DEAE-cellulose (Whatman, Clifton, N.J.) to remove endogenous ubiquitin as described by Soloman et al. (*Proc. natl. Acad. Sci. U.S.A.,* 95: 12602-7, 1998). The bound material Fraction II, which contained most of the ubiquitin conjugating enzymes were eluted with 50 mM Tris, pH 8.0 containing 0.5M NaCl and 1 mM DTT. Both crude extracts and Fraction II were dialyzed prior to use for ubiquitination assay against buffer containing 20 mM Tris, pH 8.0, 2 mM DTT, 5 mM MgCl2, and 10% glycerol and stored at 70° C. until use. Crude muscle extracts were used for ubiquitin conjugation to 125I-α-lactalbumin. Fraction II was used when rates of endogenous skeletal muscles proteins were compared and also when effects of E3α inhibitors on skeletal muscle protein ubiquitination were tested.

The Fraction II from both tumor-bearing and pair-fed control rats were subjected to ubiquitination reactions of the endogenous muscle proteins as described in Example 10 in the presence of 20 µg/ml of bestatin and 10 mM of either the E3α selective inhibitor arginine methyl ester (Arg-ME) or the control alanine methyl ester (Ala-ME) (Sigma Chemicals, St. Louis Mo.). The reactions were incubated at 37° C. for 20 minutes and the $^{125}$I-Ubiquitin conjugates were resolved by 12% SDS PAGE as described in Example 10.

Figure 6:
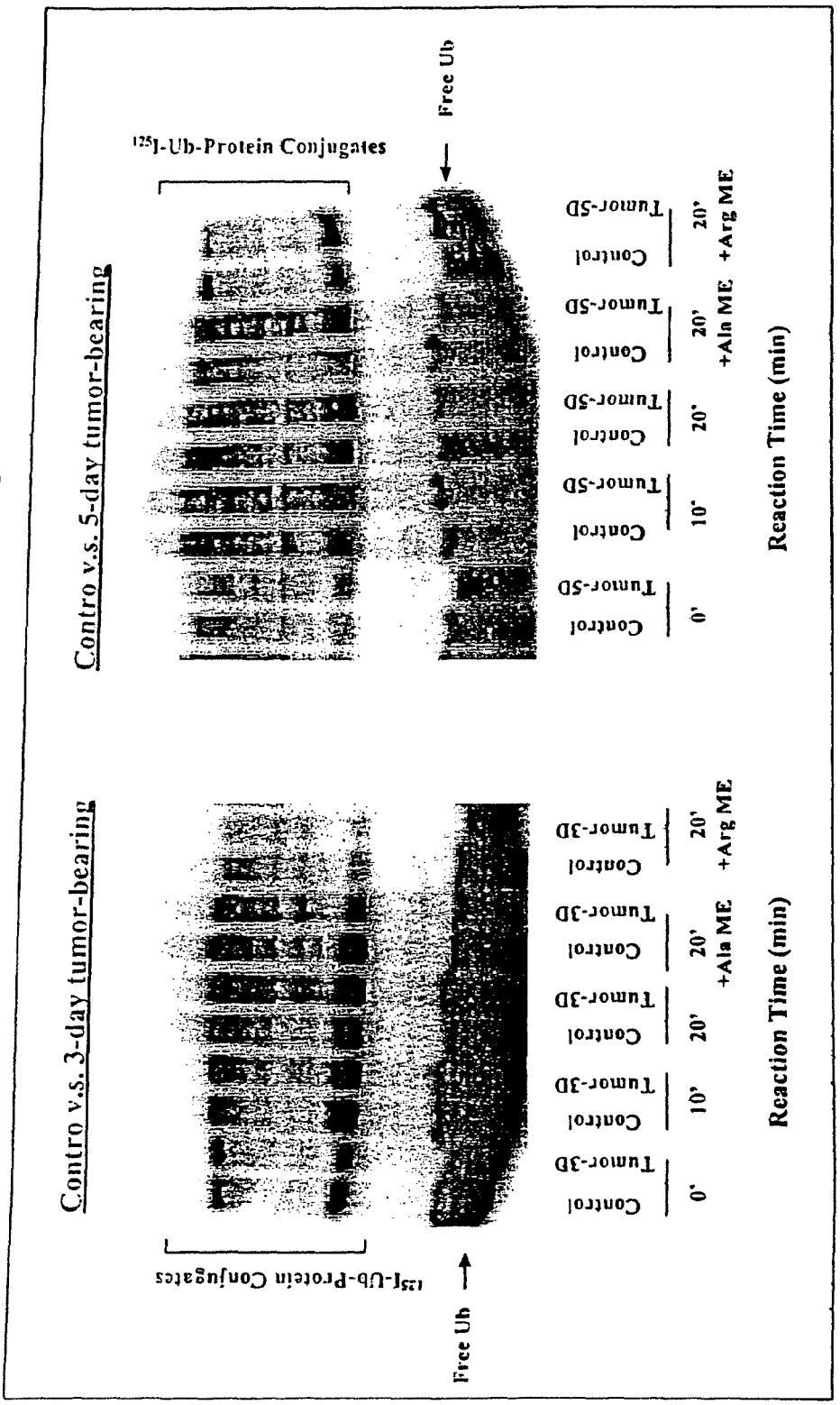
FIG. 6 shows the $^{125}$I-ubiquitin conjugation to endogenous muscle proteins and its sensitivity to selective inhibitors of E3α in muscle extracts from control and YAH-tumor bearing rats. Gel-shift assays of muscle extracts from control and tumor-bearing rats revealed the ubiquitinated high molecular weight bands (above 18 kDa) denoted as "$^{125}$I-Ubiquitin-protein conjugates". The left panel is muscle extracts collected 3 days post-implantation and the right panel is muscle extracts collected 5 days post-implantation.

As shown in FIG. 6, the tumor-bearing rats exhibited accelerated muscle protein ubquitination. The increase in ubiquitination within the rat skeletal muscles of the tumor-bearing rats was attributable to the activation of the E3α/N-end rule pathway, since the addition of E3α specific inhibitor arginine methylester virtually abolished the accelerated ubiquitination activity (see lanes 9 and 10 on FIG. 6).

Figure 7:
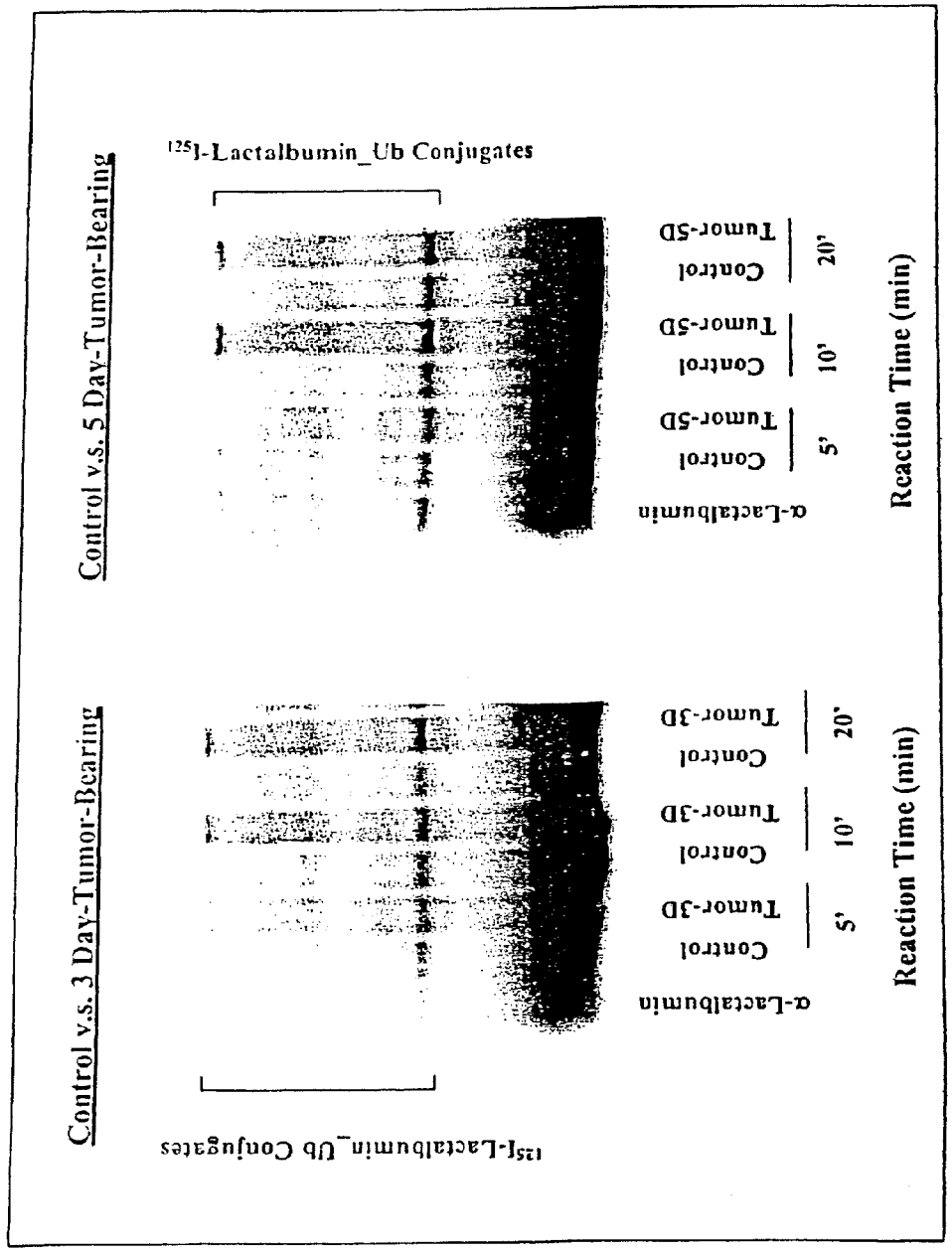
FIG. 7 shows the ubiquitin conjugation to $^{125}$I-α-lactalbumin in extracts from atrophying muscles in YAH-tumor bearing rats as western blots of muscle extracts from control and tumor-bearing rats with the ubiquitinated high molecular weight bands (above 33 kDa) as "$^{125}$I-Lactalbumin-ubiquitin conjugation". The left panel is muscle extracts collected 3 days post-implantation and the right panel is muscle extracts collected 5 days post-implantation.

To further establish the role of huE3αI and huE3αII in the N-end rule pathway in muscle wasting in the rat cachexia model, the rates of ubiquitination of N-end rule substrate α-lactalbumin was measured in skeletal muscle extracts from control and tumor-bearing mice. $^{125}$I-α-lactalbumin (0.15 mg/ml) was incubated with crude skeletal muscle extracts (2 mg/ml) in the presence of 0.25 mg/ml of ubiquitin at 37° C. for 0 or 20 minutes as described in Example 10. As shown in FIG. 7, the atrophying muscles dissected from the tumor-bearing rats exhibited increased ubiquitin conjugation to $^{125}$I-α-lactalbumin Northern blot analysis was carried out to measure the huE3αI and huE3αII mRNA expression in the gastrocnemius muscles of YAH-130 tumor-bearing mice. RNA from the dissected muscles was isolated with Trizol Reagent (Gibco, cat: 15596-018). The final RNA pellets were resuspended in DEPC-$H_2$O and 20 µg of total RNA per lane were separated by electrophoresis through 1% agarose gels. The separated RNA was transferred to nylon membranes and cross-linked to the filter by exposure to ultraviolet light.

The cDNA probes were generated by PCR with the following primers: for Hu-E3α-I probe: 5' primer, AGG AAG CTG TGG TCA TGT (SEQ ID NO: 22); 3' primer, GTT AGG AAG AAC AAC TG (SEQ ID NO: 23); for Hu-E3α-II probe: CTA AAG AAC AGC GAA GGC AAC AG (SEQ ID NO: 24); 3' primer, CGC AGC TAC CCC AAC ACA TTA T (SEQ ID NO: 25). PCR was carried out for 30 cycles at 94° C. for 45 seconds, 50-58° C. for 45 seconds, and 72° C. for 1 minutes using a commercially available kit (Boehringer Mannheim, cat: 1578553,). The PCR product was cloned into the pCR2.1 vector using the Original TA Cloning kit (Invitrogen). After digestion with EcoRI, the cloned PCR product was sequenced and confirmed.

The resulting cDNA probes were radiolabeled with [$^{32}$P] dCTP using the Prime-it RMT labeling kit (Stratagene, cat: 300392). Membranes were prehybridized and hybridized (with the cDNA probes) in buffer containing 1% BSA, 7% SDS, 0.5 M Sodium Phosphate (pH 7.0), 1 mM EDTA. Subsequently, the blots were washed in buffer containing 1% SDS, 0.04 M Sodium Phosphate, 1 M EDTA, by the method of Church and Gilbert (*Proc. Natl. Acad. Sci. U.S.A.* 81:1991-1995, 1984) and exposed to radiographic film at −70° C. overnight.

Figure 8:
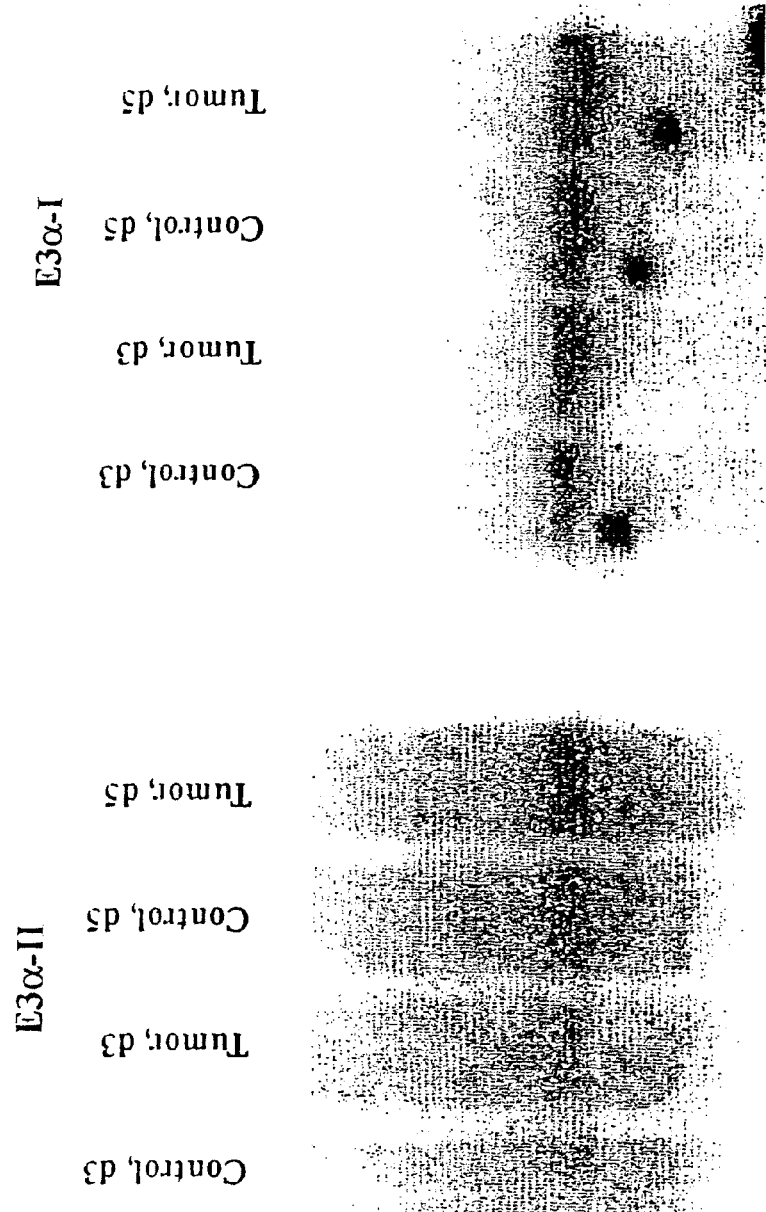
FIG. 8 shows Northern blot analysis of E3αI and E3αII expression in skeletal muscle in YAH-130 experimental cachexia model. The RNA expression from pair-fed control rats and tumor-bearing rats were compared 3 days (3d) and 5 days (5d) post-implantation.

As shown in FIG. 8, the expression of huE3αII mRNA was increased at day 3 post-tumor implantation (see left panal) but the level of huE3αI had not changed significantly at day 3 (see right panel). This coincides with the time point when the significant decrease in muscle mass was detectable in the C26 tumor-bearing mice (See Table VI in Example 12). The expression of both huE3αI and huE3αI was elevated at day 5 post-tumor implantation in the tumor bearing rats. This corresponds to a cachexia state with severe muscle wasting.

EXAMPLE 12

Expression of Human E3αI and Human E3αII in a Murine Cancer Cachexia Model of C26 Tumor Bearing Mice The Colon-26 (C-26) tumor model of cachexia was used to demonstrate the role of huE3αI and huE3αII as described in Matsumoto et al., *Brit. J. Can.* 79: 764-9 (1999) and Tanaka et al., *Can. Res.,* 50: 2290-5 (1990). Seventy-two week old male CDF1 mice were injected in the left flank with 0.2 ml containing either $0.5 \times 10^6$ C26 cells or PBS. Following injection, body weight and food intake was observed daily. The pair fed control mice (generated as described in Example 11) were fed the daily average food intake of the tumor bearing group. On the day 12 or 17 post-injection, tumor bearing mice and pair fed control mice were sacrificed by $CO_2$ asphyxiation. Subsequently, a terminal serum sample was collected and the kidney, heart and gastrocnemius muscles were rapidly dissected and weighed. The resulting C26 tumors were also weighed. The tissues were frozen on dry ice and stored at −70° C.

The wet weight of the skeletal muscles from the tumor-bearing mice were significantly less than the weight of those from the pair-fed control mice as shown below in Table VI:

| Days after Tumor Implantation | n | Pair Fed Control (in grams) | Tumor-Bearing (in grams) | Percent Change |
|---|---|---|---|---|
| 12 days | 12 | 0.127 ± 0.007 | 0.116 ± 0.0072 | −8.6% |
| 12 days | 12 | 0.117 ± 0.009 | 0.087 ± 0.001 | −26% | n = number of animals

RNA was isolated at day 12 and day 17 from the gastrocnemius muscle and cardiac muscle from the C26 tumor-bearing and pair-fed control mice as described in Example 11. Northern blot analysis was carried out by loading 20 μg of total RNA per lane and separating by electrophoresis through 1% agarose gels. The separated RNA was transferred to nylon membranes and cross-linked to the filter by exposure to ultraviolet light.

The cDNA probes were generated by PCR with the following primers: for mouse E3α-I probe: 5' primer, TTT CTT CCA TTC CCT GCA TAC A (SEQ ID NO: 26), 3' primer, CAA AAC TTT ATA AAG GTG CCC GTA A (SEQ ID NO: 27), and for Mouse E3α-II probe: 5' primer, ATT CCC TGC ATG CAC TTC AGT AA (SEQ ID NO: 28), 3' primer, CAT TCC CTG CAT GCA CTT CAG SEQ ID NO: 29). PCR was carried out for 30 cycles at 94° C. for 45 seconds, 50-58° C. for 45 seconds, and 72° C. for 1 minutes using a commercially available kit (Boehringer Mannheim cat: 1578553,). The PCR product was cloned into the pCR2.1 vector using the Original TA Cloning kit (Invitrogen). After digestion with EcoRI, the cloned PCR product was sequenced and confirmed.

The resulting cDNA probes were radiolabeled with [$^{32}$P] dCTP using the Prime-it RMT labeling kit (Stratagene, cat: 300392). Membranes were prehybridized and hybridized (with the cDNA probes) in buffer containing 1% BSA, 7% SDS, 0.5 M Sodium Phosphate (pH 7.0), 1 mM EDTA. Subsequently, the blots were washed in buffer containing 1% SDS, 0.04 M Sodium Phosphate, 1 M EDTA, by the method of Church and Gilbert (*Proc. Natl. Acad. Sci. U.S.A.* 81:1991-1995, 1984) and exposed to radiographic film at −70° C. overnight.

Figure 9:
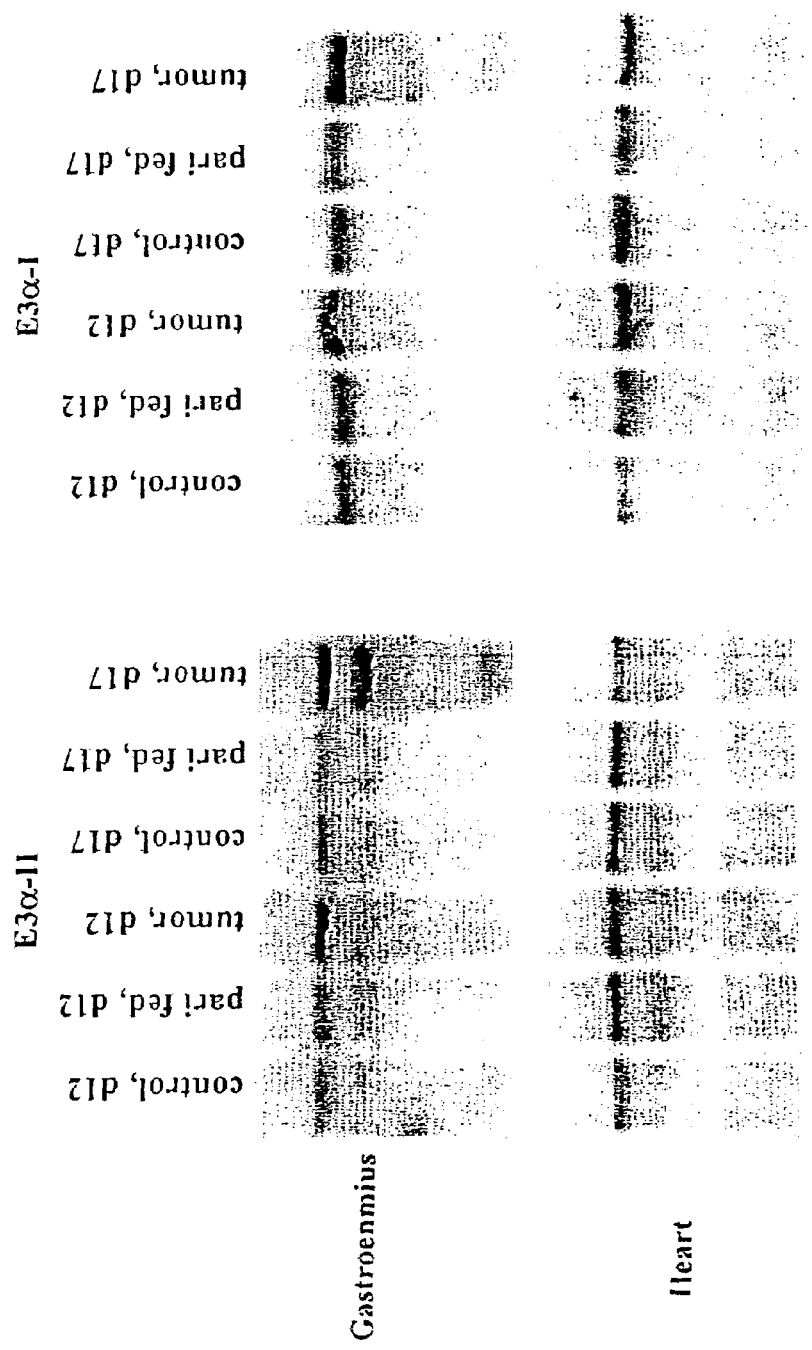
FIG. 9 shows Northern blot analysis of E3αI and E3αII expression in skeletal (gastrocnemius) muscle and cardiac muscle in the C26 experimental cacheixia model. The RNA expression from pair-fed control rats and tumor-bearing mice were compared 12 days (12d) and 17 days (17d) post-implantation.

As shown in FIG. 9, at day 12 after tumor-implantation tehrere was a clear increase in huE3αII mRNA expression in the skeletal muscles of tumor-bearing mice. Expression of both huE3αI and huE3αII was increased at day 17 post-implantation. Increased expression of huE3αII mRNA coincides with the time point when the significant decease in muscle mass became detectable in tumor-bearing mice (See Table VI above). The expression of huE3αI and huE3αII remained unchanged in the cardiac muscle of the tumor-bearing mice. This corresponds to a cachexia state with severe muscle wasting.

The data described in both Examples 11 and 12 show that in experimental cachexia models, there was a sharp rise in the rate of ubiquitination in skeletal muscle tissues. The accelerated ubiqutination is due largely to the activation of E3α, since addition of the E3α-selective inhibitor, arginine methylester, virtually abolished all the increased ubiquitination activities. In addition, the data demonstrated that in two widely used experimental models of cachexia (murine C26 tumor-bearing model and rat YAH-130 tumor-bearing model), the mRNA levels of E3α-I and E3α-II increase significantly and specifically within skeletal muscle during the course of cachexia and muscle wasting. In these disease models and during the course of cachexia, the induction of E3α-II occurred earlier than that of E3α-I and coincided with the early onset of muscle wasting. During the late stage of cachexia, both E3α-I and E3α-II were markedly induced when muscle wasting became pronounced. Therefore, the results suggest that E3α-II may play a more critical role in cachexia, although both E3α-I and E3α-II are apparently involved in the disease process.

EXAMPLE 13

Treatment of Muscle Cells with TNFα and IL-6 Leads to Increased Expression of Human E3αII and Increased Ubiquitination Treatment with the proinflammatory cytokines, TNFα and IL-6, caused the induction of huE3αII in $C_2C_{12}$ myotube cultures. $C_2C_{12}$ myoblasts were cultured in 100-mm dishes in an atmosphere of 5% $CO_2$ at 37° C. in DMEM supplemented with 10% FBS and L-glutamine to reach 100% confluence. Myoblast differentiation was induced with DMEM supplemented with 2% horse serum and L-glutamine for 96 hours. Differentiated myotubes were then treated with TNFα (10 ng/ml; R&D Systems cat no. 210-TA) or IL-6 (10 ng/ml; R&D Systems cat no. 206-IL) for 3 days and 5 days.

After the 3 or 5 day incubation, RNA from differentiated $C_2C_{12}$ cultures was isolated with Trizol Reagent and Northern blot analysis was carried out as described in Example 11. Isolated RNA from untreated $C_2C_{12}$ cultures were used as a control. The blots were hybridized with a $^{32}$P-labeled cDNA probes specific for muE3αI (lower panels) and muE3αII (upper panels). The probes were generated as described in Example 12.

Figure 10:
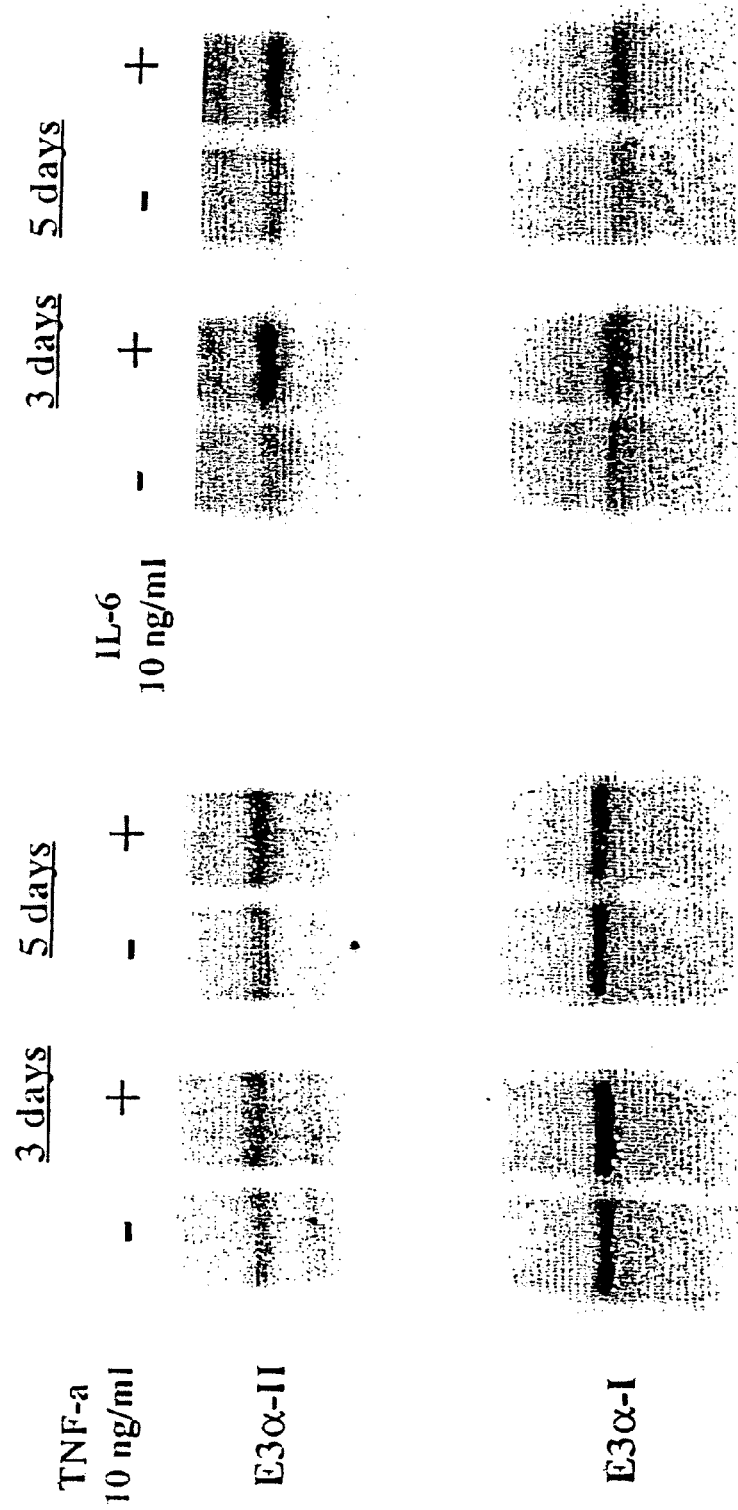
FIG. 10 shows induction of E3αII expression by proinflammatory cytokines TNFα and IL-6 in $C_2C_{12}$ myotube cultures on Northern blots. The RNA levels of E3αII (upper panel) and E3αI (lower panel) were detected 3 or 5 days after treatment with TNFα (left panel) and IL-6 (right panel).

As shown in FIG. 10, the expression of muE3αII was markedly increased in the cells treated with TNFα or IL-6 (See upper panels). Conversely, the expression of muE3αI was not drastically induced in response to proinflammatory cytokine treatment. This data indicates a role for E3αII in cytokine-mediated protein catabolism and muscle wasting.

Figure 11:
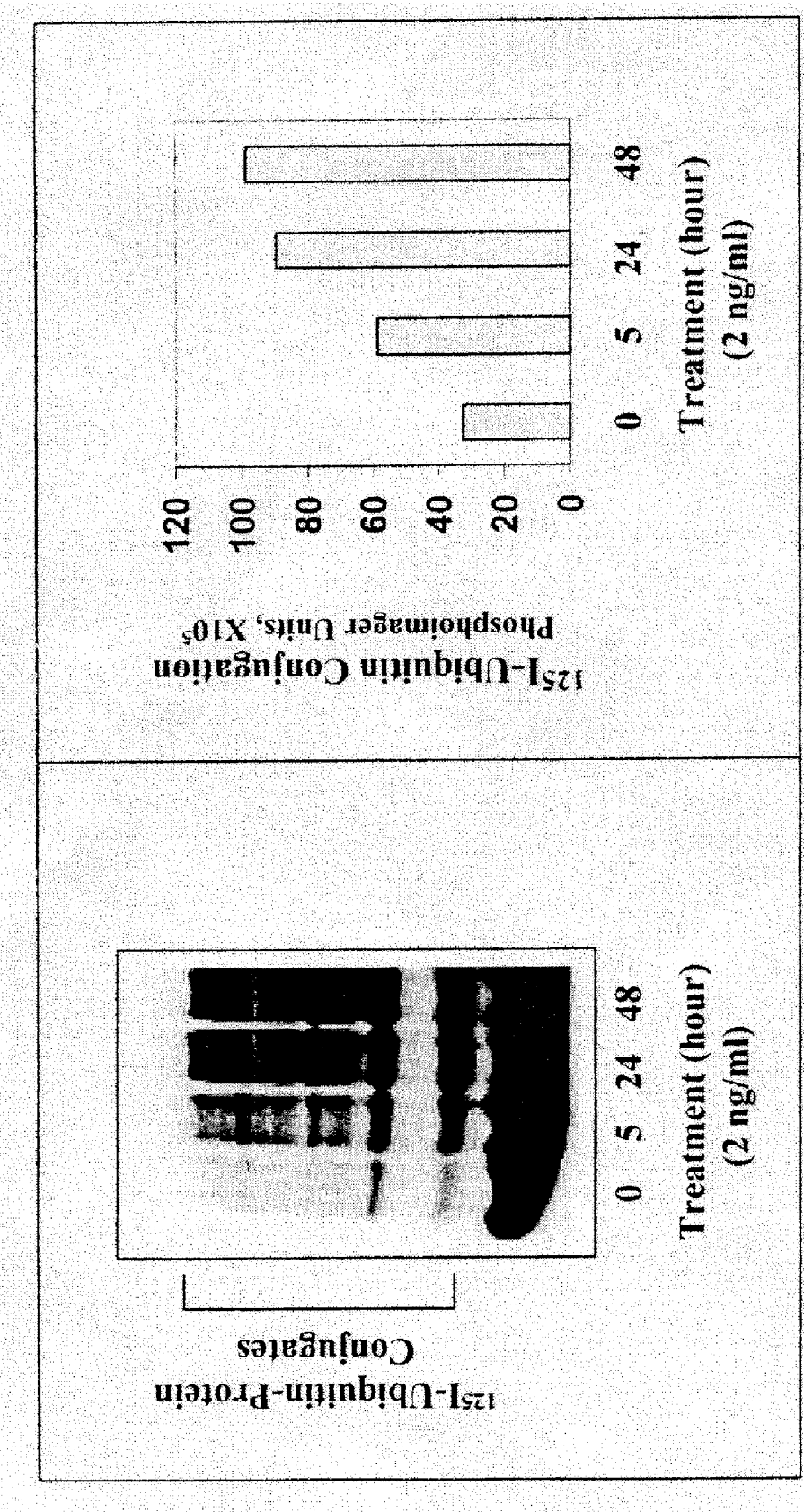
FIG. 11 shows that IL-6 treatment causes a time-dependent acceleration of ubiquitination in differentiated $C_2C_{12}$ cells. This data exhibits the results of a gel-shift assay showing the ubiquitinated high molecular weight bands denoted as "$^{125}$I-ubiquitin protein conjugates" (left panel) and is quantitated by a PhosphoImager in the right panel.

Cytokine treatment also resulted in accelerated ubiquitination in differentiated $C_2C_{12}$ cells. $C_2C_{12}$ cells were differentiated for 5 days to allow formation of myotubes. The differentiated myotubes were treated with 2 ng/ml of IL-6 for 5, 24 or 48 hours. After the incubation, the cells were lysed and $^{125}$I-Ubiquitin conjugation was carried out as described in Example 10. As shown in FIG. 11, IL-6 treatment resulted in a marked increase in ubiquination of cellular proteins (left panel) which was detectable 5 hours post-treatment. The increase in ubiquination was time dependent (see right panel).

Figure 12:
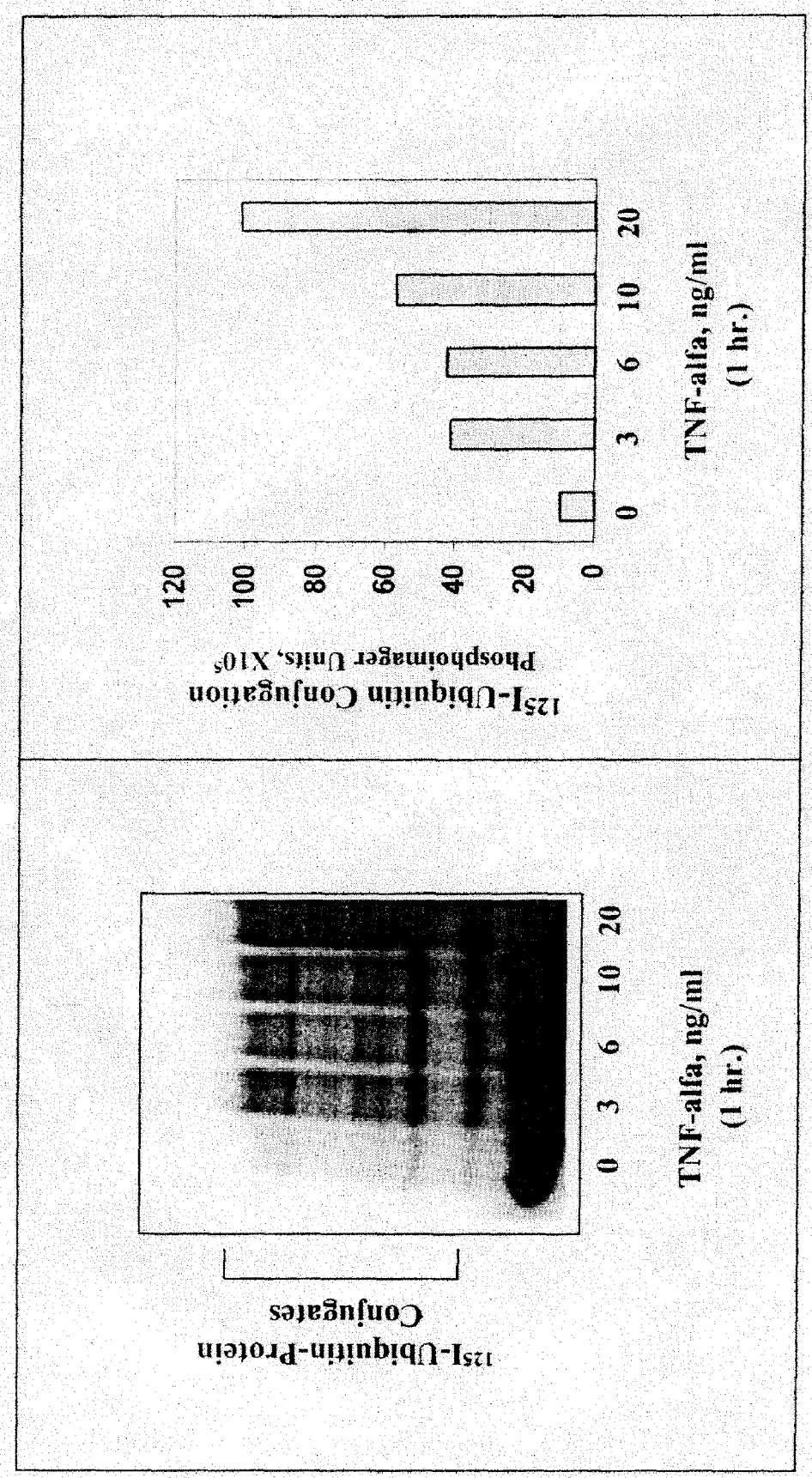
FIG. 12 shows that TNFα treatment causes a does-dependent acceleration of ubiquitination in differentiated $C_2C_{12}$ cells. This data is displayed as gel-shift assay results with the ubiquitinated high molecular weight bands denoted as "$^{125}$I-ubiquitin protein conjugates" (left panel) and is quantitated by a PhosphoImager in the right panel.

Differentiated $C_2C_{12}$ myotubes were also treated with increasing concentrations of TNFα (0, 3, 6, 10, 20 ng/ml) for one hour. This treatment resulted in a dose dependent increase in $^{125}$I-ubiquitin conjugation of cellular proteins as shown in FIG. 12.

TNFα and IL-6 are major proinflammatory cytokines known to be involved in cachexia and tissue wasting. The data reveals that these cytokines significantly upregulate the mRNA expression of E3αII in muscle cells and stimulate muscle protein ubiquitination. Proinflammatory cytokines, such as TNFα, IL-6, IL-1, interferon-gamma, CNTF and leptin, have been shown to be involved in disease states of cachexia and protein/tissue wasting, including cancer cachexia, renal cachexia (energy-protein malnutrition), burn cachexia and AIDS wasting. These findings that TNFα and IL-6 induce the expression of E3α II (FIG. 9) and stimulate protein ubiquitination in muscle cells (FIGS. 10 and 11) strongly suggest that E3α II is critical target via which various cachectic factors induce protein catabolism and cachexia/muscle wasting. This argument is further supported by our finding that recombinant expression of E3α II by cDNA transfection leads to marked protein ubiquitination in myotube cultures (FIG. 5).

While the present invention has been described in terms of the preferred embodiments, it is understood that variations and modifications will occur to those skilled in the art. Therefore, it is intended that the appended claims cover all such equivalent variations which come within the scope of the invention as claimed.

What is claimed is:

1. An isolated antibody or fragment thereof that specifically binds the polypeptide comprising the amino acid sequence selected from the group consisting of:
   (a) the amino acid sequence set forth in SEQ ID NO: 2;
   (b) an amino acid sequence that is at least 95 percent identical to the amino acid sequence of SEQ ID NO: 2, wherein the polypeptide has the E3α ubiquitin ligase activity of the polypeptide set forth in SEQ ID NO: 2; and
   (c) the amino acid sequence set forth in SEQ ID NO: 2 with 1 to about 100 conservative amino acid substitution(s), wherein the polypeptide has the E3α ubiquitin ligase activity of the polypeptide set forth in SEQ ID NO: 2.

2. The antibody or fragment thereof of claim 1 that is a humanized antibody or fragment thereof.

3. The antibody or fragment thereof of claim 1 that is a human antibody or fragment thereof.

4. The antibody or fragment thereof of claim 1 that is a polyclonal antibody or fragment thereof.

5. The antibody or fragment thereof of claim 1 that is a monoclonal antibody or fragment thereof.

6. The antibody or fragment thereof of claim 1 that is a chimeric antibody or fragment thereof.

7. The antibody or fragment thereof of claim 1 that is a CDR-grafted antibody or fragment thereof.

8. The antibody or fragment thereof of claim 1 that is an antiidiotypic antibody or fragment thereof.

9. The antibody or fragment thereof of claim 1 which is a variable region fragment.

10. The variable region fragment of claim 9 which is a Fab or a Fab' fragment.

11. The antibody or fragment thereof of claim 1 which is bound to a detectable label.

12. A method of detecting or quantitating the amount of huE3α ubiquitin ligase polypeptide in a sample using the anti-huE3α antibody or fragment thereof of claim 1, comprising:
   (a) obtaining a sample;
   (b) contacting the sample with an antibody or fragment thereof according to claim 1 under conditions which allow for the antibody to bind to the huE3α ubiquitin ligase polypeptide;
   (c) detecting antibody binding to huE3α ubiquitin lipase polypeptide in the biological sample, wherein the detection of antibody binding is indicative of the presence of huE3α ubiquitin ligase polypeptide in said sample; and
   (d) comparing the level of antibody binding to huE3α ubiquitin polypeptide within said sample and the level of the antibody binding to a known concentration of huE3α ubiquitin ligase polypeptide.

13. A method for determining the presence and/or concentration of huE3α ubiquitin ligase polypeptide in a biological sample comprising the steps of:
   (a) obtaining a biological sample;
   (b) contacting the biological sample with an antibody according to claim 1 under conditions which allow for the antibody to bind to the huE3α ubiquitin ligase polypeptide;
   (c) detecting antibody binding to huE3α ubiquitin ligase polypeptide in the biological sample, wherein the detection of antibody binding is indicative of the presence of huE3α ubiquitin ligase polypeptide in said biological sample; and
   (d) comparing the level of antibody binding to huE3α ubiquitin ligase polypeptide within said biological sample and the level of the antibody binding to a known concentration of huE3α ubiquitin ligase polypeptide.

* * * * *

UNITED STATES PATENT AND TRADEMARK OFFICE
CERTIFICATE OF CORRECTION

Page 1 of 1

PATENT NO.        : 7,745,586 B2
APPLICATION NO.   : 12/186998
DATED             : June 29, 2010
INVENTOR(S)       : Hui-Quan Han et al.

It is certified that error appears in the above-identified patent and that said Letters Patent is hereby corrected as shown below:

Column 164, Line 65, "ubiquitin polypeptide" should be changed to -- ubiquitin ligase polypeptide --

Signed and Sealed this
Second Day of October, 2012

David J. Kappos
*Director of the United States Patent and Trademark Office*